US012759996B2

(12) United States Patent
Yang et al.

(10) Patent No.: US 12,759,996 B2
(45) Date of Patent: Oct. 13, 2026

(54) GLUTARIMIDE SKELETON-BASED COMPOUNDS AND USE THEREOF

(71) Applicant: SHANGHAITECH UNIVERSITY, Pudong (CN)

(72) Inventors: Xiaobao Yang, Pudong (CN); Biao Jiang, Pudong (CN); Xing Qiu, Pudong (CN); Ning Sun, Pudong (CN); Renhong Sun, Pudong (CN); Chaowei Ren, Pudong (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 903 days.

(21) Appl. No.: 17/801,953

(22) PCT Filed: Feb. 25, 2021

(86) PCT No.: PCT/CN2021/077793
§ 371 (c)(1),
(2) Date: Aug. 24, 2022

(87) PCT Pub. No.: WO2021/170021
PCT Pub. Date: Sep. 2, 2021

(65) Prior Publication Data
US 2023/0096517 A1 Mar. 30, 2023

(30) Foreign Application Priority Data
Feb. 25, 2020 (CN) ......................... 202010115249.2

(51) Int. Cl.
*C07D 401/04* (2006.01)
*A61P 35/00* (2006.01)

(52) U.S. Cl.
CPC ............ *C07D 401/04* (2013.01); *A61P 35/00* (2018.01)

(58) Field of Classification Search
None
See application file for complete search history.

(56) References Cited

U.S. PATENT DOCUMENTS 9,938,264 B2 4/2018 Crews et al.
9,993,514 B2 6/2018 Campos
10,385,037 B2 8/2019 Ruchelman et al.
10,450,310 B2 10/2019 Gray et al.
10,759,808 B2 9/2020 Wang et al.
11,104,666 B2 8/2021 Crew et al.
11,771,709 B2 10/2023 Yang et al.
12,226,424 B2 2/2025 Yang et al.
2006/0063926 A1 3/2006 Ma et al.
2008/0167345 A1 7/2008 Jones et al.
2010/0099658 A1 4/2010 Kondoh et al.
2010/0204196 A1 8/2010 Chamberlain et al.
2012/0028924 A1 2/2012 Aquila et al.
2012/0083488 A1 4/2012 Kinoshita et al.
2012/0202776 A1 8/2012 Wang et al.
2013/0143922 A1 6/2013 Greig et al.
2013/0190298 A1 7/2013 Liang et al.
2015/0291562 A1 10/2015 Crew et al.
2016/0022642 A1 1/2016 Crews
2018/0099940 A1 4/2018 Crew et al.
2022/0041576 A1 2/2022 Chen et al.
2022/0041578 A1 2/2022 Chen et al.
2022/0117982 A1 4/2022 Yang et al.
(Continued)

FOREIGN PATENT DOCUMENTS

CN 1867331 11/2006
CN 101679380 3/2010
(Continued)

OTHER PUBLICATIONS

Steinebach, et al., "A MedChem toolbox for cereblon-directed PROTACs", MedChemComm, United Kingdom, vol. 10, No. 16, Jun. 19, 2019, 5 pages.
International Search Report for PCT/CN2021/077793, mailed May 26, 2021, 14 pages.
Written Opinion of the ISA for PCT/CN2021/077793, mailed May 26, 2021, 8 pages.
Yamazoe et al (Heterobifunctional molecules induce dephosphorylation of kinases—a proof of concept study, ChemRxiv, Jul. 31, 2019, doi.org/10.26434/chemrxiv.9177878.v1).
International Search Report for PCT/CN2020/076578 mailed Mar. 30, 2020, 9 pages.
Written Opinion of the ISA for PCT/CN2020/076578 mailed Mar. 30, 2020, 12 pages.
(Continued)

*Primary Examiner* — Samantha L Shterengarts
(74) *Attorney, Agent, or Firm* — NIXON & VANDERHYE, PC

(57) ABSTRACT

The present disclosure relates to glutarimide skeleton-based compounds of Formula (I) or a salt, an enantiomer, a stereoisomer, a solvate, or a polymorph thereof, and uses thereof. The present disclosure further relates to a pharmaceutical composition comprising, as an active ingredient, the glutarimide skeleton-based compounds of Formula (I), or a salt, an enantiomer, a stereoisomer, a solvate, or a polymorph thereof, and uses thereof. The series of compounds designed and synthesized in the present disclosure can effectively prevent and/or treat a tumor.

Formula (I)

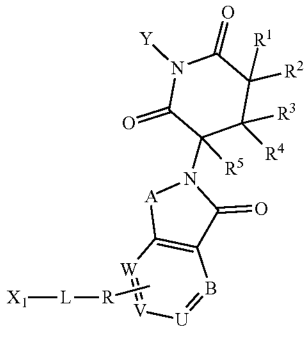

31 Claims, 1 Drawing Sheet

(56) References Cited

U.S. PATENT DOCUMENTS

| | | | |
|---|---|---|---|
| 2022/0143002 A1 | 5/2022 | Yang et al. | |
| 2022/0313829 A1 | 10/2022 | Yang | |
| 2023/0096517 A1 | 3/2023 | Yang | |
| 2023/0203022 A1 | 6/2023 | Yang | |

FOREIGN PATENT DOCUMENTS

| | | | |
|---|---|---|---|
| CN | 102822165 | 12/2012 | |
| CN | 103396397 | 11/2013 | |
| CN | 103787802 | 5/2014 | |
| CN | 105566290 | 5/2016 | |
| CN | 106432104 | 2/2017 | |
| CN | 106458993 | 2/2017 | |
| CN | 108136044 | 6/2018 | |
| CN | 108366992 | 8/2018 | |
| CN | 109311900 | 2/2019 | |
| CN | 109475528 | 3/2019 | |
| CN | 109912655 | 6/2019 | |
| CN | 109928956 | 6/2019 | |
| CN | 110204532 | 9/2019 | |
| CN | 110291087 | 9/2019 | |
| CN | 110357889 | 10/2019 | |
| CN | 110506039 | 11/2019 | |
| CN | 11051298 | 4/2020 | |
| CN | 110963994 | 4/2020 | |
| CN | 111606883 | 9/2020 | |
| JP | H02-184659 | 7/1990 | |
| JP | 2006519827 | 8/2006 | |
| JP | 2008513538 | 5/2008 | |
| JP | 2010515715 | 5/2010 | |
| JP | 2010522170 | 7/2010 | |
| JP | 2010535798 | 11/2010 | |
| JP | 2011523646 | 8/2011 | |
| JP | 2013534221 | 9/2013 | |
| JP | 2013539765 | 10/2013 | |
| JP | 2017513862 | 6/2017 | |
| JP | 2019513746 | 5/2019 | |
| JP | 2020504089 | 2/2020 | |
| JP | 2022503942 | 1/2022 | |
| JP | 2022521746 | 4/2022 | |
| WO | 2004080976 | 9/2004 | |
| WO | 2008115516 | 9/2008 | |
| WO | 2009008371 | 1/2009 | |
| WO | 2010143664 | 12/2010 | |
| WO | 2016065980 | 5/2016 | |
| WO | 2016197032 | 12/2016 | |
| WO | 2017079267 | 5/2017 | |
| WO | 2017/117474 | 7/2017 | |
| WO | 2017/185036 | 10/2017 | |
| WO | 2017176957 | 10/2017 | |
| WO | 2017176958 | 10/2017 | |
| WO | 2017185031 | 10/2017 | |
| WO | WO-2017176958 A1 * | 10/2017 | ............. A61P 35/00 |
| WO | 2017197036 | 11/2017 | |
| WO | 2017197051 | 11/2017 | |
| WO | 2017197056 | 11/2017 | |
| WO | 2018052945 | 3/2018 | |
| WO | 2018052949 | 3/2018 | |
| WO | 2018071606 | 4/2018 | |
| WO | 2018/098288 | 5/2018 | |
| WO | 2018102067 | 6/2018 | |
| WO | 2018102725 | 6/2018 | |
| WO | 2018119441 | 6/2018 | |
| WO | 2018119448 | 6/2018 | |
| WO | 2018140809 | 8/2018 | |
| WO | 2019038717 | 2/2019 | |
| WO | 2019079569 | 4/2019 | |
| WO | 2019133531 | 7/2019 | |
| WO | 2019195609 | 10/2019 | |
| WO | 2019196812 | 10/2019 | |
| WO | 2020006264 | 1/2020 | |
| WO | 2020114482 | 6/2020 | |
| WO | 2020173426 | 9/2020 | |
| WO | 2020198435 | 10/2020 | |
| WO | 2021113557 | 6/2021 | |
| WO | 2021118629 | 6/2021 | |

OTHER PUBLICATIONS

Written Opinion of the ISA for PCT/CN2021/077793, mailed May 26, 2021, 19 pages.
Donghuai Xiao et al., “Design, synthesis and biological evaluation of the thioether-containing lenalidomide analogs with anti-proliferative activities”, Science Direct, European Journal of Medicinal Chemistry 176 (available on line May 15, 2019), pp. 419-430 (12 pages).
Yiming Li et al., “A Highly Efficient Cu-Catalyzed S-Transfer Reaction: From Amine to Sulfide”, Organic Letters, pubs.acs.org/OrgLett, ASC Publications, 2014 American Chemical Society, dx.doi.org/10.1021/015009747, pp. 2692-2695, Downloaded via Shanghai Advanced Research Inst on Aug. 30, 2021 at 00:30:59 (UTC). See https://pubs.acs.org/sharingguidelines for options on how to legitimately share published articles. (4 pages).
Yiming Li et al., “Selective Late-Stage Oxygenation of Sulfides with Ground-State Oxygen by Uranyl Photocatalysis”, Angewandte Chem. Int. Ed. 2019, first published Jul. 2019, 58, pp. 13499-13506, DOI: 10.1002/anie.201906080, Wiley Online Library (8 pages).
Turk, et al., Proceedings of the National Academy of Sciences of the United States of America (1996), 93(15), 7552-7556.
Ishoey, Mette, Translation Termination Factor GSPT1 Is a Phenotypi cally Relevant Off-Target of Heterobifunctional Phthalimide Degraders, A CS Chemical Biology , 2018, 13(3), 553-560.
Zhang, Chengwei, Proteolysis Targeting Chimeras (PROTACs) of Anaplastic Lymphoma Kinase (ALK), European Journal of Medicinal Chemistry, 2018, 151, 304-314.
Lai, Ashton C., Modular PROTAC Design for the Degradation of Oncog enic BCR-ABL, Angewandte Chemie, International Edition, 2016, 55(2), 807-810.
Restriction Requirement issued in U.S. Appl. No. 17/433,462 dated Jul. 30, 2024, 13 pages.
Non-Final Office Action issued in U.S. Appl. No. 17/433,462 dated Dec. 13, 2024, 19 pages.
Restriction Requirement issued in U.S. Appl. No. 17/046,690 dated May 24, 2022, 11 pages.
Non-Final Office Action issued in U.S. Appl. No. 17/046,690 dated Sep. 14, 2022, 31 pages.
Non-Final Office Action issued in U.S. Appl. No. 17/046,690 dated May 24, 2023, 19 pages.
Non-Final Office Action issued in U.S. Appl. No. 17/046,690 dated Mar. 25, 2024, 21 pages.
Non-Final Office Action issued in U.S. Appl. No. 17/632,612 dated Nov. 27, 2024, 27 pages.
U.S. Appl. No. 17/922,124, filed Oct. 28, 2022, 89 pages.
U.S. Appl. No. 17/632,612, filed Aug. 24, 2022, 287 pages.
U.S. Appl. No. 17/433,462, filed Aug. 24, 2021, 282 pages.

* cited by examiner

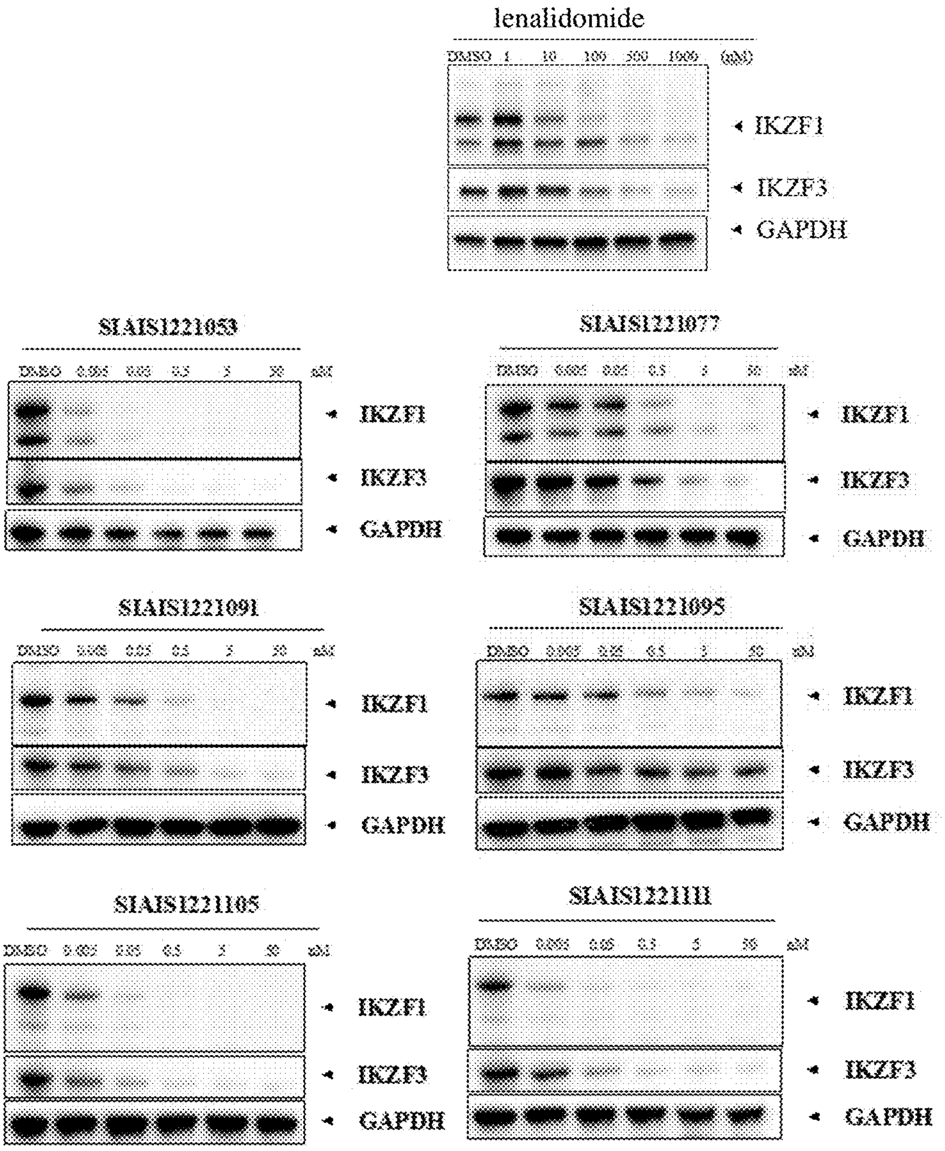
lenalidomide
DMSO 1 10 100 500 1000 (nM)
IKZF1
IKZF3
GAPDH
SIAIS1221053
IKZF1
IKZF3
GAPDH
SIAIS1221077
IKZF1
IKZF3
GAPDH
SIAIS1221091
IKZF1
IKZF3
GAPDH
SIAIS1221095
IKZF1
IKZF3
GAPDH
SIAIS1221105
IKZF1
IKZF3
GAPDH
SIAIS1221111
IKZF1
IKZF3
GAPDH

GLUTARIMIDE SKELETON-BASED COMPOUNDS AND USE THEREOF

This application is the U.S. national phase of International Application No. PCT/CN2021/077793 filed Feb. 25, 2021 which designated the U.S. and claims priority to CN Patent Application No. 202010115249.2 filed Feb. 25, 2020, the entire contents of each of which are hereby incorporated by reference.

TECHNICAL FIELD

The present disclosure relates to compounds of Formula (I) and uses thereof, especially their use for preventing and/or treating a tumor.

Formula (I)

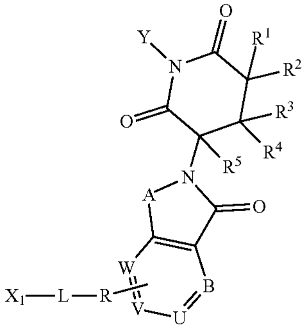

BACKGROUND

Thalidomide is the first-generation immunomodulatory drug, which was used to treat morning sickness in pregnant women in the 1950s and 1960s. However, because fetal malformation results from exposures to thalidomide, it was withdrawn from the market. As Singhal et al. first used thalidomide as a single agent for the treatment of patients with refractory multiple myeloma, it showed good clinical efficacy. Later, researchers conducted numerous clinical trials of thalidomide alone or in combination with dexamethasone in the treatment of refractory or relapsed multiple myeloma. Thalidomide has been found to have the immunomodulatory function and antitumor activities, and has attracted widespread attention again. In order to increase its immunoregulatory function and anti-cancer activity and reduce toxic and side effects, scientists have used thalidomide as the lead compound to synthesize a series of substituted phthalimide derivatives Pomalidomide and Lenalidomide. Lenalidomide, a lower toxic but higher active derivative, was approved by the FDA in 2006 in combination with dexamethasone for the treatment of relapsed or refractory multiple myeloma. In 2013, the third-generation immunomodulatory drug pomalidomide was approved for patients with relapsed/refractory multiple myeloma treated with at least two drugs including lenalidomide and bortezomib. The detailed mechanism of action of pomalidomide has not been clear until a study in 2010 using biochemical methods to affinity purify proteins that interact with thalidomide identified that Cereblon is the main target of thalidomide and its analogs; and research in related fields has become increasingly active. Subsequently, the mechanism of these drugs in the treatment of multiple myeloma was revealed: immunomodulatory drugs can bind to the CRBN protein in cells, so that CRL4A$^{CRBN}$ ubiquitin ligase ubiquitinylates and degrades transcription factors IKZF1 and IKZF3 which are essential in the development and survival of B cells. In 2014, Professor Harper discovered five endogenous ligase substrates: GRINL1A, MBOAT7, OTUD7B, C6orf141 and MEIS2 by ubiquitination analysis using protein chips. Among them, MEIS2, as a transcription factor, plays an important role in the normal development of the human body, and its increased expression can lead to shortened toe tips in chicken embryos, indicating that this molecule is a potential downstream molecule of thalidomide-induced embryonic malformation. The binding site of MEIS2 molecule in CRBN is the same as that of thalidomide, so thalidomide competes with MEIS2 for binding to CRBN. In 2015, Prof. Kranke discovered that lenalidomide is also highly effective in the treatment of myelodysplastic syndrome (MDS) caused by the deletion of 5q chromosome. Through using stable isotope labeling of amino acids in cell culture (SILAC) quantitative mass spectrometry to evaluate the global changes in ubiquitination and protein levels in del (5q) myeloid cell line KG-1, it was found that lenalidomide can uniquely degrade CK1α protein, while neither pomalidomide nor thalidomide has any effect in CK1α. In 2016, Professor Ito designed and synthesized a novel CRBN-binding drug CC-885 based on the lenalidomide skeleton, which mainly degrades the GSPT1 protein and has the potential to treat patients with acute myeloid leukemia (AML).

Thalidomide and derivatives thereof play a vital role in the treatment of other related malignant tumors such as multiple myeloma, therefore there is an urgent need to design and synthesize a series of highly active glutarimide skeleton-based drugs in order to achieve better therapeutic effect.

SUMMARY OF INVENTION

Therefore, in one aspect, the present disclosure provides a compound of Formula (I):

Formula (I)

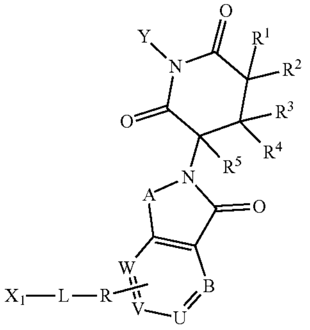

or a salt, enantiomer, diastereomer, solvate, or polymorph thereof, in which

A, R, L, $X_1$, Y, $R^1$, $R^2$, $R^3$, $R^4$, and $R^5$ and all substituents are as defined in the Detailed Description of the Invention.

The present disclosure also provides a pharmaceutical composition comprising the compound of Formula (I) or a pharmaceutically acceptable salt, enantiomer, diastereomer, solvate, or polymorph thereof, and at least one pharmaceutically acceptable carrier.

The present disclosure also provides the compound of Formula (I), or a pharmaceutically acceptable salt, enantiomer, diastereomer, solvate, or polymorph thereof for use as a medicament.

The present disclosure also provides the compound of Formula (I), or a pharmaceutically acceptable salt, enantiomer, diastereomer, solvate, or polymorph thereof for use in the prevention or treatment of a tumor.

The present disclosure further provides the use of the compound of Formula (I) or a pharmaceutically acceptable salt, enantiomer, diastereomer, solvate, polymorph thereof or the pharmaceutical composition of the present disclosure for the manufacture of a medicament for treating or preventing a tumor.

The present disclosure also provides a method for treating or preventing a tumor, comprising administering to a subject a therapeutically effective amount of the compound of Formula (I), or a pharmaceutically acceptable salt thereof, enantiomers, diastereomers, solvates, polymorphs thereof, or the pharmaceutical composition.

BRIEF DESCRIPTION OF DRAWINGS

FIG. 1 shows the degradation of IKZF1 and IKZF3 proteins caused by the compounds of the present invention in multiple myeloma cells MM.1S, as detected by Western blotting.

DETAILED DESCRIPTION OF THE INVENTION

In one aspect, the present disclosure provides Embodiment 1): the compound of Formula (I):

Formula (I)

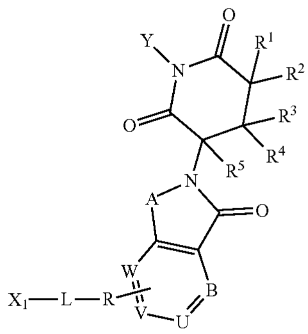

or a salt, an enantiomer, a diastereomer, a solvate, or a polymorph thereof, in which Y represents H, D, $C_{1-3}$ alkyl, or deuterated $C_{1-3}$ alkyl;

$R^1$, $R^2$, $R^3$, $R^4$, and $R^5$ are the same or different and each independently represent H or D;

A represents $CH_2$, $CD_2$, or C(O);

B, U, V, W are the same or different and each independently represent CH, CD, or N, wherein B, U, V, and W are not N at the same time, and when any of B, U, V, and W is attached to R, it is not N; and when R is O or NH, or R represents a bond, L represents a substituted or unsubstituted linear or branched $C_{5-40}$ alkylene group, wherein the substituent(s) of said substituted linear or branched $C_{5-40}$ alkylene group is one or more selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, cyano, or any combination thereof; and $X_1$ represents the Formula —$X_a$—$X_b$, wherein $X_a$ represents O, N($R^6$), C(O)N($R^6$), N($R^6$)C(O), alkynylene, or alkenylene, wherein $R^6$ represents H, $C_{1-3}$ alkyl, or deuterated $C_{1-3}$ alkyl, or $X_a$ represents a bond, and $X_b$ represents a substituted or unsubstituted $C_{3-6}$ cycloalkyl or a substituted or unsubstituted $C_{7-11}$ spiro-cycloalkyl, wherein the substituent(s) of said substituted $C_{3-6}$ cycloalkyl and the substituent (s) of said substituted $C_{7-11}$ spiro-cycloalkyl are each independently one or more selected from the group consisting of: D, $C_{1-3}$ alkyl, deuterated $C_{1-3}$ alkyl, halogenated $C_{1-3}$ alkyl, $C_{1-3}$ alkoxy, deuterated $C_{1-3}$ alkoxy, oxo, halogen, hydroxyl, cyano, $C_{1-3}$ alkylamino, amino, or any combination thereof; or when R is O or NH, or R represents a bond, L represents a substituted or unsubstituted linear or branched $C_{1-40}$ alkylene group, wherein said linear or branched $C_{1-40}$ alkylene group is optionally interrupted one or more times by a group selected from the group consisting of: N($R^7$), phenylene or any combination thereof, wherein $R^7$ represents H, $C_{1-3}$ alkyl, or deuterated $C_{1-3}$ alkyl, and the substituent(s) of said substituted linear or branched $C_{1-40}$ alkylene and the substituent(s) of said substituted phenylene are each independently one or more selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, cyano, or any combination thereof; and $X_1$ represents the Formula —$X_c$—$X_d$, wherein $X_c$ represents O, N($R^8$), C(O)N($R^8$), N($R^8$)C(O), alkynylene, or alkenylene, wherein $R^8$ represents H, $C_{1-3}$ alkyl, or deuterated $C_{1-3}$ alkyl, or $X_c$ represents a bond, and $X_d$ represents $C_{7-15}$ bridged cycloalkyl optionally substituted with from 1 to 10 substituents selected from the group consisting of: D, $C_{1-3}$ alkyl, deuterated $C_{1-3}$ alkyl, $C_{1-3}$ alkoxy, deuterated $C_{1-3}$ alkoxy, halogen, halogenated $C_{1-3}$ alkyl, hydroxyl, cyano, oxo, $C_{1-3}$ alkylamino, amino, or any combination thereof; or when R is alkynylene or alkenylene, L represents a substituted or unsubstituted linear or branched $C_{1-40}$ alkylene group, wherein the linear or branched $C_{1-40}$ alkylene group is optionally interrupted one or more times by a group selected from the group consisting of: N($R^9$), phenylene or any combination thereof, wherein $R^9$ represents H, $C_{1-3}$ alkyl or deuterated $C_{1-3}$ alkyl, and the substituent(s) of said substituted linear or branched $C_{1-40}$ alkylene and the substituent(s) of said substituted phenylene are each independently one or more selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, cyano, or any combination thereof; and $X_1$ represents the Formula —$X_e$—$X_f$, wherein $X_e$ represents O, N($R^{10}$), C(O)N($R^{10}$), N($R^{10}$)C(O), alkynylene, or alkenylene, wherein $R^{10}$ represents H, $C_{1-3}$ alkyl, or deuterated $C_{1-3}$ alkyl, or $X_e$ represents a bond, and $X_f$ represents a substituted or unsubstituted $C_{3-15}$ cycloalkyl or a substituted or unsubstituted $C_{3-15}$ heterocyclyl, wherein the substituent(s) of said substituted $C_{3-15}$ cycloalkyl and the substituent(s) of said substituted $C_{3-15}$ heterocyclyl are each independently one or more selected from the group consisting of: D, $C_{1-3}$ alkyl, deuterated $C_{1-3}$ alkyl, $C_{1-3}$ alkoxy, deuterated $C_{1-3}$ alkyloxy, halogen, halogenated $C_{1-3}$ alkyl, hydroxyl, cyano, oxo, optionally substituted phenyl, $C_{1-3}$ alkylamino, amino, or any combination thereof.

Herein, either one of both ends of the alkylene chain represented by L may be connected to the group $X_1$, while the other end may be connected to R.

Embodiment 2) relates to the compound of Formula (I) or a salt, enantiomer, stereoisomer, solvate, or polymorph thereof as described in Embodiment 1), wherein B, U, V, and W in Formula (I) are the same, and all are CH.

Embodiment 3) relates to the compound of Formula (I) or a salt, enantiomer, stereoisomer, solvate, or polymorph thereof as described in Embodiment 1), wherein one of B, U, V, and W in Formula (I) is N, and the rest are CH.

Embodiment 4) relates to the compound of Formula (I) or a salt, enantiomer, stereoisomer, solvate, or polymorph thereof as described in Embodiment 1), wherein two of B, U, V, and W in Formula (I) are N, and the rest are CH.

Embodiment 5) relates to the compound of Formula (I) or a salt, enantiomer, stereoisomer, solvate, or polymorph thereof as described in Embodiment 1), wherein three of B, U, V, and W in Formula (I) are N, and the rest is CH.

Embodiment 6) relates to the compound of Formula (I) or a salt, enantiomer, stereoisomer, solvate, or polymorph thereof as described in Embodiment 1), which is also the compound of Formula (Ia):

Formula (Ia)

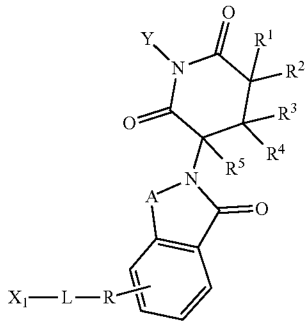

wherein the groups A, R, L, $X_1$, Y, $R^f$, $R^2$, $R^3$, $R^4$, and $R^5$ are as defined in Embodiment 1).

Embodiment 7) relates to the compound of Formula (I) or a salt, enantiomer, stereoisomer, solvate, or polymorph thereof as described in Embodiment 1), which is also the compound of Formula (Ib):

Formula (Ib)

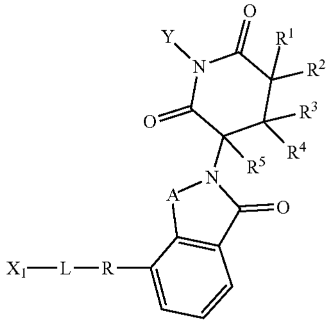

wherein the groups A, R, L, $X_1$, Y, $R^1$, $R^2$, $R^3$, $R^4$, and $R^5$ are as defined in Embodiment 1).

Embodiment 8) relates to the compound of Formula (I) or a salt, enantiomer, stereoisomer, solvate, or polymorph thereof as described in Embodiment 1), which is also the compound of Formula (Ic):

Formula (Ic)

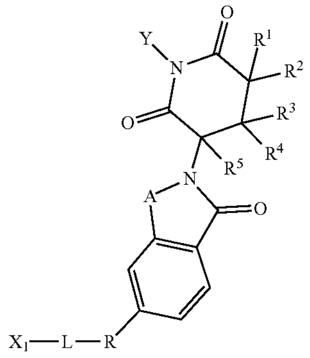

wherein the groups A, R, L, $X_1$, Y, $R^1$, $R^2$, $R^3$, $R^4$, and $R^5$ are as defined in Embodiment 1).

Embodiment 9) relates to the compound of Formula (I) or a salt, enantiomer, stereoisomer, solvate, or polymorph thereof as described in Embodiment 1), which is also the compound of Formula (Id):

Formula (Id)

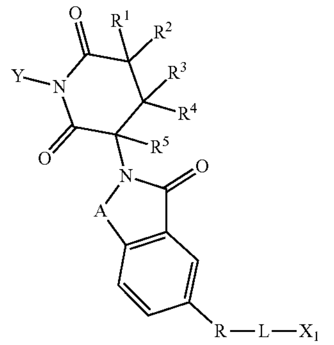

wherein the groups A, R, L, $X_1$, Y, $R^1$, $R^2$, $R^3$, $R^4$, and $R^5$ are as defined in Embodiment 1).

Embodiment 10) relates to the compound of Formula (I) or a salt, enantiomer, stereoisomer, solvate, or polymorph thereof as described in Embodiment 1), which is also the compound of Formula (Ie):

Formula (Ie)

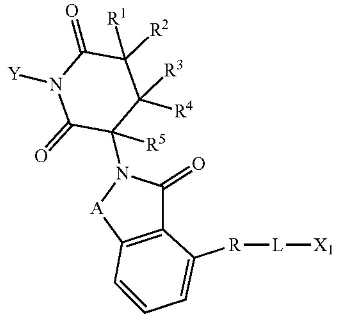

wherein the groups A, R, L, $X_1$, Y, $R^1$, $R^2$, $R^3$, $R^4$, and $R^5$ are as defined in Embodiment 1).

Embodiment 11) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-10), wherein Y represents H.

Embodiment 12) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-10), wherein Y represents D (i.e., deuterium atom).

Embodiment 13) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-10), wherein Y represents $C_{1-3}$ alkyl (optionally methyl or ethyl).

Embodiment 14) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-10), wherein Y represents methyl.

Embodiment 15) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-14), wherein A in Formula (I) represents C(O).

Embodiment 16) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-14), wherein A in Formula (I) represents $CH_2$.

Embodiment 17) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-16), wherein $R^1$, $R^2$, $R^3$, $R^4$, and $R^5$ in Formula (I) are the same, and represent H.

Embodiment 18) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-16), wherein $R^1$, $R^2$, $R^3$, $R^4$, and $R^5$ in Formula (I) are the same, and represent D.

Embodiment 19) relate to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-18), wherein when R is O or NH, or R is a bond, L represents linear or branched $C_{5-40}$ alkylene (optionally $C_{5-35}$ alkylene, $C_{5-30}$ alkylene, $C_{5-20}$ alkylene, $C_{5-10}$ alkylene, or $C_{5-10}$ alkylene), wherein the hydrogen atom(s) of one or more $CH_2$ (e.g., 1-20, 1-15, 1-10, 1-8, 1-5, 1-3, or 1-2 $CH_2$) of said linear or branched $C_{5-40}$ alkylene is optionally replaced with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof; and $X_1$ represents the Formula —$X_a$—$X_b$, wherein $X_a$ represents O, N($R^6$), C(O)N($R^6$), N($R^6$)C(O), alkynylene, or alkenylene, wherein $R^6$ represents H, $C_{1-3}$ alkyl (e.g., methyl, ethyl, or propyl), or deuterated $C_{1-3}$ alkyl, or $X_a$ represents a bond, and $X_b$ represents $C_{3-6}$ cycloalkyl or $C_{7-11}$ spiro-cycloalkyl, wherein said $C_{3-6}$ cycloalkyl and said $C_{7-11}$ spiro-cycloalkyl are each independently optionally substituted with one or more (e.g., 1-10, 1-9, 1-8, 1-7, 1-6, 1-5, 1-3, or 1-2) substituent(s) selected from the group consisting of: D, $C_{1-3}$ alkyl (e.g., methyl, ethyl, or propyl), deuterated $C_{1-3}$ alkyl, halogenated $C_{1-3}$ alkyl (e.g., trifluoromethyl), $C_{1-3}$ alkoxy (e.g., methoxy, ethoxy, or propoxy), deuterated $C_{1-3}$ alkoxy, oxo, halogen (e.g., fluorine, chlorine, bromine, or iodine), hydroxyl, cyano, $C_{1-3}$ alkylamino, amino, or any combination thereof.

Embodiment 20) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 19), wherein L represents the following groups:

$-(CH_2)_5-$, $-(CH_2)_6-$, $-(CH_2)_7-$, $-(CH_2)_8-$, $-(CH_2)_9-$, $-(CH_2)_{10}-$, $-(CH_2)_{11}-$, $-(CH_2)_{12}-$, $-(CH_2)_{13}-$, $-(CH_2)_{14}-$, $-(CH_2)_{15}-$, $-(CH_2)_{16}-$, $-(CH_2)_{17}-$, $-(CH_2)_{18}-$, $-(CH_2)_{19}-$, or $-(CH_2)_{20}-$; wherein the hydrogen atom(s) of one or more $CH_2$ (e.g., 1-20, 1-15, 1-10, 1-8, 1-5, 1-3, or 1-2 $CH_2$) of the groups are optionally further replaced with the following substituent(s) selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof.

Embodiment 21) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 19), wherein L represents the following groups: $-(CH_2)_5-$, $-(CH_2)_6-$, $-(CH_2)_7-$, $-(CH_2)_8-$, $-(CH_2)_9-$, $-(CH_2)_{10}-$, $-(CH_2)_{11}-$, $-(CH_2)_{12}-$, $-(CH_2)_{13}-$, $-(CH_2)_{14}-$, $-(CH_2)_{15}-$, $-(CH_2)_{16}-$, $-(CH_2)_{17}-$, $-(CH_2)_{18}-$, $-(CH_2)_{19}-$, or $-(CH_2)_{20}-$.

Embodiment 22) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 19)-21), wherein $X_1$ represents the Formula —$X_a$—$X_b$, wherein $X_a$ represents O, N($R^6$), C(O)N($R^6$), N($R^6$)C(O), alkynylene, or alkenylene, wherein $R^6$ represents H, $C_{1-3}$ alkyl (e.g., methyl, ethyl, or propyl), or deuterated $C_{1-3}$ alkyl, or $X_a$ represents a bond, and $X_b$ represents the following groups: cyclopropyl, cyclobutyl, cyclopentyl, cyclohexyl, spiro[3.3]heptyl, spiro[2.5]octyl, spiro[3.5]nonyl, spiro[4.4]nonyl, spiro[4.5]decyl, or spiro[5.5]undecyl, wherein the groups are optionally further substituted with one or more (e.g., 1-10, 1-9, 1-8, 1-7, 1-6, 1-5, 1-3, or 1-2) substituent(s) selected from the group consisting of D, $C_{1-3}$ alkyl (e.g., methyl, ethyl, or propyl), deuterated $C_{1-3}$ alkyl, halogenated $C_{1-3}$ alkyl (e.g., trifluoromethyl), $C_{1-3}$ alkoxy (e.g., methoxy, ethoxy, or propoxy), deuterated $C_{1-3}$ alkoxy, oxo, halogen (e.g., fluorine, chlorine, bromine, or iodine), hydroxyl, cyano, $C_{1-3}$ alkylamino, amino, or any combination thereof.

Embodiment 23) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiments 22), wherein $X_b$ represents cyclopropyl, methoxycyclopropyl, cyclobutyl, fluorocyclobutyl, cyclopentyl, fluorocyclopentyl, cyclohexyl, dimethylcyclohexyl, hydroxycyclohexyl, fluorocyclohexyl, spiro[3.3]heptyl, spiro[2.5]octyl, spiro[3.5]nonyl, spiro[4.4]nonyl, spiro[4.5]decyl, or spiro[5.5]undecyl.

Embodiment 24) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-18), wherein when R is O or NH, or R represents a bond, L represents linear or branched $C_{1-40}$ alkylene (optionally $C_{1-35}$ alkylene, $C_{1-30}$ alkylene, $C_{1-20}$ alkylene, $C_{1-15}$ alkylene, or $C_{1-10}$ alkylene), wherein the linear or branched $C_{1-40}$ alkylene is optionally interrupted one or more times (e.g., 1-10 times, 1-8 times, 1-6 times, 1-5 times, 1-3 times, 1-2 times, or 1 time) by a group selected from the group consisting of: $N(R^7)$, phenylene, or any combination thereof, wherein $R^7$ represents H, $C_{1-3}$ alkyl (e.g., methyl, ethyl, or propyl), or deuterated $C_{1-3}$ alkyl, and the hydrogen atom(s) of one or more $CH_2$ (e.g., 1-20, 1-15, 1-10, 1-8, 1-5, 1-3, or 1-2 $CH_2$) of said linear or branched $C_{1-40}$ alkylene and said phenylene are each independently optionally substituted with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof; and $X_1$ represents the Formula $—X_c—X_d$, wherein $X_c$ represents O, $N(R^8)$, $C(O)N(R^8)$, $N(R^8)C(O)$, alkynylene, or alkenylene, wherein $R^8$ represents H, $C_{1-3}$ alkyl (e.g., methyl, ethyl, or propyl), or deuterated $C_{1-3}$ alkyl, or $X_c$ represents a bond, and $X_d$ represents $C_{7-11}$ bridged cycloalkyl optionally substituted with from 1 to 10 (e.g., 1-9, 1-8, 1-7, 1-6, 1-5, 1-4, 1-3, or 1-2) substituent(s) selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), deuterated $C_{1-3}$ alkoxy, halogen (e.g., fluorine, chlorine, bromine, or iodine), halogenated $C_{1-3}$ alkyl (e.g., trifluoromethyl)), hydroxyl, cyano, oxo, $C_{1-3}$ alkylamino, amino, or any combination thereof.

Embodiment 25) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 24), wherein L represents a linear or branched $C_{1-40}$ alkylene (e.g., $C_{1-35}$ alkylene, $C_{1-30}$ alkylene, $C_{1-20}$ alkylene, $C_{1-15}$ alkylene, or $C_{1-10}$ alkylene), wherein the hydrogen atom(s) of one or more $CH_2$ (e.g., 1-20, 1-15, 1-10, 1-8, 1-5, 1-3, or 1-2 $CH_2$) of said linear or branched $C_{1-40}$ alkylene are replaced with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano or any combination thereof.

Embodiment 26) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 25), wherein L represents the following groups: $—CH_2—$, $—(CH_2)_2—$, $—(CH_2)_3—$, $—(CH_2)_4—$, $—(CH_2)_5—$, $—(CH_2)_6—$, $—(CH_2)_7—$, $—(CH_2)_8—$, $—(CH_2)_9—$, $—(CH_2)_{10}—$, $—(CH_2)_{11}—$, $—(CH_2)_{12}—$, $—(CH_2)_{13}—$, $—(CH_2)_{14}—$, $—(CH_2)_{15}—$, $—(CH_2)_{16}—$, $—(CH_2)_{17}—$, $—(CH_2)_{18}—$, $—(CH_2)_{19}—$, or $—(CH_2)_{20}—$; wherein the hydrogen atom(s) of one or more $CH_2$ (e.g., 1-20, 1-15, 1-10, 1-8, 1-5, 1-3, or 1-2 $CH_2$) of the groups are optionally further replaced by a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof.

Embodiment 27) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 24), wherein L represents a linear or branched $C_{2-40}$ alkylene (e.g., $C_{2-35}$ alkylene, $C_{2-30}$ alkylene, $C_{2-20}$ alkylene, $C_{2-15}$ alkylene, or $C_{2-10}$ alkylene), wherein said linear or branched $C_{2-40}$ alkylene is interrupted one or more times (e.g., 1-10 times, 1-8 times, 1-6 times, 1-5 times, 1-3 times, 1-2 times or 1 time) by a group selected from the group consisting of: $N(R^7)$, phenylene, or any combination thereof, wherein $R^7$ represents H, $C_{1-3}$ alkyl (e.g., methyl, ethyl, or propyl), or deuterated $C_{1-3}$ alkyl, and the hydrogen atom(s) of one or more $CH_2$ (e.g., 1-20, 1-15, 1-10, 1-8, 1-5, 1-3, or 1-2 $CH_2$) of said linear or branched $C_{2-40}$ alkylene and said phenylene are each independently optionally substituted with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof.

Embodiment 28) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 27), wherein L represents the following groups: $*—(CH_2)_{n1}—N(R^7)—(CH_2)_{n2}—$, $*—(CH_2)_{n1}$-phenylene-$(CH_2)_{n2}—$, $*—(CH_2)_{n1}—N(R^7)$-phenylene-$(CH_2)_{n2}—$, $*—(CH_2)_{n1}$-phenylene-$N(R^7)—(CH_2)_{n2}—$, $*—(CH_2)_{n1}—N(R^7)—(CH_2)_{n2}$-phenylene-$(CH_2)_{n3}—$, or $*—(CH_2)_{n1}$-phenylene-$(CH_2)_{n2}—N(R^7)—(CH_2)_{n3}—$, wherein the symbol "*" indicates the point of attachment of L to $X_1$, wherein the hydrogen atom(s) of one or more $CH_2$ (e.g., 1-20, 1-15, 1-10, 1-8, 1-5, 1-3, or 1-2 $CH_2$) of the group and said phenylene are each independently optionally substituted with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof, and wherein $R^7$ represents H, $C_{1-3}$ alkyl (e.g., methyl, ethyl, or propyl), or deuterated $C_{1-3}$ alkyl; and n1, n2, n3 each independently represent an integer of 1, 2, 3, 4, 5, 6, 7, 8, 9, 10, 11, 12, 13, 14, 15, 16, 17, 18, 19, or 20.

Embodiment 29) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 27), wherein L represents:

$*—(CH_2)_1—N(R^7)—(CH_2)_1—$, $*—(CH_2)_1—N(R^7)—(CH_2)_2—$, $*—(CH_2)_1—N(R^7)—(CH_2)_3—$, $*—(CH_2)_1—N$ $(R^7)$—$(CH_2)_4$—, *—$(CH_2)_1$—N$(R^7)$—$(CH_2)_5$—, *—$(CH_2)_1$—N$(R^7)$—$(CH_2)_6$—, *—$(CH_2)_1$—N$(R^7)$—$(CH_2)_7$—, *—$(CH_2)_1$—N$(R^7)$—$(CH_2)_8$—, *—$(CH_2)_1$—N$(R^7)$—$(CH_2)_9$—, *—$(CH_2)_1$—N$(R^7)$—$(CH_2)_{10}$—, *—$(CH_2)_2$—N$(R^7)$—$(CH_2)_1$—, *—$(CH_2)_2$—N$(R^7)$—$(CH_2)_2$—, *—$(CH_2)_2$—N$(R^7)$—$(CH_2)_3$—, *—$(CH_2)_2$—N$(R^7)$—$(CH_2)_4$—, *—$(CH_2)_2$—N$(R^7)$—$(CH_2)_5$—, *—$(CH_2)_2$—N$(R^7)$—$(CH_2)_6$—, *—$(CH_2)_2$—N$(R^7)$—$(CH_2)_7$—, *—$(CH_2)_2$—N$(R^7)$—$(CH_2)_8$—, *—$(CH_2)_2$—N$(R^7)$—$(CH_2)_9$—, *—$(CH_2)_2$—N$(R^7)$—$(CH_2)_{10}$—, *—$(CH_2)_2$—N$(R^7)$—$(CH_2)_{11}$—, *—$(CH_2)_2$—N$(R^7)$—$(CH_2)_{12}$—, *—$(CH_2)_3$—N$(R^7)$—$(CH_2)_1$—, *—$(CH_2)_3$—N$(R^7)$—$(CH_2)_2$—, *—$(CH_2)_3$—N$(R^7)$—$(CH_2)_3$—, *—$(CH_2)_4$—N$(R^7)$—$(CH_2)_1$—, *—$(CH_2)_4$—N$(R^7)$—$(CH_2)_2$—, *—$(CH_2)_5$—N$(R^7)$—$(CH_2)_1$—, *—$(CH_2)_5$—N$(R^7)$—$(CH_2)_2$—, *—$(CH_2)_5$—N$(R^7)$—$(CH_2)_3$—, *—$(CH_2)_5$—N$(R^7)$—$(CH_2)_4$—, *—$(CH_2)_5$—N$(R^7)$—$(CH_2)_5$—, *—$(CH_2)_6$—N$(R^7)$—$(CH_2)_3$—, *—$(CH_2)_7$—N$(R^7)$—$(CH_2)_3$—, *—$(CH_2)_8$—N$(R^7)$—$(CH_2)_2$—, *—CH$(CH_3)$—N$(R^7)$—$(CH_2)_1$—, *—CH$(CH_3)$—N$(R^7)$—$(CH_2)_2$—, *—CH$(CH_3)$—N$(R^7)$—$(CH_2)_3$—, *—CH$(CH_3)$—N$(R^7)$—$(CH_2)_4$—, *—CH$(CH_3)$—N$(R^7)$—$(CH_2)_5$—, *—CH$(CH_3)$—N$(R^7)$—$(CH_2)_6$—, *—CH$(CH_3)$—N$(R^7)$—$(CH_2)_7$—, *—CH$(CH_3)$—N$(R^7)$—$(CH_2)_8$—, *—CH$(CH_3)$—N$(R^7)$—$(CH_2)_9$—, *—CH$(CH_3)$—N$(R^7)$—$(CH_2)_{10}$—, *—$CH_2$-phenylene-$CH_2$—, *—$CH_2$-phenylene-$(CH_2)_2$—, *—$CH_2$-phenylene-$(CH_2)_3$—, *—$CH_2$-phenylene-$(CH_2)_4$—, *—$CH_2$-phenylene-$(CH_2)_5$—, *—$CH_2$-phenylene-$(CH_2)_6$—, *—$CH_2$-phenylene-$(CH_2)_7$—, *—$CH_2$-phenylene-$(CH_2)_8$—, *—$(CH_2)_2$-phenylene-$(CH_2)_1$—, *—$(CH_2)_2$-phenylene-$(CH_2)_2$—, *—$(CH_2)_2$-Phenylene-$(CH_2)_3$—, *—$(CH_2)_2$-phenylene-$(CH_2)_4$—, *—$(CH_2)_2$-phenylene-$(CH_2)_5$—, *—$(CH_2)_2$-phenylene-$(CH_2)_6$—, *—$(CH_2)_2$-phenylene-$(CH_2)_8$—, *—$(CH_2)_3$-phenylene-$CH_2$—, *—$(CH_2)_3$-phenylene-$(CH_2)_2$—, *—$(CH_2)_3$-phenylene-$(CH_2)_3$—, *—$(CH_2)_3$-phenylene-$(CH_2)_8$—, *—$(CH_2)_4$-phenylene-$CH_2$—, *—$(CH_2)_4$-phenylene-$(CH_2)_2$ —, *—$(CH_2)_4$-phenylene-$(CH_2)_3$—, *—$(CH_2)_4$-phenylene-$(CH_2)_8$—, *—$(CH_2)_5$-phenylene-$(CH_2)_3$—, *—$(CH_2)_5$-phenylene-$(CH_2)_8$—, *—$(CH_2)_6$-phenylene-$(CH_2)_3$—, *—$(CH_2)_6$-phenylene-$(CH_2)_8$—, *—$(CH_2)_7$-phenylene-$(CH_2)_3$—, *—$(CH_2)_7$-phenylene-$(CH_2)_8$—, *—$(CH_2)_8$-phenylene-$CH_2$—, *—$(CH_2)_8$-phenylene-$(CH_2)_2$ —, *—$(CH_2)_8$-phenylene-$(CH_2)_3$—, *—$(CH_2)_8$-phenylene-$(CH_2)_4$—, *—$(CH_2)_8$-phenylene-$(CH_2)_5$—, *—$(CH_2)_8$-phenylene-$(CH_2)_6$—, *—$(CH_2)_8$-phenylene-$(CH_2)_7$—, *—$(CH_2)_8$-phenylene-$(CH_2)_8$—, *—$CH_2$—N$(R^7)$—$CH_2$-phenylene-$CH_2$—, *—$CH_2$—N$(R^7)$—$CH_2$-phenylene-$(CH_2)_2$—, *—$CH_2$—N$(R^7)$—$CH_2$-phenylene-$(CH_2)_3$—, *—$CH_2$—N$(R^7)$—$CH_2$-phenylene-$(CH_2)_4$—, *—$CH_2$—N$(R^7)$—$CH_2$-phenylene-$(CH_2)_5$—, *—$CH_2$—N$(R^7)$—$CH_2$-phenylene-$(CH_2)_6$—, *—$CH_2$—N$(R^7)$—$CH_2$-phenylene-$(CH_2)_7$—, *—$CH_2$—N$(R^7)$—$CH_2$-phenylene-$(CH_2)_8$—, *—$CH_2$—N$(R^7)$—$(CH_2)_2$-phenylene-$CH_2$—, *—$CH_2$—N$(R^7)$—$(CH_2)_2$-phenylene-$(CH_2)_2$—, *—$CH_2$—N$(R^7)$—$(CH_2)_2$-phenylene-$(CH_2)_3$—, *—$CH_2$—N$(R^7)$—$(CH_2)_2$-phenylene-$(CH_2)_4$—, *—$CH_2$—N$(R^7)$—$(CH_2)_2$-phenylene-$(CH_2)_5$—, *—$CH_2$—N$(R^7)$—$(CH_2)_2$-phenylene-$(CH_2)_6$—, *—$CH_2$—N$(R^7)$—$(CH_2)_2$-phenylene-$(CH_2)_7$—, *—$CH_2$—N$(R^7)$—$(CH_2)_2$-phenylene-$(CH_2)_8$—, *—$(CH_2)_2$—N$(R^7)$—$CH_2$-phenylene-$CH_2$—, *—$(CH_2)_2$—N$(R^7)$—$CH_2$-phenylene-$(CH_2)_2$—, *—$(CH_2)_2$—N$(R^7)$—$CH_2$-phenylene-$(CH_2)_3$—, *—$(CH_2)_2$—N$(R^7)$—$CH_2$-phenylene-$(CH_2)_4$—, *—$(CH_2)_2$—N$(R^7)$—$CH_2$-phenylene-$(CH_2)_5$—, *—$(CH_2)_2$—N$(R^7)$—$CH_2$-phenylene-$(CH_2)_6$—, *—$(CH_2)_2$—N$(R^7)$—$CH_2$-phenylene—$(CH_2)_7$—, *—$(CH_2)_2$—N$(R^7)$—$CH_2$-phenylene-$(CH_2)_8$—, *—$(CH_2)_3$—N$(R^7)$—$CH_2$-phenylene-$CH_2$—, *—$(CH_2)_3$—N$(R^7)$—$CH_2$-phenylene-$(CH_2)_2$—, *—$(CH_2)_3$—N$(R^7)$—$CH_2$-phenylene-$(CH_2)_3$—, *—$(CH_2)_3$—N$(R^7)$—$CH_2$-phenylene—$(CH_2)_8$—, *—$(CH_2)_4$—N$(R^7)$—$CH_2$-phenylene-$CH_2$—, *—$(CH_2)_4$—N$(R^7)$—$CH_2$-phenylene-$(CH_2)_2$—, *—$(CH_2)_4$—N$(R^7)$—$CH_2$-phenylene-$(CH_2)_3$—, *—$(CH_2)_4$—N$(R^7)$—$CH_2$-phenylene-$(CH_2)_8$—, *—$(CH_2)_5$—N$(R^7)$—$CH_2$-phenylene—$(CH_2)_3$—, *—$(CH_2)_5$—N$(R^7)$—$CH_2$-phenylene-$(CH_2)_8$—, *—$(CH_2)_6$—N$(R^7)$—$CH_2$-phenylene-$(CH_2)_3$—, *—$(CH_2)_6$—N$(R^7)$—$CH_2$-phenylene-$(CH_2)_8$—, *—$(CH_2)_7$—N$(R^7)$—$CH_2$-phenylene-$(CH_2)_3$—, *—$(CH_2)_7$—N$(R^7)$—$CH_2$-phenylene-$(CH_2)_8$—, *—$(CH_2)_8$—N$(R^7)$—$CH_2$-phenylene-$CH_2$—, *—$(CH_2)_8$—N$(R^7)$—$CH_2$-phenylene-$(CH_2)_2$—, *—$(CH_2)_8$—N$(R^7)$—$CH_2$-phenylene-$(CH_2)_3$—, *—$(CH_2)_8$—N$(R^7)$—$CH_2$-phenylene-$(CH_2)_4$—, *—$(CH_2)_8$—N$(R^7)$—$CH_2$-phenylene-$(CH_2)_5$—, *—$(CH_2)_8$—N$(R^7)$—$CH_2$-phenylene-$(CH_2)_6$—, *—$(CH_2)_8$—N$(R^7)$—$CH_2$-phenylene—$(CH_2)_7$—, or *—$(CH_2)_8$—N$(R^7)$—$CH_2$-phenylene-$(CH_2)_8$—;

wherein the symbol "*" indicates the point of attachment of L to $X_1$, wherein the hydrogen atom(s) of one or more $CH_2$ (e.g., 1-20, 1-15, 1-10, 1-8, 1-5, 1-3, or 1-2 $CH_2$) of the group and said phenylene are each independently optionally substituted with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof, and wherein $R^7$ represents H, $C_{1-3}$ alkyl (e.g., methyl, ethyl, or propyl), or deuterated $C_{1-3}$ alkyl.

Embodiment 30) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 27), wherein L represents:

*—$(CH_2)_1$—NH—$(CH_2)_1$—, *—$(CH_2)_1$—NH—$(CH_2)_2$—, *—$(CH_2)_1$—NH—$(CH_2)_3$—, *—$(CH_2)_1$—NH—$(CH_2)_4$ —, *—$(CH_2)_1$—NH—$(CH_2)_5$—, *—$(CH_2)_1$—NH—$(CH_2)_6$—, *—$(CH_2)_1$—NH—$(CH_2)_7$—, *—$(CH_2)_1$—NH—$(CH_2)_8$—, *—$(CH_2)_1$—NH—$(CH_2)_9$—, *—$(CH_2)_1$ —NH—$(CH_2)_{10}$—, *—$(CH_2)_2$—NH—$(CH_2)_1$—, *—$(CH_2)_2$—NH—$(CH_2)_2$—, *—$(CH_2)_2$—NH—$(CH_2)_3$ —, *—$(CH_2)_2$—NH—$(CH_2)_4$—, *—$(CH_2)_2$—NH—$(CH_2)_5$—, *—$(CH_2)_2$—NH—$(CH_2)_6$—, *—$(CH_2)_2$—NH—$(CH_2)_7$—, *—$(CH_2)_2$—NH—$(CH_2)_8$—, *—$(CH_2)_2$ —NH—$(CH_2)_9$—, *—$(CH_2)_2$—NH—$(CH_2)_{10}$—, *—$(CH_2)_2$—NH—$(CH_2)_{11}$—, *—$(CH_2)_2$—NH—$(CH_2)_{12}$—, *—$(CH_2)_3$—NH—$(CH_2)_1$—, *—$(CH_2)_3$—NH—$(CH_2)_2$—, *—$(CH_2)_3$—NH—$(CH_2)_3$—, *—$(CH_2)_4$—NH—$(CH_2)_1$—, *—$(CH_2)_4$—NH—$(CH_2)_2$—, *—$(CH_2)_5$ —NH—$(CH_2)_1$—, *—$(CH_2)_5$—NH—$(CH_2)_2$—, *—$(CH_2)_5$—NH—$(CH_2)_3$—, *—$(CH_2)_5$—NH—$(CH_2)_4$ —, *—$(CH_2)_5$—NH—$(CH_2)_5$—, *—$(CH_2)_6$—NH—$(CH_2)_3$—, *—$(CH_2)_7$—NH—$(CH_2)_3$—, *—$(CH_2)_8$—NH—$(CH_2)_2$—, *—CH$(CH_3)$—NH—$(CH_2)_1$—, *—CH$(CH_3)$—NH—$(CH_2)_2$—, *—CH$(CH_3)$—NH—$(CH_2)_3$—, *—CH$(CH_3)$—NH—$(CH_2)_4$—, *—CH$(CH_3)$—NH—$(CH_2)_5$—, *—CH$(CH_3)$—NH—$(CH_2)_6$—, *—CH$(CH_3)$—NH—$(CH_2)_7$—, *—CH$(CH_3)$—NH—$(CH_2)_8$—, *—CH$(CH_3)$—NH—$(CH_2)_9$—, *—CH$(CH_3)$—NH—$(CH_2)_{10}$—, *—$CH_2$-phenylene-$CH_2$—, *—$CH_2$-phenylene-$(CH_2)_2$—, *—$CH_2$-phenylene-$(CH_2)_3$—, *—$CH_2$-phenylene-$(CH_2)_4$—, *—$CH_2$-phenylene-$(CH_2)_5$—, *—$CH_2$-phenylene- $(CH_2)_6$—, *—$CH_2$-phenylene-$(CH_2)_7$—, *—$CH_2$-phenylene-$(CH_2)_8$—, *—$(CH_2)_2$-phenylene-$(CH_2)_1$—, *—$(CH_2)_2$-phenylene-$(CH_2)_2$—, *—$(CH_2)_2$-phenylene-$(CH_2)_3$—, *—$(CH_2)_2$-phenylene-$(CH_2)_4$—, *—$(CH_2)_2$-phenylene-$(CH_2)_5$—, *—$(CH_2)_2$-phenylene-$(CH_2)_6$—, *—$(CH_2)_2$-phenylene-$(CH_2)_8$—, *—$(CH_2)_3$-phenylene-$CH_2$—, *—$(CH_2)_3$-phenylene-$(CH_2)_2$—, *—$(CH_2)_3$-phenylene-$(CH_2)_3$—, *—$(CH_2)_3$-phenylene-$(CH_2)_8$—, *—$(CH_2)_4$-phenylene-$CH_2$—, *—$(CH_2)_4$-phenylene-$(CH_2)_2$ —, *—$(CH_2)_4$-phenylene-$(CH_2)_3$—, *—$(CH_2)_4$-phenylene-$(CH_2)_8$—, *—$(CH_2)_5$-phenylene-$(CH_2)_3$—, *—$(CH_2)_5$-phenylene-$(CH_2)_8$—, *—$(CH_2)_6$-phenylene-$(CH_2)_3$—, *—$(CH_2)_6$-phenylene-$(CH_2)_8$—, *—$(CH_2)_7$-phenylene-$(CH_2)_3$—, *—$(CH_2)_7$-phenylene-$(CH_2)_8$—, *—$(CH_2)_8$-phenylene-$CH_2$—, *—$(CH_2)_8$-phenylene-$(CH_2)_2$ —, *—$(CH_2)_8$-phenylene-$(CH_2)_3$—, *—$(CH_2)_8$-phenylene-$(CH_2)_4$—, *—$(CH_2)_8$-phenylene-$(CH_2)_5$—, *—$(CH_2)_8$-phenylene-$(CH_2)_6$—, *—$(CH_2)_8$-phenylene-$(CH_2)_7$—, *—$(CH_2)_8$-phenylene-$(CH_2)_8$—, *—$CH_2$—NH—$CH_2$-phenylene-$CH_2$—, *—$CH_2$—NH—$CH_2$-phenylene-$(CH_2)_2$—, *—$CH_2$—NH—$CH_2$-phenylene-$(CH_2)_3$ —, *—$CH_2$—NH—$CH_2$-phenylene-$(CH_2)_4$—, *—$CH_2$—NH—$CH_2$-phenylene-$(CH_2)_5$—, *—$CH_2$—NH—$CH_2$-phenylene-$(CH_2)_6$—, *—$CH_2$—NH—$CH_2$-phenylene-$(CH_2)_7$ —, *—$CH_2$—NH—$CH_2$-phenylene-$(CH_2)_8$—, *—$CH_2$—NH—$(CH_2)_2$-phenylene-$CH_2$—, *—$CH_2$—NH—$(CH_2)_2$-phenylene-$(CH_2)_2$—, *—$CH_2$—NH—$(CH_2)_2$-phenylene-$(CH_2)_3$—, *—$CH_2$—NH—$(CH_2)_2$-phenylene-$(CH_2)_4$—, *—$CH_2$—NH—$(CH_2)_2$-phenylene-$(CH_2)_5$—, *—$CH_2$—NH—$(CH_2)_2$-phenylene-$(CH_2)_6$—, *—$CH_2$—NH —$(CH_2)_2$-phenylene-$(CH_2)_7$—, *—$CH_2$—NH—$(CH_2)_2$-phenylene-$(CH_2)_8$—, *—$(CH_2)_2$—NH—$CH_2$-phenylene-$CH_2$—, *—$(CH_2)_2$—NH—$CH_2$-phenylene-$(CH_2)_2$—, *—$(CH_2)_2$—NH—$CH_2$-phenylene-$(CH_2)_3$—, *—$(CH_2)_2$—NH—$CH_2$-phenylene-$(CH_2)_4$—, *—$(CH_2)_2$—NH—$CH_2$-phenylene-$(CH_2)_5$—, *—$(CH_2)_2$—NH—$CH_2$-phenylene-$(CH_2)_6$—, *—$(CH_2)_2$—NH—$CH_2$-phenylene-$(CH_2)_7$—, *—$(CH_2)_2$—NH—$CH_2$-phenylene-$(CH_2)_8$—, *—$(CH_2)_3$—NH—$CH_2$-phenylene-$CH_2$—, *—$(CH_2)_3$—NH—$CH_2$-phenylene-$(CH_2)_2$—, *—$(CH_2)_3$—NH—$CH_2$-phenylene-$(CH_2)_3$—, *—$(CH_2)_3$—NH—$CH_2$-phenylene-$(CH_2)_8$—, *—$(CH_2)_4$—NH—$CH_2$-phenylene-$CH_2$—, *—$(CH_2)_4$—NH—$CH_2$-phenylene-$(CH_2)_2$—, *—$(CH_2)_4$—NH—$CH_2$-phenylene-$(CH_2)_3$—, *—$(CH_2)_4$—NH—$CH_2$-phenylene-$(CH_2)_8$—, *—$(CH_2)_5$—NH—$CH_2$-phenylene-$(CH_2)_3$—, *—$(CH_2)_5$—NH—$CH_2$-phenylene-$(CH_2)_8$—, *—$(CH_2)_6$—NH—$CH_2$-phenylene-$(CH_2)_3$—, *—$(CH_2)_6$—NH—$CH_2$-phenylene-$(CH_2)_8$—, *—$(CH_2)_7$—NH—$CH_2$-phenylene-$(CH_2)_3$—, *—$(CH_2)_7$—NH—$CH_2$-phenylene-$(CH_2)_8$—, *—$(CH_2)_8$—NH—$CH_2$-phenylene-$CH_2$—, *—$(CH_2)_8$—NH—$CH_2$-phenylene-$(CH_2)_2$—, *—$(CH_2)_8$—NH—$CH_2$-phenylene-$(CH_2)_3$—, *—$(CH_2)_8$—NH—$CH_2$-phenylene-$(CH_2)_4$—, *—$(CH_2)_8$—NH—$CH_2$-phenylene-$(CH_2)_5$—, *—$(CH_2)_8$—NH—$CH_2$-phenylene-$(CH_2)_6$—, *—$(CH_2)_8$—NH—$CH_2$-phenylene-$(CH_2)_7$—, or *—$(CH_2)_8$—NH—$CH_2$-phenylene-$(CH_2)_8$—;

wherein the symbol "*" indicates the point of attachment of L to $X_1$.

Embodiment 31) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 24)-30), wherein $X_1$ represents the Formula —$X_c$—$X_d$, wherein $X_c$ represents O, $N(R^8)$, $C(O)N(R^8)$, $N(R^8)C(O)$, alkynylene, or alkenylene, wherein $R^8$ represents H, $C_{1-3}$ alkyl (e.g., methyl, ethyl, or propyl), or deuterated $C_{1-3}$ alkyl, or $X_c$ represents a bond, and $X_d$ represents adamantanyl, noradamantanyl, or bicyclo[2.2.1]heptyl, which are optionally substituted by from 1 to 10 (e.g., 1-9, 1-8, 1-7, 1-6, 1-5, 1-4, 1-3, or 1-2) substituent(s) selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), deuterated $C_{1-3}$ alkoxy, halogen (e.g., fluorine, chlorine, bromine, or iodine), halogenated $C_{1-3}$ alkyl (e.g., trifluoromethyl), hydroxyl, cyano, oxo, $C_{1-3}$ alkylamino, amino, or any combination thereof.

Embodiment 32) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 31), wherein $X_d$ represents:

adamantan-1-yl, adamantan-2-yl, adamantan-3-yl, adamantan-4-yl, adamantan-5-yl, adamantan-6-yl, adamantan-7-yl, adamantan-8-yl, adamantan-9-yl, adamantan-10-yl, halogenated adamantanyl (optionally fluoroadamantanyl, chloroadamantanyl, bromoadamantanyl, or iodoadamantanyl), hydroxyadamantanyl, dimethyladamantanyl, bicyclo[2.2.1]heptan-2-yl, bicyclo[2.2.1]heptan-3-yl, bicyclo[2.2.1]heptan-4-yl, bicyclo[2.2.1]heptan-5-yl, bicyclo[2.2.1]heptan-6-yl, 1,7,7-trimethylbicyclo[2.2.1]heptan-2-yl, 1,7,7-trimethylbicyclo[2.2.1]heptan-3-yl, 1,7,7-trimethylbicyclo[2.2.1]heptan-4-yl, 1,7,7-trimethylbicyclo[2.2.1]heptan-5-yl, 1,7,7-trimethylbicyclo[2.2.1]heptan-6-yl,

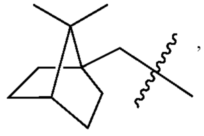
,
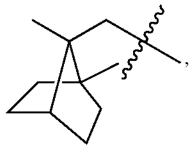
, 7,7-dimethyl-2-oxobicyclo[2.2.1]heptan-1-yl, 7,7-dimethyl-2-oxobicyclo[2.2.1]heptan-3-yl, 7,7-dimethyl-2-oxobicyclo[2.2.1]heptan-4-yl, 7,7-dimethyl-2-oxobicyclo[2.2.1]heptan-5-yl, noradamantanyl, or 7,7-dimethyl-2-oxobicyclo[2.2.1]heptan-6-yl.

Embodiment 33) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 1)-18), wherein when R is alkynylene or alkenylene, L represents linear or branched $C_{1-40}$ alkylene (e.g., $C_{1-35}$ alkylene, $C_{1-30}$ alkylene, $C_{1-20}$ alkylene, $C_{1-15}$ alkylene, or $C_{1-10}$ alkylene), wherein the linear or branched $C_{1-40}$ alkylene is optionally interrupted one or more times (e.g., 1-10 times, 1-8 times, 1-6 times, 1-5 times, 1-3 times, 1-2 times, or 1 time) by a group selected from the group consisting of: $N(R^9)$, phenylene, or any combination thereof, wherein $R^9$ represents H, $C_{1-3}$ alkyl (e.g., methyl, ethyl, or propyl), or deuterated $C_{1-3}$ alkyl, and the hydrogen atom(s) of one or more $CH_2$ (e.g., 1-20, 1-15, 1-10, 1-8, 1-5, 1-3, or 1-2 $CH_2$) of said linear or branched $C_{1-40}$ alkylene and said phenylene are each independently optionally substituted with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluoro, chloro, bromo, or iodo), halogenated $C_{1-3}$ alkyl (e.g., trifluoromethyl), hydroxyl, cyano, or any combination thereof; and $X_1$ represents the Formula —$X_e$—$X_f$, wherein $X_e$ represents O, N($R^1$%), C(O)N($R^{10}$), N($R^{10}$)C(O), alkynylene, or alkenylene, wherein $R^{10}$ represents H, $C_{1-3}$ alkyl (e.g., methyl, ethyl, or propyl), or deuterated $C_{1-3}$ alkyl, or $X_e$ represents a bond, and $X_f$ represents $C_{3-15}$ cycloalkyl or $C_{3-15}$ heterocyclyl, wherein said $C_{3-15}$ cycloalkyl and said $C_{3-15}$ heterocyclyl are each independently optionally substituted with one or more (e.g., 1-10, 1-9, 1-8, 1-7, 1-6, 1-5, 1-3, or 1-2) substituent(s) selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), deuterated $C_{1-3}$ alkoxy, halogen (e.g., fluorine, chlorine, bromine, or iodine), halogenated $C_{1-3}$ alkyl (e.g., trifluoromethyl), hydroxyl, cyano, oxo, $C_{1-3}$ alkylamino, amino, optionally substituted phenyl, or any combination thereof, wherein the optionally substituted phenyl is optionally substituted with a substituent selected from the group consisting of: cyano, halogen, $C_{1-3}$ alkoxy, halogenated $C_{1-3}$ alkyl, $C_{1-3}$ alkyl, hydroxyl, amino, $C_{1-3}$ alkylamino, or any combination thereof.

Embodiment 34) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 33), wherein L represents a linear or branched $C_{1-40}$ alkylene (e.g., $C_{1-35}$ alkylene, $C_{1-30}$ alkylene, $C_{1-20}$ alkylene, $C_{1-15}$ alkylene, or $C_{1-10}$ alkylene), and the hydrogen atom(s) of one or more $CH_2$ (e.g., 1-20, 1-15, 1-10, 1-8, 1-5, 1-3, or 1-2 $CH_2$) of said linear or branched $C_{1-40}$ alkylene are each independently optionally substituted with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof.

Embodiment 35) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 34), wherein L represents the following groups:

—$CH_2$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, —$(CH_2)_{16}$—, —$(CH_2)_{17}$—, —$(CH_2)_{18}$—, —$(CH_2)_{19}$—, or —$(CH_2)_{20}$—;

wherein the hydrogen atom(s) of one or more $CH_2$ (e.g., 1-20, 1-15, 1-10, 1-8, 1-5, 1-3, or 1-2 $CH_2$) of the groups is optionally further replaced with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof.

Embodiment 36) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 33), wherein L represents a linear or branched $C_{2-40}$ alkylene (e.g., $C_{2-35}$ alkylene, $C_{2-30}$ alkylene, $C_{2-20}$ alkylene, $C_{2-15}$ alkylene, or $C_{2-10}$ alkylene), wherein the linear or branched $C_{2-40}$ alkylene is interrupted one or more times (e.g., 1-10 times, 1-8 times, 1-6 times, 1-5 times, 1-3 times, 1-2 times, or 1 time) by a group selected from the group consisting of: N($R^9$), phenylene, or any combination thereof, wherein $R^9$ represents H, $C_{1-3}$ alkyl (e.g., methyl, ethyl, or propyl), or deuterated $C_{1-3}$ alkyl, and the hydrogen atom(s) of one or more $CH_2$ (e.g., 1-20, 1-15, 1-10, 1-8, 1-5, 1-3, or 1-2 $CH_2$) of said linear or branched $C_{2-40}$ alkylene and said phenylene are each independently optionally substituted with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof.

Embodiment 37) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 36), wherein L represents the following groups: *—$(CH_2)_{n1}$—N($R^9$)—$(CH_2)_{n2}$—, *—$(CH_2)_{n1}$-phenylene-$(CH_2)_{n2}$—, *—$(CH_2)_{n1}$—N($R^9$)-phenylene-$(CH_2)_{n2}$—, *—$(CH_2)_{n1}$-phenylene-N($R^9$)—$(CH_2)_{n2}$—, *—$(CH_2)_{n1}$—N($R^9$)—$(CH_2)_{n2}$-phenylene-$(CH_2)_{n3}$—, or *—$(CH_2)_{n1}$-phenylene-$(CH_2)_{n2}$—N($R^9$)—$(CH_2)_{n3}$—, wherein the symbol "*" represents the point of attachment of L to $X_1$, wherein the hydrogen atom(s) of one or more $CH_2$ (e.g., 1-20, 1-15, 1-10, 1-8, 1-5, 1-3, or 1-2 $CH_2$) of the group and said phenylene are each independently optionally substituted with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof, wherein $R^9$ represents H, $C_{1-3}$ alkyl (e.g., methyl, ethyl, or propyl), or deuterated $C_{1-3}$ alkyl; and n1, n2, n3 each independently represent an integer of 1, 2, 3, 4, 5, 6, 7, 8, 9, 10, 11, 12, 13, 14, 15, 16, 17, 18, 19, or 20.

Embodiment 38) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 36), wherein L represents: *—$(CH_2)_1$—N($R^7$)—$(CH_2)_1$—, *—$(CH_2)_1$—N($R^7$)—$(CH_2)_2$—, *—$(CH_2)_1$—N($R^7$)—$(CH_2)_3$—, *—$(CH_2)_1$—N($R^7$)—$(CH_2)_4$—, *—$(CH_2)_1$—N($R^7$)—$(CH_2)_5$—, *—$(CH_2)_1$—N($R^7$)—$(CH_2)_6$—, *—$(CH_2)_1$—N($R^7$)—$(CH_2)_7$—, *—$(CH_2)_1$—N($R^7$)—$(CH_2)_8$—, *—$(CH_2)_1$—N($R^7$)—$(CH_2)_9$—, *—$(CH_2)_1$—N($R^7$)—$(CH_2)_{10}$—, *—$(CH_2)_2$—N($R^7$)—$(CH_2)_1$—, *—$(CH_2)_2$—N($R^7$)—$(CH_2)_2$—, *—$(CH_2)_2$—N($R^7$)—$(CH_2)_3$—, *—$(CH_2)_2$—N($R^7$)—$(CH_2)_4$—, *—$(CH_2)_2$—N($R^7$)—$(CH_2)_5$—, *—$(CH_2)_2$—N($R^7$)—$(CH_2)_6$—, *—$(CH_2)_2$—N($R^7$)—$(CH_2)_7$—, *—$(CH_2)_2$—N($R^7$)—$(CH_2)_8$—, *—$(CH_2)_2$—N($R^7$)—$(CH_2)_9$—, *—$(CH_2)_2$—N($R^7$)—$(CH_2)_{10}$—, *—$(CH_2)_2$—N($R^7$)—$(CH_2)_{11}$—, *—$(CH_2)_2$—N($R^7$)—$(CH_2)_{12}$—, *—$(CH_2)_3$—N($R^7$)—$(CH_2)_1$—, *—$(CH_2)_3$—N($R^7$)—$(CH_2)_2$—, *—$(CH_2)_3$—N($R^7$)—$(CH_2)_3$—, *—$(CH_2)_4$—N($R^7$)—$(CH_2)_1$—, *—$(CH_2)_4$—N($R^7$)—$(CH_2)_2$—, *—$(CH_2)_5$—N($R^7$)—$(CH_2)_1$—, *—$(CH_2)_5$—N($R^7$)—$(CH_2)_2$—, *—$(CH_2)_5$—N($R^7$)—$(CH_2)_3$—, *—$(CH_2)_5$—N($R^7$)—$(CH_2)_4$—, *—$(CH_2)_5$—N($R^7$)—$(CH_2)_5$—, *—$(CH_2)_6$—N($R^7$)—

$(CH_2)_3$—, *—$(CH_2)_7$—N($R^7$)—$(CH_2)_3$—, *—$(CH_2)_8$—N($R^7$)—$(CH_2)_2$—, *—CH($CH_3$)—N($R^7$)—$(CH_2)_1$—, *—CH($CH_3$)—N($R^7$)—$(CH_2)_2$—, *—CH($CH_3$)—N($R^7$)—$(CH_2)_3$—, *—CH($CH_3$)—N($R^7$)—$(CH_2)_4$—, *—CH($CH_3$)—N($R^7$)—$(CH_2)_5$—, *—CH($CH_3$)—N($R^7$)—$(CH_2)_6$—, *—CH($CH_3$)—N($R^7$)—$(CH_2)_7$—, *—CH($CH_3$)—N($R^7$)—$(CH_2)_8$—, *—CH($CH_3$)—N($R^7$)—$(CH_2)_9$—, *—CH($CH_3$)—N($R^7$)—$(CH_2)_{10}$—, *—$CH_2$-phenylene-$CH_2$—, *—$CH_2$-phenylene-$(CH_2)_2$—, *—$CH_2$-phenylene-$(CH_2)_3$—, *—$CH_2$-phenylene-$(CH_2)_4$—, *—$CH_2$-phenylene-$(CH_2)_5$—, *—$CH_2$-phenylene-$(CH_2)_6$—, *—$CH_2$-phenylene-$(CH_2)_7$—, *—$CH_2$-phenylene-$(CH_2)_8$—, *—$(CH_2)_2$-phenylene-$(CH_2)_1$—, *—$(CH_2)_2$-phenylene-$(CH_2)_2$—, *—$(CH_2)_2$-phenylene-$(CH_2)_3$—, *—$(CH_2)_2$-phenylene-$(CH_2)_4$—, *—$(CH_2)_2$-phenylene-$(CH_2)_5$—, *—$(CH_2)_2$-phenylene-$(CH_2)_6$—, *—$(CH_2)_2$-phenylene-$(CH_2)_8$—, *—$(CH_2)_3$-phenylene-$CH_2$—, *—$(CH_2)_3$-phenylene-$(CH_2)_2$—, *—$(CH_2)_3$-phenylene-$(CH_2)_3$—, *—$(CH_2)_3$-phenylene-$(CH_2)_8$—, *—$(CH_2)_4$-phenylene-$CH_2$—, *—$(CH_2)_4$-phenylene-$(CH_2)_2$—, *—$(CH_2)_4$-phenylene-$(CH_2)_3$—, *—$(CH_2)_4$-phenylene-$(CH_2)_8$—, *—$(CH_2)_5$-phenylene-$(CH_2)_3$—, *—$(CH_2)_5$-phenylene-$(CH_2)_8$—, *—$(CH_2)_6$-phenylene-$(CH_2)_3$—, *—$(CH_2)_6$-phenylene-$(CH_2)_8$—, *—$(CH_2)_7$-phenylene-$(CH_2)_3$—, *—$(CH_2)_7$-phenylene-$(CH_2)_8$—, *—$(CH_2)_8$-phenylene-$CH_2$—, *—$(CH_2)_8$-phenylene-$(CH_2)_2$—, *—$(CH_2)_8$-phenylene-$(CH_2)_3$—, *—$(CH_2)_8$-phenylene-$(CH_2)_4$—, *—$(CH_2)_8$-phenylene-$(CH_2)_5$—, *—$(CH_2)_8$-phenylene-$(CH_2)_6$—, *—$(CH_2)_8$-phenylene-$(CH_2)_7$—, *—$(CH_2)_8$-phenylene-$(CH_2)_8$—, *—$CH_2$—N($R^7$)—$CH_2$-phenylene-$CH_2$—, *—$CH_2$—N($R^7$)—$CH_2$-phenylene-$(CH_2)_2$—, *—$CH_2$—N($R^7$)—$CH_2$-phenylene-$(CH_2)_3$—, *—$CH_2$—N($R^7$)—$CH_2$-phenylene-$(CH_2)_4$—, *—$CH_2$—N($R^7$)—$CH_2$-phenylene-$(CH_2)_5$—, *—$CH_2$—N($R^7$)—$CH_2$-phenylene-$(CH_2)_6$—, *—$CH_2$—N($R^7$)—$CH_2$-phenylene-$(CH_2)_7$—, *—$CH_2$—N($R^7$)—$CH_2$-phenylene-$(CH_2)_8$—, *—$CH_2$—N($R^7$)—$(CH_2)_2$-phenylene-$CH_2$—, *—$CH_2$—N($R^7$)—$(CH_2)_2$-phenylene-$(CH_2)_2$—, *—$CH_2$—N($R^7$)—$(CH_2)_2$-phenylene-$(CH_2)_3$—, *—$CH_2$—N($R^7$)—$(CH_2)_2$-phenylene-$(CH_2)_4$—, *—$CH_2$—N($R^7$)—$(CH_2)_2$-phenylene-$(CH_2)_5$—, *—$CH_2$—N($R^7$)—$(CH_2)_2$-phenylene-$(CH_2)_6$—, *—$CH_2$—N($R^7$)—$(CH_2)_2$-phenylene-$(CH_2)_7$—, *—$CH_2$—N($R^7$)—$(CH_2)_2$-phenylene-$(CH_2)_8$—, *—$(CH_2)_2$—N($R^7$)—$CH_2$-phenylene-$CH_2$—, *—$(CH_2)_2$—N($R^7$)—$CH_2$-phenylene-$(CH_2)_2$—, *—$(CH_2)_2$—N($R^7$)—$CH_2$-phenylene-$(CH_2)_3$—, *—$(CH_2)_2$—N($R^7$)—$CH_2$-phenylene-$(CH_2)_4$—, *—$(CH_2)_2$—N($R^7$)—$CH_2$-phenylene-$(CH_2)_5$—, *—$(CH_2)_2$—N($R^7$)—$CH_2$-phenylene-$(CH_2)_6$—, *—$(CH_2)_2$—N($R^7$)—$CH_2$-phenylene—$(CH_2)_7$—, *—$(CH_2)_2$—N($R^7$)—$CH_2$-phenylene-$(CH_2)_8$—, *—$(CH_2)_3$—N($R^7$)—$CH_2$-phenylene-$CH_2$—, *—$(CH_2)_3$—N($R^7$)—$CH_2$-phenylene-$(CH_2)_2$—, *—$(CH_2)_3$—N($R^7$)—$CH_2$-phenylene-$(CH_2)_3$—, *—$(CH_2)_3$—N($R^7$)—$CH_2$-phenylene—$(CH_2)_8$—, *—$(CH_2)_4$—N($R^7$)—$CH_2$-phenylene-$CH_2$—, *—$(CH_2)_4$—N($R^7$)—$CH_2$-phenylene-$(CH_2)_2$—, *—$(CH_2)_4$—N($R^7$)—$CH_2$-phenylene-$(CH_2)_3$—, *—$(CH_2)_4$—N($R^7$)—$CH_2$-phenylene-$(CH_2)_8$—, *—$(CH_2)_5$—N($R^7$)—$CH_2$-phenylene—$(CH_2)_3$—, *—$(CH_2)_5$—N($R^7$)—$CH_2$-phenylene-$(CH_2)_8$—, *—$(CH_2)_6$—N($R^7$)—$CH_2$-phenylene-$(CH_2)_3$—, *—$(CH_2)_6$—N($R^7$)—$CH_2$-phenylene-$(CH_2)_8$—, *—$(CH_2)_7$—N($R^7$)—$CH_2$-phenylene-$(CH_2)_3$—, *—$(CH_2)_7$—N($R^7$)—$CH_2$-phenylene-$(CH_2)_8$—, *—$(CH_2)_8$—N($R^7$)—$CH_2$-phenylene-$CH_2$—, *—$(CH_2)_8$—N($R^7$)—$CH_2$-phenylene-$(CH_2)_2$—, *—$(CH_2)_8$—N($R^7$)—$CH_2$-phenylene-$(CH_2)_3$—, *—$(CH_2)_8$—N($R^7$)—$CH_2$-phenylene-$(CH_2)_4$—, *—$(CH_2)_8$—N($R^7$)—$CH_2$-phenylene-$(CH_2)_5$—, *—$(CH_2)_8$—N($R^7$)—$CH_2$-phenylene-$(CH_2)_6$—, *—$(CH_2)_8$—N($R^7$)—$CH_2$-phenylene—$(CH_2)_7$—, or *—$(CH_2)_8$—N($R^7$)—$CH_2$-phenylene-$(CH_2)_8$—;

wherein the symbol "*" indicates the point of attachment of L to $X_1$, wherein the hydrogen atom(s) of one or more $CH_2$ (e.g., 1-20, 1-15, 1-10, 1-8, 1-5, 1-3, or 1-2 $CH_2$) of the group and said phenylene are each independently optionally substituted with a substituent selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), $C_{3-6}$ cycloalkyl (e.g., cyclopropyl, cyclobutyl, or cyclopentyl), halogen (e.g., fluorine, chlorine, bromine, or iodine), halogenated $C_{1-3}$ alkyl (e.g., trifluoromethyl), hydroxyl, cyano, or any combination thereof, wherein $R^7$ represents H, $C_{1-3}$ alkyl (e.g., methyl, ethyl, or propyl), or deuterated $C_{1-3}$ alkyl.

Embodiment 39) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 36), wherein L represents:

*—$(CH_2)_1$—NH—$(CH_2)_1$—, *—$(CH_2)_1$—NH—$(CH_2)_2$—, *—$(CH_2)_1$—NH—$(CH_2)_3$—, *—$(CH_2)_1$—NH—$(CH_2)_4$—, *—$(CH_2)_1$—NH—$(CH_2)_5$—, *—$(CH_2)_1$—NH—$(CH_2)_6$—, *—$(CH_2)_1$—NH—$(CH_2)_7$—, *—$(CH_2)_1$—NH—$(CH_2)_8$—, *—$(CH_2)_1$—NH—$(CH_2)_9$—, *—$(CH_2)_1$—NH—$(CH_2)_{10}$—, *—$(CH_2)_2$—NH—$(CH_2)_1$—, *—$(CH_2)_2$—NH—$(CH_2)_2$—, *—$(CH_2)_2$—NH—$(CH_2)_3$—, *—$(CH_2)_2$—NH—$(CH_2)_4$—, *—$(CH_2)_2$—NH—$(CH_2)_5$—, *—$(CH_2)_2$—NH—$(CH_2)_6$—, *—$(CH_2)_2$—NH—$(CH_2)_7$—, *—$(CH_2)_2$—NH—$(CH_2)_8$—, *—$(CH_2)_2$—NH—$(CH_2)_9$—, *—$(CH_2)_2$—NH—$(CH_2)_{10}$—, *—$(CH_2)_2$—NH—$(CH_2)_{11}$—, *—$(CH_2)_2$—NH—$(CH_2)_{12}$—, *—$(CH_2)_3$—NH—$(CH_2)_1$—, *—$(CH_2)_3$—NH—$(CH_2)_2$—, *—$(CH_2)_3$—NH—$(CH_2)_3$—, *—$(CH_2)_4$—NH—$(CH_2)_1$—, *—$(CH_2)_4$—NH—$(CH_2)_2$—, *—$(CH_2)_5$—NH—$(CH_2)_1$—, *—$(CH_2)_5$—NH—$(CH_2)_2$—, *—$(CH_2)_5$—NH—$(CH_2)_3$—, *—$(CH_2)_5$—NH—$(CH_2)_4$—, *—$(CH_2)_5$—NH—$(CH_2)_5$—, *—$(CH_2)_6$—NH—$(CH_2)_3$—, *—$(CH_2)_7$—NH—$(CH_2)_3$—, *—$(CH_2)_8$—NH—$(CH_2)_2$—, *—CH($CH_3$)—NH—$(CH_2)_1$—, *—CH($CH_3$)—NH—$(CH_2)_2$—, *—CH($CH_3$)—NH—$(CH_2)_3$—, *—CH($CH_3$)—NH—$(CH_2)_4$—, *—CH($CH_3$)—NH—$(CH_2)_5$—, *—CH($CH_3$)—NH—$(CH_2)_6$—, *—CH($CH_3$)—NH—$(CH_2)_7$—, *—CH($CH_3$)—NH—$(CH_2)_8$—, *—CH($CH_3$)—NH—$(CH_2)_9$—, *—CH($CH_3$)—NH—$(CH_2)_{10}$—, *—$CH_2$-phenylene-$CH_2$—, *—$CH_2$-phenylene-$(CH_2)_2$—, *—$CH_2$-phenylene-$(CH_2)_3$—, *—$CH_2$-phenylene-$(CH_2)_4$—, *—$CH_2$-phenylene-$(CH_2)_5$—, *—$CH_2$-phenylene-$(CH_2)_6$—, *—$CH_2$-phenylene-$(CH_2)_7$—, *—$CH_2$-phenylene-$(CH_2)_8$—, *—$(CH_2)_2$-phenylene-$(CH_2)_1$—, *—$(CH_2)_2$-phenylene-$(CH_2)_2$—, *—$(CH_2)_2$-phenylene-$(CH_2)_3$—, *—$(CH_2)_2$-phenylene-$(CH_2)_4$—, *—$(CH_2)_2$-phenylene-$(CH_2)_5$—, *—$(CH_2)_2$-phenylene-$(CH_2)_6$—, *—$(CH_2)_2$-phenylene-$(CH_2)_8$—, *—$(CH_2)_3$-phenylene-$CH_2$—, *—$(CH_2)_3$-phenylene-$(CH_2)_2$—, *—$(CH_2)_3$-phenylene-$(CH_2)_3$—, *—$(CH_2)_3$-phenylene-$(CH_2)_8$—, *—$(CH_2)_4$-phenylene-$CH_2$—, *—$(CH_2)_4$-phenylene-$(CH_2)_2$—, *—$(CH_2)_4$-phenylene-$(CH_2)_3$—, *—$(CH_2)_4$-phenylene-$(CH_2)_8$—, *—$(CH_2)_5$-phenylene-$(CH_2)_3$—, *—$(CH_2)_5$-phenylene-$(CH_2)_8$—, *—$(CH_2)_6$-phenylene-$(CH_2)_3$—, *—$(CH_2)_6$-phenylene-$(CH_2)_8$—, *—$(CH_2)_7$-phenylene-$(CH_2)_3$—, *—$(CH_2)_7$-phenylene-$(CH_2)_8$—, *—$(CH_2)_8$-phenylene-$CH_2$—, *—$(CH_2)_8$-phenylene-$(CH_2)_2$—, *—$(CH_2)_8$-phenylene-$(CH_2)_3$—, *—$(CH_2)_8$-phenylene-$(CH_2)_4$—, *—$(CH_2)_8$-phenylene-$(CH_2)_5$—,

*—$(CH_2)_8$-phenylene-$(CH_2)_6$—, *—$(CH_2)_8$-phenylene-$(CH_2)_7$—, *—$(CH_2)_8$-phenylene-$(CH_2)_8$—, *—$CH_2$—NH—$CH_2$-phenylene-$CH_2$—, *—$CH_2$—NH—$CH_2$-phenylene-$(CH_2)_2$—, *—$CH_2$—NH—$CH_2$-phenylene-$(CH_2)_3$—, *—$CH_2$—NH—$CH_2$-phenylene-$(CH_2)_4$—, *—$CH_2$—NH—$CH_2$-phenylene-$(CH_2)_5$—, *—$CH_2$—NH—$CH_2$-phenylene-$(CH_2)_6$—, *—$CH_2$—NH—$CH_2$-phenylene-$(CH_2)_7$—, *—$CH_2$—NH—$CH_2$-phenylene-$(CH_2)_8$—, *—$CH_2$—NH—$(CH_2)_2$-phenylene-$CH_2$—, *—$CH_2$—NH—$(CH_2)_2$-phenylene-$(CH_2)_2$—, *—$CH_2$—NH—$(CH_2)_2$-phenylene-$(CH_2)_3$—, *—$CH_2$—NH—$(CH_2)_2$-phenylene-$(CH_2)_4$—, *—$CH_2$—NH—$(CH_2)_2$-phenylene-$(CH_2)_5$—, *—$CH_2$—NH—$(CH_2)_2$-phenylene-$(CH_2)_6$—, *—$CH_2$—NH—$(CH_2)_2$-phenylene-$(CH_2)_7$—, *—$CH_2$—NH—$(CH_2)_2$-phenylene-$(CH_2)_8$—, *—$(CH_2)_2$—NH—$CH_2$-phenylene-$CH_2$—, *—$(CH_2)_2$—NH—$CH_2$-phenylene-$(CH_2)_2$—, *—$(CH_2)_2$—NH—$CH_2$-phenylene-$(CH_2)_3$—, *—$(CH_2)_2$—NH—$CH_2$-phenylene-$(CH_2)_4$—, *—$(CH_2)_2$—NH—$CH_2$-phenylene-$(CH_2)_5$—, *—$(CH_2)_2$—NH—$CH_2$-phenylene-$(CH_2)_6$—, *—$(CH_2)_2$—NH—$CH_2$-phenylene-$(CH_2)_7$—, *—$(CH_2)_2$—NH—$CH_2$-phenylene-$(CH_2)_8$—, *—$(CH_2)_3$—NH—$CH_2$-phenylene-$CH_2$—, *—$(CH_2)_3$—NH—$CH_2$-phenylene-$(CH_2)_2$—, *—$(CH_2)_3$—NH—$CH_2$-phenylene-$(CH_2)_3$—, *—$(CH_2)_3$—NH—$CH_2$-phenylene-$(CH_2)_8$—, *—$(CH_2)_4$—NH—$CH_2$-phenylene-$CH_2$—, *—$(CH_2)_4$—NH—$CH_2$-phenylene-$(CH_2)_2$—, *—$(CH_2)_4$—NH—$CH_2$-phenylene-$(CH_2)_3$—, *—$(CH_2)_4$—NH—$CH_2$-phenylene-$(CH_2)_8$—, *—$(CH_2)_5$—NH—$CH_2$-phenylene-$(CH_2)_3$—, *—$(CH_2)_5$—NH—$CH_2$-phenylene-$(CH_2)_8$—, *—$(CH_2)_6$—NH—$CH_2$-phenylene-$(CH_2)_3$—, *—$(CH_2)_6$—NH—$CH_2$-phenylene-$(CH_2)_8$—, *—$(CH_2)_7$—NH—$CH_2$-phenylene-$(CH_2)_3$—, *—$(CH_2)_7$—NH—$CH_2$-phenylene-$(CH_2)_8$—, *—$(CH_2)_8$—NH—$CH_2$-phenylene-$CH_2$—, *—$(CH_2)_8$—NH—$CH_2$-phenylene-$(CH_2)_2$—, *—$(CH_2)_8$—NH—$CH_2$-phenylene-$(CH_2)_3$—, *—$(CH_2)_8$—NH—$CH_2$-phenylene-$(CH_2)_4$—, *—$(CH_2)_8$—NH—$CH_2$-phenylene-$(CH_2)_5$—, *—$(CH_2)_8$—NH—$CH_2$-phenylene-$(CH_2)_6$—, *—$(CH_2)_8$—NH—$CH_2$-phenylene-$(CH_2)_7$—, or *—$(CH_2)_8$—NH—$CH_2$-phenylene-$(CH_2)_8$—;

wherein the symbol "*" indicates the point of attachment of L to $X_1$.

Embodiment 40) relates to the compounds of Formula (I), Formula (Ia), Formula (Ib), Formula (Ic), Formula (Id), or Formula (Ie) or a salt, enantiomer, stereoisomer, solvate, or polymorph thereof as described in any one of Embodiments 33)-39), wherein $X_1$ represents the Formula —$X_e$—$X_f$, wherein $X_e$ represents O, $N(R^{10})$, $C(O)N(R^{10})$, $N(R^{10})C(O)$, alkynylene, or alkenylene, wherein $R^{10}$ represents H, $C_{1-3}$ alkyl (e.g., methyl, ethyl, or propyl), or deuterated $C_{1-3}$ alkyl, or $X_e$ represents a bond, and $X_f$ represents the following groups:

cyclopropyl, cyclobutyl, cyclopentyl, cyclohexyl, cycloheptyl, spiro[3.3]heptyl, spiro[2.5]octyl, spiro[3.5]nonyl, spiro[4.4]nonyl, spiro[4.5]decyl, spiro[5.5]undecyl, adamantanyl, noradamantanyl, bicyclo[2.2.1]heptyl, piperidinyl, morpholinyl, piperazinyl, azetidinyl, pyrrolidinyl, azepanyl, azocanyl, diazepanyl, azaspiro-cycloalkyl, 3-azabicyclo[3.1.0]hexyl, 3-azabicyclo[4.1.0]heptyl, 3,8-diazabicyclo[3.2.1]octyl, or 2,5-diazabicyclo[2.2.2]octanyl, wherein the groups are optionally substituted with one or more (e.g., 1-10, 1-9, 1-8, 1-7, 1-6, 1-5, 1-4, 1-3, or 1-2) substituent(s) selected from the group consisting of: D, $C_{1-3}$ alkyl (e.g., methyl, ethyl, or propyl), deuterated $C_{1-3}$ alkyl, $C_{1-3}$ alkoxy (e.g., methoxy, ethoxy, or propoxy), deuterated $C_{1-3}$ alkoxy, halogen (e.g., fluorine, chlorine, bromine, or iodine), halogenated $C_{1-3}$ alkyl (e.g., trifluoromethyl), hydroxyl, cyano, oxo, optionally substituted phenyl, $C_{1-3}$ alkylamino, amino, or any combination thereof, wherein said optionally substituted phenyl is optionally substituted with a substituent selected from the group consisting of: cyano, halogen (e.g., fluorine, chlorine, bromine, or iodine), $C_{1-3}$ alkoxy (e.g., methoxy, ethoxy, or propoxy), halogenated $C_{1-3}$ alkyl (e.g., trifluoromethyl), $C_{1-3}$ alkyl (e.g., methyl, ethyl, or propyl), hydroxyl, amino, $C_{1-3}$ alkylamino (e.g., methylamino, ethylamino, or propylamino), or any combination thereof.

Embodiment 41) relates to the compounds of Formula (I), Formula (Ia), Formula (Ib), Formula (Ic), Formula (Id), or Formula (Ie) or a salt, enantiomer, stereoisomer, solvate, or polymorph thereof as described in Embodiment 40), wherein $X_f$ represents the following groups: cyclopropyl, methoxycyclopropyl, cyclobutyl, fluorocyclobutyl, cyclopentyl, fluorocyclopentyl, cyclohexyl, dimethylcyclohexyl, hydroxycyclohexyl, fluorocyclohexyl, cycloheptyl, spiro[3.3]heptyl, spiro[2.5]octyl, spiro[3.5]nonyl, spiro[4.4]nonyl, spiro[4.5]decyl, spiro[5.5]undecyl, adamantan-1-yl, adamantan-2-yl, adamantan-3-yl, adamantan-4-yl, adamantan-5-yl, adamantan-6-yl, adamantan-7-yl, adamantan-8-yl, adamantan-9-yl, adamantan-10-yl, haloadamantanyl, hydroxyadamantanyl, dimethyladamantanyl, noradamantanyl, bicyclo[2.2.1]heptan-2-yl, bicyclo[2.2.1]heptan-3-yl, bicyclo[2.2.1]heptan-4-yl, bicyclo[2.2.1]heptan-5-yl, bicyclo[2.2.1]heptan-6-yl, 1,7,7-trimethylbicyclo[2.2.1]heptan-2-yl, 1,7,7-trimethylbicyclo[2.2.1]heptan-3-yl, 1,7,7-trimethylbicyclo[2.2.1]heptan-4-yl, 1,7,7-trimethylbicyclo[2.2.1]heptan-5-yl, 1,7,7-trimethylbicyclo[2.2.1]heptane-6-yl,

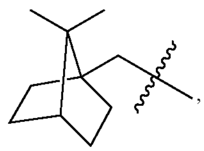, 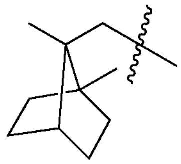, 7,7-dimethyl-2-oxobicyclo[2.2.1]heptan-1-yl, 7,7-dimethyl-2-oxobicyclo[2.2.1]heptan-3-yl, 7,7-dimethyl-2-oxobicyclo[2.2.1]heptan-4-yl, 7,7-dimethyl-2-oxobicyclo[2.2.1]heptan-5-yl, 7,7-dimethyl-2-oxobicyclo[2.2.1]heptan-6-yl, piperidinyl, morpholinyl, piperazinyl,

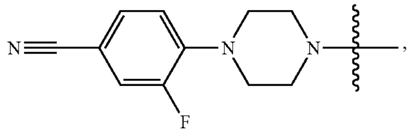 [SMILES: *N1CCN(c2ccc(C#N)cc2F)CC1], azetidinyl, pyrrolidinyl, azepanyl, azocanyl, diazepanyl, 3-azaspiro[5.5]undecyl, 5-azaspiro[2.4]heptyl, 3-azabicyclo[3.1.0]hexyl, 3-azabicyclo[4.1.0]heptyl, 6-azaspiro[2.5]octyl, 3,8-diazabicyclo[3.2.1]octyl, or 2,5-diazabicyclo[2.2.2]octyl.

Particularly preferred are the compounds of the present invention in Table 1 and their salts (especially pharmaceutically acceptable salts, such as hydrochloride, etc.), enantiomers, diastereomers, solvates, or polymorphs:

TABLE 1

Compounds of the present invention

| Compound No. | Structure of the compounds | The compound's name |
|---|---|---|
| SIAISI 221077 | 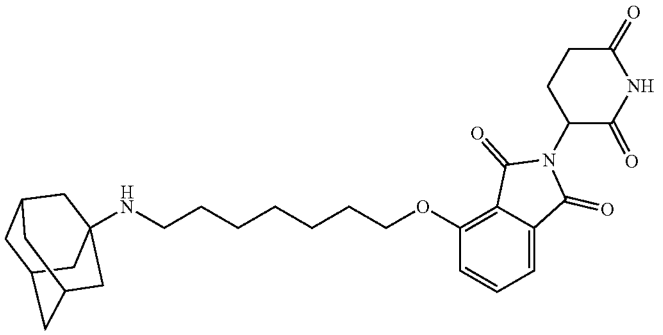 [SMILES: O=C1CCC(N2C(=O)c3cccc(OCCCCCCCNC45CC6CC(CC(C6)C4)C5)c3C2=O)C(=O)N1] | 4-((7-((adamantan-1-yl)amino)heptyl)oxy)-2-(2,6-dioxopiperidin-3-yl)isoindoline-1,3-dione |
| SIAIS3 32042 | 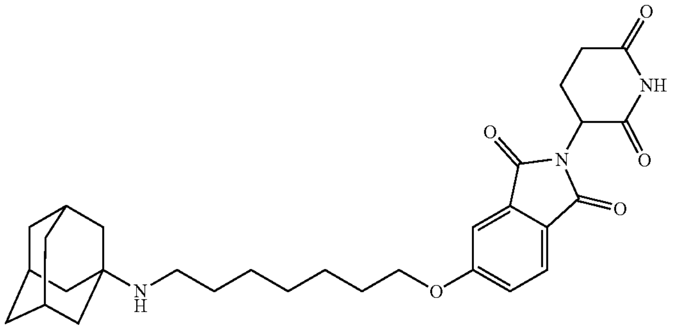 [SMILES: O=C1CCC(N2C(=O)c3ccc(OCCCCCCCNC45CC6CC(CC(C6)C4)C5)cc3C2=O)C(=O)N1] | 5-((7-((adamantan-1-yl)amino)heptyl)oxy)-2-(2,6-dioxopiperidin-3-yl)isoindoline-1,3-dione |
| SIAISI 221187 | 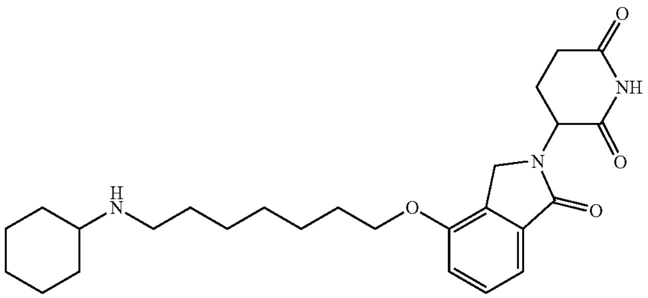 | 3-(4-((7-(cyclohexylamino)heptyl)oxy)-1-oxoisoindolin-2-yl)piperidine-2,6-dione |
| SIAIS1 224013 | 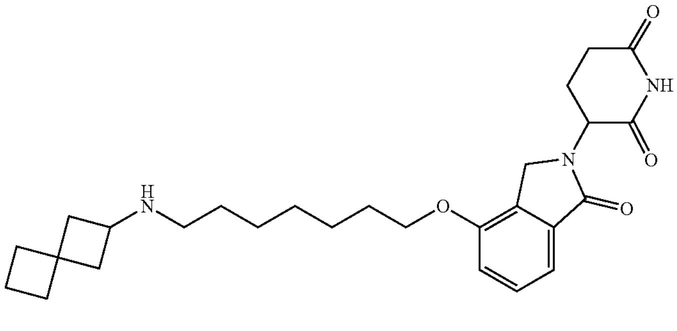 [SMILES: O=C1CCC(N2Cc3c(OCCCCCCCNC4CC5(CCC5)C4)cccc3C2=O)C(=O)N1] | 3-1(1-oxo-4-((7-(spiro [3.3]heptan-2-ylamino)heptyl)oxy)isoindolin-2-yl)piperidine-2,6-dione |

TABLE 1-continued

Compounds of the present invention

| Compound No. | Structure of the compounds | The compound's name |
| --- | --- | --- |
| SIAIS1 224009 | 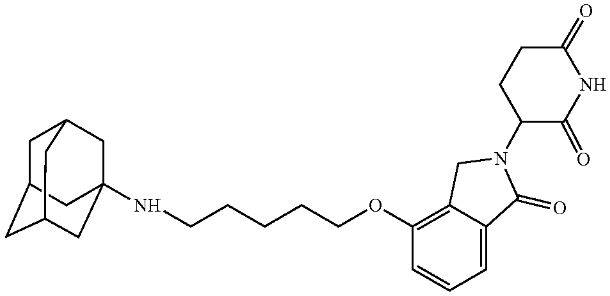 [SMILES: O=C1CCC(N2Cc3c(OCCCCCNC45CC6CC(CC(C6)C4)C5)cccc3C2=O)C(=O)N1] | 3-(4-((5-((adamantan-1-yl)amino)pentyl)oxy)-1-oxoisoindolin-2-yl)piperidine-2,6-dione |
| SIAIS1 222163 | 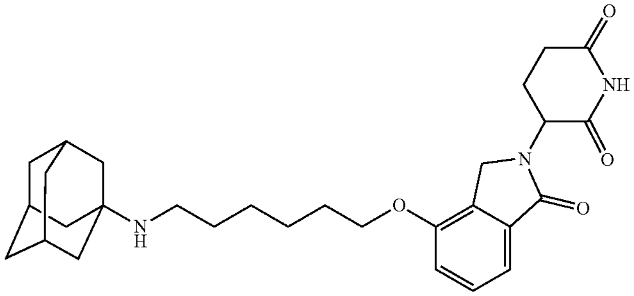 [SMILES: O=C1CCC(N2Cc3c(OCCCCCCNC45CC6CC(CC(C6)C4)C5)cccc3C2=O)C(=O)N1] | 3-(4-((6-((adamantan-1-yl)amino)hexyl)oxy)-1-oxoisoindolin-2-yl)piperidine-2,6-dione |
| SIAIS1 221111 | 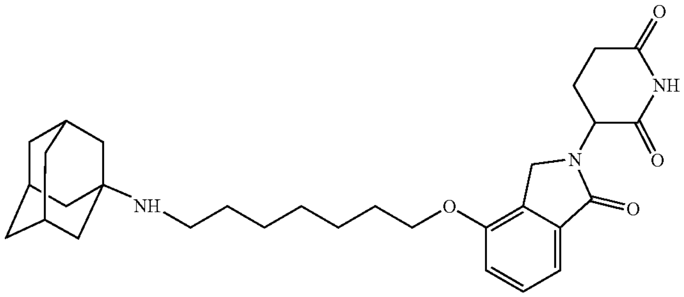 [SMILES: O=C1CCC(N2Cc3c(OCCCCCCCNC45CC6CC(CC(C6)C4)C5)cccc3C2=O)C(=O)N1] | 3-(4-((7-((adamantan-1-yl)amino)heptyl)oxy)-1-oxoisoindolin-2-yl)piperidine-2,6-dione |
| SIAIS1 222167 | 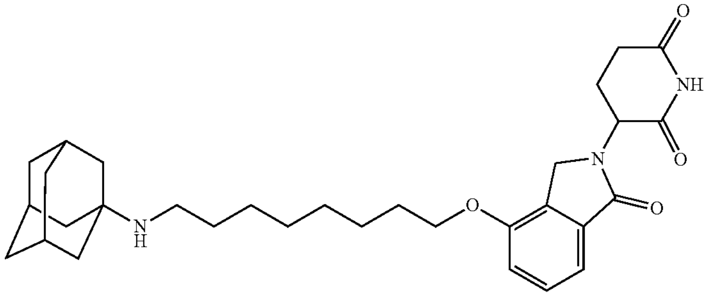 [SMILES: O=C1CCC(N2Cc3c(OCCCCCCCCNC45CC6CC(CC(C6)C4)C5)cccc3C2=O)C(=O)N1] | 3-(4-((8-((adamantan-1-yl)amino)octyl)oxy)-1-oxoisoindolin-2-yl)piperidine-2,6-dione |
| SIAIS1 222181 | 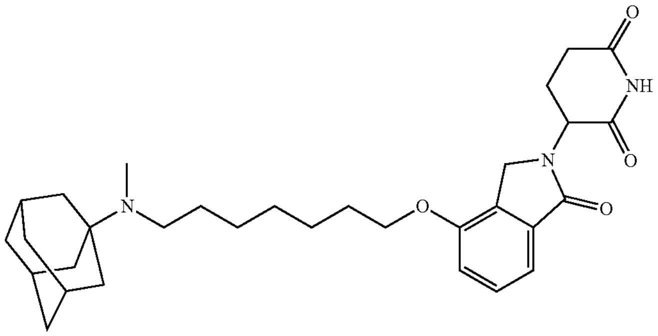 [SMILES: CN(CCCCCCCOc1cccc2c1CN(C1CCC(=O)NC1=O)C2=O)C12CC3CC(CC(C3)C1)C2] | 3-(4-((7-((adamantan-1-yl)(methyl)amino)heptyl)oxy)-1-oxoisoindolin-2-yl)piperidine-2,6-dione |

TABLE 1-continued

| Compound No. | Structure of the compounds | The compound's name |
| --- | --- | --- |
| Compounds of the present invention | | |
| SIAIS1 222165 | 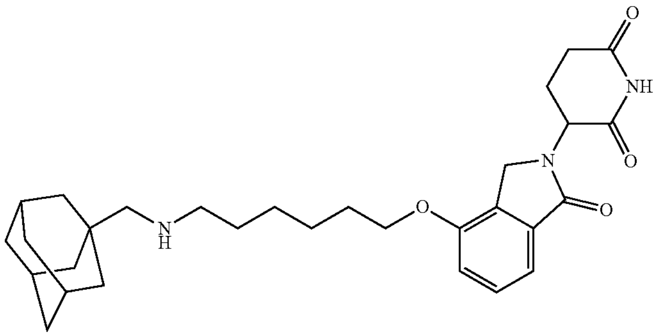 [SMILES: O=C1CCC(N2Cc3c(OCCCCCCNCC45CC6CC(CC(C6)C4)C5)cccc3C2=O)C(=O)N1] | 3-(4-((6-(((adamantan-1-yl)methyl)amino)hexyl)oxy)-1-oxoisoindolin-2-yl)piperidine-2,6-dione |
| SIAIS1 228157 | 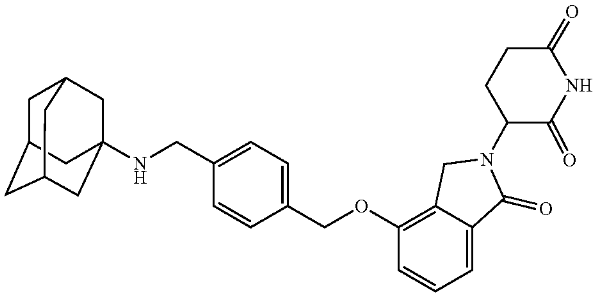 [SMILES: O=C1CCC(N2Cc3c(OCc4ccc(CNC56CC7CC(CC(C7)C5)C6)cc4)cccc3C2=O)C(=O)N1] | 3-(4-((4-(((adamantan-1-yl)amino)methyl)benzyl)oxy)-1-oxoisoindolin-2-yl)piperidine-2,6-dione |
| SIAIS1 221189 | 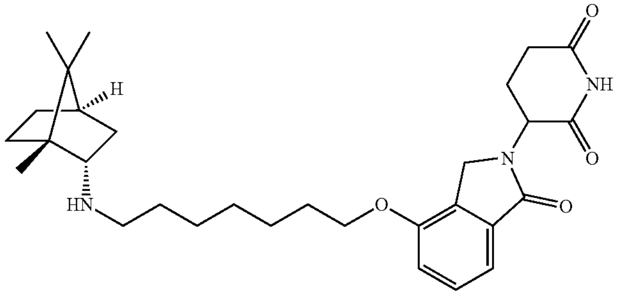 [SMILES: CC1(C)[C@@H]2CC[C@@]1(C)[C@@H](NCCCCCCCOc1cccc3c1CN(C1CCC(=O)NC1=O)C3=O)C2] | 3-(1-oxo-4-((7-(((1R,2S,4R)-1,7,7-trimethylbicyclo[2.2.1]heptan-2-yl)amino)heptyl)oxy)isoindolin-2-yl)piperidine-2,6-dione |
| SIAIS1 222095 | 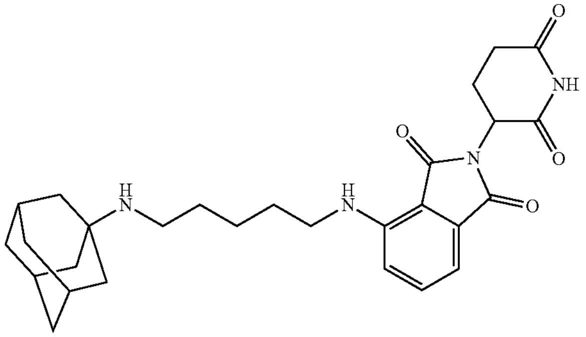 [SMILES: O=C1CCC(N2C(=O)c3cccc(NCCCCCNC45CC6CC(CC(C6)C4)C5)c3C2=O)C(=O)N1] | 4-((5 -((adamantan-1-yl)amino)pentyl)amino)-2-(2,6-dioxopiperidin-3-yl)isoindoline-1,3-dione |

TABLE 1-continued

Compounds of the present invention

| Compound No. | Structure of the compounds | The compound's name |
|---|---|---|
| SIAIS1 222093 | 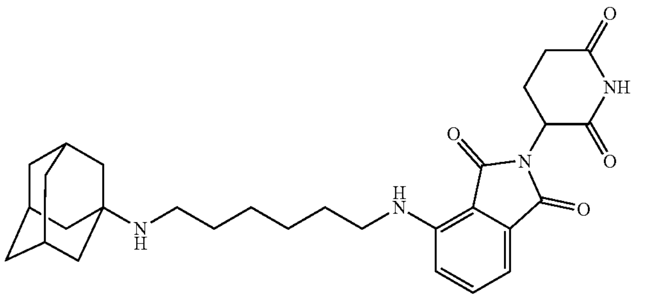 [SMILES: O=C1CCC(N2C(=O)c3cccc(NCCCCCCNC45CC6CC(CC(C6)C4)C5)c3C2=O)C(=O)N1] | 4-((6-((adamantan-1-yl)amino)hexyl)amino)-2-(2,6-dioxopiperidin-3-yl)isoindoline-1,3-dione |
| SIAIS1 221053 | 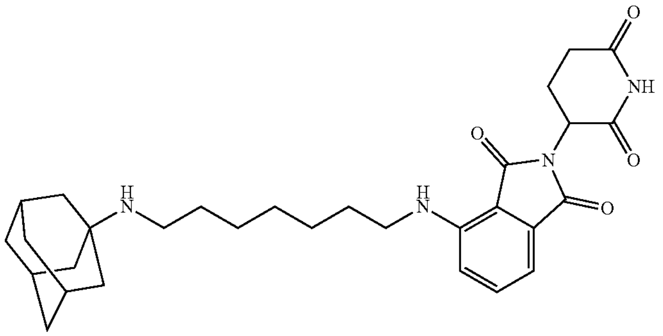 [SMILES: O=C1CCC(N2C(=O)c3cccc(NCCCCCCCNC45CC6CC(CC(C6)C4)C5)c3C2=O)C(=O)N1] | 4-((7-((adamantan-1-yl)amino)heptyl)amino)-2-(2,6-dioxopiperidin-3-yl)isoindoline-1,3-dione |
| SIAIS1 222037 | 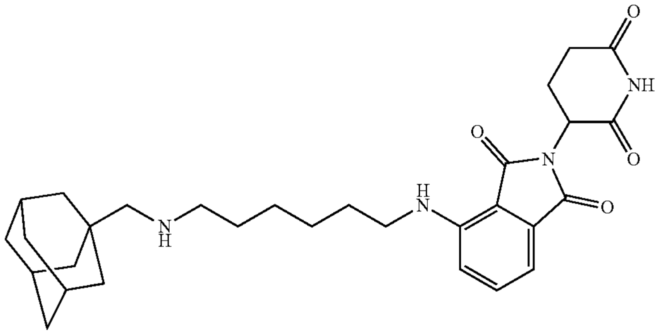 [SMILES: O=C1CCC(N2C(=O)c3cccc(NCCCCCCNCC45CC6CC(CC(C6)C4)C5)c3C2=O)C(=O)N1] | 4-((6-(((adamantan-1-yl)methyl)amino)hexyl)amino)-2-(2,6-dioxopiperidin-3-yl)isoindoline-1,3-dione |
| SIAIS1 222191 | 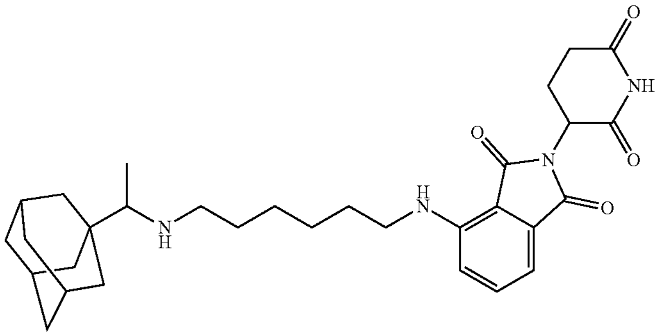 [SMILES: CC(NCCCCCCNc1cccc2c1C(=O)N(C1CCC(=O)NC1=O)C2=O)C12CC3CC(CC(C3)C1)C2] | 4-((6-((1-(adamantan-1-yl)ethyl)amino)hexyl)amino)-2-(2,6-dioxopiperidin-3-yl)isoindoline-1,3-dione |

TABLE 1-continued

| Compounds of the present invention | | |
|---|---|---|
| Compound No. | Structure of the compounds | The compound's name |
| SIAIS1 222193 | 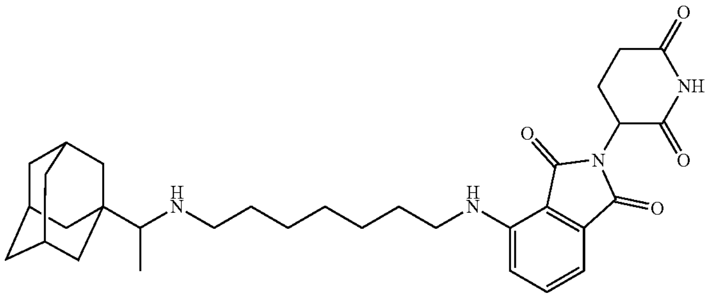 [SMILES: CC(NCCCCCCCNc1cccc2c1C(=O)N(C1CCC(=O)NC1=O)C2=O)C12CC3CC(CC(C3)C1)C2] | 4-((7-(adamantan-1-yl)ethyl)amino)heptyl) amino)-2-(2,6-dioxopiperidin-3-yl)isoindoline-1,3-dione |
| SIAIS1 222035 | 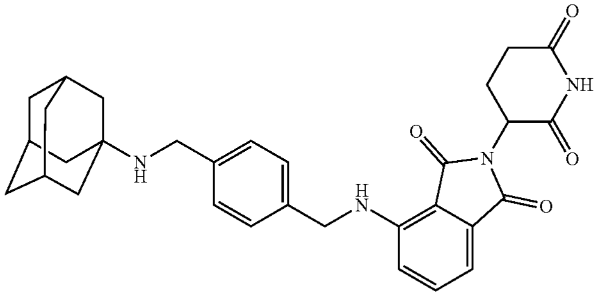 [SMILES: O=C1CCC(N2C(=O)c3cccc(NCc4ccc(CNC56CC7CC(CC(C7)C5)C6)cc4)c3C2=O)C(=O)N1] | 4-((4-(((adamantan-1-yl)amino)methyl)benzyl) amino)-2-(2,6-dioxopiperidin-3-yl)isoindoline-1,3-dione |
| SIAIS1 222041 | 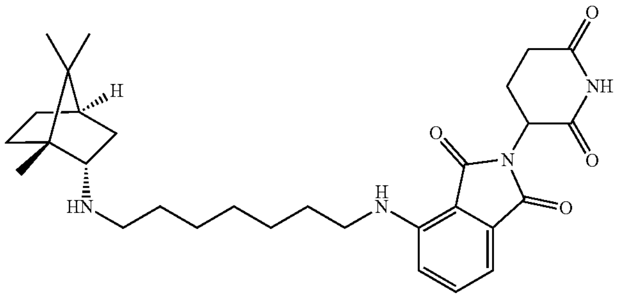 [SMILES: CC1(C)[C@@H]2CC[C@@]1(C)[C@@H](NCCCCCCCNc1cccc3c1C(=O)N(C1CCC(=O)NC1=O)C3=O)C2] | 2-(2,6-dioxopiperidin-3-yl)-4-((7-(((1R,2S,4R)-1,7,7-trimethylbicyclo[2.2.1] heptan-2-yl)amino)heptyl)amino) isoindoline-1,3-dione |
| SIAIS1 221173 | 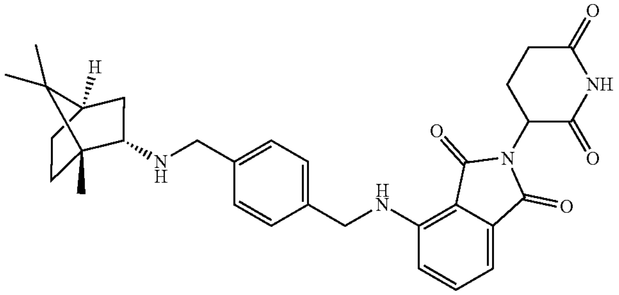 [SMILES: CC1(C)[C@@H]2CC[C@@]1(C)[C@@H](NCc1ccc(CNc3cccc4c3C(=O)N(C3CCC(=O)NC3=O)C4=O)cc1)C2] | 2-(2,6-dioxopiperidin-3-yl)-4-((4-((((1R,2S,4R)-1,7,7-trimethylbicyclo[2.2.1] heptan-2-yl)amino)methyl)benzyl) amino)isoindoline-1,3-dione |
| SIAIS1 221055 | 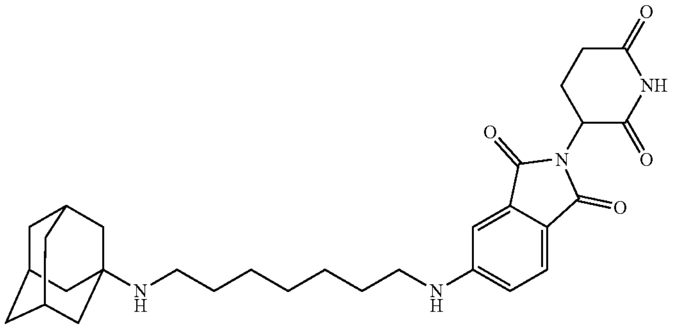 [SMILES: O=C1CCC(N2C(=O)c3ccc(NCCCCCCCNC45CC6CC(CC(C6)C4)C5)cc3C2=O)C(=O)N1] | 5-((7-((adamantan-1-yl)amino)heptyl)amino)-2-(2,6-dioxopiperidin-3-yl)isoindoline-1,3-dione |

TABLE 1-continued

| Compounds of the present invention | | |
|---|---|---|
| Compound No. | Structure of the compounds | The compound's name |
| SIAIS1 222039 | 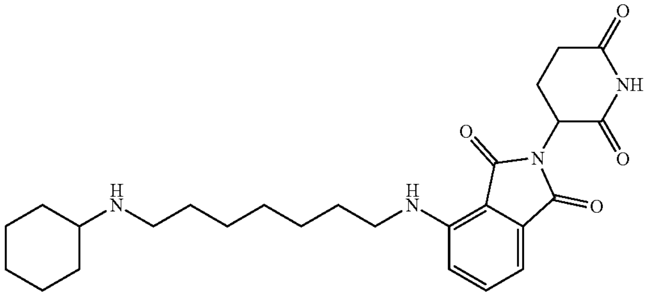 [SMILES: O=C1CCC(N2C(=O)c3cccc(NCCCCCCCNC4CCCCC4)c3C2=O)C(=O)N1] | 4-((7-(cyclohexylamino)heptyl)amino)-2-(2,6-dioxopiperidin-3-yl)isoindoline-1,3-dione |
| SIAISI 222189 | 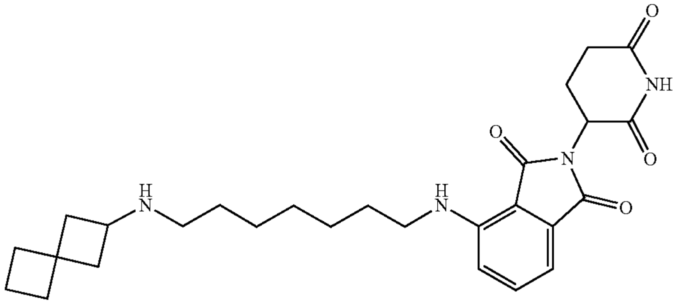 [SMILES: O=C1CCC(N2C(=O)c3cccc(NCCCCCCCNC4CC5(CCC5)C4)c3C2=O)C(=O)N1] | 2-(2,6-dioxopiperidin-3-yl)-4-(7-(spiro[3.3]heptan-2-ylamino)heptyl)amino)isoindoline-1,3-dione |
| SIAIS1 221091 | 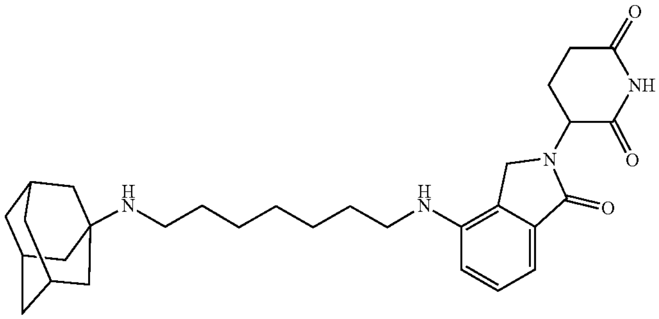 [SMILES: O=C1CCC(N2Cc3c(NCCCCCCCNC45CC6CC(CC(C6)C4)C5)cccc3C2=O)C(=O)N1] | 3-(4-((7-((adamantan-1-yl)amino)heptyl)amino)-1-oxoisoindolin-2-yl)piperidine-2,6-dione |
| SIAIS1 222045 | 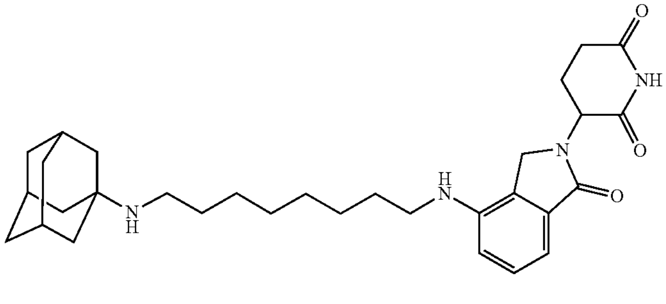 [SMILES: O=C1CCC(N2Cc3c(NCCCCCCCCNC45CC6CC(CC(C6)C4)C5)cccc3C2=O)C(=O)N1] | 3-(4-((8-((adamantan-1-yl)amino)octyl)amino)-1-oxoisoindolin-2-yl)piperidine-2,6-dione |

TABLE 1-continued

Compounds of the present invention

| Compound No. | Structure of the compounds | The compound's name |
| --- | --- | --- |
| SIAIS1 222073 | 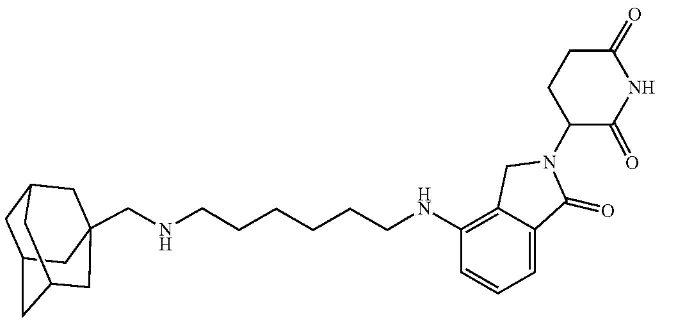 [SMILES: O=C1CCC(N2Cc3c(NCCCCCCNCC45CC6CC(CC(C6)C4)C5)cccc3C2=O)C(=O)N1] | 3-(4-((6-(((adamantan-1-yl)methyl)amino)hexyl) amino)-1-oxoisoindolin-2-yl)piperidine-2,6-dione |
| SIAIS1 222025 | 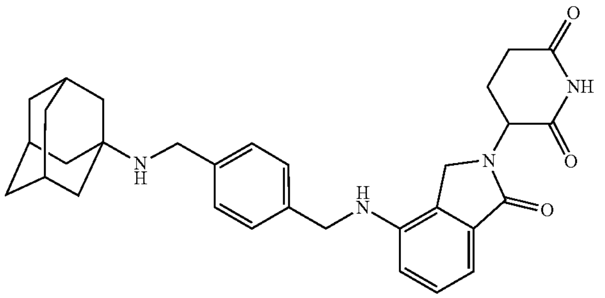 [SMILES: O=C1CCC(N2Cc3c(NCc4ccc(CNC56CC7CC(CC(C7)C5)C6)cc4)cccc3C2=O)C(=O)N1] | 3-(4-((4-(((adamantan-1-yl)amino)methyl)benzyl) amino)-1-oxoisoindolin-2-yl)piperidine-2,6-dione |
| SIAIS1 227027 | 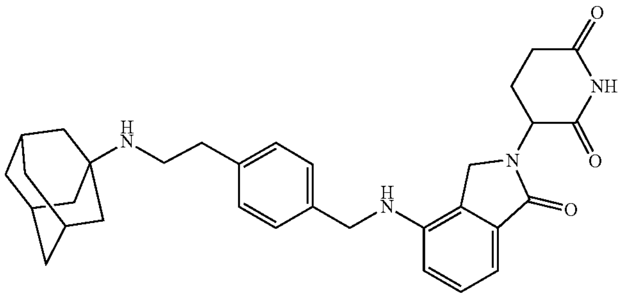 [SMILES: O=C1CCC(N2Cc3c(NCc4ccc(CCNC56CC7CC(CC(C7)C5)C6)cc4)cccc3C2=O)C(=O)N1] | 3-(4-((4-(2-((adamantan-1-yl)amino)ethyl)benzyl) amino)-1-oxoisoindolin-2-yl)piperidine-2,6-dione |
| SIAIS1 227077 | 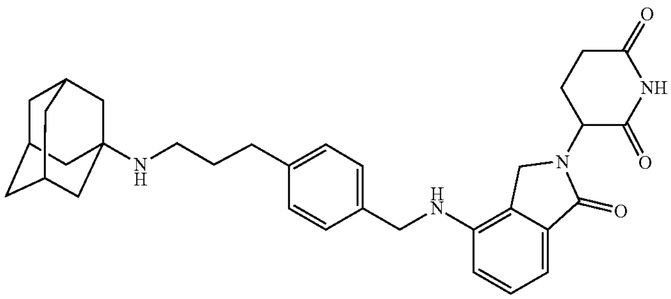 [SMILES: O=C1CCC(N2Cc3c(NCc4ccc(CCCNC56CC7CC(CC(C7)C5)C6)cc4)cccc3C2=O)C(=O)N1] | 3-(4-((4-(3-((adamantan-1-yl) amino)propyl) benzyl)amino)-1-oxoisoindolin-2-yl)piperidine-2,6-dione |
| | 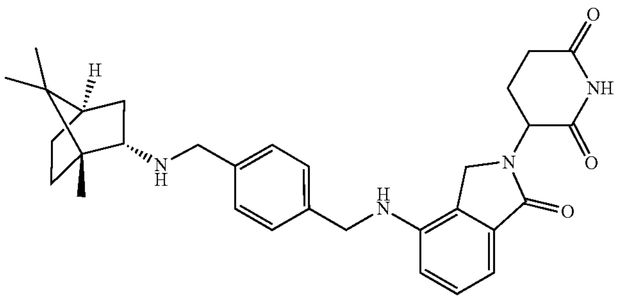 [SMILES: CC1(C)[C@@H]2CC[C@@]1(C)[C@@H](NCc1ccc(CNc3cccc4c3CN(C3CCC(=O)NC3=O)C4=O)cc1)C2] | 3-(1-oxo-4-((4-((((1R,2S,4R)-1,7,7-trimethylbicyclo[2.2.1] heptan-2-yl)amino)methyl)benzyl) amino)isoindolin-2-yl)piperidine-2,6-dione |

TABLE 1-continued

Compounds of the present invention

| Compound No. | Structure of the compounds | The compound's name |
| --- | --- | --- |
| SIAIS1 224043 | 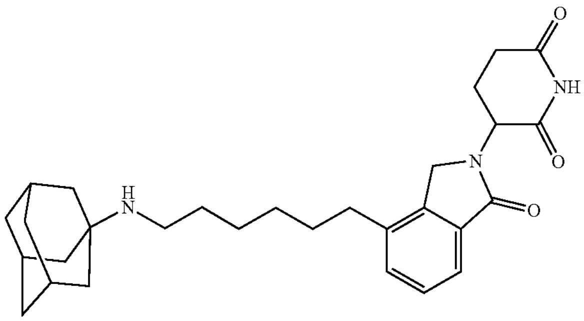 [SMILES: O=C1CCC(N2Cc3c(CCCCCCNC45CC6CC(CC(C6)C4)C5)cccc3C2=O)C(=O)N1] | 3-(4-(6-((adamantan-1-yl)amino)hexyl)-1-oxoisoindolin-2-yl)piperidine-2,6-dione |
| SIAIS1 224041 | 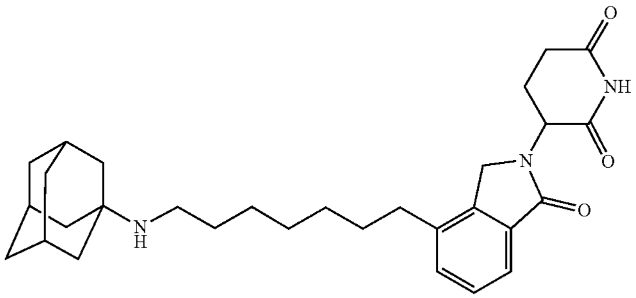 [SMILES: O=C1CCC(N2Cc3c(CCCCCCCNC45CC6CC(CC(C6)C4)C5)cccc3C2=O)C(=O)N1] | 3-(4-(7-((adamantan-1-yl)amino)heptyl)-1-oxoisoindolin-2-yl)piperidine-2,6-dione |
| SIAIS1 221169 | 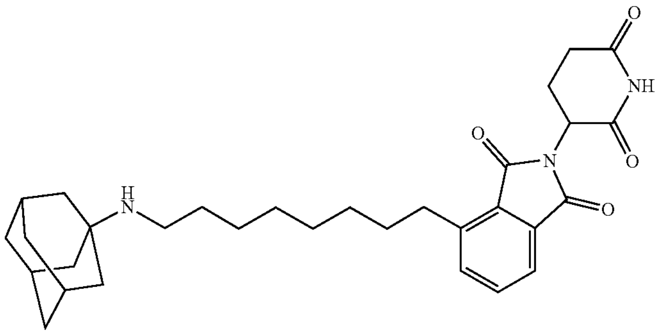 [SMILES: O=C1CCC(N2C(=O)c3cccc(CCCCCCCCNC45CC6CC(CC(C6)C4)C5)c3C2=O)C(=O)N1] | 4-(8-((adamantan-1-yl)amino)octyl)-2-(2,6-dioxopiperidin-3-yl)isoindoline-1,3-dione |
| | 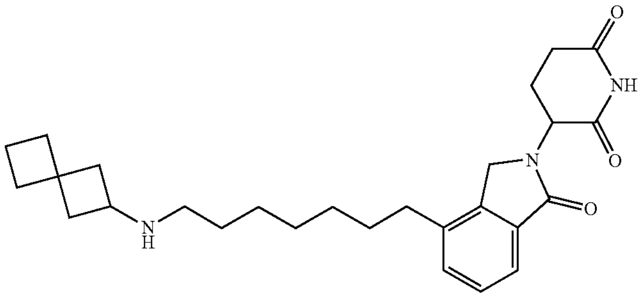 [SMILES: O=C1CCC(N2Cc3c(CCCCCCCNC4CC5(CCC5)C4)cccc3C2=O)C(=O)N1] | 3-(1-oxo-4-(7-(spiro[3.3]heptan-2-ylamino)heptyl)isoindolin-2-yl)piperidine-2,6-dione |

TABLE 1-continued

Compounds of the present invention

| Compound No. | Structure of the compounds | The compound's name |
|---|---|---|
| SIAIS1 221193 | 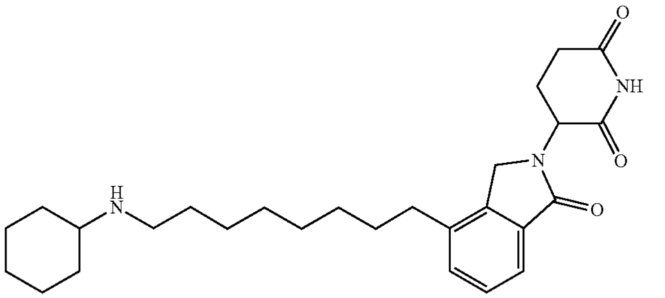 [SMILES: O=C1CCC(N2Cc3c(CCCCCCCCNC4CCCCC4)cccc3C2=O)C(=O)N1] | 3-(4-(8-(cyclohexylamino)octyl)-1-oxoisoindolin-2-yl)piperidine-2,6-dione |
| SIAIS1 222031 | 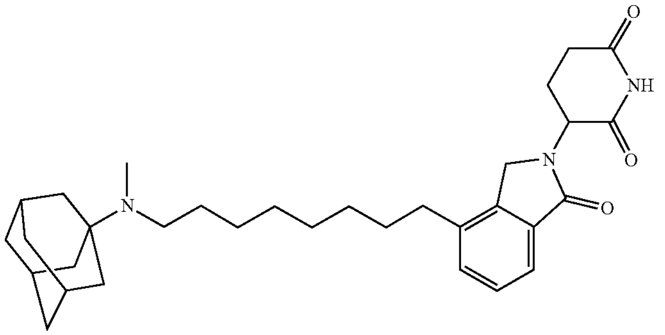 | 3-(4-(8-((adamantan-1-yl)(methyl)amino)octyl)-1-oxoisoindolin-2-yl)piperidine-2,6-dione |
| SIAIS1 221105 | 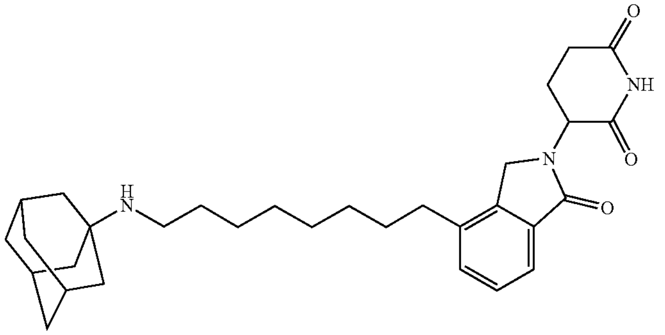 | 3-(4-(8-((adamantan-1-yl)amino)octyl)-1-oxoisoindolin-2-yl)piperidine-2,6-dione |
| SIAIS1 222021 | 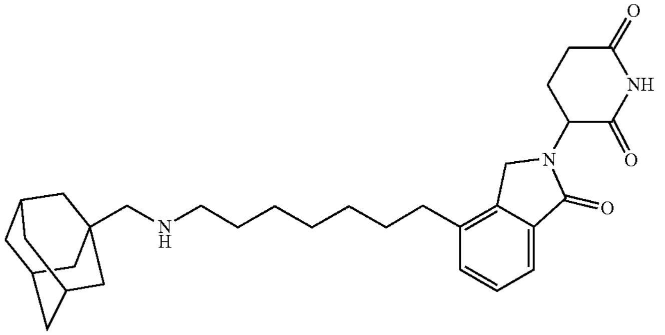 | 3-(4-(7-(((adamantan-1-yl)methyl)amino)heptyl)-1-oxoisoindolin-2-yl)piperidine-2,6-dione |

TABLE 1-continued

| Compound No. | Structure of the compounds | The compound's name |
|---|---|---|
| Compounds of the present invention | | |
| SIAIS1 222051 | 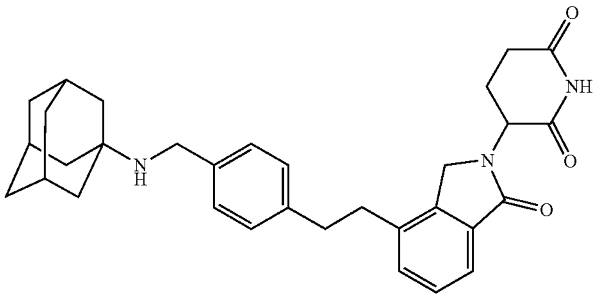 [SMILES: O=C1CCC(N2Cc3c(CCc4ccc(CNC56CC7CC(CC(C7)C5)C6)cc4)cccc3C2=O)C(=O)N1] | 3-(4-(4-(((adamantan-1-yl)amino)methyl)phenethyl)-1-oxoisoindolin-2-yl)piperidine-2,6-dione |
| SIAIS1 222053 | 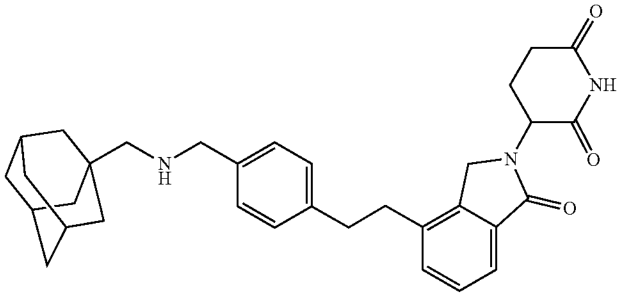 [SMILES: O=C1CCC(N2Cc3c(CCc4ccc(CNCC56CC7CC(CC(C7)C5)C6)cc4)cccc3C2=O)C(=O)N1] | 3-(4-(4-((((adamantan-1-yl)methyl)amino)methyl) phenethyl)-1-oxoisoindolin-2-yl)piperidine-2,6-dione |
| SIAIS1 222055 | 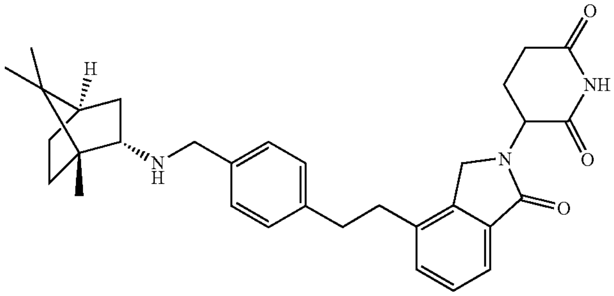 [SMILES: CC1(C)[C@@H]2CC[C@@]1(C)[C@@H](NCc1ccc(CCc3cccc4c3CN(C3CCC(=O)NC3=O)C4=O)cc1)C2] | 3-(1-oxo-4-(4-((((1R,2S,4R)-1,7,7-trimethylbicyclo[2.2.1] heptan-2-yl)amino)methyl)phenethyl)isoindolin-2-yl)piperidine-2,6-dione |
| SIAIS2 71187 | 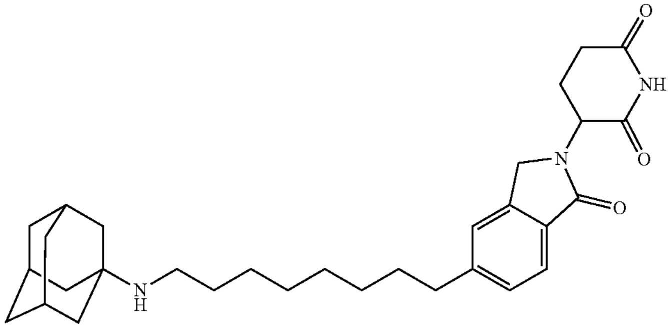 [SMILES: O=C1CCC(N2Cc3cc(CCCCCCCCNC45CC6CC(CC(C6)C4)C5)ccc3C2=O)C(=O)N1] | 3-(5-(8-((adamantan-1-yl)amino)octyl)-1-oxoisoindolin-2-yl)piperidine-2,6-dione |
| SIAIS1 221157 | 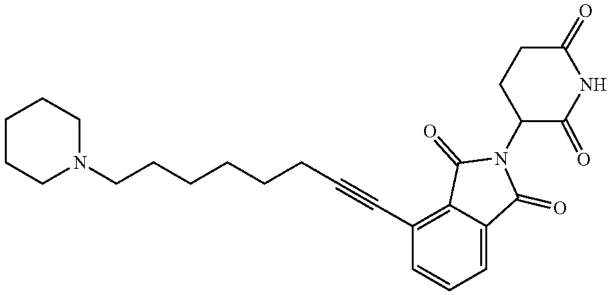 [SMILES: O=C1CCC(N2C(=O)c3cccc(C#CCCCCCCN4CCCCC4)c3C2=O)C(=O)N1] | 2-(2,6-dioxopiperidin-3-yl)-4-(8-(piperidin-1-yl)oct-1-yn-1-yl)isoindoline-1,3-dione |

TABLE 1-continued

Compounds of the present invention

| Compound No. | Structure of the compounds | The compound's name |
| --- | --- | --- |
| SIAIS1 221159 | 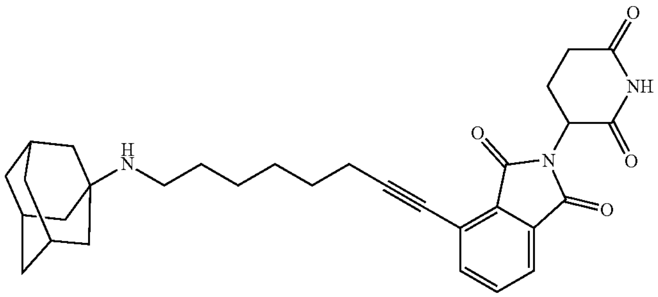 [SMILES: O=C1CCC(N2C(=O)c3cccc(C#CCCCCCCNC45CC6CC(CC(C6)C4)C5)c3C2=O)C(=O)N1] | 4-(8-((adamantan-1-yl)amino)oct-1-yn-1-yl)-2-(2,6-dioxopiperidin-3-yl)isoindoline-1,3-dione |
| SIAIS1 221035 | 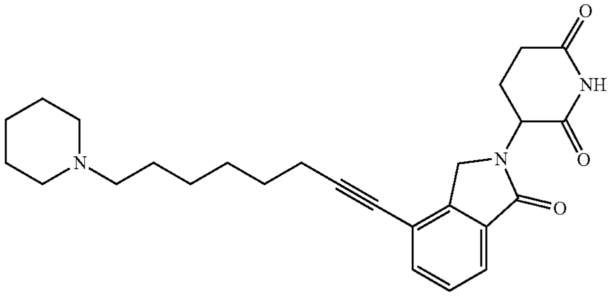 [SMILES: O=C1CCC(N2Cc3c(C#CCCCCCCN4CCCCC4)cccc3C2=O)C(=O)N1] | 3-(1-oxo-4-(8-(piperidin-1-yl)oct-1-yn-1-yl)isoindolin-2-yl)piperidine-2,6-dione |
| SIAIS1 221181 | 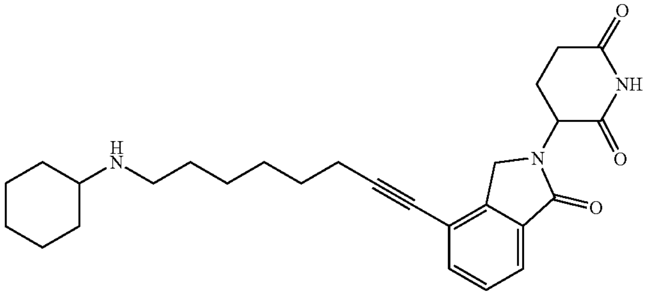 [SMILES: O=C1CCC(N2Cc3c(C#CCCCCCCNC4CCCCC4)cccc3C2=O)C(=O)N1] | 3-(4-(8-(cyclohexylamino)oct-1-yn-1-yl)-1-oxoisoindolin-2-yl)piperidine-2,6-dione |
| SIAIS1 224017 | 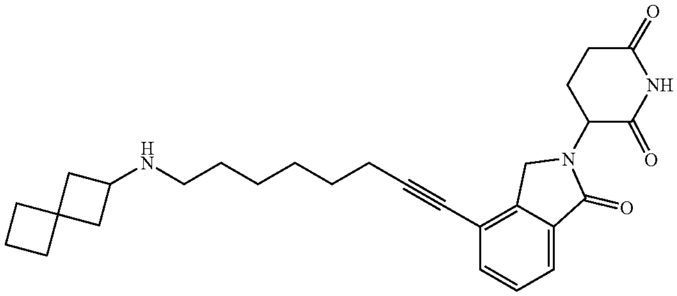 [SMILES: O=C1CCC(N2Cc3c(C#CCCCCCCNC4CC5(CCC5)C4)cccc3C2=O)C(=O)N1] | 3-(1-oxo-4-(8-(spiro[3.3]heptan-2-ylamino)oct-1-yn-1-yl)isoindolin-2-yl)piperidine-2,6-dione |
| SIAIS1 224023 | 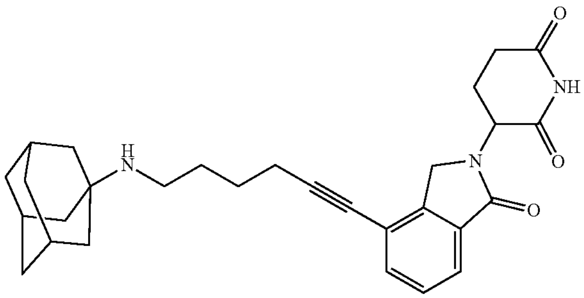 [SMILES: O=C1CCC(N2Cc3c(C#CCCCCNC45CC6CC(CC(C6)C4)C5)cccc3C2=O)C(=O)N1] | 3-(4-(6-((adamantan-1-yl)amino)hex-1-yn-1-yl)-1-oxoisoindolin-2-yl)piperidine-2,6-dione |

TABLE 1-continued

| Compounds of the present invention | | |
|---|---|---|
| Compound No. | Structure of the compounds | The compound's name |
| SIAIS1 224021 | 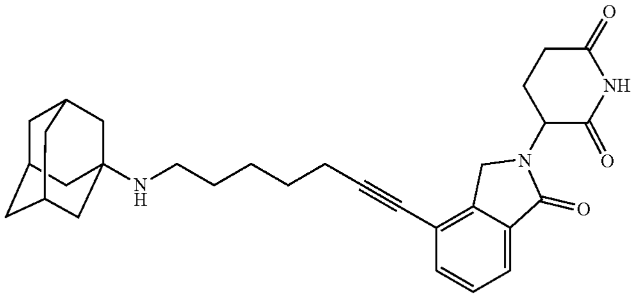 [SMILES: O=C1CCC(N2Cc3c(C#CCCCCCNC45CC6CC(CC(C6)C4)C5)cccc3C2=O)C(=O)N1] | 3-(4-(7-((adamantan-1-yl)amino)hept-1-yn-1-yl)-1-oxoisoindolin-2-yl)piperidine-2,6-dione |
| SIAISI 221095 | 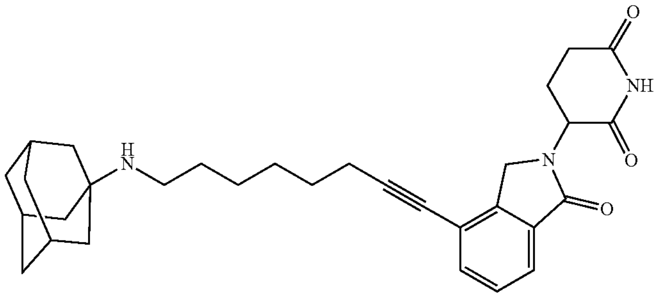 [SMILES: O=C1CCC(N2Cc3c(C#CCCCCCCNC45CC6CC(CC(C6)C4)C5)cccc3C2=O)C(=O)N1] | 3-(4-(8-((adamantan-1-yl)amino)oct-1-yn-1-yl)-1-oxoisoindolin-2-yl)piperidine-2,6-dione |
| SIAISI 222047 | 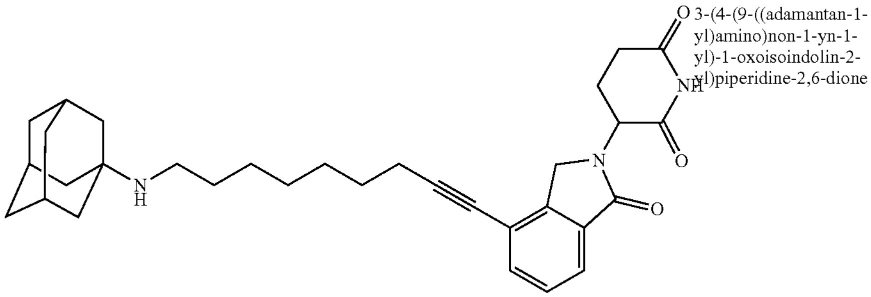 | 3-(4-(9-((adamantan-1-yl)amino)non-1-yn-1-yl)-1-oxoisoindolin-2-yl)piperidine-2,6-dione |
| SIAISI 222019 | 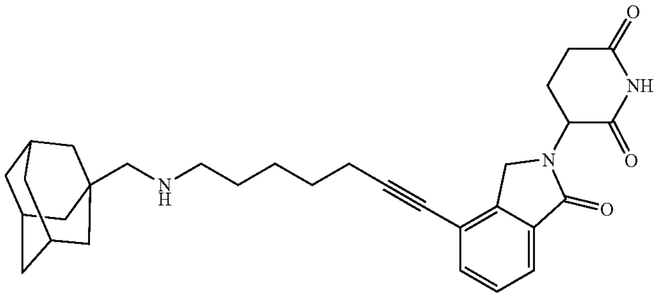 [SMILES: O=C1CCC(N2Cc3c(C#CCCCCCNCC45CC6CC(CC(C6)C4)C5)cccc3C2=O)C(=O)N1] | 3-(4-(7-(((adamantan-1-yl)methyl)amino)hept-1-yn-1-yl)-1-oxoisoindolin-2-yl)piperidine-2,6-dione |
| SIAISI 221183 | 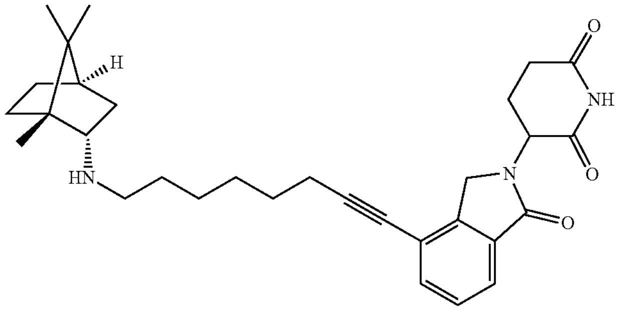 | 3-(1-oxo-4-(8-(((1R,2S,4R)-1,7,7-trimethylbicyclo[2.2.1]heptan-2-yl)amino)oct-1-yn-1-yl)isoindolin-2-yl)piperidine-2,6-dione |

TABLE 1-continued

| Compound No. | Structure of the compounds | The compound's name |
| --- | --- | --- |
| SIAIS271164 | 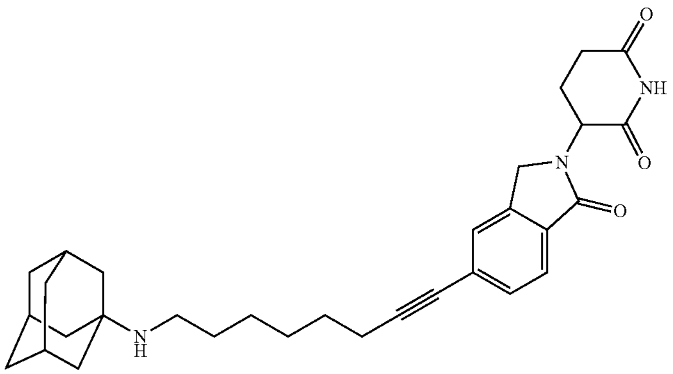 [SMILES: O=C1CCC(N2Cc3cc(C#CCCCCCCNC45CC6CC(CC(C6)C4)C5)ccc3C2=O)C(=O)N1] | 3-(5-(8-((adamantan-1-yl)amino)oct-1-yn-1-yl)-1-oxoisoindolin-2-yl)piperidine-2,6-dione |
| SIAISI228147 | 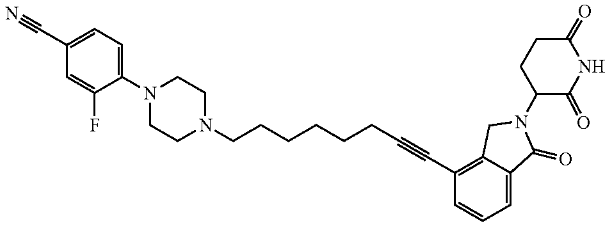 [SMILES: N#Cc1ccc(N2CCN(CCCCCCC#Cc3cccc4c3CN(C3CCC(=O)NC3=O)C4=O)CC2)c(F)c1] | 4-(4-(8-(2-(2,6-dioxopiperidin-3-yl)-1-oxoisoindolin-4-yl)oct-7-yn-1-yl)piperazin-1-yl)-3-fluorobenzonitrile |
| SIAIS1242067 | 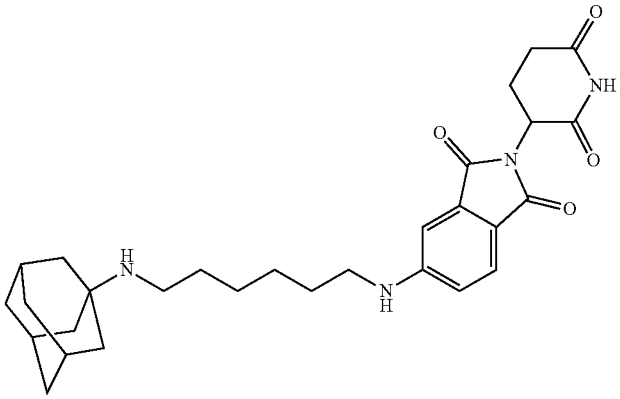 [SMILES: O=C1CCC(N2C(=O)c3ccc(NCCCCCCNC45CC6CC(CC(C6)C4)C5)cc3C2=O)C(=O)N1] | 5-((6 -((adamantan-1-yl)amino)hexyl)amino)-2-(2,6-dioxopiperidin-3-yl)isoindoline-1,3-dione |
| SIAIS1242069 | 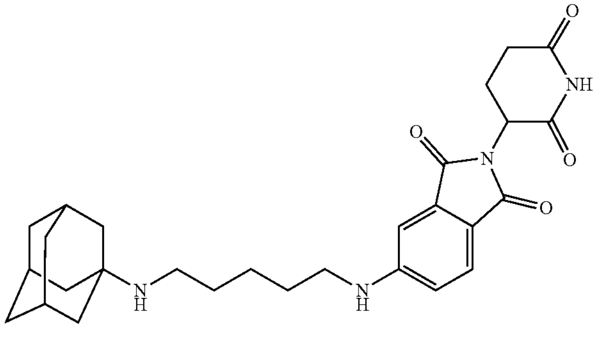 [SMILES: O=C1CCC(N2C(=O)c3ccc(NCCCCCNC45CC6CC(CC(C6)C4)C5)cc3C2=O)C(=O)N1] | 5-((5-((adamantan-1-yl)amino)pentyl)amino)-2-(2,6-dioxopiperidin-3-yl)isoindoline-1,3-dione |

TABLE 1-continued

| Compounds of the present invention | | |
|---|---|---|
| Compound No. | Structure of the compounds | The compound's name |
| | 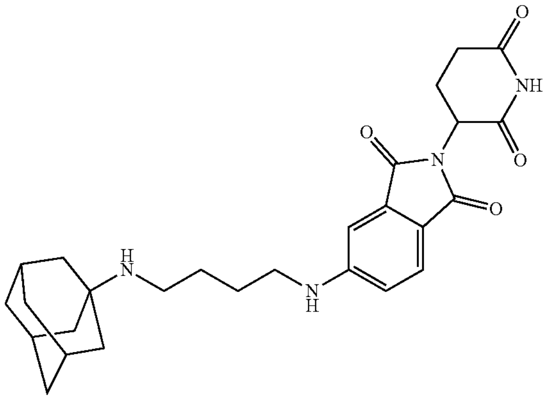 [SMILES: O=C1CCC(N2C(=O)c3ccc(NCCCCNC45CC6CC(CC(C6)C4)C5)cc3C2=O)C(=O)N1] | 5-((4-((adamantan-1-yl)amino)butyl)amino)-2-(2,6-dioxopiperidin-3-yl)isoindoline-1,3-dione |
| | 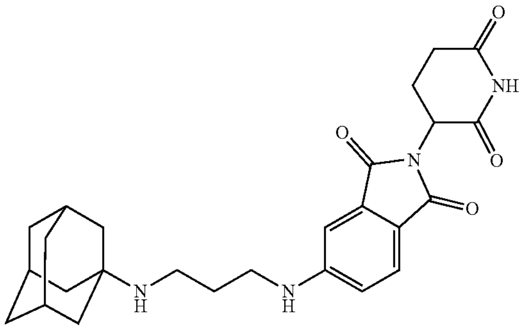 [SMILES: O=C1CCC(N2C(=O)c3ccc(NCCCNC45CC6CC(CC(C6)C4)C5)cc3C2=O)C(=O)N1] | 5-((3-((adamantan-1-yl)amino)propyl)amino)-2-(2,6-dioxopiperidin-3-yl)isoindoline-1,3-dione |
| SIAIS1 241169 | 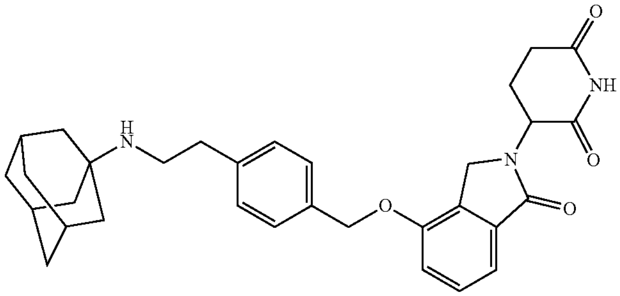 [SMILES: O=C1CCC(N2Cc3c(OCc4ccc(CCNC56CC7CC(CC(C7)C5)C6)cc4)cccc3C2=O)C(=O)N1] | 3-(4-((4-(2-((adamantan-1-yl)amino)ethyl)benzyl)oxy)-1-oxoisoindolin-2-yl)piperidine-2,6-dione |
| SIAIS1 241167 | 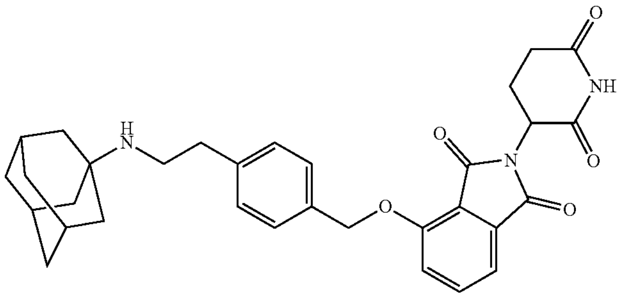 [SMILES: O=C1CCC(N2C(=O)c3cccc(OCc4ccc(CCNC56CC7CC(CC(C7)C5)C6)cc4)c3C2=O)C(=O)N1] | 4-((4-(2-((adamantan-1-yl)amino)ethyl)benzyl)oxy)-2-(2,6-dioxopiperidin-3-yl)isoindoline-1,3-dione |

TABLE 1-continued

Compounds of the present invention

| Compound No. | Structure of the compounds | The compound's name |
| --- | --- | --- |
| | 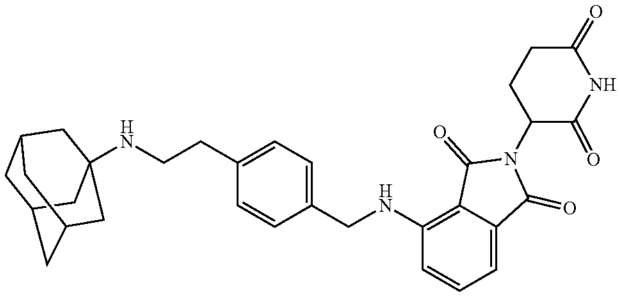 [SMILES: O=C1CCC(N2C(=O)c3cccc(NCc4ccc(CCNC56CC7CC(CC(C7)C5)C6)cc4)c3C2=O)C(=O)N1] | 4-((4-(2-((adamantan-1-yl)amino)ethyl)benzyl)amino)-2-(2,6-dioxopiperidin-3-yl)isoindoline-1,3-dione |
| SIAIS1242073 | 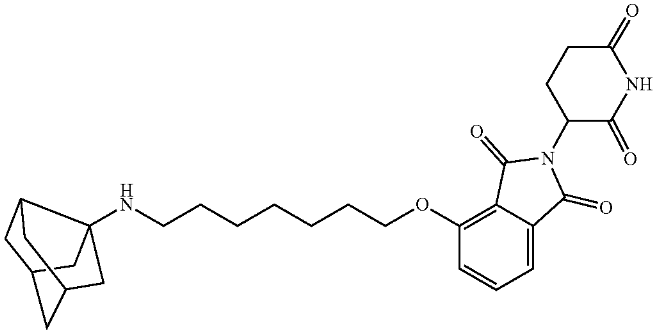 [SMILES: O=C1CCC(N2C(=O)c3cccc(OCCCCCCCNC45CC6CC(CC4C6)C5)c3C2=O)C(=O)N1] | 2-(2,6-dioxopiperidin-3-yl)-4-((7-((hexahydro-2,5-methanopentalen-3a(1H)-yl)amino)heptyl)oxy)isoindoline-1,3-dione |
| SIAIS1242043 | 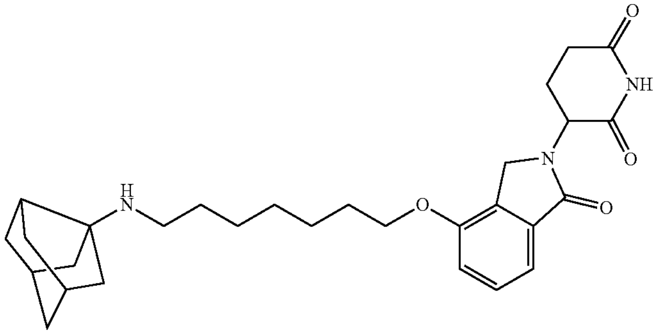 [SMILES: O=C1CCC(N2Cc3c(OCCCCCCCNC45CC6CC(CC4C6)C5)cccc3C2=O)C(=O)N1] | 3-(4-((7-((hexahydro-2,5-methanopentalen-3a(1H)-yl)amino)heptyl)oxy)-1-oxoisoindolin-2-yl)piperidine-2,6-dione |
| SIAIS1242083 | 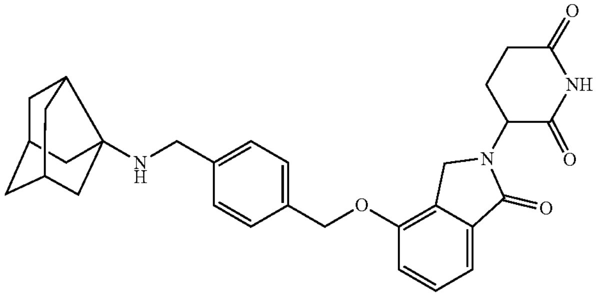 [SMILES: O=C1CCC(N2Cc3c(OCc4ccc(CNC56CC7CC(CC5C7)C6)cc4)cccc3C2=O)C(=O)N1] | 3-(4-((4-(((hexahydro-2,5-methanopentalen-3a(1H)-yl)amino)methyl)benzyl)oxy)-1-oxoisoindolin-2-yl)piperidine-2,6-dione |

TABLE 1-continued

Compounds of the present invention

| Compound No. | Structure of the compounds | The compound's name |
|---|---|---|
| SIAIS1242041 | 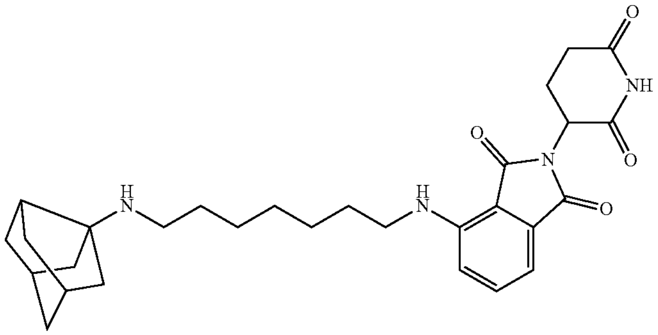 [SMILES: O=C1CCC(N2C(=O)c3cccc(NCCCCCCCNC45CC6CC(CC4C6)C5)c3C2=O)C(=O)N1] | 2-(2,6-dioxopiperidin-3-yl)-4-((7-((hexahydro-2,5-methanopentalen-3a(1H)-yl)amino)heptyl)amino)isoindoline-1,3-dione |
| | 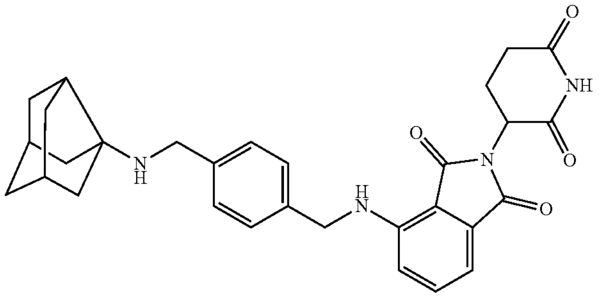 [SMILES: O=C1CCC(N2C(=O)c3cccc(NCc4ccc(CNC56CC7CC(CC5C7)C6)cc4)c3C2=O)C(=O)N1] | 2-(2,6-dioxopiperidin-3-yl)-4-((4-(((hexahydro-2,5-methanopentalen-3a(1H)-yl)amino)methyl)benzyl)amino)isoindoline-1,3-dione |
| SIAIS1242035 | 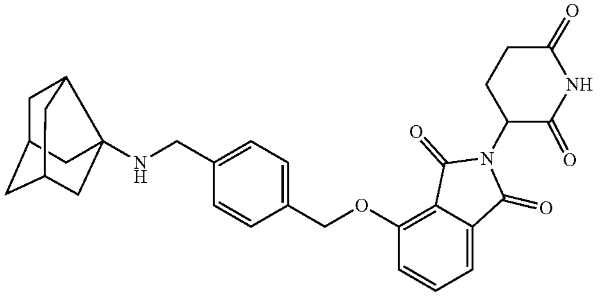 [SMILES: O=C1CCC(N2C(=O)c3cccc(OCc4ccc(CNC56CC7CC(CC5C7)C6)cc4)c3C2=O)C(=O)N1] | 2-(2,6-dioxopiperidin-3-yl)-4-((4-(((hexahydro-2,5-methanopentalen-3a(1H)-yl)amino)methyl)benzyl)oxy)isoindoline-1,3-dione |
| SIAIS1242071 | 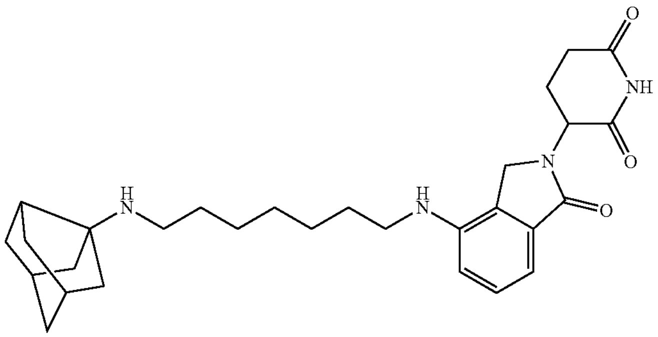 [SMILES: O=C1CCC(N2Cc3c(NCCCCCCCNC45CC6CC(CC4C6)C5)cccc3C2=O)C(=O)N1] | 3-(4-((7-((hexahydro-2,5-methanopentalen-3a(1H)-yl)amino)heptyl)amino)-1-oxoisoindolin-2-yl)piperidine-2,6-dione |

TABLE 1-continued

Compounds of the present invention

| Compound No. | Structure of the compounds | The compound's name |
|---|---|---|
| | 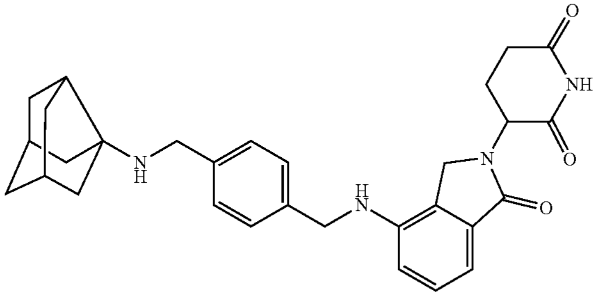 [SMILES: O=C1CCC(N2Cc3c(NCc4ccc(CNC56CC7CC(CC5C7)C6)cc4)cccc3C2=O)C(=O)N1] | 3-(4-((4-(((hexahydro-2,5-methanopentalen-3a(1H)-yl)amino)methyl)benzyl)amino)-1-oxoisoindolin-2-yl)piperidine-2,6-dione |
| | 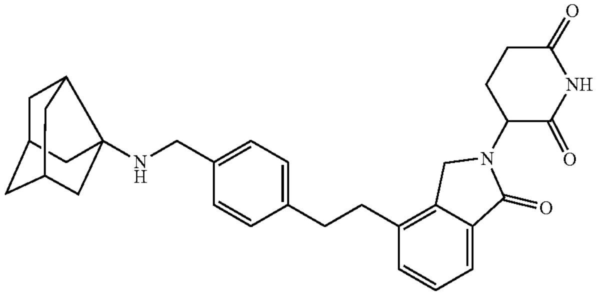 [SMILES: O=C1CCC(N2Cc3c(CCc4ccc(CNC56CC7CC(CC5C7)C6)cc4)cccc3C2=O)C(=O)N1] | 3-(4-(4-(((hexahydro-2,5-methanopentalen-3a(1H)-yl)amino)methyl)phenethyl)-1-oxoisoindolin-2-yl)piperidine-2,6-dione |
| SIAIS1242061 | 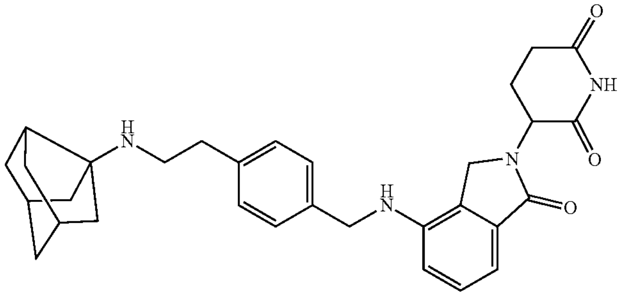 [SMILES: O=C1CCC(N2Cc3c(NCc4ccc(CCNC56CC7CC(CC5C7)C6)cc4)cccc3C2=O)C(=O)N1] | 3-(4-((4-(2-((hexahydro-2,5-methanopentalen-3a(1H)-yl)amino)ethyl)benzyl)amino)-1-oxoisoindolin-2-yl)piperidine-2,6-dione |
| | 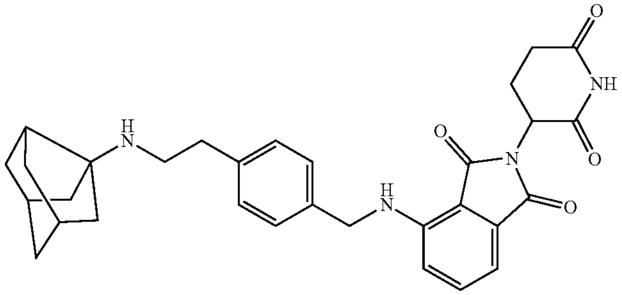 [SMILES: O=C1CCC(N2C(=O)c3cccc(NCc4ccc(CCNC56CC7CC(CC5C7)C6)cc4)c3C2=O)C(=O)N1] | 2-(2,6-dioxopiperidin-3-yl)-4-((4-(2-((hexahydro-2,5-methanopentalen-3a(1H)-yl)amino)ethyl)benzyl)amino)isoindoline-1,3-dione |
| | 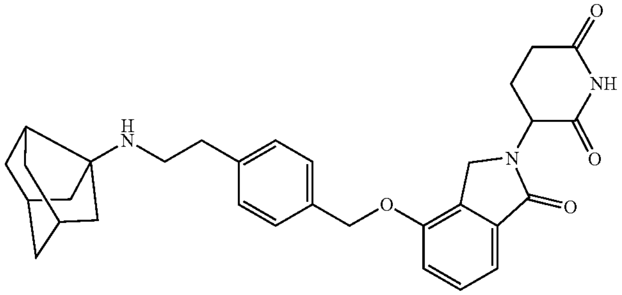 [SMILES: O=C1CCC(N2Cc3c(OCc4ccc(CCNC56CC7CC(CC5C7)C6)cc4)cccc3C2=O)C(=O)N1] | 3-(4-((4-(2-((hexahydro-2,5-methanopentalen-3a(1H)-yl)amino)ethyl)benzyl)oxy)-1-oxoisoindolin-2-yl)piperidine-2,6-dione |

TABLE 1-continued

Compounds of the present invention

| Compound No. | Structure of the compounds | The compound's name |
| --- | --- | --- |
| | 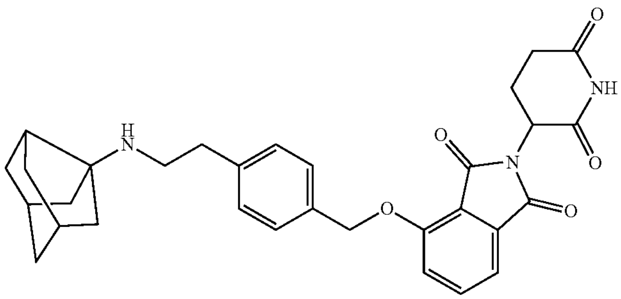 [SMILES: O=C1CCC(N2C(=O)c3cccc(OCc4ccc(CCNC56CC7CC(CC5C7)C6)cc4)c3C2=O)C(=O)N1] | 2-(2,6-dioxopiperidin-3-yl)-4-((4-(2-((hexahydro-2,5-methanopentalen-3a(1H)-yl)amino)ethyl)benzyl)oxy)isoindoline-1,3-dione |
| SIAIS1242057 | 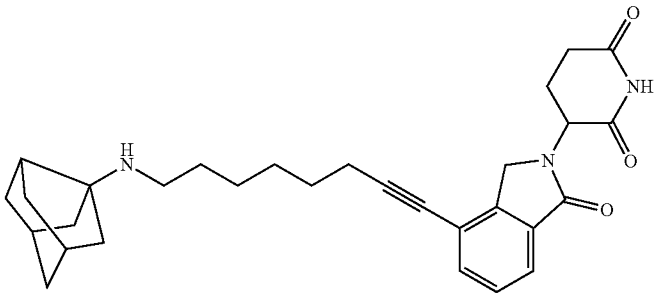 [SMILES: O=C1CCC(N2Cc3c(C#CCCCCCCNC45CC6CC(CC4C6)C5)cccc3C2=O)C(=O)N1] | 3-(4-(8-((hexahydro-2,5-methanopentalen-3a(1H)-yl)amino)oct-1-yn-1-yl)-1-oxoisoindolin-2-yl)piperidine-2,6-dione |
| SIAIS1242091 | 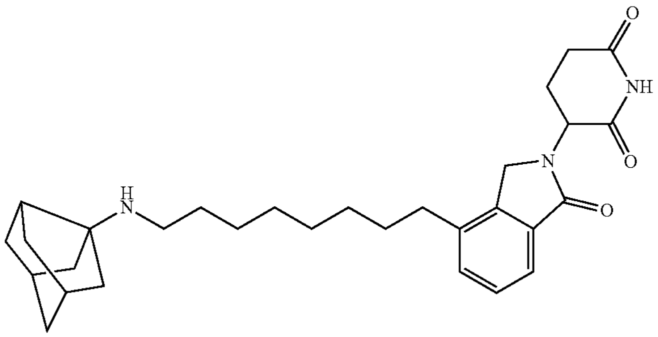 [SMILES: O=C1CCC(N2Cc3c(CCCCCCCCNC45CC6CC(CC4C6)C5)cccc3C2=O)C(=O)N1] | 3-(4-(8-((hexahydro-2,5-methanopentalen-3a(1H)-yl)amino)octyl)-1-oxoisoindolin-2-yl)piperidine-2,6-dione |
| SIAIS1242075 | 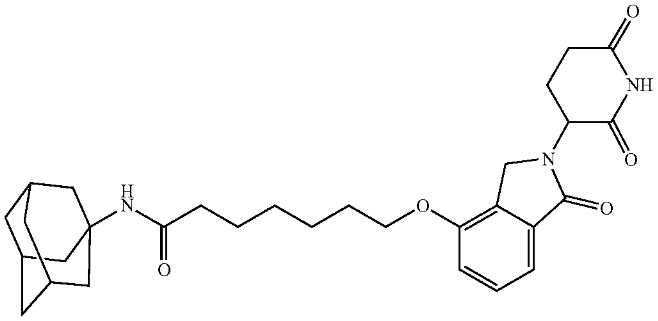 | N-(adamantan-1-yl)-7-((2-(2,6-dioxopiperidin-3-yl)-1-oxoisoindolin-4-yl)oxy)heptanamide |

TABLE 1-continued

| Compounds of the present invention | | |
|---|---|---|
| Compound No. | Structure of the compounds | The compound's name |
| | 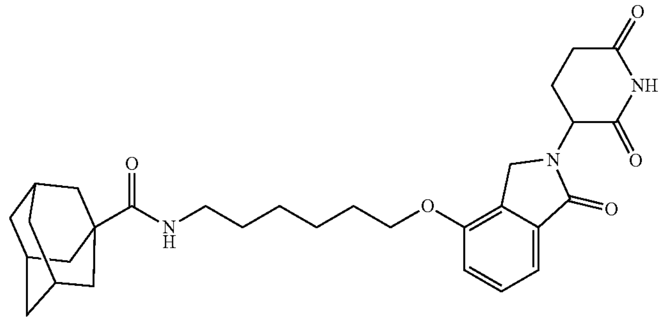 [SMILES: O=C1CCC(N2Cc3c(OCCCCCCNC(=O)C45CC6CC(CC(C6)C4)C5)cccc3C2=O)C(=O)N1] | N-(6-((2-(2,6-dioxopiperidin-3-yl)-1-oxoisoindolin-4-yl)oxy)hexyl)adamantane-1-carboxamide |
| | 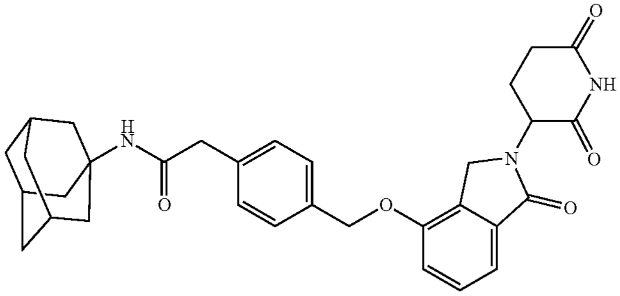 [SMILES: O=C1CCC(N2Cc3c(OCc4ccc(CC(=O)NC56CC7CC(CC(C7)C5)C6)cc4)cccc3C2=O)C(=O)N1] | N-(adamantan-1-yl)-2-(4-((2-(2,6-dioxopiperidin-3-yl)-1-oxoisoindolin-4-yl)oxy)methyl)phenyl) acetamide |
| SIAIS1 242077 | 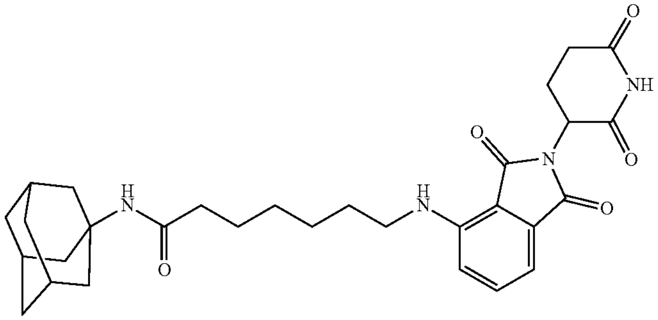 [SMILES: O=C1CCC(N2C(=O)c3cccc(NCCCCCCC(=O)NC45CC6CC(CC(C6)C4)C5)c3C2=O)C(=O)N1] | N-(adamantan-1-yl)-7-((2-(2,6-dioxopiperidin-3-yl)-1,3-dioxoisoindolin-4-yl)amino)heptanamide |
| | 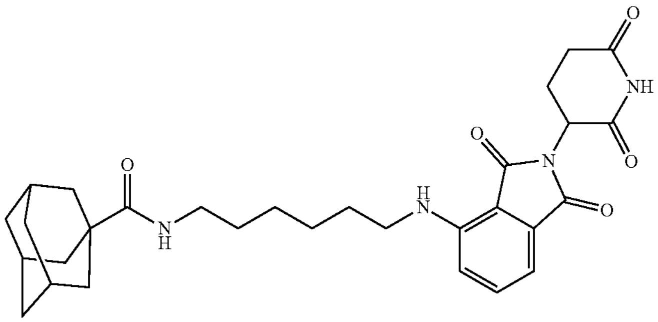 [SMILES: O=C1CCC(N2C(=O)c3cccc(NCCCCCCNC(=O)C45CC6CC(CC(C6)C4)C5)c3C2=O)C(=O)N1] | N-(6-((2-(2,6-dioxopiperidin-3-yl)-1,3-dioxoisoindolin-4-yl)amino)hexyl)adamantane-1-carboxamide |

TABLE 1-continued

| Compounds of the present invention | | |
|---|---|---|
| Compound No. | Structure of the compounds | The compound's name |
| | 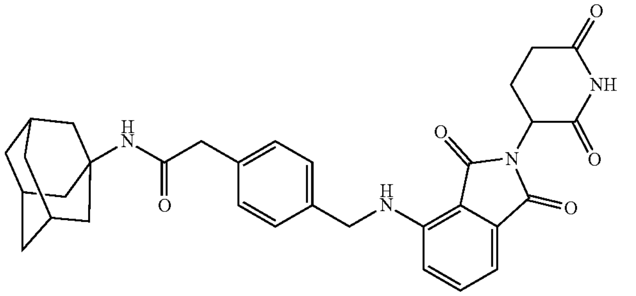 [SMILES: O=C1CCC(N2C(=O)c3cccc(NCc4ccc(CC(=O)NC56CC7CC(CC(C7)C5)C6)cc4)c3C2=O)C(=O)N1] | N-(adamantan-1-yl)-2-(4-(((2-(2,6-dioxopiperidin-3-yl)-1,3-dioxoisoindolin-4-yl)amino)methyl)phenyl) acetamide |
| | 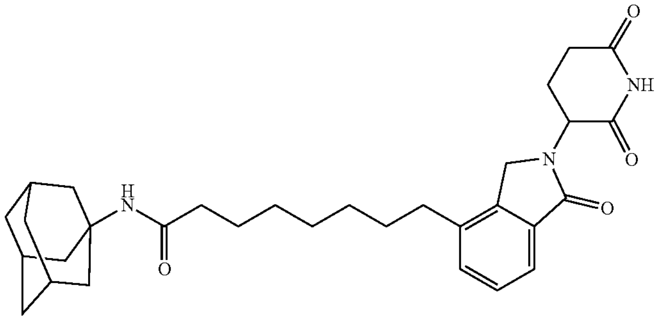 [SMILES: O=C1CCC(N2Cc3c(CCCCCCCC(=O)NC45CC6CC(CC(C6)C4)C5)cccc3C2=O)C(=O)N1] | N-(adamantan-1-yl)-8-(2-(2,6-dioxopiperidin-3-yl)-1-oxoisoindolin-4-yl)octanamide |
| | 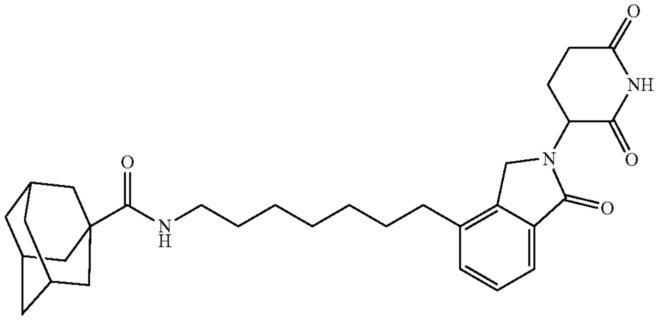 [SMILES: O=C1CCC(N2Cc3c(CCCCCCCNC(=O)C45CC6CC(CC(C6)C4)C5)cccc3C2=O)C(=O)N1] | N-(7-(2-(2,6-dioxopiperidin-3-yl)-1-oxoisoindolin-4-yl)heptyl)adamantane-1-carboxamide |

It is to be understood that the compounds of Formula (I), (Ia), (Ib), (Ic), (Id), (Ie) of the present invention may have a stereo configuration and thus can be in more than one stereoisomeric form. The present invention also relates to compounds having a stereo configuration in substantially pure isomeric form, e.g., greater than about 90% enantiomeric/diastereomeric excess ("ee"), such as about 95% ee or 97% ee, or greater than 99% ee, and mixtures thereof, including racemic mixtures. These isomers can be prepared by using asymmetric synthesis (e.g., by using chiral intermediates) or by chiral resolution.

In another aspect, the present invention also provides a pharmaceutical composition comprising, as an active ingredient, the compound of Formula (I) of the present invention or pharmaceutically acceptable salts, racemates, enantiomers, diastereomers, solvates, or polymorphs thereof, and a pharmaceutically acceptable carrier.

The pharmaceutical composition of the present invention further comprises at least one additional therapeutic agent for the treatment or prevention of a cancer or tumor. In one embodiment, the cancer or tumor includes, but is not limited to, myeloma (also known as plasmacytoma), multiple myeloma, myelodysplastic syndrome (MDS), previously treated myelodysplastic syndrome, plasma cell myeloma, transplantation-related cancer, myelofibrosis, plasma cell myeloma, bone marrow disease, neutropenia, leukemia, acute myeloid leukemia, anemia, chronic myeloid leukemia, B-cell chronic lymphocytic leukemia, acute myeloid leukemia (AML), lymphoma, CD20 positive lymphoma, primary lymphoma, B-cell lymphoma, relapsed B-cell non-Hodgkin's lymphoma, relapsed diffuse large B-cell lymphoma, relapsed primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B cell lymphoma, refractory transformed non-Hodgkin's lymphoma, smoldering myeloma; smoldering multiple myeloma, or Unverricht syndrome.

The pharmaceutical composition of the present invention comprising, as an active ingredient, the compound of Formula (I) of the present invention or a pharmaceutically acceptable salt thereof can be formulated into any suitable formulations such as sprays, patches, tablets, capsules, dragees, troches, powders, granules, powder injections, or liquid formulations (such as suspensions, solutions, emulsions, or syrups), or conventional injection dosage forms such as lyophilized injectable formulation and the like, depending upon a suitable route of administration (including, but not limited to, nasal administration, inhalation administration, topical administration, oral administration, oral mucosal administration, rectal administration, intrapleural administration, intraperitoneal administration, vaginal administration, intramuscular administration, subcutaneous administration, transdermal administration, epidural administration, intrathecal administration, and intravenous administration.

In another aspect, the present invention provides the compound of Formula (I), or pharmaceutically acceptable salts, racemates, enantiomers, diastereomer, solvates, or polymorphs thereof for use as a medicament.

In another aspect, the present invention provides the compound of Formula (I), or pharmaceutically acceptable salts, racemates, enantiomers, diastereomers, solvates, or polymorphs thereof for use in the prevention and/or treatment of a cancer or tumor. In one embodiment, the cancer or tumor includes, but is not limited to, myeloma, multiple myeloma, myelodysplastic syndrome (MDS), previously treated myelodysplastic syndrome, plasma cell myeloma, smoldering myeloma, smoldering multiple myeloma, transplantation-related cancer, myelofibrosis, plasma cell myeloma, bone marrow disease, neutropenia; leukemia, including acute myeloid leukemia, anemia (e.g., leukemia-related anemia), chronic myeloid leukemia, B-cell chronic lymphocytic leukemia, acute myeloid leukemia (AML); lymphoma, including CD20 positive lymphoma, primary lymphoma, B-cell lymphoma, relapsed B-cell non-Hodgkin's lymphoma, relapsed diffuse large B-cell lymphoma, relapsed primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B cell lymphoma, refractory transformed non-Hodgkin's lymphoma, or Unverricht syndrome.

In another aspect, the present invention provides the use of the compound of Formula (I) or a pharmaceutically acceptable salt, racemate, enantiomer, diastereomer, solvates, or polymorphs thereof, for the manufacture of a medicament for the prevention and/or treatment of a cancer or tumor. In one embodiment, the cancer or tumor includes, but is not limited to, myeloma, multiple myeloma, myelodysplastic syndrome (MDS), previously treated myelodysplastic syndrome, plasma cell myeloma, transplantation-related cancer, myelofibrosis, plasma cell myeloma, smoldering myeloma, smoldering multiple myeloma, bone marrow disease, neutropenia; leukemia, including acute myeloid leukemia, anemia, chronic myeloid leukemia, B-cell chronic lymphocytic leukemia, acute myeloid leukemia (AML); lymphoma, including CD20-positive lymphoma, primary lymphoma, B-cell lymphoma, relapsed B-cell non-Hodgkin's lymphoma, relapsed diffuse large B-cell lymphoma, relapsed primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B cell lymphoma, refractory transformed non-Hodgkin's lymphoma, or Unverricht syndrome.

In another aspect, the present invention also provides a method for treating or preventing a cancer or tumor, comprising administering to a subject a therapeutically effective amount of the compound of Formula (I) of the present invention or a pharmaceutically acceptable salt, racemate, enantiomer, diastereomer, solvate, or polymorph thereof, or the pharmaceutical composition of the present invention. In one embodiment, the cancer or tumor includes, but is not limited to, myeloma, multiple myeloma, myelodysplastic syndrome (MDS), previously treated myelodysplastic syndrome, plasma cell myeloma, smoldering myeloma, smoldering multiple myeloma, transplantation-related cancer, myelofibrosis, plasma cell myeloma, bone marrow disease, neutropenia; leukemia, including acute myeloid leukemia, anemia, chronic myeloid leukemia, B-cell chronic lymphocytic leukemia, acute myeloid leukemia (AML); lymphoma, including CD20 positive lymphoma, primary lymphoma, B-cell lymphoma, relapsed B-cell non-Hodgkin's lymphoma, relapsed diffuse large B-cell lymphoma, relapsed primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B cell lymphoma, refractory transformed non-Hodgkin's lymphoma, or Unverricht syndrome.

The method for treating or preventing a cancer or tumor of the present invention comprises that: the compound of Formula (I) of the present invention, or a pharmaceutically acceptable salt, racemate, enantiomer, diastereomer, solvate, or polymorph thereof, or said pharmaceutical composition is administered to the subject by at least one mode of administration selected from the group consisting of: nasal, inhalation, topical, oral, oral mucosal, rectal, pleural, peritoneal, vaginal, intramuscular, subcutaneous, transdermal, epidural, intrathecal, and intravenous administration.

Definition

Unless otherwise specified, the following words, phrases and symbols used herein generally have the meanings as described below.

In general, the nomenclature used herein (such as the IUPAC nomenclature) and the laboratory procedures described below (including those used in cell culture, organic chemistry, analytical chemistry, and pharmacology, etc.) are those well known and commonly used in the art. Unless otherwise defined, all scientific and technical terms used herein in connection with the present disclosure described herein have the same meaning as commonly understood by one skill in the art. In addition, the use of the word "a" or "an" when used in conjunction with the term "comprising" or nouns in the claims and/or the specification may mean "one", but it is also consistent with the meaning of "one or more", "at least one", and "one or more than one". Similarly, the terms "another" or "other" can mean at least a second or more.

It is to be understood that whenever the terms "comprising" or "containing" are used herein to describe various aspects, other similar aspects recited by "consisting of" and/or "consisting essentially of" are also provided.

The term "about" used herein refers to approximately, roughly, nearly, or around. When the term "about" is used in conjunction with a numerical range, it modifies that range by extending the boundaries above and below the stated numerical value. In general, the term "about" can modify a numerical value above and below the stated value by an upward or downward (increasing or decreasing) variation, e.g., 10%, 5%, 2%, or 1%.

The wording " . . . represents a bond" used herein means that it is a chemical bond linker (i.e., that it is absent). For example, the term "R represents a bond" means that R is a bond linker. In other words, when R represents a bond, the L of the compound of Formula (I) is directly connected to any one of B, U, V and W in Formula (I).

As used herein, the term "interrupted" of the wording "linear or branched alkylene chain is interrupted by . . . " used alone or in combination has the definition known in the art, i.e., can mean that there is a group as defined herein (e.g., selected from the group consisting of $N(R^7)$, phenylene, or any combination thereof, as defined herein) inserted between any two adjacent carbon atoms in the backbone of the linear or branched alkylene chain. For example, the wording "the linear or branched alkylene group is optionally interrupted one or more times by phenylene group(s)" refers to that there is a phenylene group inserted between any one or more pairs of two adjacent carbon atoms of the main backbone of the linear or branched alkylene chain, such that a linear or branched alkylene chain containing one or more (e.g., 1-10, 1-8, 1-7, 1-6, 1-5, 1-4, 1-3. 1-2, or 1) fragment "—$CH_2$-phenylene-$CH_2$—" is formed.

In the context of the present disclosure, it is to be understood that the wording "the linear or branched $C_{1-40}$ alkylene group is optionally interrupted one or more times by a phenylene group" includes embodiments with phenylene inserted and embodiments without phenylene insertion. In the case of embodiments with phenylene inserted, $C_1$ alkylene group that does not meet the definition of the term "interrupted" and the valence bond theory is excluded, i.e., the embodiments include linear or branched $C_{2-40}$ alkylene.

Herein, bonds interrupted by wavy lines show the point of attachment of the depicted group to the rest of the molecule. For example, the group represented by $X_d$ depicted below

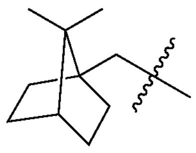 [SMILES: *CC12CCC(CC1)C2(C)C]

means the methylene in said group is bonded to $X_c$ in the group $X_1$ of the compound of Formula (I).

In some embodiments, the term "one or more" when used in conjunction with "the hydrogen atom(s) of $CH_2$ of $C_{1-40}$ alkylene" may refer to 1-80 hydrogen atom(s) of the plurality of hydrogen atoms of $C_{1-40}$ alkylene group. In some embodiments, the term "one or more" may refer to 1-30, optionally 1-25, 1-20, 1-15, 1-10, 1-5, 1-4, 1-3, 1-1, or 1 of the plurality of hydrogen atoms of the $C_{1-40}$ alkylene group mentioned. In some embodiments, the term "one or more" may refer to 1-3 of the plurality of hydrogen atoms of the referenced alkylene group.

As used herein, the term "halogen atom" or "halogen", used alone or in combination, refers to fluorine, chlorine, bromine, or iodine, and optionally F, Cl, or Br.

As used herein, the term "alkyl", used alone or in combination, refers to a linear or branched alkyl group. The term "$C_x$-$C_y$ alkyl" or "$C_{x-y}$ alkyl" (x and y each being an integer) refers to a linear or branched alkyl group containing from x to y carbon atoms. The term "$C_{1-10}$ alkyl" used alone or in combination in the present disclosure refers to a linear or branched alkyl group containing from 1 to 10 carbon atoms. The $C_{1-10}$ alkyl of the present disclosure is optionally a $C_{1-9}$ alkyl, such as $C_{1-8}$ alkyl, $C_{2-8}$ alkyl, $C_{1-7}$ alkyl, $C_{1-6}$ alkyl, $C_{1-5}$ alkyl, or $C_{1-4}$ alkyl. Representative examples include methyl, ethyl, n-propyl, isopropyl, n-butyl, isobutyl, sec-butyl, tert-butyl, pentyl, isopentyl, neopentyl, tert-pentyl, hexyl, heptyl, octyl, nonyl, and decyl. The term "$C_{1-3}$ alkyl" in the present disclosure refers to an alkyl group containing from 1 to 3 carbon atoms, and representative examples thereof include methyl, ethyl, n-propyl, and isopropyl. In the present invention, the "alkyl" is optionally substituted, and the substituent may be one or more selected from D, halogen, hydroxyl, cyano, $C_{1-3}$ alkyl, $C_{1-3}$ alkoxy, trifluoromethyl, heterocyclyl, or a combination thereof.

As used herein, the term "the hydrogen atom(s) of one or more $CH_2$ of the linear or branched $C_{x-y}$ alkylene group is replaced by . . . ", used alone or in combination, means that the hydrogen atom(s) of one or more $CH_2$ of the linear or branched $C_{x-y}$ alkylene group is replaced with a substituent as defined herein.

As used herein, the term "deuterated", used alone or in combination, refers to that a hydrogen atom on the carbon of a hydrocarbyl group in the group mentioned is replaced with its isotope deuterium (i.e., D). As used herein, the term "deuterated $C_{1-3}$ alkyl", used alone or in combination, means that one or more hydrogen atoms in a "$C_{1-3}$ alkyl" have been replaced by its isotope deuterium.

As used herein, the term "halogenated alkyl" or "haloalkyl", used alone or in combination, refers to a linear or branched alkyl group substituted with one or more halogens, wherein one or more hydrogen atom(s) of the alkyl group is replaced with one or more halogens. The term "halogenated $C_x$-$C_y$ alkyl" or "halogenated $C_{x-y}$ alkyl" (x and y are each an integer) refers to a linear or branched alkyl containing from x to y carbon atoms substituted with one or more halogens. The term "halogenated $C_{1-10}$ alkyl" used alone or in combination in the present invention refers to a linear or branched alkyl group containing from 1 to 10 carbon atoms substituted with one or more halogens. The halogenated $C_{1-10}$ alkyl group of the present invention is optionally a halogenated $C_{1-9}$ alkyl group, such as a halogenated $C_{1-8}$ alkyl group, a halogenated $C_{2-s}$ alkyl group, a halogenated $C_{1-7}$ alkyl group, a halogenated $C_{1-6}$ alkyl, halogenated $C_{1-5}$ alkyl, or halogenated $C_{1-4}$ alkyl. Representative examples include halomethyl, haloethyl, halo-n-propyl, haloisopropyl, halo-n-butyl, haloisobutyl, halo-sec-butyl, halo-tert-butyl, halopentyl, haloisoamyl, haloneopentyl, halo-tert-pentyl, halohexyl, haloheptyl, halooctyl, halononyl, and halodecyl. The term "halo-$C_{1-3}$ alkyl" of the present invention refers to an alkyl group containing from 1 to 3 carbon atoms substituted by one or more halogens, and its representative examples include halomethyl, haloethyl, halo-n-propyl and haloisopropyl.

As used herein, the term "alkylene" (which is used interchangeably with "alkylene chain"), used alone or in combination, refers to a linear or branched divalent saturated hydrocarbon group composed of carbon and hydrogen atoms. The term "$C_x$-$C_y$ alkylene" or "$C_{x-y}$ alkylene" (x and y each being an integer) refers to a linear or branched alkylene group containing from x to y carbon atoms. The $C_1$-$C_{40}$ alkylene in the present disclosure can optionally be $C_1$-$C_{35}$ alkylene, $C_1$-$C_{30}$ alkylene, $C_1$-$C_{29}$ alkylene, $C_1$-$C_{28}$ alkylene, $C_1$-$C_{27}$ alkylene, $C_1$-$C_{26}$ alkylene, $C_1$-$C_{25}$ alkylene, $C_1$-$C_{24}$ alkylene, $C_1$-$C_{23}$ alkylene, $C_1$-$C_{22}$ alkylene, $C_1$-$C_{21}$ alkylene, $C_1$-$C_{20}$ alkylene, $C_1$-$C_{19}$ alkylene, $C_1$-$C_{18}$ alkylene, $C_1$-$C_{17}$ alkylene, $C_1$-$C_{16}$ alkylene, $C_1$-$C_{15}$ alkylene, $C_1$-$C_{14}$ alkylene, $C_1$-$C_{13}$ alkylene, $C_1$-$C_{12}$ alkylene, $C_1$-$C_{11}$ alkylene, $C_1$-$C_{10}$ alkylene, $C_1$-$C_9$ alkylene, $C_1$-$C_8$ alkylene, $C_1$-$C_7$ alkylene, $C_1$-$C_6$ alkylene, $C_1$-$C_5$ alkylene, $C_1$-$C_4$ alkylene, $C_1$-$C_3$ alkylene, or $C_1$-$C_2$ alkylene. Representative examples include, but are not limited to, methylene, ethylene, propylene, isopropylene, butylene, isobutylene, sec-butylene, tert-butylene, n-pentylene, isopentylene, neopentylidene, tertpentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, heneicosylene, docosylene, tricosylene, tetracosylene, pentacosylene, hexacosylene, peptacosylene, octacosylene, nonacosylene, and triacontylene. In the present invention, the "alkylene" is optionally substituted, and the substituent may be one or more selected from D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, cyano, or any combination thereof.

As used herein, the term "phenyl", used alone or in combination, is optionally substituted. Substituted phenyl refers to phenyl substituted with 1-3 substituents, wherein the substituents can optionally be selected from D, $C_{1-3}$ alkyl, deuterated $C_{1-3}$ alkyl, $C_{1-3}$ alkoxy, $C_{3-6}$ cycloalkyl, halogen, halogenated $C_{1-3}$alkyl, hydroxyl, cyano, or any combination thereof.

As used herein, the term "phenylene", used alone or in combination, is optionally substituted. Substituted phenylene refers to phenylene substituted with 1-3 substituents, wherein the substituents can optionally be selected from D, $C_{1-3}$ alkyl, deuterated $C_{1-3}$ alkyl, $C_{1-3}$ alkoxy, $C_{3-6}$ cycloalkyl, halogen, halogenated $C_{1-3}$alkyl, hydroxyl, cyano, or any combination thereof.

As used herein, the term "alkoxy", used alone or in combination, refers to a linear or branched alkoxy group having structural Formula of —O-alkyl. Optionally, the alkyl portion of the alkoxy group may contain 1-10 carbon atoms. Representative examples of "alkoxy" include, but are not limited to, methoxy, ethoxy, propoxy, isopropoxy, n-butoxy, isobutoxy, tert-butoxy, pentyloxy, 2-pentyloxy, isopentyloxy, neopentyloxy, hexyloxy, 2-hexyloxy, 3-hexyloxy, 3-methylpentyloxy, etc. The term "$C_1$-$C_3$ alkoxy" or "$C_{1-3}$ alkoxy" refers to a linear or branched alkoxy group containing from 1 to 3 carbon atoms. Representative examples of $C_{1-3}$ alkoxy include, but are not limited to, methoxy, ethoxy, n-propoxy, and isopropoxy. Optionally Representative examples of $C_{1-3}$ alkoxy are methoxy and ethoxy.

As used herein, the term "cycloalkyl", used alone or in combination, refers to a saturated or partially unsaturated (i.e., containing one or more double bonds, but not having a fully conjugated π-electron system) monocyclic or bicyclic or polycyclic cyclic hydrocarbon radical, which in some embodiments has from 3 to 20 carbon atoms (i.e., $C_{3-20}$ cycloalkyl), or from 3 to 15 carbon atoms (i.e., $C_{3-15}$ cycloalkyl), or from 3 to 12 carbon atoms (i.e., $C_{3-12}$ cycloalkyl), or from 3 to 11 carbon atoms (i.e., $C_{3-11}$ cycloalkyl), or from 3 to 10 carbon atoms (i.e., $C_{3-10}$ cycloalkyl), or from 3 to 8 carbon atoms (i.e., $C_{3-8}$ cycloalkyl), or from 3 to 7 carbon atoms (i.e., $C_{3-7}$ cycloalkyl), or from 3 to 6 carbon atoms (i.e., $C_{3-6}$ cycloalkyl). The term "cycloalkyl" includes monocyclic, bicyclic or tricyclic cyclic hydrocarbon radical having from 3 to 20 carbon atoms. Representative examples of monocyclic cycloalkyl groups include, but are not limited to, cyclopropyl, cyclobutyl, cyclopentyl, cyclopentenyl, cyclohexyl, cyclohexenyl, cycloheptyl, and cyclooctyl. Bicyclic and tricyclic cycloalkyl groups include bridged cycloalkyl, fused cycloalkyl and spiro-cycloalkyl groups such as, but not limited to, decalinyl, octahydropentalenyl, octahydro-1H-indenyl, spiro-cycloalkyl, adamantanyl, noradamantanyl, bornyl, norbornyl (also named as bicyclo[2.2.1]heptyl by the IUPAC system). As used herein, the "cycloalkyl" is optionally mono- or poly-substituted, such as, but not limited to, 2,2-, 2,3-, 2,4-, 2,5-, or 2,6-disubstituted cyclohexyl. The substituents of the substituted "cycloalkyl" can be optionally one or more (e.g., 1-5, 1-4, 1-3, 1-2, or 1) selected from D, $C_{1-3}$ alkyl, deuterated $C_{1-3}$ alkyl, halo $C_{1-3}$ alkyl, $C_{1-3}$ alkoxy, deuterated $C_{1-3}$ alkoxy, oxo, halogen, hydroxyl, cyano, $C_{1-3}$ alkyl amino, amino, or any combination thereof.

As used herein, the term "$C_{x-y}$ spiro-cycloalkyl" (x and y each being an integer), used alone or in combination, refers to a spiro-cycloalkyl group containing from x to y carbon atoms. As used herein, the term "$C_7$-11 spiro-cycloalkyl", used alone or in combination, refers to a spiro-cycloalkyl group containing from 7 to 11 (e.g., 7-10, 7-9) carbon atoms. Representative examples of the term "$C_7$-11 spiro-cycloalkyl" include, but are not limited to, spiro[3.3]heptyl, spiro[2.5]octyl, spiro[3.5]nonyl, spiro[4.4]nonyl, spiro[4.5]decyl, or spiro[5.5]undecyl. The "$C_7$-11 spiro-cycloalkyl" is optionally further substituted with one or more substituents selected from the group consisting of D, $C_{1-3}$ alkyl, deuterated $C_{1-3}$ alkyl, halogenated $C_{1-3}$ alkyl, $C_{1-3}$ alkoxy, deuterated $C_{1-3}$ alkoxy, $C_{1-3}$ alkylamino, amino, oxo, halogen, hydroxyl, cyano, or any combination thereof.

As used herein, the term "$C_{x-y}$ bridged cycloalkyl" (x and y each being an integer), used alone or in combination, refers to a bridged cycloalkyl group containing from x to y carbon atoms. As used herein, the term "$C_{7-15}$ bridged cycloalkyl", used alone or in combination, refers to bridged cycloalkyl containing from 7 to 15 (e.g., 7-11, 7-10, 7-9, 7-8) carbon atoms. Representative examples of the term "$C_7$-15 bridged cycloalkyl" include, but are not limited to, adamantanyl, noradamantanyl, bornyl, norbornyl (also named as bicyclo[2.2.1]heptyl by the IUPAC system). The "bridged cycloalkyl" is optionally substituted with 1 to 10 substituents selected from the group consisting of D, $C_{1-3}$ alkyl, deuterated $C_{1-3}$ alkyl, $C_{1-3}$ alkoxy, deuterated $C_{1-3}$ alkoxy, halogen, halogenated $C_{1-3}$ alkyl, $C_{1-3}$ alkylamino, amino, hydroxyl, cyano, oxo, or any combination thereof.

As used herein, the term "heterocyclyl" or "heterocyclic group", used alone or in combination, refers to a 3- to 20-membered saturated or partially unsaturated (i.e., containing one or more double bonds, but not having a fully conjugated π-electron system) monocyclic, bicyclic, or tricyclic cyclic hydrocarbon group containing one or more (e.g., from 1 to 5, or from 1 to 4) heteroatoms independently selected from sulfur, oxygen, and nitrogen. In some embodiments, "heterocyclyl" may preferably refer to a 3- to 15-membered (optionally 3- to 8-membered, or 3- to 6-membered) saturated or partially unsaturated (i.e., containing one or more double bonds, but not having a fully conjugated π-electron system) monocyclic cyclic hydrocarbon group containing one or more heteroatoms independently selected from sulfur, oxygen, and nitrogen. Representative examples of the heterocyclyl include, but are not limited to, azetidinyl, oxetanyl, pyrrolidinyl, imidazolidinyl, pyrazolidyl, triazolyl, tetrahydrofuranyl, tetrahydropyranyl, tetrahydrothienyl, tetrahydrothiopyranyl, oxazolidinyl, thiazolidinyl, piperidinyl, piperazinyl, morpholinyl, thiomorpholinyl, dioxocyclohexyl, 1,4-diazacycloheptane-1-yl, 3,8-diazabicyclo[3.2.1]octan-3-yl, 2,5-diazabicyclo[2.2.2]octan-2-yl, and azaspirocycloalkyl (especially 3-azaspiro[5.5]undecan-3-yl). The heterocyclyl may be unsubstituted or substituted as explicitly defined, and the substituent(s) of the heterocyclyl can be optionally selected from the group consisting of D, $C_{1-3}$ alkyl, deuterated $C_{1-3}$ alkyl, $C_{1-3}$ alkoxy, deuterated $C_{1-3}$ alkoxy, halogen, halogenated $C_{1-3}$ alkyl, hydroxyl, cyano, oxo, $C_{1-3}$ alkylamino, amino, or any combination thereof.

As used herein, the term "alkynylene", used alone or in combination, refers to a linear or branched divalent hydrocarbon group containing from 2 to 6 (optionally from 2 to 4, or 2) carbon atoms and having one or more carbon-carbon triple bonds. Examples of alkynylene include, but are not limited to, ethynylene, 1-propynylene, 1-butynylene, and 1,3-diynylene.

As used herein, the term "alkenylene", used alone or in combination, refers to a linear or branched divalent hydrocarbon group containing from 2 to 6 (optionally from 2 to 6 or from 2 to 5, e.g., from 2 to 4, or from 2 to 3, or 2) carbon atoms and having one or more carbon-carbon double bonds. Examples of alkenylene groups include, but are not limited to, vinylene (e.g., —CH═CH—), 1-propenylene, allylidene, 1-butenylene, 2-butenylene, 3-butenylene, isobutenylene, pentenylene, n-pent-2,4-dienylene, 1-methyl-but-1-enylene, 2-methyl-but-1-enylene, 3-methyl-but-1-enylene, 1-methyl-but-2-enylene, 2-methyl-but-2-enylene, 3-methyl-but-2-enylene, 1-methyl-but-3-enylene, 2-methyl-but-3-enylene, 3-methyl-but-3-enylene, and hexenylene.

As used herein, "bornylane" or "bornane" (also known as 1,7,7-trimethylbicyclo[2.2.1]heptane; camphane; bornylane) has a definition known to those skilled in the art. As used herein, "camphanyl" or "bornyl" refers to a monovalent group of bornane, i.e., the group remaining after any one of the hydrogens in bornane is removed. Representative examples include, but are not limited to, 1,7,7-trimethylbicyclo[2.2.1]heptan-2-yl, 1,7,7-trimethylbicyclo[2.2.1]heptan-3-yl, 1,7,7-trimethylbicyclo[2.2.1]heptan-4-yl, 1,7,7-trimethylbicyclo[2.2.1]heptan-5-yl, or 1,7,7-trimethylbicyclo[2.2.1]heptan-6-yl,

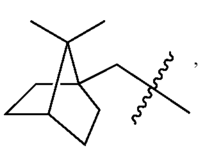

, or

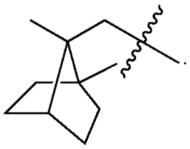

.

or

As used herein, "bicyclo[2.2.1]heptane" also known as bicyclo[2.2.1]heptane or "norbornane". As used herein, "bicyclo[2.2.1]heptyl" or "norbornyl" refers to a monovalent group of bicyclo[2.2.1]heptane, i.e., the group remaining after any hydrogen in bicyclo[2.2.1]heptane is removed. Representative examples include, but are not limited to, bicyclo[2.2.1]heptan-2-yl, bicyclo[2.2.1]heptan-3-yl, bicyclo[2.2.1]heptan-4-yl, bicyclo[2.2.1]heptan-4-yl, bicyclo[2.2.1]heptan-5-yl, or bicyclo[2.2.1]heptan-6-yl.

As used herein, "adamantane" (also known as tricyclo[3.3.1.$1^{3,7}$]decane) has a definition known to those skilled in the art. As used herein, "adamantanyl" refers to a monovalent group of adamantane, that is, the group remaining after any hydrogen in adamantane is removed. Representative examples include, but are not limited to, 1-adamantanyl, 2-adamantanyl, 3-adamantanyl, 4-adamantanyl, 5-adamantanyl, 6-adamantanyl, 7-adamantanyl, 8-adamantanyl, 9-adamantanyl, or 10-adamantanyl.

As used herein, "noradamantane" (also known as noradamantane) has a definition known to those skilled in the art, and its structural formula is as follows:

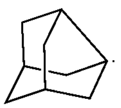

.

As used herein, "noradamantanyl" refers to a monovalent group of noradamantane, that is, the group remaining after any hydrogen in noradamantane is removed. Representative examples include, but are not limited to, 1-noradamantanyl, 2-noradamantanyl, 3-noradamantanyl, 4-noradamantanyl, 5-noradamantanyl, 6-noradamantanyl, 7-noradamantanyl, 8-noradamantanyl or 9-noradamantanyl.

As used herein, "adamantanamine" has the definitions known to those skilled in the art, namely referring to an adamantane having an amino substituent, wherein the amino substituent can replace a hydrogen on a carbon at any position in the adamantane. An example of "adamantanamine" can be adamantan-1-amine (corresponding English chemical name is adamantan-1-amine or Tricyclo[3.3.1.$1^{3,7}$]decan-1-amine; CAS No.: 768-94-5), with the following structural Formula:

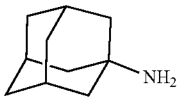

Salts or pharmaceutically acceptable salts, enantiomers, diastereomers, solvates, polymorphs of the compounds of Formula (I) of the present disclosure are also encompassed within the scope of the present invention.

In all embodiments of the present disclosure, the salts or pharmaceutically acceptable salts of the compounds of Formula (I) refer to non-toxic inorganic or organic acid and/or base addition salts. Examples include: sulfate, hydrochloride, citrate, maleate, sulfonate, citrate, lactate, tartrate, fumarate, phosphate, dihydrogenphosphate, pyrophosphate, metaphosphate, oxalate, malonate, benzoate, mandelate, succinate, glycolate, or p-toluenesulfonate, etc.

"Pharmaceutically acceptable carrier" refers to a pharmaceutically acceptable material, such as a filler, stabilizer, dispersant, suspending agent, diluent, excipient, thickener, solvent, or encapsulating material, with which the useful compounds according to the present disclosure are carried or transported into or administered to a patient so that they can perform their intended function. Generally, such constructs are carried or transported from one organ or part of the body to another organ or part of the body. The carrier is compatible with the other ingredients of the formulation, including the compounds useful in the present disclosure, and is not harmful to the patient, and the carrier must be "acceptable". Some examples of materials that can be used as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository wax; oils such as peanut oil, cottonseed oil, safflower oil, sesame oil, olive oil, corn oil and soybean oil; glycols such as propylene glycol; polyols such as glycerol, sorbitol, mannitol, and polyethylene glycol; esters such as ethyl oleate and ethyl laurate; agar; buffers such as magnesium hydroxide and aluminum hydroxide; surfactant phosphate buffer solution; and other common non-toxic compatible substances used in pharmaceutical formulations.

The term "treatment" or "treating" refers to the administration of the compound of Formula (I) or a pharmaceutically acceptable salt thereof according to the present disclosure, or the pharmaceutical composition containing, as an active ingredient, the compound of Formula I or a pharmaceutically acceptable salt thereof, to a subject to mitigate (alleviate) undesirable diseases or conditions, such as the development of a cancer or tumor. The beneficial or desired clinical results of the present disclosure include, but are not limited to: alleviating symptoms, reducing the severity of the disease, stabilizing the state of the disease, slowing down or delaying the progression of the disease, improving or alleviating the condition, and alleviating the disease.

A "therapeutically effective amount" of a compound of the present disclosure depends on the age, sex, and weight of the patient, the patient's current medical condition, and the cancer progression of the patient being treated. Those skilled in the art will be able to determine appropriate dosages based on these and other factors.

It is to be understood that the choice of using one or more active compounds and/or compositions and their dosage depends on the basic situations of the individual (which should generally render the individual situation to achieve the best effect). Dosing and dosing regimens should be within the ability of those skilled in the art, and the appropriate dosage depends on many factors including the knowledge and ability of the physicians, veterinarians or researchers (Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)).

The term "room temperature" used herein refers to the ambient temperature, such as a temperature of 20-30° C.

EXAMPLES

In the following description, numerous specific details are set forth in order to provide a thorough understanding of the present disclosure. The present disclosure may be practiced without some or all of these specific details. In other cases, well-known process operations have not been described in detail in order not to unnecessarily obscure the present disclosure. Although the present disclosure will be described in conjunction with specific embodiments, it should be understood that this is not intended to limit the present disclosure to these embodiments.

The Following Abbreviations are Used Throughout the Specification and Examples:

- Ar Argon
- ACN Acetonitrile
- BnCl benzyl chloride
- Boc tert-butoxycarbonyl
- DCM dichloromethane
- DIEA N,N-diisopropylethylamine
- DIPEA N,N-diisopropylethylamine
- DMF N,N-dimethylformamide
- DMAP N,N-dimethylpyridin-4-amine
- DMSO dimethyl sulfoxide
- equiv equivalent
- ESI electrospray ionization
- HBTU O-benzotriazol-1-yl-N,N,N',N'-tetramethyluronium hexafluorophosphate
- HPLC high performance liquid chromatography
- HRMS high-resolution mass spectrometry
- LAH lithium aluminum hydride
- LC-MS liquid chromatography-mass spectrometry
- LRMS low resolution mass spectrometry
- LC liquid chromatography
- MsCl methylsulfonyl chloride
- MsO methylsulfonyloxy
- MW microwave
- NaAc sodium acetate
- NMP N-methylpyrrolidone
- $^1H$ NMR proton nuclear magnetic resonance spectroscopy
- OMe methoxy
- rt room temperature
- TEA triethylamine
- TFA trifluoroacetate
- THE tetrahydrofuran
- TLC thin layer chromatography
- TMS tetramethylsilane
- TsOH p-toluenesulfonic acid
- TsO—p-toluenesulfonyloxy In the present disclosure, the $^1H$ NMR spectrum was recorded on a Bruker-500 MHz nuclear magnetic resonance instrument, by using, as a solvent, $CD_3OD$ (δ=3.31 ppm) containing 0.1% TMS (as an internal standard); or using, as a solvent, $CDCl_3$ (δ=7.26 ppm) containing 0.1% TMS (as an internal standard); or using, as a solvent, DMSO-$d_6$ (δ=2.50 ppm) containing 0.03% TMS (as an internal standard). HRMS spectrum was recorded on an AB Triple 4600 mass spectrometer, and HPLC purity was measured on a SHIMADZU LC-30AP or Waters 1525 type instrument. Unless otherwise specified, all reactions were performed in the air atmosphere. The reactions were followed by TLC or LC-MS, intermediates were isolated and purified by column chromatography using an ISCO or Biotage, and the designed and synthesized target products were separated and purified by the Waters 2767 preparative HPLC.

Solvents and Reagents are Processed as Follows:

The solvents used in the reaction such as DCM, DMF, anhydrous EtOH, and anhydrous MeOH were purchased from Chinese Sinopharm Group; Preparative grade $CH_3CN$ and deionized water were used in HPLC preparation. Unless otherwise specified, other reaction instruments, separation and purification equipment, reaction substrates, reagents, compounds (such as SIAIS1221097, etc.) and medicines were commercially available and used directly.

"Bornylamine" (also known as (1R,2S,4R)-born-2-ylamine; (1R,2S,4R)-1,7,7-Trimethylbicyclo[2.2.1]heptane-2-amine; CAS No.: 32511-34-5) used in the Examples of the present disclosure has a definition known to those skilled in the art and has the structural Formula as follows:

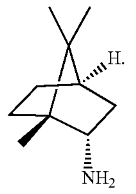

General Synthetic Methods

The compounds described herein and/or pharmaceutically acceptable salts thereof can be synthesized using commercially available raw materials by synthetic techniques known in the art. The pharmaceutically acceptable salts of the compounds described herein can be converted into the free forms of the compounds by techniques known in the art. The synthetic schemes described below illustrate the preparation of most compounds. The starting materials or reagents used in each scheme can be commercially available or prepared by methods known to those skilled in the art.

General Synthesis Method for Preparing Substituted Oxy-Pomalidomide with Carbon Chain Linker:

Scheme 1

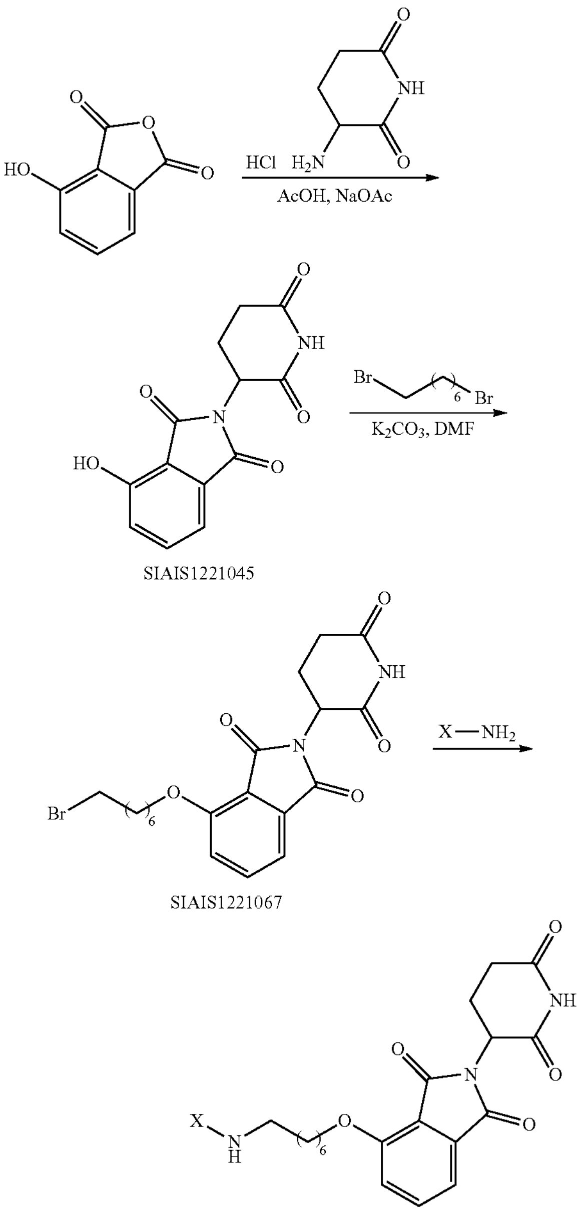

SIAIS1221045

SIAIS1221067

The X—NH— moiety in the product of Scheme 1 corresponds to the corresponding embodiments of the $X_1$ group in the Formula (I) herein.

Step 1: A 100 mL egg-shaped flask was charged with 3-hydroxyphthalic anhydride (984.7 mg, 6 mmol), followed by addition of 3-aminopiperidine-2,6-dione hydrochloride (1086.3 mg, 6.6 mmol), sodium acetate (1476.5 mg, 3 mmol) and acetic acid (15 mL). After the completion of addition, the mixture was reacted in an oil bath at 90° C. overnight. After the reaction was complete as monitored by TCL, the reaction mixture was directly mixed with silica gel powder, and the obtained sample was subjected to ISCO column chromatography (eluent (v/v):dichloromethane/methanol=20:1) for separation. The collected fractions were concentrated and dried under reduced pressure to give the compound SIAIS1221045 (white solid, 920 mg, yield 56%).

Step 2: A 100 mL egg-shaped flask was charged with the intermediate compound SIAIS1221045 (1 mmol, 1 equiv), followed by addition of anhydrous N,N-dimethylformamide (10 mL) and anhydrous potassium carbonate (6.8 mmol, 2 equiv), and then slow addition dropwise of the corresponding brominated substrate (1.5 mmol, 1.5 equiv) with stirring at room temperature. The mixture was reacted at 60° C. overnight. The mixture was filtered, and then subjected to ISCO reverse-phase column chromatography (eluent (v/v): acetonitrile/water=10%-100%) to give the compound SIAIS1221067 (white solid, 170 mg, yield 37%). $^1H$ NMR (500 MHz, DMSO) δ 11.10 (s, 1H), 7.81 (dd, J=8.4, 7.3 Hz, 1H), 7.51 (d, J=8.5 Hz, 1H), 7.44 (d, J=7.2 Hz, 1H), 5.08 (dd, J=12.8, 5.4 Hz, 1H), 4.20 (t, J=6.4 Hz, 2H), 3.53 (t, J=6.7 Hz, 2H), 2.94-2.84 (m, 1H), 2.63-2.57 (m, 1H), 2.55-2.51 (m, 1H), 2.07-1.99 (m, 1H), 1.84-1.73 (m, 4H), 1.50-1.35 (m, 6H). $^{13}C$ NMR (126 MHz, DMSO) δ 173.26, 170.43, 167.33, 165.79, 156.48, 137.50, 133.72, 120.25, 116.69, 115.60, 69.22, 49.21, 35.66, 32.65, 31.44, 28.76, 28.19, 27.92, 25.62, 22.48. HRMS (ESI) m/z: calcd for $C_{20}H_{24}BrN_2O_5^+$ $[M+H]^+$, 451.0863; found, 451.0872.

Step 3: A 15 mL sample vial was charged with the intermediate compound SIAIS1221067 (1 mmol, 1 equiv), followed by addition of amine substrate (X—$NH_2$; 2 mmol, 2 equiv). The mixture was reacted at 40° C. overnight. The mixture was filtered, and then subjected to Waters 2767 preparative HPLC (eluent (v/v):acetonitrile/(water+0.05% HCl)=10%-100%) for separation. The collected fractions were concentrated, and lyophilized by lyophilizer to give the solid of hydrochloride of the target compound.

General Synthesis Method for Preparing Substituted Oxy-Lenalidomide with Carbon Chain Linker:

Scheme 2

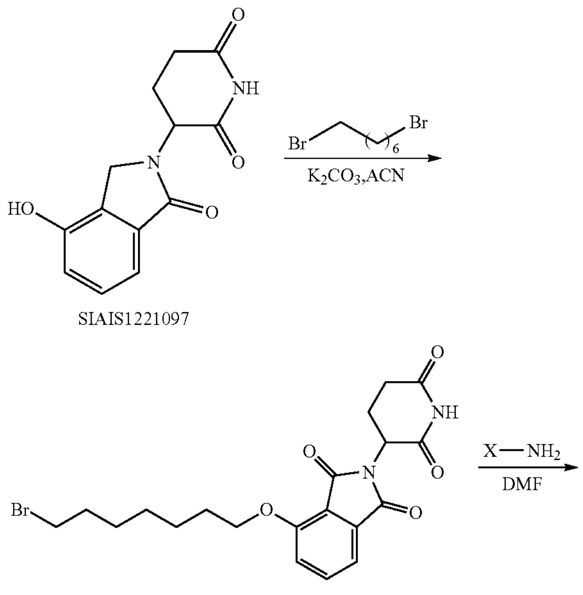

SIAIS1221097

SIAIS1221099

-continued

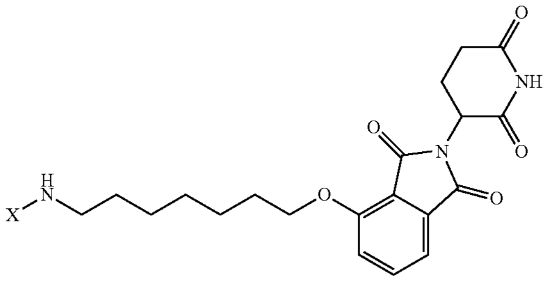

The X—NH— moiety in the product of Scheme 2 corresponds to the corresponding embodiments of the $X_1$ group in the Formula (I) herein.

Step 1: A 100 mL egg-shaped flask was charged with SIAIS1221097 (CAS No.: 1061604-41-8)(2 mmol, 1 equiv), followed by addition of anhydrous potassium carbonate (6 mmol, 3 equiv) and acetonitrile (10 mL), and then slow addition dropwise of 1,7-dibromoheptane (4 mmol, 2 equiv) with stirring at room temperature. After the completion of addition, the mixture was reacted at 50° C. for 12 h. After the reaction was complete, the mixture was poured into ice water, extracted with EA. The organic phase was washed with water and saturated brine, dried over anhydrous sodium sulfate, and rotary evaporated to dryness. To the resulting residue was added a small amount of DMF, and the resulting mixture was subjected to ISCO reverse-phase column chromatography (eluent (v/v):acetonitrile/water=10%-100%) for separation to give the compound SIAIS1221099 (white solid, 323 mg, yield 37%). $^1H$ NMR (500 MHz, DMSO) δ 10.98 (s, 1H), 7.47 (t, J=7.8 Hz, 1H), 7.31 (d, J=7.4 Hz, 1H), 7.23 (d, J=8.2 Hz, 1H), 5.11 (dd, J=13.2, 5.0 Hz, 1H), 4.37 (d, J=17.3 Hz, 1H), 4.23 (d, J=17.3 Hz, 1H), 4.11 (t, J=6.2 Hz, 2H), 3.53 (t, J=6.7 Hz, 2H), 2.96-2.86 (m, 1H), 2.59 (d, J=17.2 Hz, 1H), 2.49-2.41 (m, 1H), 2.03-1.96 (m, 1H), 1.83-1.70 (m, 4H), 1.48-1.32 (m, 6H). $^{13}C$ NMR (126 MHz, DMSO) δ 173.37, 171.52, 168.61, 154.29, 133.67, 130.36, 130.15, 115.38, 114.99, 68.35, 52.09, 45.55, 35.66, 32.65, 31.69, 28.93, 28.27, 27.91, 25.75, 22.87. HRMS (ESI) m/z: calcd for $C_{20}H_{26}BrN_2O_4^+$ $[M+H]^+$, 437.1070; found, 437.1062.

Step 2: A 15 mL sample vial was charged with the intermediate compound SIAIS1221099 (0.04 mmol, 1 equiv), followed by addition of the amine substrate ($X—NH_2$; 0.08 mmol, 2 equiv) and DMF (2 mL). The mixture was reacted at 40° C. overnight. The mixture was filtered, and then subjected to Waters 2767 preparative HPLC (eluent (v/v):acetonitrile/(water+0.05% HCl)=10%-100%) for separation. The collected fractions were concentrated, and lyophilized by lyophilizer to give the solid of hydrochloride of the target compound.

General Synthesis Method for Preparing Substituted Pomalidomide with Carbon Chain Linker:

Scheme 3

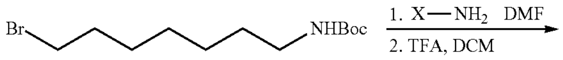

-continued

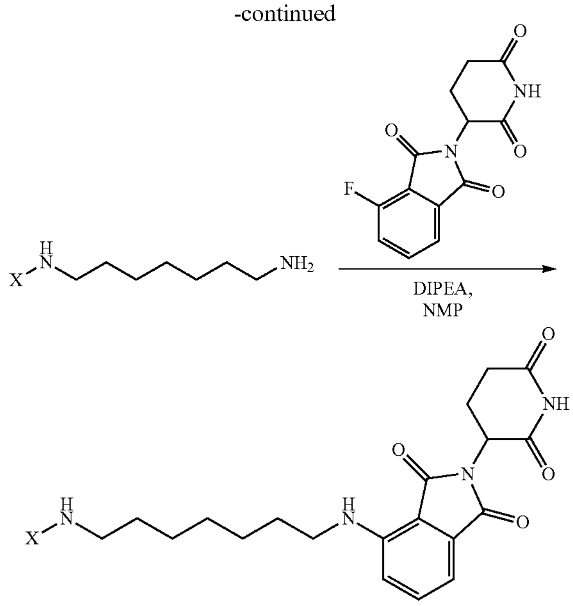

The X—NH— moiety in the intermediates and the final product of Scheme 3 corresponds to the corresponding embodiments of the $X_1$ group in the Formula (I) herein.

Step 1: A 15 mL sample vial was charged with tert-butyl (7-bromoheptyl)carbamate (1 mmol, 1 equiv), followed by addition of the amine substrate ($X—NH_2$; 2 mmol, 2 equiv) and DMF (2 mL). The mixture was reacted at 40° C. overnight. The mixture was filtered, and then subjected to Waters 2767 preparative HPLC (eluent (v/v):acetonitrile/(water+0.05% HCl)=10%-100%) for separation to obtain an intermediate. To the intermediate was added TFA (1 mL) and DCM (3 mL), and the mixture was reacted at room temperature for one hour, and then rotary evaporated to remove the solvent. The resulting residue was treated by addition of a small amount of water and lyophilized to give the intermediate with terminal amino.

Step 2: A 15 mL sample vial was charged with the product from the previous step (0.15 mmol, 1 equiv), followed by addition of 2-(2,6-dioxopiperidin-3-yl)-4-fluoroisoindoline-1,3-dione (0.3 mmol, 2 equiv), DIPEA (0.45 mmol, 3 equiv), and NMP (3 mL). The mixture was reacted at 110° C. for 1 h. The mixture was filtered, and then subjected to Waters 2767 preparative HPLC (eluent (v/v):acetonitrile/(water+0.05% HCl)=10%-100%) for separation. The collected fractions were concentrated, and lyophilized by lyophilizer to give the solid of hydrochloride of the target compound.

General Synthesis Method for Preparing Substituted Lenalidomide with Carbon Chain Linker:

Scheme 4

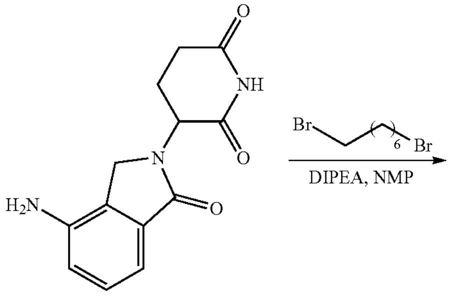

-continued

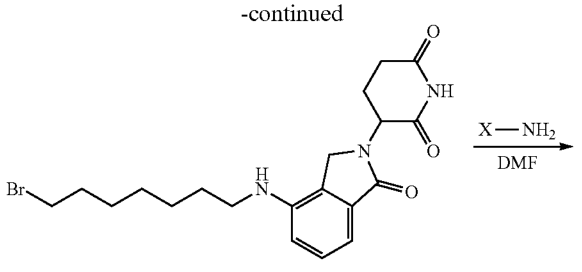

SIAIS1220113

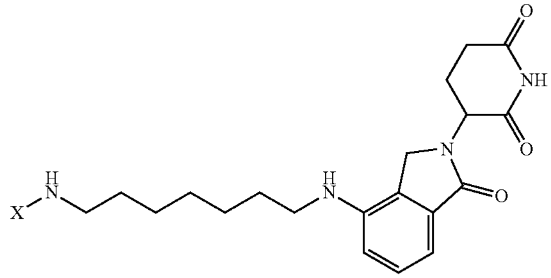

The X—NH— moiety in the final product of Scheme 4 corresponds to the corresponding embodiments of the $X_1$ group in the Formula (I) herein.

Step 1: A 50 mL egg-shaped flask was charged with Lenalidomide (2 mmol, 1 equiv), followed by addition of NMP (6 mL) and DIPEA (6 mmol, 3 equiv), and then slow addition dropwise of the corresponding brominated substrate (6 mmol, 3 equiv) with stirring at room temperature. The mixture was reacted at 100° C. overnight. The mixture was subjected to ISCO reverse phase column chromatography (eluent (v/v):acetonitrile/water=10%-100%) for separation to give the compound SIAIS1220113 (pale yellow solid, 237 mg, yield 27%). $^1$H NMR (500 MHz, DMSO) δ 11.00 (s, 1H), 7.28 (t, J=7.7 Hz, 1H), 6.92 (d, J=6.9 Hz, 1H), 6.74 (d, J=8.0 Hz, 1H), 5.56 (t, J=5.5 Hz, 1H), 5.11 (dd, J=13.3, 5.1 Hz, 1H), 4.23 (d, J=17.2 Hz, 1H), 4.12 (d, J=17.1 Hz, 1H), 3.53 (t, J=6.7 Hz, 2H), 3.11 (dd, J=12.8, 6.8 Hz, 2H), 2.97-2.88 (m, 1H), 2.62 (d, J=17.6 Hz, 1H), 2.35-2.24 (m, 1H), 2.06-2.00 (m, 1H), 1.83-1.76 (m, 2H), 1.62-1.53 (m, 2H), 1.43-1.32 (m, 6H). $^{13}$C NMR (126 MHz, DMSO) δ 173.40, 171.72, 169.41, 144.20, 132.49, 129.70, 126.92, 112.23, 110.41, 51.96, 46.22, 43.16, 35.71, 32.68, 31.71, 28.88, 28.43, 27.98, 26.95, 23.28. HRMS (ESI) m/z: calcd for $C_{20}H_{27}BrN_3O_5^+$ [M+H]$^+$, 436.1230; found, 436.1231.

Step 2: A 15 mL sample vial was charged with the intermediate compound SIAIS1220113 (1 mmol, 1 equiv), followed by addition of amine substrate (X—$NH_2$; 2 mmol, 2 equiv) and DMF (2 mL). The mixture was reacted at 40° C. overnight. The mixture was filtered, and then subjected to Waters 2767 preparative HPLC (eluent (v/v):acetonitrile/(water+0.05% HCl)=10%-100%) for separation. The collected fractions were concentrated, and lyophilized by lyophilizer to give the hydrochloride of the target compound.

General Synthesis Method for Preparing Substituted Alkynyl-Lenalidomide with Carbon Chain Linker:

Scheme 5

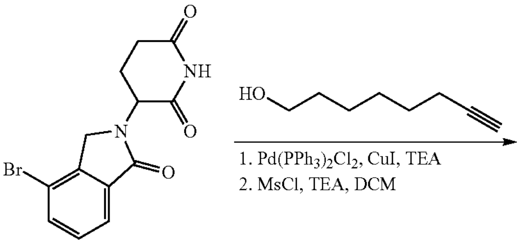

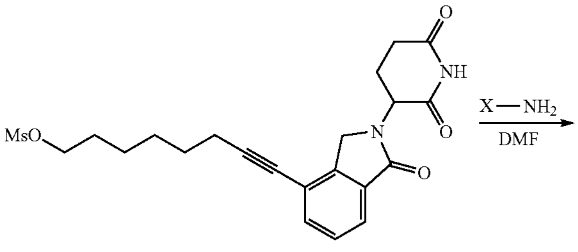

SIAIS268071

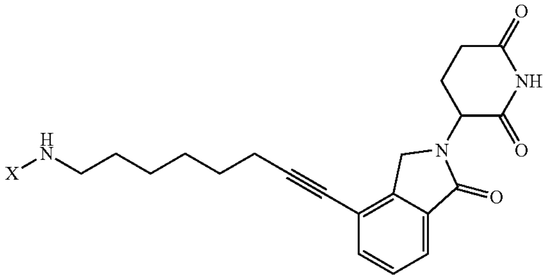

The X—NH— moiety in the final product of Scheme 5 corresponds to the corresponding embodiments of the $X_1$ group in the Formula (I) herein.

Step 1: Argon gas was bubbled through a solution of 3-(4-bromo-1-oxoisoindolin-2-yl)piperidine-2,6-dione (0.50 g, 1.5 mmol) in 5 mL DMF for 5 min, followed by sequentially addition of 7-octyn-1-ol (0.38 g, 3.0 mmol), $Pd(PPh_3)_2Cl_2$ (0.10 g, 0.15 mmol) and CuI (57 mg, 0.30 mmol). After stirring for 5 min, to the mixture was added 2.5 mL of triethylamine. The mixture was then heated to 80° C., and reacted overnight. The resulting mixture was cooled to room temperature, and the reaction was quenched with 50 mL of water. The resulting mixture was extracted with ethyl acetate (3×50 mL). The organic phases were combined, washed with water (2×30 mL) and saturated brine (50 mL), dried over anhydrous $Na_2SO_4$, evaporated under reduced pressure to remove the solvent. The crude product was subjected to Biotage column chromatography (DCM/MeOH=5/1) to give the alcohol intermediate (pale yellow solid, m=0.50 g).

Step 2: To a solution of the intermediate from step 1 in 15 mL of DCM were sequentially added triethylamine (0.44 g, 4.4 mmol) and methylsulfonyl chloride (0.25 g, 2.2 mmol), and the reaction system became clear. The mixture was reacted overnight. The reaction solution was washed with saturated brine, and evaporated under reduced pressure to remove solvent. The resulting residue was subjected to Biotage column chromatography (DCM/MeOH=5/1) to give the compound SIAIS268071 (pale yellow solid, m=0.35 g). $^1$H NMR (500 MHz, DMSO) δ 10.99 (s, 1H), 7.70 (dd, J=7.6, 0.7 Hz, 1H), 7.63 (dd, J=7.6, 0.9 Hz, 1H), 7.51 (dd, J=9.7, 5.5 Hz, 1H), 5.14 (dd, J=13.3, 5.1 Hz, 1H), 4.45 (d, J=17.7 Hz, 1H), 4.31 (d, J=17.6 Hz, 1H), 4.18 (dt, J=6.5, 4.1 Hz, 2H), 2.90 (tt, J=19.0, 5.4 Hz, 1H), 2.60 (d, J=17.6 Hz, 1H), 2.49-2.46 (m, 2H), 2.46-2.40 (m, 1H), 2.05-1.98 (m, 1H), 1.68 (dd, J=14.3, 6.8 Hz, 2H), 1.58 (dd, J=14.7, 7.2 Hz, 2H), 1.48-1.38 (m, 4H).

Step 3: A 15 mL sample vial was charged with the intermediate compound SIAIS268071 (0.1 mmol, 1 equiv), followed by addition of amine substrate (X—$NH_2$; 0.1 mmol, 2 equiv), DIPEA (0.15 mmol, 3 equiv) and NMP (2 mL). The mixture was reacted at 50° C. overnight. The mixture was filtered, and then subjected to Waters 2767 preparative HPLC (eluent (v/v):acetonitrile/(water+0.05% HCl)=10%-100%) for separation. The collected fractions were concentrated, and lyophilized by lyophilizer to give the solid of hydrochloride of the target compound.

General Synthesis Method for Preparing Substituted Lenalidomide with Alkylene Chain Linker:

Scheme 6

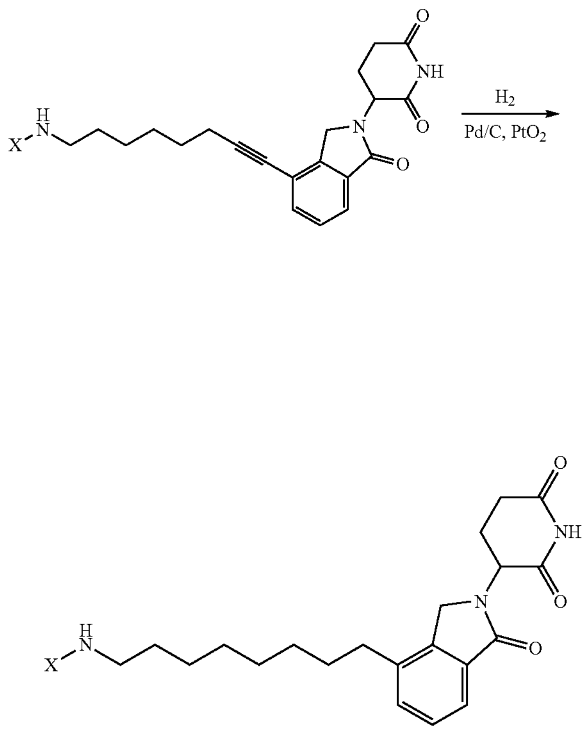

The X—NH— moiety in the final product of Scheme 6 corresponds to the corresponding embodiments of the $X_1$ group in the Formula (I) herein.

A 50 mL single necked flask was charged with the corresponding alkynyl precursor compound (1 equiv), then palladium on carbon, platinum dioxide and methanol (5 mL), followed by evacuation and refilling with hydrogen three times with a hydrogen balloon. The mixture was stirred and reacted at room temperature overnight. The mixture was filtered, and then subjected to Waters 2767 preparative HPLC (eluent (v/v):acetonitrile/(water+0.05% HCl)=10%-100%) for separation. The collected fractions were concentrated, and lyophilized by lyophilizer to give the solid of hydrochloride of the reduced target compound.

General Synthesis Method for Preparing Substituted Pomalidomide with Carbon Chain Linker:

Scheme 7

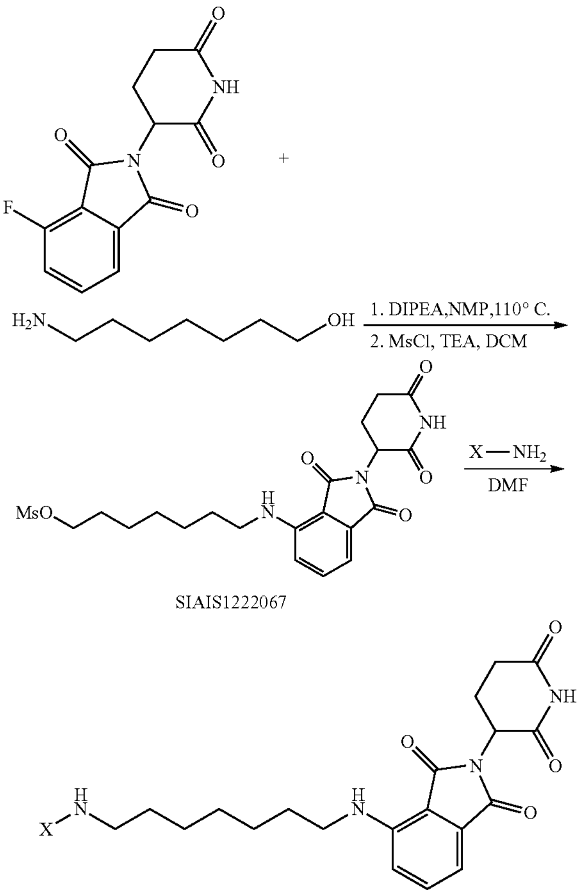

SIAIS1222067

The X—NH— moiety in the intermediate and the final product of Scheme 7 corresponds to the corresponding embodiments of the $X_1$ group in the Formula (I) herein.

Step 1: A 15 mL sample vial was charged with 7-amino-heptan-1-ol (2.4 mmol, 1.2 equiv), followed by addition of 2-(2,6-dioxopiperidin-3-yl)-4-fluoroisoindoline-1,3-dione (2.0 mmol, 1 equiv), DIPEA (4.0 mmol, 2 equiv), and NMP (5 mL). The mixture was reacted at 110° C. for 1 h. The mixture was filtered, and then subjected to ISCO reversed-phase column chromatography (ISCO CombiFlash EZ Prep preparative HPLC, USA)(eluent (v/v):acetonitrile/water=10%-100%) for separation, to give the intermediate with terminal hydroxy.

Step 2: To a solution of the intermediate from step 1 in 15 mL of DCM were sequentially added triethylamine (2.0 mmol, 1 equiv) and methylsulfonyl chloride (2.0 mmol, 1 equiv), and the reaction system became clear. The mixture was reacted overnight. The mixture was evaporated under reduced pressure to remove solvent, and the resulting residue was subjected to ISCO reverse phase column chromatography (eluent (v/v):acetonitrile/water=10%-100%) for separation to give the compound SIAIS1222067 (a bright yellow solid, 340 mg, 37% in total in two steps). $^1H$ NMR (500 MHz, DMSO) δ 11.10 (s, 1H), 7.58 (dd, J=8.5, 7.2 Hz, 1H), 7.09 (d, J=8.6 Hz, 1H), 7.02 (d, J=7.0 Hz, 1H), 6.53 (t, J=5.3 Hz, 1H), 5.05 (dd, J=12.7, 5.4 Hz, 1H), 4.19 (t, J=6.5

Hz, 2H), 3.30 (dd, J=12.3, 6.6 Hz, 2H), 3.15 (s, 3H), 2.94-2.84 (m, 1H), 2.62-2.51 (m, 2H), 2.07-2.00 (m, 1H), 1.70-1.62 (m, 2H), 1.61-1.54 (m, 2H), 1.35 (s, 6H). $^{13}$C NMR (126 MHz, DMSO) δ 173.29, 170.58, 169.43, 167.78, 146.90, 136.75, 132.67, 117.65, 110.85, 109.49, 70.90, 49.02, 42.26, 37.01, 31.46, 29.04, 28.92, 28.62, 26.63, 25.33, 22.63, 1.63.

Step 3: A 15 mL sample vial was charged with the intermediate compound SIAIS1222067 (0.1 mmol, 1 equiv), followed by addition of amine substrate (X—$NH_2$; 0.1 mmol, 2 equiv), DIPEA (0.15 mmol, 3 equiv) and NMP (2 mL). The mixture was reacted at 50° C. overnight. The mixture was filtered, and then subjected to Waters 2767 preparative HPLC (eluent (v/v):acetonitrile/(water+0.05% HCl)=10%-100%) for separation. The collected fractions were concentrated, and lyophilized by lyophilizer to give the solid of hydrochloride of the target compound.

Depending on target compounds, each of the above-mentioned schemes and their reaction substrates, reaction conditions (comprising amounts of reactants, reaction temperature, time etc.), work up procedures etc.) can be appropriately modified and adjusted by techniques and methods well known to those skilled in the art to obtain the desired target compound. The obtained target compounds can be further modified e.g., by substituents and the like, to obtain other target compounds according to methods well known to those skilled in the art.

Example 1: preparation of hydrochloride of 4-((7-((adamantan-1-yl)amino)heptyl)oxy)-2-(2,6-dioxopiperidin-3-yl)isoindoline-1,3-dione (SIAIS1221077)

Referring to the preparation method of Scheme 1, the compound SIAIS1221077 was prepared under appropriate conditions that will be recognized by one skilled in the art, except that the amine substrate employed in the last step was 1-adamantanamine. The hydrochloride of compound SIAIS1221077 was obtained (white solid, 7 mg, yield 27%). $^1$H NMR (500 MHz, DMSO) δ 11.11 (s, 1H), 8.52 (s, 2H), 7.82 (t, J=7.9 Hz, 1H), 7.52 (d, J=8.5 Hz, 1H), 7.45 (d, J=7.2 Hz, 1H), 5.08 (dd, J=12.7, 5.3 Hz, 1H), 4.21 (t, J=6.2 Hz, 2H), 2.92-2.80 (m, 3H), 2.59 (d, J=18.0 Hz, 1H), 2.11 (s, 3H), 2.06-2.00 (m, 1H), 1.84 (s, 6H), 1.80-1.74 (m, 2H), 1.69-1.55 (m, 8H), 1.47 (s, 2H), 1.37 (s, 4H), 1.23 (s, 1H). HRMS (ESI) m/z: calcd for $C_{30}H_{40}N_3O_5^+$ [M+H]$^+$, 522.2962; found, 522.2946.

Example 2: preparation of hydrochloride of 5-((7-((adamantan-1-yl)amino)heptyl)oxy)-2-(2,6-dioxopiperidin-3-yl)isoindoline-1,3-dione (SIAIS332042)

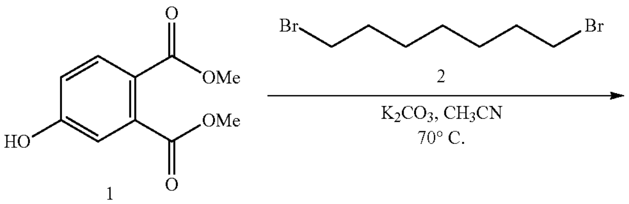

1

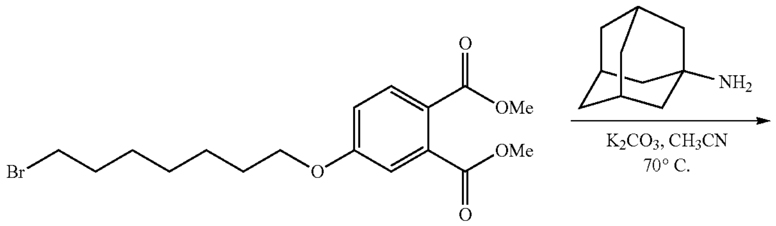

3

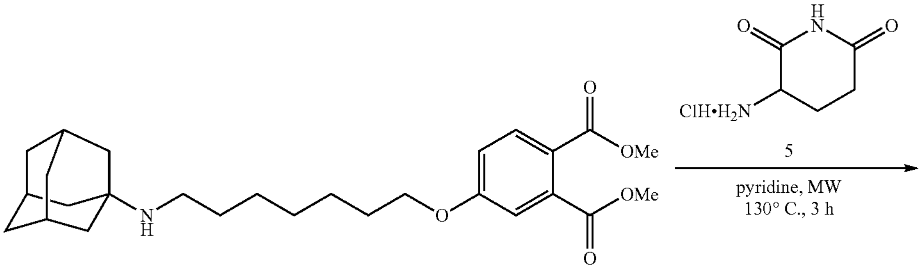

SIAIS332041

-continued

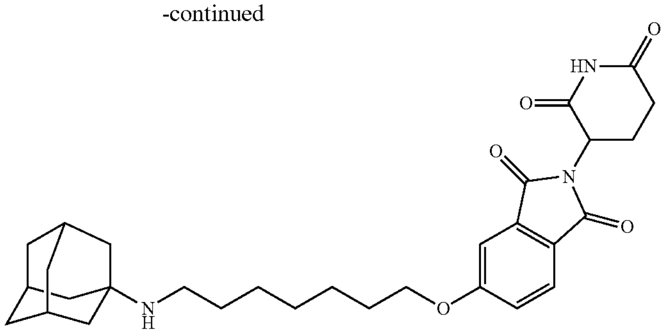

SIAIS332042

Step 1: To a solution of compound 1 (500 mg, 2.38 mmol) and compound 2 (736 mg, 2.85 mmol) dissolved in acetonitrile (10 mL) was added potassium carbonate (657 mg, 4.76 mmol) at room temperature. The mixture was warmed to 70° C. and stirred for 18 hours. The mixture was filtered, and the filtrate was concentrated under reduced pressure. The resulting residue was subjected to Biotage column chromatography (dichloromethane:methanol=10:1) for separation to give the compound 3 (400 mg, yield 43%) as a colorless oil.

Step 2: To a solution of the compound 3 (400 mg, 1.03 mmol) and 1-adamantanamine (234 mg, 1.55 mmol) dissolved in acetonitrile (6 mL) was added potassium carbonate (284 mg, 2.06 mmol) at room temperature. The mixture was warmed to 70° C. and stirred for 18 hours. The mixture was filtered, and the filtrate was concentrated under reduced pressure. The resulting residue was subjected to Biotage column chromatography (dichloromethane:methanol=10:1) for separation to give the compound SIAIS332041 (260 mg, yield 55%) as a colorless oil.

Step 3: To a solution of the compound SIAIS332041 (50 mg, 0.11 mmol) dissolved in pyridine (1 mL) was added the compound 5 (165 mg, 1.00 mmol). The mixture was stirred in microwave at 130° C. for 3 h, and concentrated under reduced pressure. The resulting residue was subjected to Waters 2767 preparative HPLC (eluent (v/v):acetonitrile/(water+0.05% HCl)=10%-100%) for separation to give the hydrochloride of the final compound SIAIS332042 (white solid, 11 mg). $^1$H NMR (500 MHz, MeOD) δ 7.80 (d, J=10.0 Hz, 1H), 7.38 (s, 1H), 7.30 (d, J=10.0 Hz, 1H), 5.15-5.06 (m, 1H), 4.17 (t, J=10.0 Hz, 2H), 2.96 (t, J=10.0 Hz, 2H), 2.92-2.81 (m, 1H), 2.80-2.65 (m, 2H), 2.21 (s, 3H), 2.16-2.08 (m, 1H), 1.90 (s, 6H), 1.86 (t, J=10.0 Hz, 2H), 1.79-1.83 (m, 3H), 1.76-1.64 (m, 5H), 1.52-1.59 (m, 2H), 1.48 (s, 4H). HRMS (ESI) m/z: calcd for $C_{30}H_{40}N_3O_5^+$ [M+H]$^+$, 522.2962; found, 522.3018.

Example 3: Preparation of hydrochloride of 3-(4-((7-((adamantan-1-yl)amino)heptyl)oxy)-1-oxoisoindolin-2-yl)piperidine-2,6-dione (SIAIS1221111)

Referring to the preparation method of Scheme 2, the compound SIAIS1221111 was prepared under appropriate conditions that will be recognized by one skilled in the art, except that the amine substrate employed in the last step was 1-adamantanamine. The hydrochloride of compound SIAIS1221111 was obtained (white solid, 7 mg, yield 35%). $^1$H NMR (500 MHz, DMSO) δ 10.98 (s, 1H), 8.53 (s, 2H), 7.48 (t, J=7.7 Hz, 1H), 7.31 (d, J=7.5 Hz, 1H), 7.24 (d, J=8.1 Hz, 1H), 5.12 (dd, J=13.3, 5.0 Hz, 1H), 4.37 (d, J=17.3 Hz, 1H), 4.22 (d, J=17.3 Hz, 1H), 4.12 (t, J=6.2 Hz, 2H), 2.96-2.87 (m, 1H), 2.82 (s, 2H), 2.58 (d, J=17.4 Hz, 1H), 2.47-2.41 (m, 1H), 2.11 (s, 3H), 2.02-1.96 (m, 1H), 1.84 (s, 6H), 1.78-1.72 (m, 2H), 1.68-1.55 (m, 8H), 1.44 (s, 2H), 1.36 (s, 4H). HRMS (ESI) m/z: calcd for $C_{30}H_{42}N_3O_4^+$ [M+H]$^+$, 508.3170; found, 508.3170.

Example 4: Preparation of hydrochloride of 3-(1-oxo-4-((7-(spiro[3.3]heptan-2-ylamino)heptyl)oxy)isoindolin-2-yl)piperidine-2,6-dione (SIAIS1224013)

Referring to the preparation method of Scheme 2, the compound SIAIS1224013 was prepared under appropriate conditions that will be recognized by one skilled in the art, except that the amine substrate employed was spiro[3.3]heptan-2-amine hydrochloride. The hydrochloride of compound SIAIS1224013 was obtained (white solid, 10 mg, yield 36%). $^1$H NMR (500 MHz, DMSO) δ 10.98 (s, 1H), 8.74 (s, 2H), 7.48 (t, J=7.6 Hz, 1H), 7.31 (d, J=6.3 Hz, 1H), 7.24 (d, J=8.1 Hz, 1H), 5.12 (dd, J=13.3, 5.0 Hz, 1H), 4.36 (d, J=17.3 Hz, 1H), 4.21 (d, J=17.2 Hz, 1H), 4.12 (s, 2H), 3.50 (s, 1H), 2.97-2.87 (m, 1H), 2.71 (s, 2H), 2.58 (d, J=17.6 Hz, 1H), 2.48-2.39 (m, 1H), 2.26 (t, J=8.9 Hz, 2H), 2.10 (t, J=9.4 Hz, 2H), 2.01 (t, J=6.4 Hz, 3H), 1.92 (t, J=7.0 Hz, 2H), 1.82-1.71 (m, 4H), 1.55 (s, 2H), 1.43 (s, 2H), 1.33 (s, 4H). HRMS (ESI) m/z: calcd for $C_{27}H_{38}N_3O_4S^+$ [M+H]$^+$, 468.2857; found, 468.2855.

Example 5: Preparation of hydrochloride of 3-(4-((5-((adamantan-1-yl)amino)pentyl)oxy)-1-oxoisoindolin-2-yl)piperidine-2,6-dione (SIAIS1224009)

Referring to the preparation method of Scheme 2, the compound SIAIS1224009 was prepared under appropriate conditions that will be recognized by one skilled in the art, except that the brominated substrate used was 1,5-dibromopentane, and the amine substrate used was 1-adamantanamine. The hydrochloride of compound SIAIS1224009 was obtained (white solid, 18.3 mg, yield 36%). $^1$H NMR (500 MHz, DMSO) δ 10.98 (s, 1H), 8.57 (s, 2H), 7.49 (t, J=7.4 Hz, 1H), 7.32 (d, J=7.1 Hz, 1H), 7.25 (d, J=7.9 Hz, 1H), 5.12 (dd, J=13.2, 3.9 Hz, 1H), 4.39 (d, J=17.4 Hz, 1H), 4.23 (d, J=17.3 Hz, 1H), 4.13 (t, J=5.3 Hz, 2H), 2.97-2.89 (m, 1H), 2.85 (s, 2H), 2.59 (d, J=17.8 Hz, 1H), 2.47-2.39 (m, 1H), 2.11 (s, 3H), 2.03-1.97 (m, 1H), 1.84 (s, 6H), 1.81-1.76 (m, 2H), 1.66 (d, J=13.1 Hz, 5H), 1.58 (d, J=12.0 Hz, 3H), 1.55-1.48 (m, 2H). HRMS (ESI) m/z: calcd for $C_{28}H_{38}N_3O_4^+$ [M+H]$^+$, 480.2857; found, 480.2855.

Example 6: Preparation of hydrochloride of 3-(4-((6-((adamantan-1-yl)amino)hexyl)oxy)-1-oxoisoindolin-2-yl)piperidine-2,6-dione (SIAIS1222163)

Referring to the preparation method of Scheme 2, the compound SIAIS1222163 was prepared under appropriate conditions that will be recognized by one skilled in the art, except that the brominated substrate used was 1,6-dibromohexane, and the amine substrate used was 1-adamantanamine. The hydrochloride of compound SIAIS1222163 was obtained (pale yellow solid, 12 mg, yield 49%). $^1$H NMR (500 MHz, DMSO) δ 10.99 (d, J=7.6 Hz, 1H), 8.66 (s, 2H), 7.50 (d, J=7.7 Hz, 1H), 7.33 (s, 1H), 7.26 (s, 1H), 5.13 (s, 1H), 4.43-4.33 (m, 1H), 4.28-4.20 (m, 1H), 4.14 (s, 2H), 2.92 (s, 1H), 2.84 (s, 2H), 2.65-2.56 (m, 2H), 2.12 (s, 3H), 2.01 (s, 1H), 1.87 (d, J=6.5 Hz, 6H), 1.76 (s, 2H), 1.71-1.55 (m, 8H), 1.53-1.38 (m, 4H). HRMS (ESI) m/z: calcd for $C_{29}H_{40}N_3O_4^+$ [M+H]$^+$, 494.3013; found, 494.3016.

Example 7: Preparation of hydrochloride of 3-(4-((6-(((adamantan-1-yl)methyl)amino)hexyl)oxy)-1-oxoisoindolin-2-yl)piperidine-2,6-dione (SIAIS1222165)

Referring to the preparation method of Scheme 2, the compound SIAIS1222165 was prepared under appropriate conditions that will be recognized by one skilled in the art, except that the brominated substrate used was 1,6-dibromohexane, and the amine substrate used was (adamantan-1-yl) methanamine (CAS No.: 17768-41-1). The hydrochloride of compound SIAIS1222165 was obtained (pale yellow solid, 8.5 mg, yield 49%). $^1$H NMR (500 MHz, DMSO) δ 10.99 (d, J=8.7 Hz, 1H), 8.36 (s, 2H), 7.49 (s, 1H), 7.32 (s, 1H), 7.26 (s, 1H), 5.13 (s, 1H), 4.43-4.34 (m, 1H), 4.28-4.19 (m, 1H), 4.14 (s, 2H), 3.54-3.40 (m, 2H), 3.00-2.82 (m, 3H), 2.70-2.55 (m, 4H), 1.98 (s, 4H), 1.81-1.65 (m, 6H), 1.62-1.54 (m, 8H), 1.47 (s, 2H), 1.37 (s, 2H). HRMS (ESI) m/z: calcd for $C_{30}H_{42}N_3O_4^+$ [M+H]$^+$, 508.3170; found, 508.3150.

Example 8: Preparation of hydrochloride of 3-(4-((8-((adamantan-1-yl)amino)octyl)oxy)-1-oxoisoindolin-2-yl)piperidine-2,6-dione (SIAIS1222167)

Referring to the preparation method of Scheme 2, the compound SIAIS1222167 was prepared under appropriate conditions that will be recognized by one skilled in the art, except that the brominated substrate used was 1,8-dibromooctane, and the amine substrate used was 1-adamantanamine. The hydrochloride of compound SIAIS1222167 was obtained (pale yellow solid, 12.4 mg, yield 48%). $^1$H NMR (500 MHz, DMSO) δ 10.97 (s, 1H), 8.61 (s, 2H), 7.48 (t, J=7.5 Hz, 1H), 7.30 (d, J=7.4 Hz, 1H), 7.24 (d, J=7.9 Hz, 1H), 5.11 (d, J=10.7 Hz, 1H), 4.37 (d, J=17.4 Hz, 1H), 4.22 (d, J=17.1 Hz, 1H), 4.12 (s, 2H), 2.96-2.86 (m, 1H), 2.84-2.76 (m, 2H), 2.58 (d, J=17.5 Hz, 1H), 2.48-2.40 (m, 1H), 2.11 (s, 3H), 2.02-1.95 (m, 1H), 1.85 (s, 6H), 1.78-1.70 (m, 2H), 1.68-1.55 (m, 8H), 1.44 (s, 2H), 1.32 (s, 6H). HRMS (ESI) m/z: calcd for $C_{31}H_{44}N_3O_4^+$ [M+H]$^+$, 522.3326; found, 522.3326.

Example 9: Preparation of hydrochloride of 3-(4-((7-((adamantan-1-yl)(methyl)amino)heptyl)oxy)-1-oxoisoindolin-2-yl)piperidine-2,6-dione (SIAIS1222181)

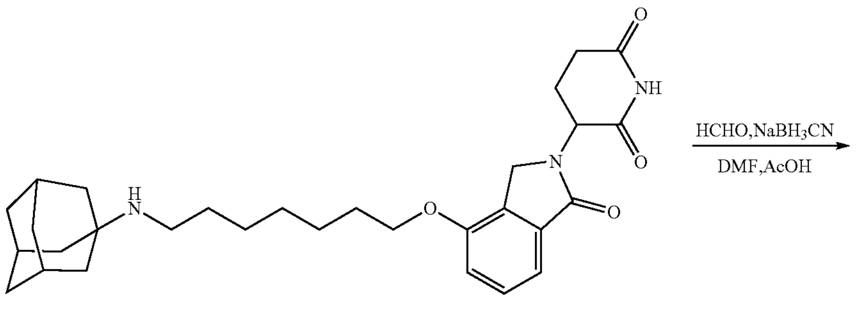

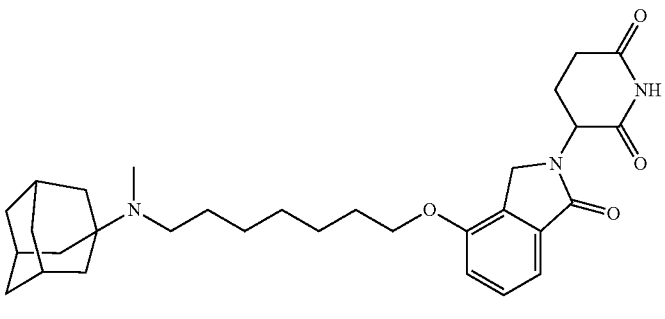

A 15 mL sample vial was charged with the intermediate compound SIAIS1221111 (1 mmol, 1 equiv), followed by addition of formaldehyde (2 mmol, 2 equiv), $NaBH_3CN$ (2 mmol, 2 equiv), DMF (2 mL) and a drop of acetic acid. The mixture was reacted at room temperature overnight. The mixture was filtered, and then subjected to preparative HPLC (eluent (v/v):acetonitrile/(water+0.05% HCl)=10%-100%) for separation to give the hydrochloride of the compound SIAIS1222181 (white solid, 12.3 mg, yield 61%). $^1$H NMR (500 MHz, DMSO) δ 10.99 (d, J=7.6 Hz, 1H), 10.16 (s, 1H), 7.52-7.46 (m, 1H), 7.33-29 (m, 1H), 7.27-7.22 (m, 1H), 5.12 (s, 1H), 4.38 (s, 1H), 4.28-4.20 (m, 1H), 4.12 (s, 2H), 3.32-3.23 (m, 1H), 2.92 (s, 1H), 2.72-2.65 (m, 1H), 2.60 (s, 5H), 2.14 (s, 3H), 2.00 (s, 4H), 1.96-1.90 (m, 3H), 1.77 (s, 2H), 1.62 (s, 8H), 1.50-135 (m, 6H). HRMS (ESI) m/z: calcd for $C_{31}H_{44}N_3O_4^+$ [M+H]$^+$, 522.3326; found, 522.3328.

Example 10: Preparation of hydrochloride of 4-((7-((adamantan-1-yl)amino)heptyl)amino)-2-(2,6-dioxopiperidin-3-yl)isoindoline-1,3-dione (SIAIS1221053)

Referring to the preparation method of Scheme 3, the compound SIAIS1221053 was prepared under appropriate conditions that will be recognized by one skilled in the art, except that the amine substrate used was 1-adamantanamine. The hydrochloride of compound SIAIS1221053 was obtained (bright yellow solid, 4 mg, yield 6%). $^1$H NMR (500 MHz, DMSO) δ 11.10 (s, 1H), 8.38 (s, 2H), 7.59 (t, J=7.8 Hz, 1H), 7.10 (d, J=8.7 Hz, 1H), 7.03 (d, J=7.0 Hz, 1H), 6.53 (s, 1H), 5.05 (dd, J=12.9, 5.2 Hz, 1H), 2.93-2.80 (m, 3H), 2.70 (s, 1H), 2.59 (d, J=18.5 Hz, 1H), 2.11 (s, 3H), 2.05-2.00 (m, 1H), 1.83 (s, 6H), 1.66 (d, J=12.0 Hz, 4H), 1.59 (d, J=10.5 Hz, 8H), 1.34 (s, 6H). HRMS (ESI) m/z: calcd for $C_{30}H_{41}N_4O_4^+$ [M+H]$^+$, 521.3122; found, 521.3122.

Example 11: Preparation of hydrochloride of 4-((6-(((adamantan-1-yl)methyl)amino)hexyl)amino)-2-(2,6-dioxopiperidin-3-yl)isoindoline-1,3-dione (SIAIS1222037)

Referring to the preparation method of Scheme 3, the compound SIAIS1222037 was prepared under appropriate conditions that will be recognized by one skilled in the art, except that the brominated substrate used was tert-butyl (6-bromohexyl)carbamate, and the amine substrate used was (adamantan-1-yl)methanamine. The hydrochloride of compound SIAIS1222037 was obtained (yellow solid, 16.6 mg, yield 12%). $^1$H NMR (500 MHz, DMSO) δ 11.10 (s, 1H), 8.05 (s, 2H), 7.59 (t, J=7.4 Hz, 1H), 7.11 (d, J=8.6 Hz, 1H), 7.04 (d, J=6.9 Hz, 1H), 6.53 (s, 1H), 5.05 (dd, J=12.6, 4.9 Hz, 1H), 3.31 (d, J=6.5 Hz, 4H), 2.94-2.81 (m, 3H), 2.66-2.57 (m, 3H), 2.06-2.00 (m, 1H), 1.97 (s, 3H), 1.67 (t, J=12.1 Hz, 4H), 1.60 (d, J=11.0 Hz, 5H), 1.55 (s, 6H), 1.35 (s, 4H). HRMS (ESI) m/z: calcd for $C_{30}H_{41}N_4O_4^+$ [M+H]$^+$, 521.3122; found, 521.3124.

Example 12: Preparation of hydrochloride of 4-((6-((adamantan-1-yl)amino)hexyl)amino)-2-(2,6-dioxopiperidin-3-yl)isoindoline-1,3-dione (SIAIS1222093)

Referring to the preparation method of Scheme 3, the compound SIAIS1222093 was prepared under appropriate conditions that will be recognized by one skilled in the art, except that the brominated substrate used was tert-butyl (6-bromohexyl)carbamate, and the amine substrate used was 1-adamantanamine. The hydrochloride of compound SIAIS1222093 was obtained (yellow solid, 12 mg, yield 47%). $^1$H NMR (500 MHz, DMSO) δ 11.10 (s, 1H), 8.42 (s, 2H), 7.59 (t, J=7.7 Hz, 1H), 7.11 (d, J=8.5 Hz, 1H), 7.04 (d, J=7.0 Hz, 1H), 6.54 (s, 1H), 5.05 (dd, J=12.7, 4.8 Hz, 1H), 3.32 (s, 3H), 2.94-2.78 (m, 3H), 2.59 (d, J=17.2 Hz, 1H), 2.11 (s, 3H), 2.06-2.00 (m, 1H), 1.83 (s, 6H), 1.70-1.55 (m, 10H), 1.38 (s, 4H). HRMS (ESI) m/z: calcd for $C_{29}H_{39}N_4O_4^+$ [M+H]$^+$, 507.2966; found, 507.2969.

Example 13: Preparation of hydrochloride of 4-((5-((adamantan-1-yl)amino)pentyl)amino)-2-(2,6-dioxopiperidin-3-yl)isoindoline-1,3-dione (SIAIS1222095)

Referring to the preparation method of Scheme 3, the compound SIAIS1222095 was prepared under appropriate conditions that will be recognized by one skilled in the art, except that the brominated substrate used was tert-butyl (5-bromopentyl)carbamate, and the amine substrate used was 1-adamantanamine. The hydrochloride of compound SIAIS1222095 was obtained (yellow solid, 15.4 mg, yield 63%). $^1$H NMR (500 MHz, DMSO) δ 11.11 (s, 1H), 8.39 (s, 2H), 7.60 (t, J=7.6 Hz, 1H), 7.12 (d, J=9.5 Hz, 1H), 7.04 (d, J=7.2 Hz, 1H), 6.57 (t, J=6.8 Hz, 1H), 5.10-5.02 (m, 1H), 3.34-3.30 (m, 2H), 2.94-2.81 (m, 3H), 2.60 (d, J=17.8 Hz, 2H), 2.12 (s, 3H), 2.07-2.00 (m, 1H), 1.83 (s, 6H), 1.70-1.57 (m, 10H), 1.47-1.39 (m, 2H). HRMS (ESI) m/z: calcd for $C_{28}H_{37}N_4O_4^+$ [M+H]$^+$, 493.2809; found, 593.2803.

Example 14: Preparation of hydrochloride of 4-((6-((1-(adamantan-1-yl)ethyl)amino)hexyl)amino)-2-(2,6-dioxopiperidin-3-yl)isoindoline-1,3-dione (SIAIS1222191)

Referring to the preparation method of Scheme 3, the compound SIAIS1222191 was prepared under appropriate conditions that will be recognized by one skilled in the art, except that the brominated substrate used was tert-butyl (6-bromohexyl)carbamate, and the amine substrate used was 1-(adamantan-1-yl)ethan-1-amine hydrochloride (CAS No.: 1501-84-4). The hydrochloride of compound SIAIS1222191 was obtained (yellow solid, 14 mg, yield 58%). $^1$H NMR (500 MHz, DMSO) δ 11.10 (s, 1H), 8.42 (s, 1H), 7.59 (t, J=7.7 Hz, 1H), 7.42 (s, 1H), 7.11 (d, J=8.6 Hz, 1H), 7.03 (d, J=6.6 Hz, 1H), 6.54 (s, 1H), 5.05 (dd, J=12.6, 4.8 Hz, 1H), 3.30 (s, 1H), 3.00-2.82 (m, 3H), 2.73 (s, 1H), 2.59 (d, J=17.5 Hz, 1H), 2.55-2.48 (m, 1H), 2.06-2.01 (m, 1H), 1.98 (s, 3H), 1.78-1.53 (m, 14H), 1.49 (d, J=11.8 Hz, 3H), 1.37 (s, 4H), 1.12 (d, J=6.4 Hz, 3H). HRMS (ESI) m/z: calcd for $C_{31}H_{43}N_4O_4^+$ [M+H]$^+$, 535.3279; found, 535.3275.

Example 15: Preparation of hydrochloride of 4-((7-(adamantan-1-yl)ethyl)amino)heptyl)amino)-2-(2,6-dioxopiperidin-3-yl)isoindoline-1,3-dione (SIAIS1222193)

Referring to the preparation method of Scheme 3, the compound SIAIS1222193 was prepared under appropriate conditions that will be recognized by one skilled in the art, except that the amine substrate used was 1-(adamantan-1-yl)ethan-1-amine hydrochloride. The hydrochloride of compound SIAIS1222193 was obtained (yellow solid, 10 mg, yield 36%). $^1$H NMR (500 MHz, DMSO) δ 11.10 (s, 1H), 8.41 (s, 1H), 7.59 (t, J=7.8 Hz, 1H), 7.42 (s, 1H), 7.10 (d, J=8.3 Hz, 1H), 7.03 (d, J=7.0 Hz, 1H), 6.53 (s, 1H), 5.05 (dd, J=12.1, 4.2 Hz, 1H), 3.00-2.84 (m, 3H), 2.76-2.68 (m, 1H), 2.62-2.54 (m, 3H), 2.03 (d, J=12.7 Hz, 1H), 1.98 (s, 3H), 1.75-1.54 (m, 14H), 1.49 (d, J=11.5 Hz, 3H), 1.35 (s, 6H), 1.12 (d, J=6.6 Hz, 3H). HRMS (ESI) m/z: calcd for $C_{32}H_{45}N_4O_4^+$ [M+H]$^+$, 549.3435; found, 549.3434.

Example 16: Preparation of hydrochloride of 2-(2,6-dioxopiperidin-3-yl)-4-((7-(spiro[3.3]heptan-2-ylamino)heptyl)amino)isoindoline-1,3-dione (SIAIS1222189)

Referring to the preparation method of Scheme 3, the compound SIAIS1222189 was prepared under appropriate conditions that will be recognized by one skilled in the art, except that the amine substrate used was spiro[3.3]heptan-2-amine hydrochloride. The hydrochloride of compound SIAIS1222189 was obtained (yellow solid, 14 mg, yield 58%). $^1$H NMR (500 MHz, DMSO) δ 11.10 (s, 1H), 8.97 (s, 2H), 7.59 (t, J=7.7 Hz, 1H), 7.10 (d, J=8.6 Hz, 1H), 7.03 (d, J=7.1 Hz, 1H), 6.53 (s, 1H), 5.05 (dd, J=12.7, 5.2 Hz, 1H), 3.50-3.46 (m, 1H), 3.30 (t, J=6.5 Hz, 2H), 2.93-2.84 (m, 1H), 2.69 (s, 2H), 2.59 (d, J=18.7 Hz, 1H), 2.55-2.48 (m, 1H), 2.25 (t, J=8.8 Hz, 2H), 2.14 (t, J=9.7 Hz, 2H), 2.00 (t, J=7.3 Hz, 3H), 1.92 (t, J=7.3 Hz, 2H), 1.82-1.74 (m, 2H), 1.57 (d, J=6.5 Hz, 4H), 1.32 (s, 6H). HRMS (ESI) m/z: calcd for $C_{27}H_{37}N_4O_4^+$ [M+H]$^+$, 481.2809; found, 481.2804.

Example 17: Preparation of hydrochloride of 4-((7-(cyclohexylamino)heptyl)amino)-2-(2,6-dioxopiperidin-3-yl)isoindoline-1,3-dione (SIAIS1222039)

Referring to the preparation method of Scheme 3, the compound SIAIS1222039 was prepared under appropriate conditions that will be recognized by one skilled in the art, except that the amine substrate used was cyclohexylamine. The hydrochloride of compound SIAIS1222039 was obtained (yellow solid, 22 mg, yield 96%). $^1$H NMR (500 MHz, DMSO) δ 11.11 (s, 1H), 8.58 (s, 2H), 7.60 (d, J=6.2 Hz, 1H), 7.11 (s, 1H), 7.04 (s, 1H), 6.54 (s, 1H), 5.10-5.02 (m, 1H), 3.32 (s, 2H), 3.00-2.85 (m, 4H), 2.65-2.55 (m, 2H), 2.02 (s, 3H), 1.77 (s, 2H), 1.60 (s, 5H), 1.35 (s, 7H), 1.30-2.22 (m, 3H), 1.11 (s, 1H). HRMS (ESI) m/z: calcd for $C_{26}H_{37}N_4O_4^+$ [M+H]$^+$, 469.2809; found, 469.2803.

Example 18: Preparation of hydrochloride of 2-(2,6-dioxopiperidin-3-yl)-4-((7-(((1R,2S,4R)-1,7,7-trimethylbicyclo[2.2.1]heptan-2-yl)amino)heptyl)amino)isoindoline-1,3-dione (SIAIS1222041)

Referring to the preparation method of Scheme 3, the compound SIAIS1222041 was prepared under appropriate conditions that will be recognized by one skilled in the art, except that the amine substrate used was bornylamine. The hydrochloride of compound SIAIS1222041 was obtained (yellow solid, 8 mg, yield 31%). $^1$H NMR (500 MHz, DMSO) δ 11.11 (d, J=8.6 Hz, 1H), 8.65 (s, 1H), 8.23 (s, 1H), 7.60 (s, 1H), 7.18-7.08 (m, 1H), 7.08-7.00 (m, 1H), 6.54 (s, 1H), 5.06 (s, 1H), 3.31 (s, 2H), 3.22 (s, 1H), 2.89 (s, 3H), 2.67-2.56 (m, 2H), 2.37 (s, 1H), 2.26 (s, 1H), 2.18 (s, 1H), 2.04 (s, 1H), 1.70 (s, 4H), 1.61 (s, 2H), 1.36 (s, 7H), 1.25 (s, 1H), 0.98 (d, J=9.1 Hz, 3H), 0.85 (d, J=7.5 Hz, 6H). HRMS (ESI) m/z: calcd for $C_{30}H_{43}N_4O_4^+$ [M+H]$^+$, 523.3279; found, 523.3272.

Example 19: Preparation of hydrochloride of 4-((4-(((adamantan-1-yl)amino)methyl)benzyl)amino)-2-(2,6-dioxopiperidin-3-yl)isoindoline-1,3-dione (SIAIS1222035)

Referring to the preparation method of Scheme 3, the compound SIAIS1222035 was prepared under appropriate conditions that will be recognized by one skilled in the art, except that the brominated substrate used was tert-butyl (4-(bromomethyl)benzyl)carbamate, and the amine substrate used was 1-adamantanamine. The hydrochloride of compound SIAIS1222035 was obtained (yellow solid, 6.3 mg, yield 12%). $^1$H NMR (500 MHz, DMSO) δ 11.11 (s, 1H), 8.66 (s, 2H), 7.50 (dd, J=13.2, 7.1 Hz, 3H), 7.45 (d, J=7.5 Hz, 2H), 7.28 (t, J=7.1 Hz, 1H), 7.03 (d, J=6.5 Hz, 1H), 6.95 (d, J=8.6 Hz, 1H), 5.07 (dd, J=12.6, 4.9 Hz, 1H), 4.59 (d, J=5.8 Hz, 2H), 4.07 (s, 2H), 2.94-2.85 (m, 1H), 2.63 (d, J=9.0 Hz, 1H), 2.56 (d, J=25.3 Hz, 1H), 2.15 (s, 3H), 2.08-2.02 (m, 1H), 1.93 (s, 6H), 1.68 (d, J=11.8 Hz, 3H), 1.61 (d, J=11.6 Hz, 3H). HRMS (ESI) m/z: calcd for $C_{31}H_{35}N_4O_4^+$ [M+H]$^+$, 527.2653; found, 527.2654.

Example 20: Preparation of hydrochloride of 2-(2,6-dioxopiperidin-3-yl)-4-((4-((((1R,2S,4R)-1,7,7-trimethylbicyclo[2.2.1]heptan-2-yl)amino)methyl)benzyl)amino)isoindoline-1,3-dione (SIAIS1221173)

Referring to the preparation method of Scheme 3, the compound SIAIS1221173 was prepared under appropriate conditions that will be recognized by one skilled in the art, except that the amine substrate used was bornylamine, and the brominated substrate used was tert-butyl (4-(bromomethyl)benzyl)carbamate. The hydrochloride of compound SIAIS1221173 was obtained (yellow solid, 6.2 mg, yield 8%). $^1$H NMR (500 MHz, DMSO) δ 11.10 (s, 1H), 9.19 (s, 1H), 8.69 (s, 1H), 7.57 (d, J=6.8 Hz, 2H), 7.48 (t, J=7.9 Hz, 1H), 7.43 (d, J=6.7 Hz, 2H), 7.27 (s, 1H), 7.02 (d, J=6.3 Hz, 1H), 6.91 (d, J=8.8 Hz, 1H), 5.07 (d, J=12.9 Hz, 1H), 4.59 (s, 2H), 4.21-4.14 (m, 1H), 4.13-4.04 (m, 1H), 3.09 (s, 1H), 2.88 (d, J=13.8 Hz, 1H), 2.62 (d, J=11.5 Hz, 2H), 2.05 (s, 1H), 1.94 (s, 1H), 1.64 (d, J=11.8 Hz, 3H), 1.39 (s, 2H), 1.16 (d, J=15.6 Hz, 1H), 0.87 (s, 3H), 0.80 (s, 3H), 0.70 (s, 3H). HRMS (ESI) m/z: calcd for $C_{31}H_{37}N_4O_4^+$ [M+H]$^+$, 529.2809; found, 529.2803.

Example 21: Preparation of hydrochloride of 5-((7-((adamantan-1-yl)amino)heptyl)amino)-2-(2,6-dioxopiperidin-3-yl)isoindoline-1,3-dione (SIAIS1221055)

Referring to the preparation method of Scheme 3, the compound SIAIS1221055 was prepared under appropriate conditions that will be recognized by one skilled in the art, except that the amine substrate used was 1-adamantanamine, and the fluorinated substrate used was 2-(2,6-dioxopiperidin-3-yl)-5-fluoroisoindoline-1,3-dione. The hydrochloride of compound SIAIS1221055 was obtained (yellow solid, 3 mg, yield 4%). $^1$H NMR (500 MHz, DMSO) δ 11.08 (s, 1H), 8.18 (s, 2H), 7.59 (t, J=8.8 Hz, 1H), 7.13 (s, 1H), 6.87 (s, 1H), 6.55 (s, 1H), 5.04 (s, 1H), 2.93-2.80 (m, 3H), 2.41-2.35 (m, 2H), 2.14 (s, 3H), 2.05-1.96 (m, 1H), 1.82 (s, 6H), 1.71-1.52 (m, 8H), 1.42-1.32 (m, 6H), 1.19-1.13 (m, 4H). HRMS (ESI) m/z: calcd for $C_{30}H_{41}N_4O_4^+$ [M+H]$^+$, 521.3122; found, 521.3124.

Example 22: Preparation of hydrochloride of 3-(4-((7-((adamantan-1-yl)amino)heptyl)amino)-1-oxoisoindolin-2-yl)piperidine-2,6-dione (SIAIS1221091)

Referring to the preparation method of Scheme 4, the compound SIAIS1221091 was prepared under appropriate conditions that will be recognized by one skilled in the art, except that the amine substrate used was 1-adamantanamine.

The hydrochloride of compound SIAIS1221091 was obtained (pale yellow solid, 8 mg, yield 32%). $^1H$ NMR (500 MHz, DMSO) δ 11.01 (s, 1H), 8.61 (s, 2H), 7.29 (t, J=7.7 Hz, 1H), 6.95 (d, J=7.4 Hz, 1H), 6.77 (d, J=7.9 Hz, 1H), 5.12 (dd, J=13.2, 4.9 Hz, 1H), 4.25 (d, J=17.1 Hz, 1H), 4.14 (d, J=17.2 Hz, 1H), 3.13 (t, J=6.9 Hz, 2H), 2.97-2.89 (m, 1H), 2.81 (s, 2H), 2.62 (d, J=16.3 Hz, 1H), 2.30 (dt, J=13.2, 8.9 Hz, 1H), 2.11 (s, 3H), 2.07-2.01 (m, 1H), 1.85 (s, 6H), 1.68-1.56 (m, 10H), 1.34 (s, 6H). HRMS (ESI) m/z: calcd for $C_{30}H_{43}N_4O_3^+$ [M+H]$^+$, 507.3330; found, 507.3333.

Example 23: Preparation of hydrochloride of 3-(4-((6-(((adamantan-1-yl)methyl)amino)hexyl)amino)-1-oxoisoindolin-2-yl)piperidine-2,6-dione (SIAIS1222073)

Referring to the preparation method of Scheme 4, the compound SIAIS1222073 was prepared under appropriate conditions that will be recognized by one skilled in the art, except that the brominated substrate used was 1,6-dibromohexane, and the amine substrate used was (adamantan-1-yl) methanamine. The hydrochloride of compound SIAIS1222073 was obtained (white solid, 12.5 mg, yield 25%). $^1H$ NMR (500 MHz, DMSO) δ 11.02 (s, 1H), 8.26 (s, 2H), 7.30 (t, J=7.7 Hz, 1H), 6.96 (d, J=7.2 Hz, 1H), 6.79 (d, J=7.8 Hz, 1H), 5.11 (dd, J=13.1, 4.8 Hz, 1H), 4.25 (d, J=17.3 Hz, 1H), 4.14 (d, J=17.2 Hz, 1H), 3.14 (t, J=6.6 Hz, 2H), 2.97-2.88 (m, 1H), 2.85 (s, 2H), 2.66-2.56 (m, 3H), 2.35-2.25 (m, 1H), 2.07-2.00 (m, 1H), 1.96 (s, 3H), 1.68 (d, J=10.7 Hz, 5H), 1.60 (d, J=12.4 Hz, 5H), 1.56 (s, 6H), 1.44-1.37 (m, 2H), 1.36-1.28 (m, 2H). HRMS (ESI) m/z: calcd for $C_{30}H_{43}N_4O_3^+$ [M+H]$^+$, 507.3330; found, 507.3335.

Example 24: Preparation of hydrochloride of 3-(4-((8-((adamantan-1-yl)amino)octyl)amino)-1-oxoisoindolin-2-yl)piperidine-2,6-dione (SIAIS1222045)

Referring to the preparation method of Scheme 4, the compound SIAIS1222045 was prepared under appropriate conditions that will be recognized by one skilled in the art, except that the brominated substrate used was 1,8-dibromooctane, and the amine substrate used was 1-adamantanamine. The hydrochloride of compound SIAIS1222045 was obtained (white solid, 12.7 mg, yield 49%). $^1H$ NMR (500 MHz, DMSO) δ 11.01 (s, 1H), 8.46 (s, 2H), 7.30 (t, J=7.2 Hz, 1H), 6.95 (d, J=7.5 Hz, 1H), 6.76 (d, J=8.0 Hz, 1H), 5.11 (dd, J=13.1, 4.3 Hz, 1H), 4.24 (d, J=17.1 Hz, 1H), 4.13 (d, J=17.3 Hz, 1H), 3.12 (t, J=6.9 Hz, 2H), 2.93 (t, J=12.8 Hz, 1H), 2.81 (s, 2H), 2.63 (d, J=17.1 Hz, 1H), 2.35-2.25 (m, 1H), 2.11 (s, 3H), 2.07-2.00 (m, 1H), 1.84 (s, 6H), 1.66 (d, J=12.1 Hz, 3H), 1.59 (d, J=12.3 Hz, 7H), 1.41-1.28 (m, 8H). HRMS (ESI) m/z: calcd for $C_{31}H_{45}N_4O_3^+$ [M+H]$^+$, 521.3486; found, 521.3396.

Example 25: Preparation of hydrochloride of 3-(4-((4-(((adamantan-1-yl)amino)methyl)benzyl)amino)-1-oxoisoindolin-2-yl)piperidine-2,6-dione (SIAIS1222025)

Referring to the preparation method of Scheme 4, the compound SIAIS1222025 was prepared under appropriate conditions that will be recognized by one skilled in the art, except that the brominated substrate used was 1,4-dibromomethylbenzene, and the amine substrate used was 1-adamantanamine. The hydrochloride of compound SIAIS1222025 was obtained (white solid, 19.3 mg, yield 75%). $^1H$ NMR (500 MHz, DMSO) δ 11.03 (d, J=8.9 Hz, 1H), 9.01 (s, 2H), 7.54 (s, 2H), 7.45 (s, 2H), 7.18 (s, 2H), 6.95-6.86 (m, 1H), 6.64-6.56 (m, 1H), 5.13 (s, 1H), 4.42 (s, 2H), 4.38-4.30 (m, 1H), 4.25-4.15 (m, 1H), 4.04 (s, 2H), 2.93 (s, 1H), 2.65 (s, 1H), 2.40-2.25 (m, 1H), 2.14 (s, 3H), 1.97 (d, J=6.6 Hz, 7H), 1.68 (s, 3H), 1.61 (s, 3H). HRMS (ESI) m/z: calcd for $C_{31}H_{37}N_4O_3^+$ [M+H]$^+$, 513.2860; found, 513.2854.

Example 26: Preparation of hydrochloride of 3-(4-((4-(2-((adamantan-1-yl)amino)ethyl)benzyl)amino)-1-oxoisoindolin-2-yl)piperidine-2,6-dione (SIAIS1227027)

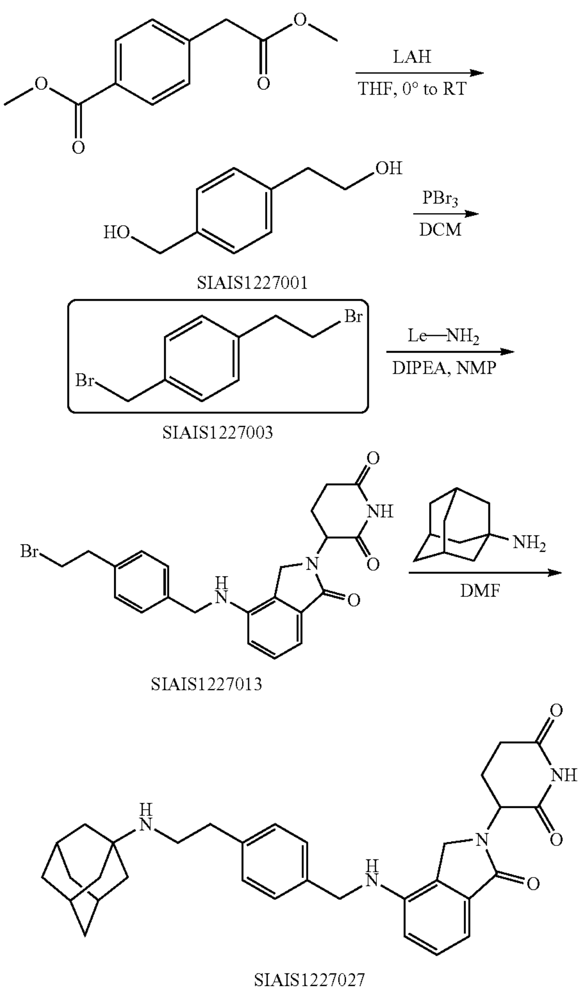

SIAIS1227001

SIAIS1227003

SIAIS1227013

SIAIS1227027

Step 1: preparation of 2-(4-(hydroxymethyl)phenyl)ethan-1-ol (SIAIS1227001)

A 100 mL egg-shaped flask was charged with methyl 4-(2-methoxy-2-oxoethyl)benzoate (10 mmol, 1 equiv), followed by addition of anhydrous tetrahydrofuran (20 mL), and slowly addition of lithium aluminum hydride (25 mmol, 2.5 equiv) in an ice bath. The mixture was warmed to room temperature, stirred and reacted overnight. After the reaction was complete as monitored by TCL, to the mixture were sequentially added 1 mL of water, 2 mL of 10% NaOH and 3 mL of water. The mixture was filtered to remove the insoluble substances, and the filtrate was directly rotary evaporated to give the compound SIAIS1227001 (pale yellow oil, 1.4 g, yield 90%).

Step 2: preparation of 1-(2-bromoethyl)-4-(bromomethyl)benzene (SIAIS1227003)

A 100 mL egg-shaped flask was charged with the compound SIAIS1227001 (8 mmol, 1 equiv), followed by addition of dichloromethane (10 mL), and slowly addition of phosphorus tribromide (8 mmol, 1 equiv) in an ice bath. The mixture was warmed to room temperature, stirred and reacted overnight. After the reaction was complete as monitored by TCL, the reaction was quenched with a small amount of water. The reaction mixture was directly mixed with silica gel powder, and the obtained sample was subjected to ISCO column chromatography for separation, and the product was eluted out with PE:EA=9:1. The collected fractions were concentrated under reduced pressure to remove the solvent to give the corresponding target compound SIAIS1227003 (pale yellow solid, 277 mg, yield 12%).

Step 3: preparation of 3-(4-((4-(2-bromoethyl)benzyl)amino)-1-oxoisoindolin-2-yl)piperidine-2,6-dione (SIAIS1227013)

A 50 mL single necked flask was charged with Lenalidomide (Le-$NH_2$)(0.25 mmol, 1 equiv), DIPEA (0.75 mmol, 3 equiv) and NMP (5 mL), and SIAIS1227003 (0.25 mmol, 1.0 equiv). The mixture was then stirred and reacted at room temperature for 3 h. After the reaction was complete, the mixture was filtered to remove the insoluble substances. The filtrate was subjected to Waters 2767 preparative HPLC (eluent (v/v):acetonitrile/water=10%-100%) for separation. The collected fractions were concentrated under reduced pressure to remove the solvent to give the corresponding target compound (pale yellow solid, 48 mg, yield 42%).

Step 4: preparation of hydrochloride of the final compound 3-(4-((4-(2-((adamantan-1-yl)amino)ethyl)benzyl)amino)-1-oxoisoindolin-2-yl)piperidine-2,6-dione (SIAIS1227027)

A 15 mL sample vial was charged with the intermediate compound SIAIS1227013 (0.05 mmol, 1 equiv), followed by addition of 1-adamantanamine (0.1 mmol, 2 equiv), DIPEA (0.15 mmol, 3 equiv) and DMF (2 mL). The mixture was reacted at 40° C. overnight. The mixture was filtered, and then subjected to Waters 2767 preparative HPLC (eluent (v/v):acetonitrile/(water+0.05% HCl)=10%-100%) for separation. The collected fractions were concentrated, and lyophilized by lyophilizer to give the hydrochloride of the compound SIAIS1227027 (pale yellow solid, 6 mg, yield 10%). $^1$H NMR (500 MHz, DMSO) δ 11.02 (s, 1H), 8.87 (s, 2H), 7.36 (d, J=6.6 Hz, 2H), 7.23 (d, J=6.9 Hz, 2H), 7.19 (d, J=5.8 Hz, 1H), 6.92 (d, J=6.8 Hz, 1H), 6.63 (d, J=7.5 Hz, 1H), 5.12 (d, J=8.3 Hz, 1H), 4.38 (s, 2H), 4.31 (d, J=17.2 Hz, 1H), 4.19 (d, J=17.0 Hz, 1H), 3.04 (s, 2H), 2.93 (s, 3H), 2.63 (d, J=16.5 Hz, 1H), 2.32 (d, J=12.5 Hz, 1H), 2.10 (s, 3H), 2.07-2.03 (m, 1H), 1.88 (s, 6H), 1.69-1.55 (m, 6H). $^{13}$C NMR (126 MHz, DMSO) δ 173.40, 171.72, 169.25, 143.61, 138.68, 136.29, 132.58, 129.53, 129.10, 127.82, 127.29, 112.97, 110.87, 56.63, 52.03, 46.31, 38.02, 35.67, 32.25, 31.74, 28.90, 23.28. HRMS (ESI) m/z: calcd for $C_{32}H_{39}N_4O_3^+$ [M+H]$^+$, 527.3017; found, 527.3014.

Example 27: Preparation of hydrochloride of 3-(4-((4-(3-((adamantan-1-yl)amino)propyl)benzyl)amino)-1-oxoisoindolin-2-yl)piperidine-2,6-dione (SIAIS1227077)

Referring to the preparation method of Example 26, the compound SIAIS1227077 was prepared under appropriate conditions that will be recognized by one skilled in the art, except that the ester substrate used in the first step was methyl 4-(3-methoxy-3-oxopropyl)benzoate. The hydrochloride of compound SIAIS1227077 was obtained (pale yellow solid, 5 mg, yield 31%). $^1$H NMR (500 MHz, DMSO) δ 11.01 (s, 1H), 8.60 (s, 2H), 7.32 (d, J=7.3 Hz, 2H), 7.19 (t, J=8.6 Hz, 3H), 6.92 (d, J=7.4 Hz, 1H), 6.63 (d, J=7.9 Hz, 1H), 5.12 (dd, J=13.0, 4.0 Hz, 1H), 4.36 (s, 2H), 4.31 (d, J=17.0 Hz, 1H), 4.19 (d, J=17.2 Hz, 1H), 2.98-2.88 (m, 1H), 2.85 (s, 2H), 2.67-2.60 (m, 3H), 2.34-2.26 (m, 1H), 2.11 (s, 3H), 2.09-2.02 (m, 1H), 1.92-1.85 (m, 2H), 1.82 (s, 6H), 1.66 (d, J=12.3 Hz, 3H), 1.58 (d, J=12.0 Hz, 3H). HRMS (ESI) m/z: calcd for $C_{33}H_{41}N_4O_3^+$ [M+H]$^+$, 541.3173; found, 541.3169.

Example 28: Preparation of hydrochloride of 3-(1-oxo-4-(8-(piperidin-1-yl)oct-1-yn-1-yl)isoindolin-2-yl)piperidine-2,6-dione (SIAIS1221035)

Referring to the preparation method of Scheme 5, the compound SIAIS1221035 was prepared under appropriate conditions that will be recognized by one skilled in the art, except that the amine substrate used was piperidine. The hydrochloride of compound SIAIS1221035 was obtained (pale yellow solid, 27 mg, yield 61%). $^1$H NMR (500 MHz, DMSO) δ 11.00 (s, 1H), 9.61 (s, 1H), 7.71 (d, J=7.5 Hz, 1H), 7.63 (d, J=7.6 Hz, 1H), 7.53 (t, J=7.5 Hz, 1H), 5.15 (dd, J=13.2, 5.0 Hz, 1H), 4.45 (d, J=17.7 Hz, 1H), 4.31 (d, J=17.6 Hz, 1H), 3.39 (d, J=12.3 Hz, 2H), 2.99-2.90 (m, 3H), 2.84-2.77 (m, 2H), 2.60 (d, J=16.9 Hz, 1H), 2.48-2.40 (m, 1H), 2.05-1.99 (m, 1H), 1.76 (s, 2H), 1.69 (d, J=10.3 Hz, 6H), 1.60 (dt, J=14.4, 7.3 Hz, 2H), 1.49-1.43 (m, 2H), 1.34 (dd, J=14.4, 7.7 Hz, 4H). HRMS (ESI) m/z: calcd for $C_{26}H_{34}N_3O_3^+$ [M+H]$^+$, 436.2595; found, 436.2596.

Example 29: Preparation of hydrochloride of 3-(4-(8-((adamantan-1-yl)amino)oct-1-yn-1-yl)-1-oxoisoindolin-2-yl)piperidine-2,6-dione (SIAIS1221095)

Referring to the preparation method of Scheme 5, the compound SIAIS1221095 was prepared under appropriate conditions that will be recognized by one skilled in the art, except that the amine substrate used was 1-adamantanamine. The hydrochloride of compound SIAIS1221095 was obtained (pale yellow solid, 25 mg, yield 50%). $^1$H NMR (500 MHz, DMSO) δ 11.00 (s, 1H), 8.41 (s, 2H), 7.71 (d, J=7.6 Hz, 1H), 7.63 (d, J=7.6 Hz, 1H), 7.52 (t, J=7.6 Hz, 1H), 5.15 (dd, J=13.3, 5.1 Hz, 1H), 4.45 (d, J=17.6 Hz, 1H), 4.31 (d, J=17.7 Hz, 1H), 3.40-3.34 (m, 2H), 2.97-2.88 (m, 1H), 2.83 (s, 2H), 2.60 (d, J=16.7 Hz, 1H), 2.48-2.40 (m, 1H), 2.10 (s, 3H), 2.05-1.98 (m, 1H), 1.82 (s, 6H), 1.68-1.55 (m, 10H), 1.50-1.43 (m, 2H), 1.43-1.36 (m, 2H). HRMS (ESI) m/z: calcd for $C_{31}H_{40}N_3O_3^+$ [M+H]$^+$, 502.3064; found, 502.3076.

Example 30: Preparation of hydrochloride of 3-(4-(7-(((adamantan-1-yl)methyl)amino)hept-1-yn-1-yl)-1-oxoisoindolin-2-yl)piperidine-2,6-dione (SIAIS1222019)

Referring to the preparation method of Scheme 5, the compound SIAIS1222019 was prepared under appropriate conditions that will be recognized by one skilled in the art, except that the alcohol substrate used is hept-6-yn-1-ol, and the amine substrate used was (adamantan-1-yl)methanamine. The hydrochloride of compound SIAIS1222019 was obtained (yellow solid, 28 mg, yield 56%). $^1$H NMR (500 MHz, DMSO) δ 11.02 (s, 1H), 8.17 (s, 2H), 7.74 (t, J=7.9 Hz, 1H), 7.66 (t, J=8.1 Hz, 1H), 7.58-7.51 (m, 1H), 5.18 (s, 1H), 4.52-4.43 (m, 1H), 4.38-4.29 (m, 1H), 2.91 (s, 3H), 2.62 (s, 3H), 2.37 (s, 1H), 2.03 (s, 1H), 1.98 (s, 3H), 1.70 (s, 6H), 1.62 (s, 5H), 1.57 (d, J=6.7 Hz, 7H), 1.48 (s, 2H). HRMS (ESI) m/z: calcd for $C_{31}H_{40}N_3O_3^+$ [M+H]$^+$, 502.3064; found, 502.3073.

Example 31: Preparation of hydrochloride of 3-(4-(9-((adamantan-1-yl)amino)non-1-yn-1-yl)-1-oxoisoindolin-2-yl)piperidine-2,6-dione (SIAIS1222047)

Referring to the preparation method of Scheme 5, the compound SIAIS1222047 was prepared under appropriate conditions that will be recognized by one skilled in the art, except that the alcohol substrate used is non-8-yn-1-ol, and the amine substrate used was 1-adamantanamine. The hydrochloride of compound SIAIS1222047 was obtained (pale yellow solid, 11.5 mg, yield 22%). $^1$H NMR (500 MHz, DMSO) δ 11.01 (s, 1H), 8.42 (s, 2H), 7.71 (d, J=7.6 Hz, 1H), 7.63 (d, J=7.3 Hz, 1H), 7.52 (t, J=7.3 Hz, 1H), 5.16 (dd, J=13.4, 4.3 Hz, 1H), 4.45 (d, J=17.5 Hz, 1H), 4.30 (d, J=17.5 Hz, 1H), 2.93 (t, J=12.9 Hz, 1H), 2.82 (s, 2H), 2.60 (d, J=16.1 Hz, 1H), 2.42 (d, J=12.7 Hz, 1H), 2.11 (s, 3H), 2.03 (s, 1H), 1.83 (s, 6H), 1.66 (d, J=12.4 Hz, 3H), 1.59 (d, J=9.2 Hz, 7H), 1.44 (s, 2H), 1.35 (s, 6H). HRMS (ESI) m/z: calcd for $C_{32}H_{42}N_3O_3^+$ [M+H]$^+$, 516.3221; found, 516.3225.

Example 32: Preparation of hydrochloride of 3-(4-(7-((adamantan-1-yl)amino)hept-1-yn-1-yl)-1-oxoisoindolin-2-yl)piperidine-2,6-dione (SIAIS1224021)

Referring to the preparation method of Scheme 5, the compound SIAIS1224021 was prepared under appropriate conditions that will be recognized by one skilled in the art, except that the alcohol substrate used is hept-6-yn-1-ol, and the amine substrate used was 1-adamantanamine. The hydrochloride of compound SIAIS1224021 was obtained (pale yellow solid, 26 mg, yield 53%). $^1$H NMR (500 MHz, DMSO) δ 11.02 (d, J=8.2 Hz, 1H), 8.42 (s, 2H), 7.74 (s, 1H), 7.66 (s, 1H), 7.56 (s, 1H), 5.18 (s, 1H), 4.53-4.44 (m, 1H), 4.38-4.30 (m, 1H), 2.95-2.82 (m, 3H), 2.67-2.60 (m, 1H), 2.40-2.30 (m, 1H), 2.13 (s, 3H), 2.05 (s, 1H), 1.86 (s, 6H), 1.72-1.57 (m, 12H), 1.53 (s, 2H). HRMS (ESI) m/z: calcd for $C_{30}H_{38}N_3O_3^+$ [M+H]$^+$, 488.2908; found, 488.2905.

Example 33: Preparation of hydrochloride of 3-(4-(6-((adamantan-1-yl)amino)hex-1-yn-1-yl)-1-oxoisoindolin-2-yl)piperidine-2,6-dione (SIAIS1224023)

Referring to the preparation method of Scheme 5, the compound SIAIS1224023 was prepared under appropriate conditions that will be recognized by one skilled in the art, except that the alcohol substrate used is hex-5-yn-1-ol, and the amine substrate used was 1-adamantanamine. The hydrochloride of compound SIAIS1224023 was obtained (pale yellow solid, 21.6 mg, yield 46%). $^1$H NMR (500 MHz, DMSO) δ 11.02 (s, 1H), 8.47 (s, 2H), 7.75 (s, 1H), 7.67 (s, 1H), 7.55 (s, 1H), 5.18 (s, 1H), 4.55-4.46 (m, 1H), 4.39-4.30 (m, 1H), 3.00-2.85 (m, 3H), 2.70-2.64 (m, 1H), 2.39 (s, 1H), 2.13 (s, 3H), 2.04 (s, 1H), 1.86 (s, 6H), 1.78 (s, 2H), 1.68 (s, 6H), 1.61 (s, 4H). HRMS (ESI) m/z: calcd for $C_{29}H_{36}N_3O_3^+$ [M+H]$^+$, 474.2751; found, 474.2743.

Example 34: Preparation of hydrochloride of 3-(1-oxo-4-(8-(spiro[3.3]heptan-2-ylamino)oct-1-yn-1-yl)isoindolin-2-yl)piperidine-2,6-dione (SIAIS1224017)

Referring to the preparation method of Scheme 5, the compound SIAIS1224017 was prepared under appropriate conditions that will be recognized by one skilled in the art, except that the amine substrate used was spiro[3.3]heptan-2-amine hydrochloride. The hydrochloride of compound SIAIS1224017 was obtained (white solid, 13.2 mg, yield 29%). $^1$H NMR (500 MHz, DMSO) δ 11.00 (s, 1H), 8.71 (s, 2H), 7.71 (d, J=7.5 Hz, 1H), 7.63 (d, J=7.6 Hz, 1H), 7.52 (t, J=7.5 Hz, 1H), 5.15 (dd, J=13.2, 4.8 Hz, 1H), 4.44 (d, J=17.5 Hz, 1H), 4.30 (d, J=17.8 Hz, 1H), 3.50 (s, 1H), 3.30 (s, 2H), 2.97-2.88 (m, 1H), 2.72 (s, 2H), 2.60 (d, J=16.4 Hz, 1H), 2.48-2.40 (m, 1H), 2.26 (t, J=8.8 Hz, 2H), 2.09 (t, J=9.5 Hz, 2H), 2.00 (t, J=7.1 Hz, 3H), 1.92 (t, J=7.2 Hz, 2H), 1.82-1.74 (m, 2H), 1.60-1.53 (m, 4H), 1.47-1.39 (m, 2H), 1.38-1.31 (m, 2H). HRMS (ESI) m/z: calcd for $C_{28}H_{36}N_3O_3^+$ [M+H]$^+$, 462.2751; found, 462.2755.

Example 35: Preparation of hydrochloride of 3-(4-(8-(cyclohexylamino)oct-1-yn-1-yl)-1-oxoisoindolin-2-yl)piperidine-2,6-dione (SIAIS1221181)

Referring to the preparation method of Scheme 5, the compound SIAIS1221181 was prepared under appropriate conditions that will be recognized by one skilled in the art, except that the amine substrate used was cyclohexylamine. The hydrochloride of compound SIAIS1221181 was obtained (pale yellow solid, 28.2 mg, yield 63%). $^1$H NMR (500 MHz, DMSO) δ 11.02 (d, J=7.4 Hz, 1H), 8.57 (s, 2H), 7.77-7.70 (m, 1H), 7.66-7.62 (m, 1H), 7.57-7.50 (m, 1H), 5.17 (s, 1H), 4.51-4.41 (m, 1H), 4.35 (d, J=8.0 Hz, 1H), 2.92 (d, J=25.5 Hz, 4H), 2.59 (s, 2H), 2.34 (d, J=30.3 Hz, 1H), 2.02 (s, 3H), 1.76 (s, 2H), 1.61 (s, 5H), 1.33 (d, J=61.5 Hz, 9H), 1.11 (s, 1H). HRMS (ESI) m/z: calcd for $C_{27}H_{36}N_3O_3^+$ [M+H]$^+$, 450.2751; found, 450.2745.

Example 36: Preparation of hydrochloride of 3-(1-oxo-4-(8-(((1R,2S,4R)-1,7,7-trimethylbicyclo[2.2.1]heptan-2-yl)amino)oct-1-yn-1-yl)isoindolin-2-yl)piperidine-2,6-dione (SIAIS1221183)

Referring to the preparation method of Scheme 5, the compound SIAIS1221183 was prepared under appropriate conditions that will be recognized by one skilled in the art, except that the amine substrate used was bornylamine. The hydrochloride of compound SIAIS1221183 was obtained (white solid, 29.9 mg, yield 59%). $^1$H NMR (500 MHz, DMSO) δ 11.01 (s, 1H), 8.53 (s, 1H), 8.16 (s, 1H), 8.16 (s, 1H), 7.77-7.70 (m, 1H), 7.68-7.62 (m, 1H), 7.58-7.51 (m, 1H), 5.17 (s, 1H), 4.52-4.40 (m, 1H), 4.40-4.28 (m, 1H), 3.24 (s, 1H), 2.91 (s, 3H), 2.58 (s, 3H), 2.17 (s, 1H), 2.04 (s, 1H), 1.70 (s, 4H), 1.63 (s, 3H), 1.48 (s, 2H), 1.40 (s, 4H), 1.22 (s, 1H), 0.98 (d, J=9.8 Hz, 3H), 0.85 (d, J=6.0 Hz, 6H). HRMS (ESI) m/z: calcd for $C_{31}H_{42}N_3O_3^+$ [M+H]$^+$, 504.3221; found, 504.3214.

Example 37: Preparation of hydrochloride of 2-(2,6-dioxopiperidin-3-yl)-4-(8-(piperidin-1-yl)oct-1-yn-1-yl)isoindoline-1,3-dione (SIAIS1221157)

Referring to the preparation method of Scheme 5, the compound SIAIS1221157 was prepared under appropriate conditions that will be recognized by one skilled in the art, except that the brominated substrate used in step 1 was 4-bromo-2-(2,6-dioxopiperidin-3-yl)isoindoline-1,3-dione. The hydrochloride of compound SIAIS1221157 was obtained (pale yellow solid, 37 mg, yield 55%. $^1$H NMR (500 MHz, DMSO) δ 11.14 (s, 1H), 9.69 (s, 1H), 7.90 (d, J=7.8 Hz, 1H), 7.85 (d, J=7.5 Hz, 2H), 5.16 (dd, J=12.9, 5.3 Hz, 1H), 2.99-2.81 (m, 5H), 2.65-2.56 (m, 2H), 2.09-2.04 (m, 1H), 1.82-1.65 (m, 10H), 1.64-1.55 (m, 2H), 1.49-1.45 (m, 2H), 1.40-1.30 (m, 4H). HRMS (ESI) m/z: calcd for $C_{26}H_{32}N_3O_4S^+$ [M+H]$^+$, 450.5585; found, 450.5583.

Example 38: Preparation of hydrochloride of 4-(8-((adamantan-1-yl)amino)oct-1-yn-1-yl)-2-(2,6-dioxopiperidin-3-yl)isoindoline-1,3-dione (SIAIS1221159)

Referring to the preparation method of Scheme 5, the compound SIAIS1221159 was prepared under appropriate conditions that will be recognized by one skilled in the art, except that the brominated substrate used in step 1 was 4-bromo-2-(2,6-dioxopiperidin-3-yl)isoindoline-1,3-dione, and the amine substrate used in step 2 was 1-adamantanamine. The hydrochloride of compound SIAIS1221159 was obtained (pale yellow solid, 42 mg, yield 55%). $^1$H NMR (500 MHz, DMSO) δ 11.14 (s, 1H), 8.43 (s, 2H), 7.90 (d, J=7.8 Hz, 1H), 7.86 (d, J=6.2 Hz, 2H), 5.16 (dd, J=13.1, 5.4 Hz, 1H), 2.93-2.80 (m, 3H), 2.61 (d, J=17.9 Hz, 1H), 2.53 (d, J=6.5 Hz, 1H), 2.12-2.05 (m, 4H), 1.84 (d, J=11.3 Hz, 8H), 1.67-1.58 (m, 10H), 1.50-1.44 (m, 2H), 1.42-1.37 (m, 2H). HRMS (ESI) m/z: calcd for $C_{31}H_{38}N_3O_4^+$ [M+H]$^+$, 516.2857; found, 516.2850.

Example 39: Preparation of hydrochloride of 3-(5-(8-((adamantan-1-yl)amino)oct-1-yn-1-yl)-1-oxoisoindolin-2-yl)piperidine-2,6-dione (SIAIS271164)

Referring to the preparation method of Scheme 5, the compound SIAIS271164 was prepared under appropriate conditions that will be recognized by one skilled in the art, except that the brominated substrate used in step 1 was 3-(5-bromo-1-oxoisoindolin-2-yl)piperidine-2,6-dione, and the amine substrate used in step 2 was 1-adamantanamine. The hydrochloride of compound SIAIS271164 was obtained (white solid, 11 mg, yield 54.5%). $^1$H NMR (500 MHz, DMSO) δ 11.00 (s, 1H), 8.55 (s, 2H), 7.74-7.57 (m, 2H), 7.50 (d, J=7.8 Hz, 1H), 5.11 (dd, J=13.2, 4.9 Hz, 1H), 4.38 (dd, J=61.7, 17.4 Hz, 2H), 3.03-2.76 (m, 3H), 2.60 (d, J=17.0 Hz, 1H), 2.48 (s, 2H), 2.39 (dt, J=13.2, 9.0 Hz, 1H), 2.10 (s, 3H), 2.04-1.93 (m, 1H), 1.84 (s, 6H), 1.70-1.52 (m, 10H), 1.44 (ddd, J=30.4, 14.3, 7.0 Hz, 4H). HRMS (ESI) m/z: calcd for $C_{31}H_{40}N_3O_3^+$ [M+H]$^+$, 502.3064; found, 502.3064.

Example 40: Preparation of hydrochloride of 3-(4-(8-(cyclohexylamino)octyl)-1-oxoisoindolin-2-yl)piperidine-2,6-dione (SIAIS1221193)

Referring to the preparation method of Scheme 6, the compound SIAIS1221193 was prepared under appropriate conditions that will be recognized by one skilled in the art, except that the alkynyl precursor compound used was the compound SIAIS1221181. The hydrochloride of compound SIAIS1221193 was obtained (white solid, 11 mg, yield 55%). $^1$H NMR (500 MHz, DMSO) δ 10.99 (s, 1H), 8.58 (s, 2H), 7.59-7.55 (m, 1H), 7.46 (d, J=4.2 Hz, 2H), 5.14 (dd, J=13.2, 5.0 Hz, 1H), 4.46 (d, J=17.1 Hz, 1H), 4.30 (d, J=17.1 Hz, 1H), 2.97-2.89 (m, 2H), 2.84 (s, 2H), 2.67-2.58 (m, 3H), 2.48-2.38 (m, 1H), 2.01 (d, J=11.4 Hz, 3H), 1.75 (d, J=12.0 Hz, 2H), 1.60 (d, J=7.6 Hz, 5H), 1.30 (d, J=9.0 Hz, 9H), 1.27-1.17 (m, 3H), 1.13-1.04 (m, 1H). HRMS (ESI) m/z: calcd for $C_{29}H_{40}N_3O_3S^+$ [M+H]$^+$, 454.3064; found, 454.3060.

Example 41: Preparation of hydrochloride of 3-(4-(8-((adamantan-1-yl)amino)octyl)-1-oxoisoindolin-2-yl)piperidine-2,6-dione (SIAIS1221105)

Referring to the preparation method of Scheme 6, the compound SIAIS1221105 was prepared under appropriate conditions that will be recognized by one skilled in the art, except that the alkynyl precursor compound used was the compound SIAIS1221095. The hydrochloride of compound SIAIS1221105 was obtained (pale yellow solid, 13 mg, yield 62%). $^1$H NMR (500 MHz, DMSO) δ 10.99 (s, 1H), 8.52 (s, 2H), 7.59-7.55 (m, 1H), 7.46 (d, J=4.2 Hz, 2H), 5.14 (dd, J=13.2, 5.0 Hz, 1H), 4.46 (d, J=17.1 Hz, 1H), 4.30 (d, J=17.1 Hz, 1H), 2.97-2.89 (m, 1H), 2.80 (s, 2H), 2.68-2.58 (m, 3H), 2.48-2.39 (m, 1H), 2.11 (s, 3H), 2.04-1.98 (m, 1H), 1.84 (s, 6H), 1.68-1.55 (m, 10H), 1.31 (s, 8H). HRMS (ESI) m/z: calcd for $C_{31}H_{44}N_4O_3^+$ [M+H]$^+$, 506.3377; found, 506.3375.

Example 42: Preparation of hydrochloride of 3-(4-(7-(((adamantan-1-yl)methyl)amino)heptyl)-1-oxoisoindolin-2-yl)piperidine-2,6-dione (SIAIS1222021)

Referring to the preparation method of Scheme 6, the compound SIAIS1222021 was prepared under appropriate conditions that will be recognized by one skilled in the art, except that the alkynyl precursor compound used was the compound SIAIS1222019. The hydrochloride of compound SIAIS1222021 was obtained (white solid, 14.8 mg, yield 59%). $^1$H NMR (500 MHz, DMSO) δ 11.00 (s, 1H), 8.06 (s, 2H), 7.61-7.54 (m, 1H), 7.46 (s, 2H), 5.14 (dd, J=13.1, 4.8 Hz, 1H), 4.46 (d, J=17.1 Hz, 1H), 4.30 (d, J=17.2 Hz, 1H), 2.92 (dd, J=22.1, 9.5 Hz, 1H), 2.85 (s, 2H), 2.67-2.62 (m, 3H), 2.60 (s, 2H), 2.43 (d, J=13.6 Hz, 1H), 2.06-2.00 (m, 1H), 1.97 (s, 3H), 1.68 (d, J=12.1 Hz, 4H), 1.60 (d, J=11.4 Hz, 6H), 1.54 (s, 6H), 1.32 (s, 4H), 1.29 (s, 2H). HRMS (ESI) m/z: calcd for $C_{31}H_{44}N_3O_3S^+$ [M+H]$^+$, 506.3377; found, 506.3375.

Example 43: Preparation of hydrochloride of 3-(4-(7-((adamantan-1-yl)amino)heptyl)-1-oxoisoindolin-2-yl)piperidine-2,6-dione (SIAIS1224041)

Referring to the preparation method of Scheme 6, the compound SIAIS1224041 was prepared under appropriate conditions that will be recognized by one skilled in the art, except that the alkynyl precursor compound used was the compound SIAIS1224021. The hydrochloride of compound SIAIS1224041 was obtained (pale yellow solid, 12.9 mg, yield 64%). $^1$H NMR (500 MHz, DMSO) δ 10.99 (s, 1H), 8.46 (s, 2H), 7.56 (s, 1H), 7.46 (s, 2H), 5.14 (d, J=13.9, 5.0 Hz, 1H), 4.46 (d, J=18.1 Hz, 1H), 4.30 (d, J=17.1 Hz, 1H), 2.93 (t, J=12.9 Hz, 1H), 2.81 (s, 2H), 2.68-2.62 (m, 3H), 2.45-2.38 (m, 1H), 2.11 (s, 3H), 2.03 (s, 1H), 1.83 (s, 6H), 1.66 (d, J=12.6 Hz, 4H), 1.58 (d, J=11.4 Hz, 6H), 1.33 (s, 6H). HRMS (ESI) m/z: calcd for $C_{30}H_{41}N_3O_3^+$ [M+H]$^+$, 492.3221; found, 492.3226.

Example 44: Preparation of hydrochloride of 3-(4-(6-((adamantan-1-yl)amino)hexyl)-1-oxoisoindolin-2-yl)piperidine-2,6-dione (SIAIS1224043)

Referring to the preparation method of Scheme 6, the compound SIAIS1224043 was prepared under appropriate conditions that will be recognized by one skilled in the art, except that the alkynyl precursor compound used was the compound SIAIS1224023. The hydrochloride of compound SIAIS1224043 was obtained (pale yellow solid, 8 mg, yield 44%). $^1$H NMR (500 MHz, DMSO) δ 11.00 (s, 1H), 8.82 (s, 2H), 7.57 (s, 1H), 7.47 (d, J=3.4 Hz, 2H), 5.14 (dd, J=13.0, 4.5 Hz, 1H), 4.48 (d, J=16.7 Hz, 1H), 4.32 (d, J=17.1 Hz, 1H), 2.98-2.88 (m, 1H), 2.79 (s, 2H), 2.68-2.64 (m, 2H), 2.61 (d, J=17.8 Hz, 1H), 2.48-2.40 (m, 1H), 2.10 (s, 3H), 2.05-2.00 (m, 1H), 1.87 (s, 6H), 1.65 (d, J=10.9 Hz, 6H), 1.58 (d, J=12.3 Hz, 4H), 1.37 (s, 4H). HRMS (ESI) m/z: calcd for $C_{29}H_{40}N_3O_3^+$ [M+H]$^+$, 478.3064; found, 478.3066.

Example 45: Preparation of hydrochloride of 3-(5-(8-((adamantan-1-yl)amino)octyl)-1-oxoisoindolin-2-yl)piperidine-2,6-dione (SIAIS271187)

Referring to the preparation method of Scheme 6, the compound SIAIS271187 was prepared under appropriate conditions that will be recognized by one skilled in the art, except that the alkynyl precursor compound used was the compound SIAIS271164. The hydrochloride of compound SIAIS271187 was obtained (white solid, 1.6 mg, yield 34.0%). $^1$H NMR (500 MHz, MeOD) δ 7.71 (d, J=7.7 Hz, 1H), 7.41 (s, 1H), 7.35 (d, J=7.9 Hz, 1H), 5.14 (dd, J=13.3, 5.1 Hz, 1H), 4.46 (q, J=16.8 Hz, 2H), 2.97-2.85 (m, 3H), 2.77 (dd, J=18.8, 11.5 Hz, 3H), 2.56-2.43 (m, 1H), 2.20 (s, 3H), 2.03 (s, 1H), 1.90 (s, 6H), 1.76 (dd, J=41.6, 12.9 Hz, 8H), 1.62 (s, 2H), 1.38 (s, 4H), 1.31 (d, J=22.6 Hz, 4H). HRMS (ESI) m/z: calcd for $C_{31}H_{44}N_4O_3^+$ [M+H]$^+$, 506.3377; found, 506.3368.

Example 46: Preparation of hydrochloride of 3-(4-(4-(((adamantan-1-yl)amino)methyl)phenethyl)-1-oxoisoindolin-2-yl)piperidine-2,6-dione (SIAIS1222051)

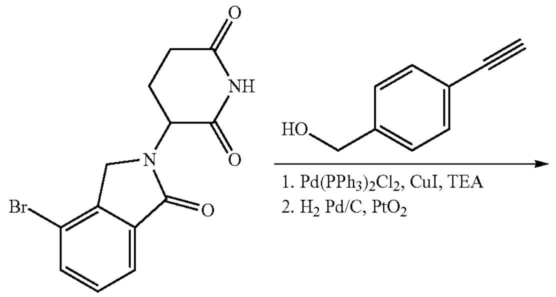

-continued

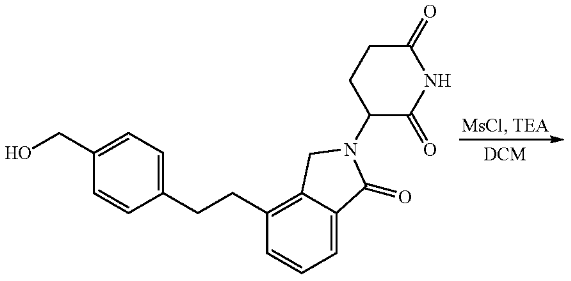

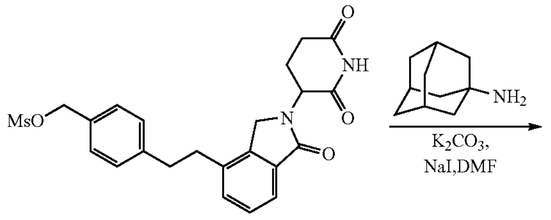

SIAIS292102

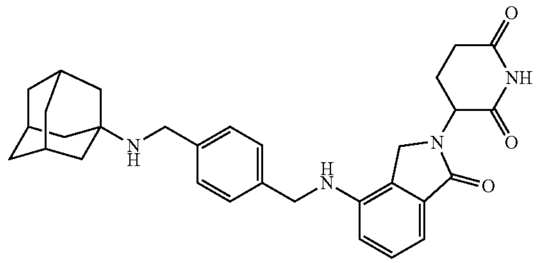

SIAIS1222051

Referring to the preparation method of Example 28, the compound SIAIS292102 was prepared under appropriate conditions that will be recognized by one skilled in the art, except that: (1) the alcohol substrate used was (4-ethynylphenyl)methanol; and (2) after the two starting material underwent coupling reaction, the resulting intermediate was first hydrogenated and then methanesulfonyloxylation. The compound SIAIS292102 was obtained as pale yellow solid (67 mg, 9.4% in total in three steps).

A 15 mL sample vial was charged with the intermediate compound SIAIS292102 (0.04 mmol, 1 equiv), followed by addition of 1-adamantanamine (0.08 mmol, 2 equiv), potassium carbonate (0.08 mmol, 2 equiv), sodium iodide (0.08 mmol, 2 equiv) and NMP (2 mL). The mixture was reacted at 50° C. overnight. The mixture was filtered, and then subjected to reverse phase C18 column chromatography (eluent (v/v):acetonitrile/(water+0.05% HCl)=10%-100%) for separation. The collected fractions were concentrated, and lyophilized by lyophilizer to give the hydrochloride of the compound SIAIS1222051 (yellow solid, 4.9 mg, yield 24%). $^1$H NMR (500 MHz, DMSO) δ 11.01 (s, 1H), 8.69 (s, 2H), 7.58 (d, J=6.9 Hz, 1H), 7.51 (d, J=7.6 Hz, 1H), 7.46 (t, J=6.4 Hz, 1H), 7.43 (d, J=7.3 Hz, 2H), 7.32 (d, J=7.3 Hz, 2H), 5.16-5.10 (dd, J=13.6, 3.7 Hz, 1H), 4.40 (d, J=17.1 Hz, 1H), 4.26 (d, J=16.9 Hz, 1H), 4.06 (s, 2H), 3.00-2.87 (m, 5H), 2.62 (d, J=16.0 Hz, 1H), 2.45-2.37 (m, 1H), 2.15 (s, 3H), 2.00 (d, J=13.3 Hz, 1H), 1.94 (s, 6H), 1.69 (d, J=12.0 Hz, 3H), 1.62 (d, J=11.0 Hz, 3H). HRMS (ESI) m/z: calcd for $C_{32}H_{38}N_3O_3^+$ [M+H]$^+$, 512.2908; found, 512.2899.

Example 47: Preparation of hydrochloride of 3-(4-(4-((((adamantan-1-yl)methyl)amino)methyl)phenethyl)-1-oxoisoindolin-2-yl)piperidine-2,6-dione (SIAIS1222053)

Referring to the preparation method of Example 46, the compound SIAIS1222053 was prepared under appropriate conditions that will be recognized by one skilled in the art, except that the amine substrate used was (adamantan-1-yl) methanamine. The hydrochloride of compound SIAIS1222053 was obtained (pale yellow solid, 6.7 mg, yield 32%). $^1$H NMR (500 MHz, DMSO) δ 11.01 (s, 1H), 8.89 (s, 1H), 8.50 (s, 1H), 7.57 (d, J=6.1 Hz, 1H), 7.50-7.40 (m, 4H), 7.30 (d, J=7.2 Hz, 2H), 5.13 (dd, J=12.9, 4.1 Hz, 1H), 4.41 (d, J=17.1 Hz, 1H), 4.28 (d, J=18.4 Hz, 1H), 4.20-4.05 (m, 2H), 3.12 (s, 1H), 3.00-2.85 (m, 5H), 2.62 (d, J=18.3 Hz, 1H), 2.40 (dd, J=26.3, 12.8 Hz, 1H), 1.98 (s, 2H), 1.63 (d, J=27.8 Hz, 3H), 1.38 (dd, J=24.4, 11.9 Hz, 2H), 1.10 (d, J=13.8 Hz, 1H), 0.87 (s, 3H), 0.82 (s, 3H), 0.73 (s, 3H). HRMS (ESI) m/z: calcd for $C_{33}H_{40}N_3O_3^+$ [M+H]$^+$, 526.3064; found, 526.3061.

Example 48: Preparation of hydrochloride of 3-(1-oxo-4-(4-((((1R,2S,4R)-1,7,7-trimethylbicyclo[2.2.1] heptan-2-yl)amino)methyl)phenethyl)isoindolin-2-yl)piperidine-2,6-dione (SIAIS1222055)

Referring to the preparation method of Example 46, the compound SIAIS1222055 was prepared under appropriate conditions that will be recognized by one skilled in the art, except that the amine substrate used was bornylamine. The hydrochloride of compound SIAIS1222055 was obtained (pale yellow solid, 7.6 mg, yield 37%). $^1$H NMR (500 MHz, DMSO) δ 11.01 (s, 1H), 8.63 (s, 2H), 7.58 (d, J=6.9 Hz, 1H), 7.49-7.40 (m, 4H), 7.31 (d, J=7.5 Hz, 2H), 5.13 (dd, J=13.0, 4.9 Hz, 1H), 4.40 (d, J=17.2 Hz, 1H), 4.26 (d, J=16.8 Hz, 1H), 4.09 (s, 2H), 3.00-2.88 (m, 5H), 2.62 (d, J=17.4 Hz, 1H), 2.40 (dd, J=25.0, 12.3 Hz, 1H), 1.99 (d, J=12.9 Hz, 1H), 1.94 (s, 4H), 1.66 (d, J=11.9 Hz, 3H), 1.58 (d, J=11.8 Hz, 3H), 1.52 (s, 1H), 1.49 (s, 6H). HRMS (ESI) m/z: calcd for $C_{32}H_{40}N_3O_3^+$ [M+H]$^+$, 514.3073; found, 526.3061.

Example 49: Preparation of hydrochloride of 3-(4-((7-(cyclohexylamino)heptyl)oxy)-1-oxoisoindolin-2-yl)piperidine-2,6-dione (SIAIS1221187)

Referring to the preparation method of Scheme 2, the compound SIAIS1221187 was prepared under appropriate conditions that will be recognized by one skilled in the art, except that the amine substrate used in the last step was cyclohexylamine. The hydrochloride of compound SIAIS1221187 was obtained (white solid, 15.4 mg, yield 68%). $^1$H NMR (500 MHz, DMSO) δ 10.98 (s, 1H), 8.56 (s, 2H), 7.49 (t, J=8.1 Hz, 1H), 7.31 (d, J=7.6 Hz, 1H), 7.25 (d, J=8.3 Hz, 1H), 5.12 (dd, J=13.7, 5.1 Hz, 1H), 4.37 (d, J=17.3 Hz, 1H), 4.22 (d, J=17.3 Hz, 1H), 4.13 (t, J=6.4 Hz, 2H), 2.98-2.83 (m, 4H), 2.63-2.56 (m, 1H), 2.49-2.41 (m, 1H), 2.05-1.96 (m, 3H), 1.79-1.71 (m, 4H), 1.65-1.56 (m, 3H), 1.45 (t, J=7.5 Hz, 2H), 1.39-1.32 (m, 4H), 1.31-1.19 (m, 4H), 1.15-1.04 (m, 1H). HRMS (ESI) m/z: calcd for $C_{26}H_{38}N_3O_4^+$ [M+H]$^+$, 456.2857; found, 456.2855.

Example 50: Preparation of hydrochloride of 3-(1-oxo-4-((7-(((1R,2S,4R)-1,7,7-trimethylbicyclo[2.2.1] heptan-2-yl)amino)heptyl)oxy)isoindolin-2-yl)piperidine-2,6-dione (SIAIS1221189)

Referring to the preparation method of Scheme 2, the compound SIAIS1221189 was prepared under appropriate conditions that will be recognized by one skilled in the art, except that the amine substrate used in the last step was bornylamine. The hydrochloride of compound SIAIS1221189 was obtained (white solid, 7 mg, yield 35%). $^1$H NMR (500 MHz, DMSO) δ 10.98 (s, 1H), 8.41 (s, 1H), 8.08 (s, 1H), 7.80 (t, J=5.7 Hz, 1H), 7.47-7.43 (m, 1H), 7.33-7.29 (m, 1H), 5.12 (dd, J=13.2, 5.3 Hz, 1H), 4.61-4.56 (m, 2H), 4.35 (d, J=17.2 Hz, 1H), 4.28 (d, J=17.2 Hz, 1H), 4.12 (t, J=6.4 Hz, 2H), 3.22 (s, 1H), 2.93-2.83 (m, 1H), 2.62-2.55 (m, 2H), 2.30-2.25 (m, 2H), 2.21-2.13 (m, 1H), 2.03-1.96 (m, 1H), 1.68 (s, 4H), 1.50-1.10 (m, 10H), 0.95 (s, 3H), 0.84 (d, J=2.4 Hz, 6H). HRMS (ESI) m/z: calcd for $C_{30}H_{44}N_3O_4^+$ [M+H]$^+$, 510.3326; found, 510.3325.

Example 51: Preparation of hydrochloride of 3-(4-(8-((adamantan-1-yl)(methyl)amino)octyl)-1-oxoisoindolin-2-yl)piperidine-2,6-dione (SIAIS1222031)

Referring to the preparation method of Example 9, the compound SIAIS1222031 was prepared under appropriate conditions that will be recognized by one skilled in the art, except that the precursor used was the compound SIAIS1221105. The hydrochloride of compound SIAIS1222031 was obtained (white solid, 11.0 mg, yield 71%). $^1$H NMR (500 MHz, DMSO) δ 11.00 (s, 1H), 9.61 (s, 1H), 7.60-7.52 (m, 1H), 7.50-43 (m, 2H), 5.15 (s, 1H), 4.84 (s, 1H), 4.55-4.40 (m, 4H), 4.36-4.28 (m, 1H), 3.32-3.25 (m, 2H), 2.94 (s, 1H), 2.66-2.60 (m, 3H), 2.28 (s, 2H), 2.16 (s, 3H), 1.98 (s, 4H), 1.91 (s, 3H), 1.72-1.60 (m, 10H), 1.40-1.25 (m, 6H). HRMS (ESI) m/z: calcd for $C_{32}H_{46}N_3O_3^+$ [M+H]$^+$, 520.3234; found, 520.3238.

Example 52: Preparation of hydrochloride of 4-(4-(8-(2-(2,6-dioxopiperidin-3-yl)-1-oxoisoindolin-4-yl)oct-7-yn-1-yl)piperazin-1-yl)-3-fluorobenzonitrile (SIAIS1228147)

Referring to the preparation method of Scheme 5, the compound SIAIS1228147 was prepared under appropriate conditions that will be recognized by one skilled in the art, except that the amine substrate used was 3-fluoro-4-(piperazin-1-yl)benzonitrile. The hydrochloride of compound SIAIS1228147 was obtained (white solid, 32.2 mg, yield 58%). $^1$H NMR (500 MHz, DMSO) δ 11.00 (s, 1H), 10.23 (s, 1H), 7.79 (d, J=13.1 Hz, 1H), 7.72 (d, J=7.6 Hz, 1H), 7.64 (d, J=8.0 Hz, 2H), 7.53 (t, J=7.8 Hz, 1H), 7.25 (d, J=8.7 Hz, 1H), 5.16 (dd, J=13.5, 5.1 Hz, 1H), 4.45 (d, J=16.5 Hz, 1H), 4.31 (d, J=17.6 Hz, 1H), 3.70 (d, J=12.9 Hz, 2H), 3.60-3.54 (m, 2H), 3.30-3.08 (m, 8H), 2.98-2.87 (m, 1H), 2.65-2.57 (m, 1H), 2.44 (s, 1H), 2.05-1.98 (m, 1H), 1.76-1.68 (m, 2H), 1.65-1.57 (m, 2H), 1.51-1.44 (m, 2H), 1.40-1.34 (m, 2H). HRMS (ESI) m/z: calcd for $C_{32}H_{35}FN_5O_3^+$ [M+H]$^+$, 556.2718; found, 556.2712.

Example 53: Preparation of hydrochloride of 4-((4-(2-((adamantan-1-yl)amino)ethyl)benzyl)oxy)-2-(2,6-dioxopiperidin-3-yl)isoindoline-1,3-dione (SIAIS1241167)

To a solution of compound 4-(2-bromoethyl)benzoic acid (800 mg, 3.49 mmol) in dichloromethane (10 mL) and methanol (10 mL) was added dropwise trimethylsilyldiazomethane (1.92 ml, 3.84 mmol, 2 M in cyclohexane) at 0° C. The mixture was warmed to room temperature and stirred for 2 hours. The reaction solution was quenched with water (10 mL), extracted with dichloromethane (20 mL×3). The organic phases were combined, dried over anhydrous sodium sulfate, and filtered. The filtrate was concentrated under reduced pressure, and the residue was separated by column chromatography (petroleum ether:ethyl acetate=2:1) to give methyl 4-(2-bromoethyl)benzoate (colorless oily, 0.72 g, yield 85%). $^1$H NMR (500 MHz, chloroform-d) δ 7.99 (d, J=10.0 Hz, 2H), 7.29 (d, J=10.0 Hz, 2H), 3.91 (s, 3H), 3.59 (t, J=10.0 Hz, 2H), 3.22 (t, J=10.0 Hz, 2H).

To a solution of methyl 4-(2-bromoethyl)benzoate (400 mg, 1.65 mmol) and 1-adamantanamine (309 mg, 1.65 mmol) in acetonitrile (10 mL) was added potassium carbonate (682 mg, 4.94 mmol) at room temperature. The mixture was warmed to 70° C. and stirred for 16 hours. The mixture was filtered, and the filtrate was concentrated under reduced pressure. The residue was washed with water (10 mL), extracted with dichloromethane (20 mL×3). The organic phases were combined, and dried over anhydrous sodium sulfate, and filtered. The filtrate was concentrated under reduced pressure, and the residue was separated by column chromatography (dichloromethane:methanol=10:1) to give methyl 4-(2-((adamantan-1-yl)amino)ethyl)benzoate (pale yellow solid, 240 mg, yield 46%). MS m/z: 314.3 [M+H].

To a solution of methyl 4-(2-((adamantan-1-yl)amino) ethyl)benzoate (100 mg, 0.32 mmol) in anhydrous tetrahydrofuran (4 mL) was added Lithium aluminum hydride (24 mg, 0.64 mmol) at 0° C. The reaction solution was stirred at 0° C. for 1 hour. The reaction solution was quenched with water (0.1 mL), stirred for 10 minutes, dried over anhydrous sodium sulfate. The mixture was filtered, and the filtrate was concentrated under reduced pressure to give the crude product (4-(2-((adamantan-1-yl)amino)ethyl)phenyl)methanol (pale yellow solid, 102 mg), which was used directly in the next step. MS m/z: 286.3 [M+H].

To a solution of (4-(2-((adamantan-1-yl)amino)ethyl)phenyl)methanol (110 mg, 0.39 mmol) in anhydrous tetrahydrofuran (4 mL) was added Phosphorus tribromide (104 mg, 0.39 mmol) at 0° C. The reaction solution was stirred at 0° C. for 2 hours. The reaction solution was quenched with water (10 mL), and extracted with dichloromethane (20 mL×3). The organic phases were combined, dried over anhydrous sodium sulfate, filtered, and the resulting filtrate was concentrated under reduced pressure to give the crude product N-(4-(bromomethyl)phenethyl)adamantan-1-amine (white solid, 150 mg), which was used directly in the next step. MS m/z: 348.2, 350.2 [M+H].

A 15 mL sample vial was charged with N-(4-(bromomethyl)phenethyl)adamantan-1-amine (0.1 mmol, 1 equiv), followed by addition of the compound SIAIS1221045 (0.1 mmol, 1 equiv). The mixture was reacted overnight at 50° C. The mixture was filtered, and then subjected to Waters 2767 preparative HPLC (eluent (v/v):acetonitrile/(water+0.05% HCl)=10%-100%) for separation. The collected fractions were concentrated, and lyophilized to give the hydrochloride of the compound SIAIS1241167(26.2 mg, white solid, yield 48%). $^1$H NMR (500 MHz, DMSO) δ 11.11 (s, 1H), 8.97 (s, 2H), 7.86-7.78 (m, 1H), 7.61 (d, J=8.6 Hz, 1H), 7.48 (t, J=6.3 Hz, 3H), 7.35 (d, J=8.0 Hz, 2H), 5.35 (s, 2H), 5.09 (dd, J=12.8, 5.4 Hz, 1H), 3.07 (s, 2H), 3.01 (s, 2H), 2.93-2.84 (m, 1H), 2.59 (d, J=17.7 Hz, 1H), 2.56-2.51 (m, 1H), 2.11 (s, 3H), 2.07-2.01 (m, 1H), 1.91 (s, 6H), 1.66 (d, J=12.2 Hz, 3H), 1.59 (d, J=12.0 Hz, 3H). $^{13}$C NMR (126 MHz, DMSO) δ 173.27, 170.42, 167.26, 165.81, 155.99, 137.52, 135.09, 133.76, 129.32, 128.28, 120.70, 117.07, 116.03, 70.34, 56.70, 49.25, 38.03, 35.67, 32.32, 31.42, 28.91, 22.48. HRMS (ESI) m/z: calcd for $C_{32}H_{36}N_3O_5^+$ [M+H]$^+$, 542.2649; found, 542.2669.

Example 54: Preparation of hydrochloride of 3-(4-((4-(2-((adamantan-1-yl)amino)ethyl)benzyl)oxy)-1-oxoisoindolin-2-yl)piperidine-2,6-dione (SIAIS1241169)

A 15 mL sample vial was charged with N-(4-(bromomethyl)phenethyl)adamantan-1-amine (0.12 mmol, 1.2 equiv), followed by addition of the compound SIAIS1221097 (0.1 mmol, 1 equiv). The mixture was reacted at 80° C. overnight. The mixture was concentrated under reduced pressure to remove acetonitrile. The resulting residue was dissolved in DMF, filtered, and subjected to Waters 2767 preparative HPLC (eluent (v/v):acetonitrile/(water+0.05% HCl)=10%-100%) for separation. The collected fractions were concentrated, and lyophilized to give the hydrochloride of the compound SIAIS1241169 (4.4 mg, white solid, yield 7%). $^1$H NMR (500 MHz, DMSO) δ 10.97 (s, 1H), 8.86 (s, 1H), 7.50-7.44 (m, 3H), 7.32 (d, J=7.9 Hz, 4H), 5.24 (s, 2H), 5.11 (dd, J=13.3, 5.1 Hz, 1H), 4.40 (d, J=17.4 Hz, 1H), 4.25 (d, J=17.4 Hz, 1H), 3.07 (s, 2H), 3.00-2.87 (m, 3H), 2.58 (d, J=17.0 Hz, 1H), 2.46-2.38 (m, 1H), 2.11 (s, 3H), 2.02-1.96 (m, 1H), 1.89 (s, 6H), 1.66 (d, J=12.3 Hz, 3H), 1.59 (d, J=11.9 Hz, 3H). $^{13}$C NMR (126 MHz, DMSO) δ 173.36, 171.50, 168.49, 153.88, 137.65, 135.64, 133.81, 130.45, 130.32, 129.32, 128.54, 115.75, 115.53, 69.71, 56.74, 52.08, 45.56, 38.08, 35.65, 32.36, 31.70, 28.90, 22.86. HRMS (ESI) m/z: calcd for $C_{32}H_{38}N_3O_4^+$ [M+H]$^+$, 528.2857; found, 528.2851.

Example 55: Preparation of hydrochloride of 2-(2,6-dioxopiperidin-3-yl)-4-((4-(((hexahydro-2,5-methanopentalen-3a(1H)-yl)amino)methyl)benzyl)oxy)isoindoline-1,3-dione (SIAIS1242035)

Referring to the preparation method of Scheme 1, the compound SIAIS1242035 was prepared under appropriate conditions that will be recognized by one skilled in the art, except that the halogenated substrate used was 1,4-dibromomethylbenzene, and the amine substrate used was 3-noradamantanamine hydrochloride. The hydrochloride of compound SIAIS1242035 was obtained (white solid, 7 mg, yield 27%). $^1$H NMR (500 MHz, DMSO) δ 11.11 (s, 1H), 9.75 (s, 2H), 7.83 (t, J=7.8 Hz, 1H), 7.68 (d, J=7.9 Hz, 2H), 7.61 (d, J=8.5 Hz, 1H), 7.57 (d, J=7.9 Hz, 2H), 7.48 (d, J=7.2 Hz, 1H), 5.42 (s, 2H), 5.10 (dd, J=12.8, 5.3 Hz, 1H), 4.12 (d, J=5.7 Hz, 2H), 2.93-2.84 (m, 1H), 2.59 (d, J=18.6 Hz, 1H), 2.55-2.51 (m, 2H), 2.33 (s, 2H), 2.11-2.01 (m, 3H), 1.98-1.90 (m, 4H), 1.63-1.54 (m, 3H), 1.50 (d, J=12.8 Hz, 1H). $^{13}$C NMR (126 MHz, DMSO) δ 173.26, 170.42, 167.26, 165.82, 155.86, 137.52, 137.30, 133.77, 132.90, 130.75, 127.96, 120.73, 117.16, 116.12, 70.27, 70.12, 49.27, 46.73, 45.06, 42.62, 41.99, 37.21, 34.20, 31.44, 22.47. HRMS (ESI) m/z: calcd for $C_{30}H_{32}N_3O_5^+$ [M+H]$^+$, 514.2336; found, 514.2335.

Example 56: Preparation of hydrochloride of 2-(2,6-dioxopiperidin-3-yl)-4-((7-((hexahydro-2,5-methanopentalen-3a(1H)-yl)amino)heptyl)amino)isoindoline-1,3-dione (SIAIS1242041)

Referring to the preparation method of Scheme 7, the compound SIAIS1242041 was prepared under appropriate conditions that will be recognized by one skilled in the art, except that the amine substrate used was 3-noradamantanamine hydrochloride. The hydrochloride of compound SIAIS1242041 was obtained (bright yellow solid, 20.4 mg, yield 57%). $^1$H NMR (500 MHz, DMSO) δ 11.10 (s, 1H), 9.33 (s, 2H), 7.59 (dd, J=8.3, 7.3 Hz, 1H), 7.11 (d, J=8.6 Hz, 1H), 7.03 (d, J=7.0 Hz, 1H), 6.53 (s, 1H), 5.05 (dd, J=12.8, 5.4 Hz, 1H), 3.31 (t, J=6.7 Hz, 2H), 2.93-2.78 (m, 3H), 2.63-2.52 (m, 2H), 2.42 (t, J=6.5 Hz, 1H), 2.29 (s, 2H), 2.06-2.01 (m, 1H), 1.96 (d, J=9.7 Hz, 2H), 1.93-1.84 (m, 4H), 1.66 (s, 2H), 1.62-1.52 (m, 5H), 1.46 (d, J=12.8 Hz, 1H), 1.35 (s, 6H). $^{13}$C NMR (126 MHz, DMSO) δ 173.29, 170.58, 169.44, 167.77, 146.91, 136.79, 132.66, 117.69, 110.88, 109.47, 69.60, 49.02, 44.86, 43.25, 42.63, 42.27, 41.81, 37.13, 34.14, 31.46, 29.07, 28.79, 26.64, 26.59, 22.64, 18.44, 17.18. HRMS (ESI) m/z: calcd for $C_{29}H_{39}N_4O_4^+$ [M+H]$^+$, 507.2966; found, 507.2965.

Example 57: Preparation of hydrochloride of 3-(4-((7-((hexahydro-2,5-methanopentalen-3a(1H)-yl)amino)heptyl)oxy)-1-oxoisoindolin-2-yl)piperidine-2,6-dione (SIAIS1242043)

Referring to the preparation method of Scheme 2, the compound SIAIS1242043 was prepared under appropriate conditions that will be recognized by one skilled in the art, except that the amine substrate used was 3-noradamantanamine hydrochloride. The hydrochloride of compound SIAIS1242043 was obtained (white solid, 10.3 mg, yield 30%). $^1$H NMR (500 MHz, DMSO) δ 10.98 (s, 1H), 9.31 (s, 2H), 7.48 (t, J=7.8 Hz, 1H), 7.30 (d, J=7.4 Hz, 1H), 7.24 (d, J=8.1 Hz, 1H), 5.12 (dd, J=13.3, 5.1 Hz, 1H), 4.37 (d, J=17.4 Hz, 1H), 4.23 (d, J=17.4 Hz, 1H), 4.12 (t, J=6.3 Hz, 2H), 2.96-2.87 (m, 1H), 2.86-2.79 (m, 2H), 2.58 (d, J=17.4 Hz, 1H), 2.49-2.43 (m, 1H), 2.42 (t, J=5.8 Hz, 1H), 2.29 (s, 2H), 2.02-1.97 (m, 1H), 1.95 (d, J=10.1 Hz, 2H), 1.86 (t, J=11.2 Hz, 4H), 1.79-1.72 (m, 2H), 1.67 (s, 2H), 1.56 (t, J=13.2 Hz, 3H), 1.46 (d, J=12.8 Hz, 3H), 1.37 (d, J=3.0 Hz, 4H). $^{13}$C NMR (126 MHz, DMSO) δ 173.36, 171.54, 168.56, 154.30, 133.72, 130.37, 130.15, 115.40, 115.03, 69.61, 68.35, 52.10, 45.56, 44.87, 43.24, 42.63, 41.81, 37.12, 34.12, 31.71, 28.96, 28.72, 26.58, 26.54, 25.72, 22.89. HRMS (ESI) m/z: calcd for $C_{29}H_{40}N_3O_4^+$ [M+H]$^+$, 494.3013; found, 494.3015.

Example 58: Preparation of hydrochloride of 3-(4-((7-((hexahydro-2,5-methanopentalen-3a(1H)-yl)amino)heptyl)amino)-1-oxoisoindolin-2-yl)piperidine-2,6-dione (SIAIS1242071)

Referring to the preparation method of Scheme 4, the compound SIAIS1242071 was prepared under appropriate conditions that will be recognized by one skilled in the art, except that the amine substrate used was 3-noradamantanamine hydrochloride. The hydrochloride of compound SIAIS1242071 was obtained (white solid, 18 mg, yield 53%). $^1$H NMR (500 MHz, DMSO) δ 11.03 (s, 1H), 9.43 (s, 2H), 7.41 (t, J=7.7 Hz, 1H), 7.21 (d, J=6.6 Hz, 1H), 7.12 (s, 1H), 5.13 (dd, J=13.3, 5.1 Hz, 1H), 4.45 (d, J=17.4 Hz, 1H), 4.32 (d, J=17.4 Hz, 1H), 3.19 (t, J=7.3 Hz, 2H), 2.98-2.88 (m, 1H), 2.85-2.77 (m, 2H), 2.63 (d, J=16.7 Hz, 1H), 2.43 (t, J=6.7 Hz, 1H), 2.37-2.30 (m, 1H), 2.29 (s, 2H), 2.07-2.01 (m, 1H), 1.98 (d, J=10.0 Hz, 2H), 1.93-1.83 (m, 4H), 1.71-1.68 (m, 4H), 1.56 (t, J=14.0 Hz, 3H), 1.46 (d, J=12.9 Hz, 1H), 1.35 (s, 6H). $^{13}$C NMR (126 MHz, DMSO) δ 173.35, 171.57, 168.69, 133.14, 129.89, 69.57, 52.06, 46.44, 44.83, 43.21, 42.62, 41.81, 37.12, 34.16, 31.68, 28.77, 27.90, 26.68, 26.56, 26.52, 23.23. HRMS (ESI) m/z: calcd for $C_{29}H_{41}N_4O_3^+$ [M+H]$^+$, 493.3173; found, 493.3176.

Example 59: Preparation of hydrochloride of 2-(2,6-dioxopiperidin-3-yl)-4-((7-((hexahydro-2,5-methanopentalen-3a(1H)-yl)amino)heptyl)oxy)isoindoline-1,3-dione (SIAIS1242073)

Referring to the preparation method of Scheme 1, the compound SIAIS1242073 was prepared under appropriate conditions that will be recognized by one skilled in the art, except that the amine substrate used was 3-noradamantanamine hydrochloride. The hydrochloride of compound SIAIS1242073 was obtained (white solid, 25.5 mg, yield 72%). $^1$H NMR (500 MHz, DMSO-$d_6$) δ 11.10 (s, 1H), 9.24 (s, 2H), 7.80 (dd, J=8.5, 7.3 Hz, 1H), 7.51 (d, J=8.5 Hz, 1H), 7.43 (d, J=7.2 Hz, 1H), 5.08 (dd, J=12.8, 5.4 Hz, 1H), 4.20 (t, J=6.2 Hz, 2H), 3.63 (t, J=6.6 Hz, 2H), 2.94-2.79 (m, 2H), 2.62-2.56 (m, 1H), 2.53 (d, J=4.5 Hz, 1H), 2.29 (s, 1H), 2.06-1.99 (m, 1H), 1.90-1.84 (d, J=11.2 Hz, 1H), 1.78-1.64 (m, 2H), 1.79-1.62 (m, 6H), 1.60-1.53 (m, 2H), 1.50-1.43 (m, 4H), 1.42-1.34 (m, 6H). $^{13}$C NMR (126 MHz, DMSO) δ 173.26, 170.43, 167.33, 165.79, 156.48, 137.51, 133.72, 120.26, 116.69, 115.61, 69.64, 69.22, 49.21, 45.86, 44.90, 43.27, 42.64, 41.82, 37.13, 34.11, 32.44, 31.43, 28.76, 28.32, 26.66, 25.63, 22.48. HRMS (ESI) m/z: calcd for $C_{29}H_{38}N_3O_5^+$ [M+H]$^+$, 508.2806; found, 508.2800.

Example 60: Preparation of hydrochloride of 3-(4-(8-((hexahydro-2,5-methanopentalen-3a(1H)-yl)amino)oct-1-yn-1-yl)-1-oxoisoindolin-2-yl)piperidine-2,6-dione (SIAIS1242057)

Referring to the preparation method of Scheme 5, the compound SIAIS1242057 was prepared under appropriate conditions that will be recognized by one skilled in the art, except that the amine substrate used was 3-noradamantanamine hydrochloride. The hydrochloride of compound SIAIS1242057 was obtained (white solid, 33.6 mg, yield 46%). $^1$H NMR (500 MHz, DMSO) δ 11.00 (s, 1H), 9.40 (s, 2H), 7.71 (d, J=7.1 Hz, 1H), 7.66-7.63 (m, 1H), 7.52 (t, J=7.6 Hz, 1H), 5.15 (dd, J=13.3, 5.1 Hz, 1H), 4.46 (d, J=17.7 Hz, 1H), 4.33 (d, J=17.7 Hz, 1H), 3.10-3.02 (m, 3H), 2.97-2.88 (m, 1H), 2.86-2.79 (m, 2H), 2.60 (d, J=17.6 Hz, 1H), 2.49-2.40 (m, 2H), 2.28 (s, 2H), 2.06-1.99 (m, 1H), 1.96 (d, J=9.8 Hz, 2H), 1.89 (s, 2H), 1.84 (d, J=10.0 Hz, 2H), 1.73-1.65 (m, 2H), 1.62-1.51 (m, 5H), 1.50-1.39 (m, 4H). $^{13}$C NMR (126 MHz, DMSO) δ 173.40, 171.72, 169.25, 143.61, 138.68, 136.29, 132.58, 129.53, 129.10, 127.82, 127.29, 112.97, 110.87, 56.63, 52.03, 46.31, 38.02, 35.67, 32.25, 31.74, 28.90, 23.28. HRMS (ESI) m/z: calcd for $C_{30}H_{38}N_3O_3^+$ [M+H]$^+$, 488.2908; found, 488.2916.

Example 61: Preparation of hydrochloride of 3-(4-(8-((hexahydro-2,5-methanopentalen-3a(1H)-yl)amino)octyl)-1-oxoisoindolin-2-yl)piperidine-2,6-dione (SIAIS1242091)

Referring to the preparation method of Scheme 6, the compound SIAIS1242091 was prepared under appropriate conditions that will be recognized by one skilled in the art, except that the alkynyl precursor substrate used was the compound SIAIS1242057. The hydrochloride of compound SIAIS1242091 was obtained (pale yellow solid, 16 mg, yield 94%). $^1$H NMR (500 MHz, DMSO) δ 10.99 (s, 1H), 9.21 (s, 2H), 7.57 (t, J=4.3 Hz, 1H), 7.46 (d, J=4.3 Hz, 2H), 5.14 (dd, J=13.3, 5.1 Hz, 1H), 4.47 (d, J=17.1 Hz, 1H), 4.31 (d, J=17.1 Hz, 1H), 2.98-2.88 (m, 1H), 2.85-2.77 (m, 2H), 2.68-2.57 (m, 3H), 2.49-2.38 (m, 2H), 2.30 (s, 2H), 2.05-1.98 (m, 1H), 1.94 (d, J=10.0 Hz, 2H), 1.86 (d, J=9.8 Hz, 4H), 1.65-1.53 (m, 7H), 1.47 (d, J=12.9 Hz, 1H), 1.32 (s, 8H). $^{13}$C NMR (126 MHz, DMSO) δ 173.39, 171.55, 168.84, 140.97, 137.98, 132.02, 131.95, 128.75, 121.09, 69.63, 52.01, 46.71, 44.89, 43.28, 42.64, 41.82, 37.13, 34.10, 31.71, 29.75, 29.29, 29.13, 29.01, 26.66, 26.58, 22.99. HRMS (ESI) m/z: calcd for $C_{30}H_{42}N_3O_3^+$ [M+H]$^+$, 492.3221; found, 492.3225.

Example 62: Preparation of hydrochloride of N-(adamantan-1-yl)-7-((2-(2,6-dioxopiperidin-3-yl)-1-oxoisoindolin-4-yl)oxy)heptanamide (SIAIS1242075)

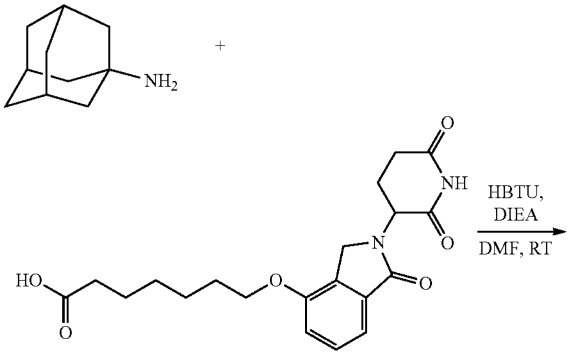

SIAIS1222151

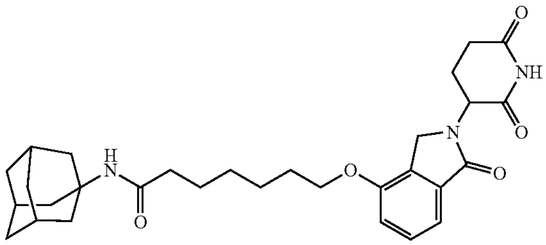

SIAIS1242075

A 50 mL egg-shaped flask was charged with the compound SIAIS1221097 (CAS No.: 1061604-41-8)(2 mmol, 1 equiv), followed by addition of acetonitrile (10 mL) and potassium carbonate (4 mmol, 2 equiv), and tert-butyl 7-bromoheptanoate (2.4 mmol, 1.2 equiv) with stirring at room temperature. The mixture was refluxed and reacted at 80° C. overnight. After the reaction was complete, the mixture was concentrated under reduced pressure to remove acetonitrile. The resulting residue was dissolved a small amount of DMSO, and then subjected to C18 reversed-phase column chromatography (eluent (v1/v2):acetonitrile/water=10%-100%) for separation. The collected fractions were concentrated under reduced pressure to remove solvents to give the corresponding tert-butoxycarbonyl intermediate. The corresponding tert-butoxycarbonyl intermediate was added to a 25 mL egg-shaped flask, followed by addition of dichloromethane (1 mL) and trifluoroacetic acid (3 mL). The mixture was stirred and reacted at room temperature for 1 h, and evaporated under reduced pressure to remove solvent. The resulting residue was treated by addition of water and lyophilized to give the corresponding target compound 7-((2-(2,6-dioxopiperidin-3-yl)-1-oxoisoindolin-4-yl)oxy) heptanoic acid (SIAIS1222151)(pale yellow solid, 250 mg, yield 32%). $^1$H NMR (500 MHz, DMSO) δ 10.97 (s, 1H), 7.48 (t, J=7.8 Hz, 1H), 7.31 (d, J=7.4 Hz, 1H), 7.24 (d, J=8.1 Hz, 1H), 5.11 (dd, J=13.2, 4.9 Hz, 1H), 4.38 (d, J=17.3 Hz, 1H), 4.23 (d, J=17.3 Hz, 1H), 4.11 (t, J=6.2 Hz, 2H), 2.95-2.87 (m, 1H), 2.59 (d, J=18.3 Hz, 1H), 2.49-2.41 (m, 1H), 2.22 (t, J=7.3 Hz, 2H), 2.03-1.96 (m, 1H), 1.77-1.70 (m, 2H), 1.56-1.49 (m, 2H), 1.48-1.40 (m, 2H), 1.38-1.30 (m, 2H). $^{13}$C NMR (126 MHz, DMSO) δ 174.95, 173.35, 171.52, 168.58, 154.30, 133.71, 130.35, 130.18, 115.38, 114.97, 68.34, 52.08, 45.53, 34.06, 31.71, 28.92, 28.74, 25.66, 24.89, 22.85. HRMS (ESI) calcd for $C_{20}H_{25}N_2O_6$ [M+H]$^+$, 389.1707; found, 389.1702.

A 15 mL sample vial was sequentially charged with 7-((2-(2,6-dioxopiperidin-3-yl)-1-oxoisoindolin-4-yl)oxy) heptanoic acid (SIAIS1222151)(19.4 mg, 0.05 mmol), 1-adamantanamine (7.6 mg, 0.05 mmol) and HBTU (37.9 mg, 0.1 mmol), followed by addition of DMF (2 mL) for dissolution, and N,N-diisopropylethylamine (12.9 mg, 0.1 mmol) with stirring. The mixture was reacted at room temperature for 12 h. The mixture was filtered using filtering membrane, and subjected to preparative HPLC (eluent (v/v): acetonitrile/(water+0.05% HCl)=10%-100%) for separation. The collected fractions were rotary evaporated to remove acetonitrile, and lyophilized to give the target compound SIAIS1242075 (white solid, 21.9 mg, yield 84%). $^1$H NMR (500 MHz, DMSO) δ 10.97 (s, 1H), 7.47 (t, J=7.8 Hz, 1H), 7.30 (d, J=7.4 Hz, 1H), 7.22 (d, J=8.1 Hz, 1H), 7.19 (s, 1H), 5.11 (dd, J=13.3, 5.1 Hz, 1H), 4.38 (d, J=17.4 Hz, 1H), 4.23 (d, J=17.4 Hz, 1H), 4.10 (t, J=6.3 Hz, 2H), 2.96-2.87 (m, 1H), 2.58 (d, J=17.7 Hz, 1H), 2.49-2.41 (m, 1H), 2.00 (t, J=7.2 Hz, 3H), 1.96 (s, 3H), 1.88 (d, J=2.4 Hz, 6H), 1.76-1.70 (m, 2H), 1.62-1.55 (m, 6H), 1.52-1.39 (m, 4H), 1.33-1.26 (m, 2H). $^{13}$C NMR (126 MHz, DMSO) δ 173.33, 171.98, 171.52, 168.57, 154.31, 133.71, 130.33, 130.17, 115.37, 114.93, 68.32, 52.08, 50.91, 45.54, 43.13, 41.51, 36.54, 35.96, 31.71, 29.84, 29.26, 28.95, 28.67, 25.81, 25.69, 22.87. HRMS (ESI) m/z: calcd for $C_{30}H_{40}N_3O_5^+$ [M+H]$^+$, 522.2962; found, 522.2965.

Example 63: Preparation of hydrochloride of N-(adamantan-1-yl)-7-((2-(2,6-dioxopiperidin-3-yl)-1,3-dioxoisoindolin-4-yl)amino)heptanamide (SIAIS1242077)

Referring to the preparation method of Example 62, the compound SIAIS1242077 was prepared under appropriate conditions that will be recognized by one skilled in the art, except that the carboxylic acid precursor substrate used was 7-((2-(2,6-dioxopiperidin-3-yl)-1,3-dioxoisoindolin-4-yl) amino)heptanoic acid (SIAIS1231169, CAS No.: 2225940-50-9). The hydrochloride of compound SIAIS1242077 was obtained as bright yellow solid (21.8 mg, yield 82%). $^1$H NMR (500 MHz, DMSO) δ 11.10 (s, 1H), 7.58 (dd, J=8.5, 7.1 Hz, 1H), 7.19 (s, 1H), 7.09 (d, J=8.6 Hz, 1H), 7.02 (d, J=7.0 Hz, 1H), 5.05 (dd, J=12.7, 5.4 Hz, 1H), 3.28 (t, J=7.0 Hz, 2H), 2.94-2.83 (m, 1H), 2.63-2.51 (m, 2H), 2.06-1.95 (m, 6H), 1.90 (d, J=2.5 Hz, 6H), 1.62-1.53 (m, 8H), 1.49-1.43 (m, 2H), 1.37-1.23 (m, 4H). $^{13}$C NMR (126 MHz, DMSO) δ 173.28, 171.98, 170.56, 169.42, 167.77, 146.90, 136.74, 132.67, 117.63, 110.86, 109.50, 50.92, 49.01, 42.28, 41.52, 36.54, 36.52, 31.45, 29.28, 29.05, 28.74, 26.56, 25.83, 22.63. HRMS (ESI) m/z: calcd for $C_{30}H_{39}N_4O_5^+$ [M+H]$^+$, 535.2915; found, 535.2925.

Example 64: Preparation of hydrochloride of 3-(4-((4-(2-((hexahydro-2,5-methanopentalen-3a(1H)-yl) amino)ethyl)benzyl)amino)-1-oxoisoindolin-2-yl) piperidine-2,6-dione (SIAIS1242061)

Referring to the preparation method of Example 26, the compound SIAIS1242061 was prepared under appropriate conditions that will be recognized by one skilled in the art, except that the amine substrate used was 3-noradamantanamine hydrochloride. The hydrochloride of compound SIAIS1242061 was obtained as pale yellow solid (7 mg, yield 15%). $^1$H NMR (500 MHz, DMSO) δ 11.02 (s, 1H), 9.52 (s, 2H), 7.36 (d, J=8.1 Hz, 2H), 7.25 (d, J=8.1 Hz, 2H), 7.19 (t, J=7.7 Hz, 1H), 6.92 (d, J=7.4 Hz, 1H), 6.64 (d, J=8.1 Hz, 1H), 5.12 (dd, J=13.3, 5.1 Hz, 1H), 4.38 (s, 2H), 4.31 (d, J=17.2 Hz, 1H), 4.19 (d, J=17.2 Hz, 1H), 3.05 (s, 2H), 3.00-2.89 (m, 3H), 2.63 (d, J=16.4 Hz, 1H), 2.45 (t, J=6.6 Hz, 1H), 2.37-2.27 (m, 3H), 2.08-2.02 (m, 1H), 1.98 (d, J=9.7 Hz, 2H), 1.88 (d, J=9.0 Hz, 4H), 1.56 (t, J=11.6 Hz, 3H), 1.45 (d, J=12.8 Hz, 1H). $^{13}$C NMR (126 MHz, DMSO) δ 173.40, 171.72, 169.25, 143.62, 138.73, 136.15, 132.59, 129.54, 129.15, 127.85, 127.29, 112.97, 110.88, 69.73, 52.03, 46.30, 46.22, 44.85, 44.33, 42.65, 41.82, 40.59, 40.49, 37.14, 34.11, 32.29, 31.73, 23.28. HRMS (ESI) m/z: calcd for $C_{31}H_{37}N_4O_3^+$ [M+H]$^+$, 513.2860; found, 513.2865.

Example 65: Preparation of hydrochloride of 5-((6-((adamantan-1-yl)amino)hexyl)amino)-2-(2,6-dioxopiperidin-3-yl)isoindoline-1,3-dione (SIAIS1242067)

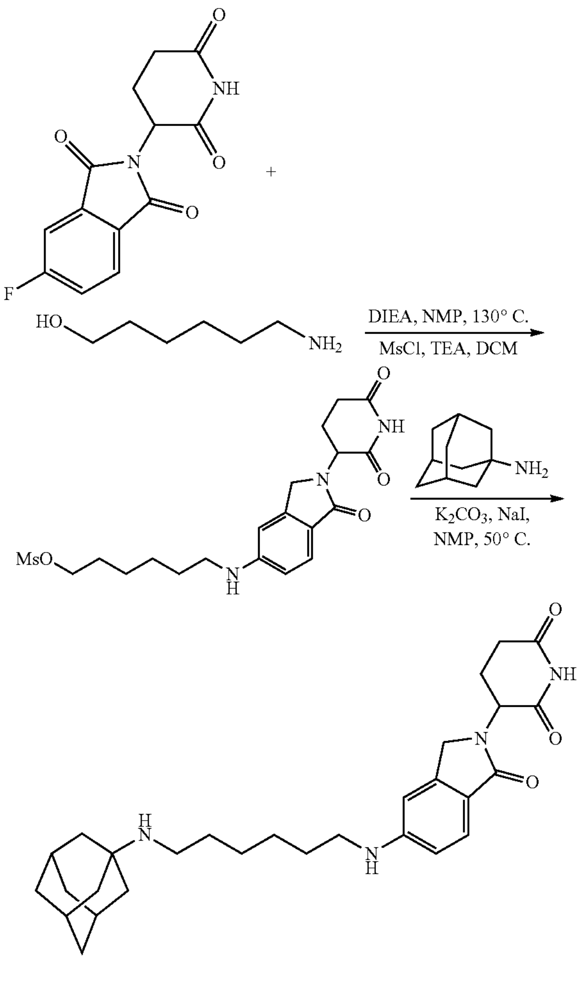

Referring to the preparation method of Scheme 7, the compound SIAIS1242067 was prepared under appropriate conditions that will be recognized by one skilled in the art, except that the starting materials used in the first step were 2-(2,6-dioxopiperidin-3-yl)-5-fluoroisoindoline-1,3-dione and 6-aminohexan-1-ol, and the amine substrate used in the last step was 3-noradamantanamine hydrochloride. The hydrochloride of compound SIAIS1242067 was obtained as bright yellow solid (6.7 mg, yield 26%). $^1$H NMR (500 MHz, DMSO) δ 11.06 (s, 1H), 8.67 (s, 2H), 7.56 (d, J=8.4 Hz, 1H), 6.96 (s, 1H), 6.86 (dd, J=8.4, 1.7 Hz, 1H), 5.03 (dd, J=12.7, 5.4 Hz, 1H), 3.17 (t, J=6.9 Hz, 2H), 2.92-2.78 (m, 3H), 2.61-2.52 (m, 2H), 2.11 (s, 3H), 2.03-1.96 (m, 1H), 1.86 (s, 6H), 1.69-1.55 (m, 10H), 1.40 (d, J=3.2 Hz, 4H). HRMS (ESI) m/z: calcd for $C_{29}H_{39}N_4O_4^+$ [M+H]$^+$, 507.2966; found, 507.2975.

Example 66: Preparation of hydrochloride of 5-((5-((adamantan-1-yl)amino)pentyl)amino)-2-(2,6-dioxopiperidin-3-yl)isoindoline-1,3-dione (SIAIS1242069)

Referring to the preparation method of Scheme 7, the compound SIAIS1242069 was prepared under appropriate conditions that will be recognized by one skilled in the art, except that the starting materials used in the first step were 2-(2,6-dioxopiperidin-3-yl)-5-fluoroisoindoline-1,3-dione and 5-aminopentan-1-ol, and the amine substrate used in the last step was 3-noradamantanamine hydrochloride. The hydrochloride of compound SIAIS1242069 was obtained as bright yellow solid (4.6 mg, yield 19%). $^1$H NMR (500 MHz, DMSO) δ 11.06 (s, 1H), 8.78 (s, 2H), 7.57 (d, J=8.4 Hz, 1H), 6.97 (s, 1H), 6.87 (dd, J=8.4, 1.9 Hz, 1H), 5.03 (dd, J=12.7, 5.4 Hz, 1H), 3.17 (t, J=6.8 Hz, 2H), 2.92-2.79 (m, 3H), 2.61-2.52 (m, 2H), 2.11 (s, 3H), 2.02-1.96 (m, 1H), 1.88 (s, 6H), 1.70-1.56 (m, 10H), 1.49-1.42 (m, 2H). $^{13}$C NMR (126 MHz, DMSO) δ 173.30, 170.66, 168.18, 167.63, 154.93, 134.68, 128.22, 125.59, 120.95, 116.29, 56.47, 49.09, 42.64, 40.58, 39.11, 37.97, 35.70, 31.46, 28.87, 28.08, 26.28, 24.13, 22.71. calcd for HRMS (ESI) m/z: $C_{28}H_{37}N_4O_4^+$ [M+H]$^+$, 493.2809; found, 493.2806.

Example 67: Preparation of hydrochloride of 3-(4-((4-(((adamantan-1-yl)amino)methyl)benzyl)oxy)-1-oxoisoindolin-2-yl)piperidine-2,6-dione (SIAIS1228157)

Referring to the preparation method of Scheme 1, the compound SIAIS1228157 was prepared under appropriate conditions that will be recognized by one skilled in the art, except that the brominated substrate used was 1,4-dibromomethylbenzene, and the amine substrate used was 1-adamantanamine. The hydrochloride of compound SIAIS1228157 was obtained as pale yellow solid (13 mg, yield 51%). $^1$H NMR (500 MHz, DMSO) δ 11.00 (s, 1H), 8.73 (s, 2H), 7.59-7.54 (m, 4H), 7.48 (t, J=7.8 Hz, 1H), 7.32 (t, J=8.1 Hz, 2H), 5.35-5.29 (m, 2H), 5.12 (dd, J=13.3, 5.1 Hz, 1H), 4.43 (d, J=17.4 Hz, 1H), 4.27 (d, J=17.4 Hz, 1H), 4.12 (d, J=6.4 Hz, 2H), 2.97-2.87 (m, 1H), 2.59 (d, J=18.4 Hz, 1H), 2.47-2.39 (m, 1H), 2.16 (s, 3H), 2.03-1.98 (m, 1H), 1.95 (s, 6H), 1.70 (d, J=12.1 Hz, 3H), 1.62 (d, J=11.9 Hz, 3H). HRMS (ESI) m/z: calcd for $C_{31}H_{36}N_3O_4^+$ [M+H]$^+$, 514.2700; found, 514.2691.

Example 68: Preparation of hydrochloride of 3-(4-((4-(((hexahydro-2,5-methanopentalen-3a(1H)-yl)amino)methyl)benzyl)oxy)-1-oxoisoindolin-2-yl)piperidine-2,6-dione (SIAIS1242083)

Referring to the preparation method of Scheme 1, the compound SIAIS1242083 was prepared under appropriate conditions that will be recognized by one skilled in the art, except that the brominated substrate used was 1,4-dibromomethylbenzene, and the amine substrate used was 3-noradamantanamine hydrochloride. The hydrochloride of compound SIAIS1242083 was obtained as white solid (4.4 mg, yield 18%). $^1H$ NMR (500 MHz, DMSO) δ 10.97 (s, 1H), 9.58 (s, 2H), 7.63 (d, J=8.1 Hz, 2H), 7.56 (d, J=8.1 Hz, 2H), 7.47 (t, J=7.8 Hz, 1H), 7.32 (dd, J=7.7, 5.2 Hz, 2H), 5.31 (s, 2H), 5.11 (dd, J=13.3, 5.1 Hz, 1H), 4.43 (d, J=17.4 Hz, 1H), 4.28 (d, J=17.4 Hz, 1H), 4.14-4.08 (m, 2H), 2.96-2.87 (m, 1H), 2.59 (d, J=17.0 Hz, 1H), 2.48-2.40 (m, 2H), 2.34 (s, 2H), 2.09-2.03 (m, 2H), 2.03-1.98 (m, 1H), 1.98-1.87 (m, 4H), 1.59 (t, J=14.9 Hz, 3H), 1.50 (d, J=12.9 Hz, 1H). $^{13}C$ NMR (126 MHz, DMSO) δ 173.37, 171.50, 168.47, 153.75, 137.86, 133.87, 132.81, 130.68, 130.50, 130.29, 128.28, 115.83, 115.57, 70.30, 69.47, 52.12, 46.76, 45.61, 45.09, 42.62, 41.99, 37.21, 34.15, 31.71, 22.85. HRMS (ESI) m/z: calcd for $C_{30}H_{34}N_3O_4^+$ [M+H]$^+$, 500.2544; found, 500.2543.

Comparative Example 1: Preparation of hydrochloride of 2-(2,6-dioxopiperidin-3-yl)-4-((7-(piperidin-1-yl)heptyl)oxy)isoindoline-1,3-dione (SIAIS1221079)

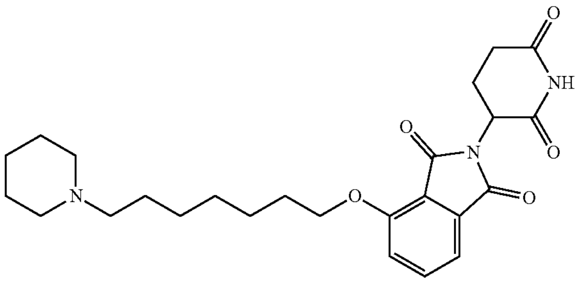 [SMILES: O=C1CCC(N2C(=O)c3cccc(OCCCCCCCN4CCCCC4)c3C2=O)C(=O)N1]

Referring to the preparation method of Scheme 1, the compound SIAIS1221079 was prepared under appropriate conditions that will be recognized by one skilled in the art, except that the amine substrate used was piperidine. The hydrochloride of compound SIAIS1221079 was obtained as white solid (21.5 mg, yield 94%). $^1H$ NMR (500 MHz, DMSO) δ 11.11 (s, 1H), 9.91 (s, 1H), 7.81 (t, J=7.9 Hz, 1H), 7.52 (d, J=8.6 Hz, 1H), 7.45 (d, J=7.3 Hz, 1H), 5.08 (dd, J=12.8, 5.4 Hz, 1H), 4.21 (t, J=6.2 Hz, 2H), 3.00-2.94 (m, 3H), 2.93-2.84 (m, 1H), 2.80 (d, J=9.6 Hz, 3H), 2.59 (d, J=17.8 Hz, 1H), 2.52 (s, 1H), 2.06-2.00 (m, 1H), 1.76 (d, J=4.7 Hz, 6H), 1.69 (d, J=7.9 Hz, 4H), 1.50-1.46 (m, 2H), 1.39 (d, J=6.9 Hz, 2H), 1.32 (d, J=7.0 Hz, 2H). HRMS (ESI) m/z: calcd for $C_{25}H_{34}N_3O_5^+$ [M+H]$^+$, 456.2493; found, 456.2491.

Comparative Example 2: Preparation of hydrochloride of 3-(1-oxo-4-((7-(piperidin-1-yl)heptyl)oxy) isoindolin-2-yl)piperidine-2,6-dione (SIAIS1221109)

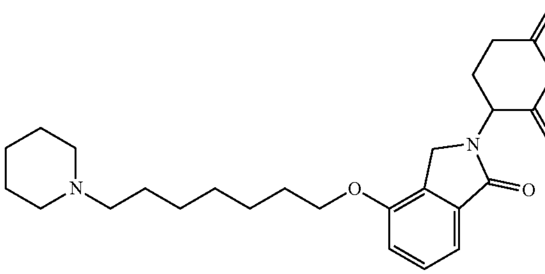

Referring to the preparation method of Scheme 2, the compound SIAIS1221109 was prepared under appropriate conditions that will be recognized by one skilled in the art, except that the amine substrate used in the last step was piperidine. The hydrochloride of compound SIAIS1221109 was obtained as pale yellow solid (12 mg, yield 66%). $^1H$ NMR (500 MHz, DMSO) δ 10.98 (s, 1H), 10.06 (s, 1H), 7.48 (t, J=7.7 Hz, 1H), 7.31 (d, J=7.4 Hz, 1H), 7.24 (d, J=8.0 Hz, 1H), 5.12 (dd, J=13.2, 4.8 Hz, 1H), 4.37 (d, J=17.3 Hz, 1H), 4.22 (d, J=17.3 Hz, 1H), 4.12 (t, J=6.0 Hz, 2H), 2.98-2.87 (m, 3H), 2.79 (s, 2H), 2.58 (d, J=17.7 Hz, 1H), 2.48-2.41 (m, 1H), 2.03-1.96 (m, 1H), 1.80-1.65 (m, 10H), 1.48-1.42 (m, 2H), 1.38-1.28 (m, 5H). HRMS (ESI) m/z: calcd for $C_{25}H_{36}N_3O_4^+$ [M+H]$^+$, 442.2700; found, 442.2703.

Comparative Example 3: Preparation of hydrochloride of 2-(2,6-dioxopiperidin-3-yl)-4-((7-(piperidin-1-yl)heptyl)amino)isoindoline-1,3-dione (SIAIS1221047)

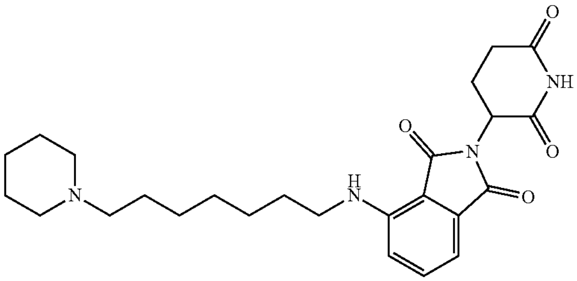 [SMILES: O=C1CCC(N2C(=O)c3cccc(NCCCCCCCN4CCCCC4)c3C2=O)C(=O)N1]

Referring to the preparation method of Scheme 3, the compound SIAIS1221047 was prepared under appropriate conditions that will be recognized by one skilled in the art, except that the amine substrate used in the last step was piperidine. The hydrochloride of compound SIAIS1221047 was obtained as yellow solid (3 mg, yield 4%). $^1H$ NMR (500 MHz, DMSO) δ 11.10 (s, 1H), 9.69 (s, 1H), 7.59 (t, J=7.8 Hz, 1H), 7.10 (d, J=8.5 Hz, 1H), 7.03 (d, J=7.0 Hz, 1H), 6.53 (t, J=5.5 Hz, 1H), 5.05 (dd, J=12.7, 5.3 Hz, 1H), 3.41-3.28 (m, 2H), 2.99-2.93 (m, 2H), 2.92-2.76 (m, 3H), 2.62-2.53 (m, 2H), 2.06-2.00 (m, 1H), 1.81-1.55 (m, 10H), 1.41-1.21 (m, 8H). HRMS (ESI) m/z: calcd for $C_{25}H_{35}N_4O_4^+$ [M+H]$^+$, 455.2653; found, 455.2653.

Comparative Example 4: Preparation of hydrochloride of 3-(1-oxo-4-((7-(piperidin-1-yl)heptyl)amino) isoindolin-2-yl)piperidine-2,6-dione (SIAIS1220125)

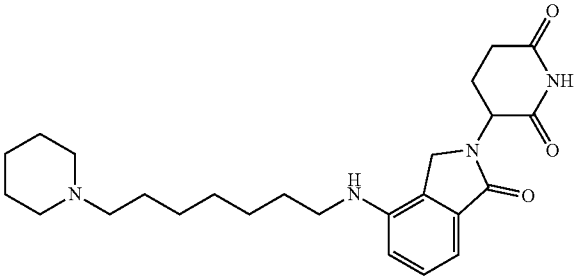 [SMILES: O=C1CCC(N2Cc3c(NCCCCCCCN4CCCCC4)cccc3C2=O)C(=O)N1]

Referring to the preparation method of Scheme 4, the compound SIAIS1220125 was prepared under appropriate conditions that will be recognized by one skilled in the art, except that the amine substrate used in the last step was piperidine. The hydrochloride of compound SIAIS1220125 was obtained as white solid (14.6 mg, yield 66%). $^1$H NMR (500 MHz, DMSO) δ 11.04 (s, 1H), 9.90 (s, 1H), 7.30 (t, J=7.7 Hz, 1H), 6.95 (d, J=7.4 Hz, 1H), 6.77 (d, J=8.0 Hz, 1H), 5.12 (dd, J=13.3, 5.1 Hz, 1H), 4.25 (d, J=17.2 Hz, 1H), 4.14 (d, J=17.2 Hz, 1H), 3.38 (d, J=11.8 Hz, 2H), 3.13 (t, J=7.0 Hz, 2H), 2.98-2.91 (m, 3H), 2.84-2.75 (m, 2H), 2.62 (d, J=17.8 Hz, 1H), 2.34-2.24 (m, 1H), 2.07-2.00 (m, 1H), 1.79-1.62 (m, 8H), 1.62-1.55 (m, 2H), 1.40-1.36 (m, 6H). HRMS (ESI) m/z: calcd for $C_{25}H_{37}N_4O_3^+$ [M+H]$^+$, 441.2860; found, 441.2863.

Comparative Example 5: Preparation of hydrochloride of 3-(1-oxo-4-(8-(piperidin-1-yl)octyl)isoindolin-2-yl)piperidine-2,6-dione (SIAIS1221107)

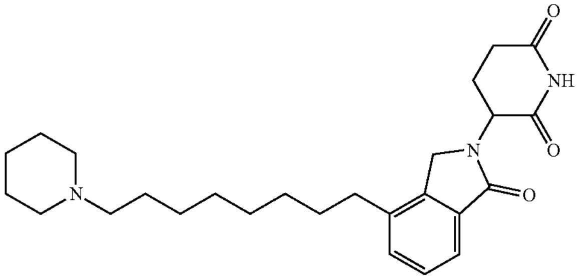 [SMILES: O=C1CCC(N2Cc3c(CCCCCCCCN4CCCCC4)cccc3C2=O)C(=O)N1]

Referring to the preparation method of Scheme 6, the compound SIAIS1221107 was prepared under appropriate conditions that will be recognized by one skilled in the art, except that the alkynyl precursor used was the compound SIAIS1221035. The hydrochloride of compound SIAIS1221107 was obtained as pale yellow (9 mg, yield 45%). $^1$H NMR (500 MHz, DMSO) δ 11.00 (s, 1H), 10.02 (s, 1H), 7.59-7.55 (m, 1H), 7.46 (d, J=4.4 Hz, 2H), 5.14 (dd, J=13.2, 4.9 Hz, 1H), 4.46 (d, J=17.5 Hz, 1H), 4.30 (d, J=17.0 Hz, 1H), 2.96-2.90 (m, 3H), 2.83-2.76 (m, 2H), 2.66-2.62 (m, 3H), 2.46-2.39 (m, 1H), 2.05-1.98 (m, 1H), 1.75 (s, 4H), 1.70-1.62 (m, 6H), 1.34-1.22 (m, 10H). HRMS (ESI) m/z: calcd for $C_{26}H_{38}N_3O_3^+$ [M+H]$^+$, 440.2908; found, 440.2903.

Biological Activity Assay

Experimental Materials

| | |
|---|---|
| Halt proteosome and phosphatase inhibitors | Thermo Fisher Company |
| Cell TITER BLUE detection kits | Promega Company |
| Cell TITER GLO detection kits | Promega Company |
| CCK8 (WST) reagent | DOJINDO LABORATORIES, Japan |
| RPMI1640 | GIBICO Company |
| Fetal bovine serum (FBS) | GIBICO Company |
| Penicillin-Streptomycin | GIBICO Company |
| SuperSignal West Pico Chemiluminescent Substrate | Thermo Fisher Company |
| SuperSignal West Femto Maximum Sensitivity Substrate | Thermo Fisher Company |
| Cycloheximide | Sigma Company |

Antibodies:

Most antibodies were purchased from Cell Signaling Technology Company, including IKZF1 (#9034S), IKZF3 (#15103S). CK1α(#ab108296) and GAPDH antibodies were purchased from Abcam Company.

Cell Culture

Multiple myeloma cell line: MM.1S (B lymphoblast), purchased from ATCC (American Type Culture Collection). Culture medium was RPMI1640 supplemented with 10% FBS and 1% Penicillin-Streptomycin. The cells used were identified as correct cells by STR cells and negative for *mycoplasma* by routine inspections.

Western Blotting Assay (Western Blot)

Tumor cells were seeded in 24-well plates at a cell seeding density of $3\times10^5$ cells/mL, with 1 mL culture medium per well. After 24 h, the cells were treated with different concentrations of the compounds of the present disclosure. After 16 hours, the cells were collected, and washed with PBS. The supernatant was discarded, and the cells were placed on ice, and treated with RIPA protein lysate containing Halt protease and phosphatase inhibitor. The lysate was centrifuged at 10000 RPM at 4° C. for 10 minutes, and the supernatant was collected. An equal amount of proteins were loaded in 4× SDS sample solution, denatured at 95° C. for 5 minutes, and then freezed to −20° C. or directly subjected to protein electrophoresis (Bio-rad precast gel, 4-15% gradient gel, Bio-rad company). Electrophoresis apparatus and related components were purchased from Bio-rad company, and electrophoresis set at a constant pressure of 120V for 1 h. Then transferring membrane was conducted by using PVDF membrane at 400 mA for 1 h on ice. Afterwards, the membranes were block for 30 minutes by using T7131A Western Blot Blocking Buffer (TarKara company) at room temperature. Western blotting was conducted according to the antibody product manual of Cell Signaling Technology Company. Results were shown in FIG. 1.

Determination of Half Inhibitory Concentration ($IC_{50}$) of the Compounds of the Present Disclosure $IC_{50}$ values of the compounds of the present disclosure were measured using Cell Titer Blue, Cell Titer GLO, or WST reagent from Promega Company. Assay details are as follows: Cells were seeded in 100 μL RPMI1640 complete medium containing serum at a density of 15,000 cells/well. After 24 h, the inoculated cells were treated with commercial inhibitors, the compounds of the present disclosure to be tested (comprising examples 1-68) and comparative examples 1-5 which were serially diluted. After the cells were treated with the compounds of the present disclosure to be tested (comprising examples 1-68) for 72 h, cell viability was determined after adding the cell viability detection kit listed above to the culture medium according to the reagent operating instructions. The negative control was DMSO, and the positive controls were commercial inhibitors and comparative examples 1-5, all of which were used to treat the cells through the same method as that of the compounds of the present disclosure. The growth inhibition of the compounds of the present disclosure (comprising examples 1-68) on cells was plotted by Prism Graphpad software, and the $IC_{50}$ values of the compounds of the present disclosure (comprising examples 1-68) were calculated therefrom. Results were shown in Table 2.

1. Evaluation of Proliferation Inhibition of the Compounds of the Present Invention Based on Pomalidomide and Lenalidomide Derivatives in Multiple Myeloma Cells We tested the activities of the compounds of the present invention (comprising examples 1-68) in MM.1S cell (which overexpressed IKZF1/3 and is highly sensitive to immunomodulatory drugs) through a dose-dependent manner. The cells were treated with the compounds of the present invention (comprising examples 1-68) at 10 different successively decreasing concentrations (starting at the highest concentration of 10 M; 5-fold serial dilutions) for 72 h, and then the cell viability determination was performed in accordance with CCK-8 reagent operating instructions. The experiment was repeated more than three times. Results were shown in Table 2.

The compounds of the present invention (comprising examples 1-68) designed on the basis of lenalidomide showed satisfying anti-proliferation of MM.1S (Table 2). Compared with the $IC_{50}$ of lenalidomide against MM.1S cells of 19.6 nM, the compounds of the present invention (comprising examples 1-68) greatly increased the inhibitory effect. Many compounds of the present invention have $IC_{50}$ significantly lower than that of lenalidomide. For example, $IC_{50}$ of compound SIAIS1221111 was about 0.09 nM, which was 217 times lower than lenalidomide.

TABLE 2

$IC_{50}$ values of the compounds of the present invention in multiple myeloma cells (half inhibitory concentration)

| Cell line | Compounds | Reagent | $IC_{50}$ (nM) |
|---|---|---|---|
| MM.1S | pomalidomide | WST | 9.4 ± 1.3 |
| MM.1S | lenalidomide | WST | 19.6 ± 3.3 |
| MM.1S | SIAIS1222095 | WST | 1.104 |
| MM.1S | SIAIS1222093 | WST | 1.577 |
| MM.1S | SIAIS1221053 | WST | 0.16 ± 0.03 |
| MM.1S | SIAIS1222037 | WST | 0.13 |
| MM.1S | SIAIS1222191 | WST | 2.219 |
| MM.1S | SIAIS1222193 | WST | 2.693 |
| MM.1S | SIAIS1222189 | WST | 0.324 |
| MM.1S | SIAIS1222039 | WST | 0.326 |
| MM.1S | SIAIS1221047 (comparative example) | WST | 0.78 |
| MM.1S | SIAIS1222041 | WST | 0.383 |
| MM.1S | SIAIS1222035 | WST | 2.457 |
| MM.1S | SIAIS1221173 | WST | 1.094 |
| MM.1S | SIAIS1221055 | WST | 1.43 |
| MM.1S | SIAIS1221091 | WST | 1.508 |
| MM.1S | SIAIS1220125 (comparative example) | WST | 697 |
| MM.1S | SIAIS1222045 | WST | 3.778 |
| MM.1S | SIAIS1222073 | WST | 1.259 |
| MM.1S | SIAIS1222025 | WST | 3.24 |
| MM.1S | SIAIS1227027 | WST | 0.32 ± 0.09 |
| MM.1S | SIAIS1227077 | WST | 1.93 ± 0.31 |
| MM.1S | SIAIS1221077 | WST | 5.531 |
| MM.1S | SIAIS1221079 (comparative example) | WST | 65.91 |
| MM.1S | SIAIS1221187 | WST | 1.126 |
| MM.1S | SIAIS1221109 (comparative example) | WST | 17.55 |
| MM.1S | SIAIS1224013 | WST | 0.534 |
| MM.1S | SIAIS1222167 | WST | 0.426 |
| MM.1S | SIAIS1221111 | WST | 0.089 |
| MM.1S | SIAIS1222181 | WST | 0.052 |
| MM.1S | SIAIS1222165 | WST | 0.204 |
| MM.1S | SIAIS1222163 | WST | 2.106 |
| MM.1S | SIAIS1221189 | WST | 1.2 |
| MM.1S | SIAIS1221105 | WST | 0.044 |
| MM.1S | SIAIS1222031 | WST | 0.27 |
| MM.1S | SIAIS1224041 | WST | 1.11 |
| MM.1S | SIAIS1224043 | WST | 0.63 |
| MM.1S | SIAIS1222021 | WST | 0.781 |
| MM.1S | SIAIS1221193 | WST | 0.854 |
| MM.1S | SIAIS1221107 (comparative example) | WST | 3.926 |
| MM.1S | SIAIS1222051 | WST | 4.101 |
| MM.1S | SIAIS1222053 | WST | 1.614 |
| MM.1S | SIAIS1222055 | WST | 0.239 |
| MM.1S | SIAIS271187 | WST | 16.98 |

TABLE 2-continued $IC_{50}$ values of the compounds of the present invention in multiple myeloma cells (half inhibitory concentration)

| Cell line | Compounds | Reagent | $IC_{50}$ (nM) |
|---|---|---|---|
| MM.1S | SIAIS1221095 | WST | 2.215 |
| MM.1S | SIAIS1222047 | WST | 13.04 |
| MM.1S | SIAIS1242077 | WST | 0.241 |
| MM.1S | SIAIS1241167 | WST | 1.95 |
| MM.1S | SIAIS1241169 | WST | 0.123 |
| MM.1S | SIAIS1242041 | WST | 0.076 |
| MM.1S | SIAIS1242043 | WST | 0.069 |
| MM.1S | SIAIS1242057 | WST | 0.267 |
| MM.1S | SIAIS1242061 | WST | 0.107 |
| MM.1S | SIAIS1242067 | WST | 17.68 |
| MM.1S | SIAIS1242069 | WST | 2.269 |
| MM.1S | SIAIS1242071 | WST | 2.457 |
| MM.1S | SIAIS1242075 | WST | 0.877 |
| MM.1S | SIAIS1228157 | WST | 0.280 |

2. Studies on the IKZF Degradation of the Compounds of the Present Invention Based on Pomalidomide and Lenalidomide We studied the abundance of IKZF1 and IKZF3 in MM.15S cells which overexpress IKZF1/3 after treatment by the compounds of the present invention (comprising examples 1-68). Firstly, we treated the MM.1S cells with lenalidomide at different concentrations (1, 10, 100, 500, and 1000 nM) for 16 h. After cell lysis, the effects of lenalidomide on IKZF1 and IKZF3 protein contents were detected by western blot (FIG. 1). The results showed that half IKZF1/3 degradation concentration of lenalidomide was around 10-100 nM.

$DC_{50}$ value (the drug concentration required for degrading proteins by 50%, abbreviated as $DC_{50}$) reads method: comparing the gray values of the Western blotting bands for the drug treatment with the gray values of the Western blotting band for the DMSO control, and reading the drug concentration range corresponding to the gray value of the Western blotting bands for the drug treatment which is equal to half of the gray value of the Western blotting band for the DMSO control.

$DC_{50}$ value could also be calculated as follows: using software ImageJ to quantify the gray values of the Western blotting bands for the drug treatment, fitting the relationship curve between drug concentrations and gray values, and from the fitted curve, calculating the drug concentration corresponding to half of the gray value of the Western blotting band for the DMSO control.

The compounds of the present invention (comprising examples 1-68) based on lenalidomide have significant degradation effects on IKZF1 and IKZF3 proteins. As shown in FIG. 1, Compound SIAIS1221053, SIAIS1221105 and SIAIS1221111 showed significant degradation effects below 0.5 nM. Compared with lenalidomide, the compounds of the present invention (comprising examples 1-68) significantly improves both proliferation inhibition and protein degradation activities in MM.1S cells (FIG. 2).

The basic principles, main features and advantages of the present disclosure are shown and described above. Those skilled in the art should understand that the present disclosure is not limited by the foregoing embodiments, and they can make various changes, substitutions and alterations herein without departing from the spirit and scope of the present disclosure. These changes, substitutions and alterations fall within the scope of the present disclosure. The claimed scope of the present disclosure is defined by the appended claims and their equivalents.

The invention claimed is:

1. A compound of Formula (I)

Formula (I)

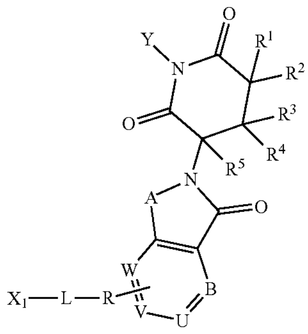

or a salt, or an enantiomer thereof, wherein

Y represents H, D, $C_{1-3}$ alkyl, or deuterated $C_{1-3}$ alkyl; $R^1$, $R^2$, $R^3$, $R^4$, and $R^5$ are the same or different and each independently represent H or D;

A represents $CH_2$, $CD_2$, or C(O);

B, U, V, W are the same or different and independently represent CH, CD, or N, wherein B, U, V, and W are not N at the same time, and when any of B, U, V, and W is attached to R, it is not N; and (1) when R is O or NH, or R represents a bond, L represents a linear or branched $C_{5-40}$ alkylene group, wherein a hydrogen atom of one or more $CH_2$ of the linear or branched $C_{5-40}$ alkylene group is optionally replaced with a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano, or any combination thereof; and $X_1$ represents the Formula —$X_a$—$X_b$, wherein $X_a$ represents O, N($R^6$), C(O)N($R^6$), N($R^6$)C(O), alkynylene, or alkenylene, wherein $R^6$ represents H, $C_{1-3}$ alkyl, or deuterated $C_{1-3}$ alkyl, or $X_a$ represents a bond, and $X_b$ represents $C_{3-6}$ cycloalkyl or $C_{7-11}$ spiro-cycloalkyl, wherein said $C_{3-6}$ cycloalkyl and said $C_{7-11}$ spiro-cycloalkyl are each independently optionally substituted with one or more substituents selected from the group consisting of: D, $C_{1-3}$ alkyl, $C_{1-3}$ alkylamino, amino, deuterated $C_{1-3}$ alkyl, halogenated $C_{1-3}$ alkyl, $C_{1-3}$ alkoxy, deuterated $C_{1-3}$ alkoxy, oxo, halogen, hydroxyl, and cyano, or any combination thereof; or (2) when R is O or NH, or R represents a bond, L represents a linear or branched $C_{1-40}$ alkylene group, wherein the linear or branched $C_{1-40}$ alkylene group is optionally interrupted one or more times by a group selected from the group consisting of: N($R^7$), phenylene, and combinations thereof, wherein $R^7$ represents H, $C_{1-3}$ alkyl or deuterated $C_{1-3}$ alkyl, and a hydrogen atom of one or more $CH_2$ of the linear or branched $C_{1-40}$ alkylene group and the phenylene are each independently optionally substituted with a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano; and $X_1$ represents the Formula —$X_c$—$X_d$, wherein $X_c$ represents O, N($R^8$), C(O)N($R^8$), N($R^8$)C(O), alkynylene, or alkenylene, wherein $R^8$ represents H, $C_{1-3}$ alkyl, or deuterated $C_{1-3}$ alkyl, or $X_c$ represents a bond, and $X_d$ represents $C_{7-15}$ bridged cycloalkyl optionally substituted with from 1 to 10 substituents selected from the group consisting of: D, $C_{1-3}$ alkyl, deuterated $C_{1-3}$ alkyl, $C_{1-3}$ alkoxy, deuterated $C_{1-3}$ alkoxy, halogen, halogenated $C_{1-3}$ alkyl, $C_{1-3}$ alkylamino, amino, hydroxyl, cyano, and oxo; or (3) when R is alkynylene or alkenylene, L represents a linear or branched $C_{1-40}$ alkylene group, wherein the linear or branched $C_{1-40}$ alkylene group is optionally interrupted one or more times by a group selected from the group consisting of: N($R^9$), phenylene and combinations thereof, wherein $R^9$ represents H, $C_{1-3}$ alkyl or deuterated $C_{1-3}$ alkyl, and a hydrogen atom of one or more $CH_2$ of the linear or branched $C_{1-40}$ alkylene group and the phenylene are each independently optionally substituted with a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano; and $X_1$ represents the Formula —$X_e$—$X_f$, wherein $X_e$ represents —N($R^{10}$), C(O)N($R^{10}$), N($R^{10}$)C(O), alkynylene, or alkenylene, wherein $R^{10}$ represents H, $C_{1-3}$ alkyl or deuterated $C_{1-3}$ alkyl, and $X_f$ represents $C_{3-15}$ cycloalkyl, wherein said $C_{3-15}$ cycloalkyl is bicyclic, tricyclic or polycyclic cycloalkyl and is optionally substituted with a substituent selected from the group consisting of: D, $C_{1-3}$ alkyl, deuterated $C_{1-3}$ alkyl, $C_{1-3}$ alkoxy, deuterated $C_{1-3}$ alkoxy, halogen, halogenated $C_{1-3}$ alkyl, hydroxyl, cyano, oxo, optionally substituted phenyl, $C_{1-3}$ alkylamino, and amino, and wherein the optionally substituted phenyl is optionally substituted with a substituent selected from the group consisting of: cyano, halogen, $C_{1-3}$ alkoxy, halogenated $C_{1-3}$ alkyl, $C_{1-3}$ alkyl, hydroxyl, amino, and $C_{1-3}$ alkylamino.

2. The compound of Formula (I) or a salt, an enantiomer thereof as claimed in claim 1, which is also a compound of Formula (Ia) Formula (Ib), Formula (Ic), Formula (Id), or Formula (Ie):

(Ia)

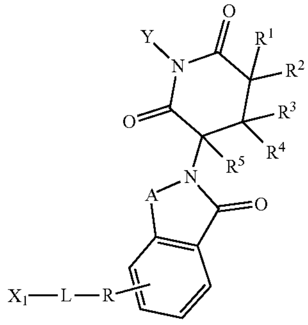

(Ib)

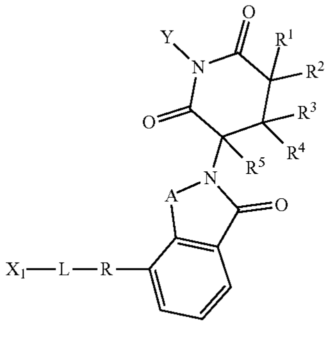

-continued (Ic)

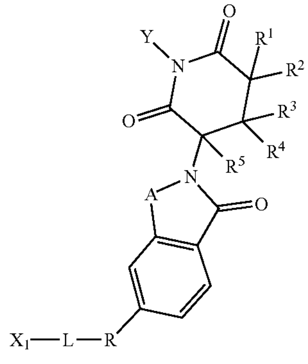

(Id)

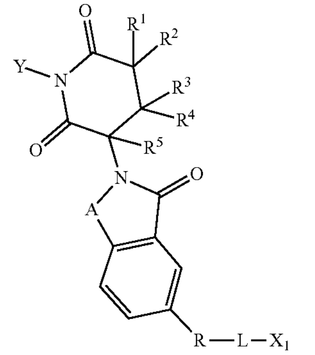

(Ie)

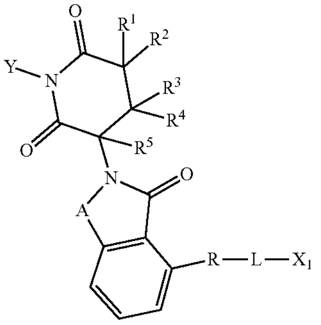

wherein the groups A, R, L, $X_1$, Y, $R^1$, $R^2$, $R^3$, $R^4$, and $R^5$ are as defined in claim 1.

3. The compound of Formula (I) or a salt, or an enantiomer thereof as claimed in claim 1, wherein R is O or NH, or R represents a bond, L represents a linear or branched $C_{5-30}$ alkylene group, wherein the hydrogen atom of one or more $CH_2$ of the linear or branched $C_{5-30}$ alkylene group is optionally replaced with a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano; and $X_1$ represents the Formula —$X_a$—$X_b$, wherein $X_a$ represents O, $N(R^6)$, $C(O)N(R^6)$, $N(R^6)C(O)$, alkynylene, or alkenylene, wherein $R^6$ represents H, $C_{1-3}$ alkyl, or deuterated $C_{1-3}$ alkyl, and $X_b$ represents $C_{3-6}$ cycloalkyl or $C_{7-11}$ spiro-cycloalkyl, wherein said $C_{3-6}$ cycloalkyl and said $C_{7-11}$ spiro-cycloalkyl are each independently optionally substituted with one or more substituents selected from the group consisting of: D, $C_{1-3}$ alkyl, deuterated $C_{1-3}$ alkyl, halogenated $C_{1-3}$ alkyl, $C_{1-3}$ alkoxy, deuterated $C_{1-3}$ alkoxy, $C_{1-3}$ alkylamino, amino, oxo, halogen, hydroxyl, and cyano.

4. The compound of Formula (I) or a salt, or an enantiomer, thereof as claimed in claim 3, wherein L represents one of the following groups:

$—(CH_2)_5—$, $—(CH_2)_6—$, $—(CH_2)_7—$, $—(CH_2)_8—$, $—(CH_2)_9—$, $—(CH_2)_{10}—$, $—(CH_2)_{11}—$, $—(CH_2)_{12}—$, $—(CH_2)_{13}—$, $—(CH_2)_{14}—$, $—(CH_2)_{15}—$, $—(CH_2)_{16}—$, $—(CH_2)_{17}—$, $—(CH_2)_{18}—$, $—(CH_2)_{19}—$, or $—(CH_2)_{20}—$; wherein the hydrogen atom of one or more $CH_2$ of the group is optionally further replaced with a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano; and/or wherein $X_1$ represents the Formula —$X_a$—$X_b$, wherein $X_a$ represents O, $N(R^6)$, $C(O)N(R^6)$, $N(R^6)C(O)$, alkynylene, or alkenylene, wherein $R^6$ represents H, $C_{1-3}$ alkyl, or deuterated $C_{1-3}$ alkyl, and $X_b$ represents one of the following groups: cyclopropyl, cyclobutyl, cyclopentyl, cyclohexyl, spiro[3.3]heptyl, spiro[2.5]octyl, spiro[3.5]nonyl, spiro[4.4]nonyl, spiro[4.5]decyl, or spiro[5.5]undecyl, wherein the groups are optionally further substituted with one or more substituents selected from the group consisting of: D, $C_{1-3}$ alkyl, deuterated $C_{1-3}$ alkyl, halogenated $C_{1-3}$ alkyl, $C_{1-3}$ alkoxy, deuterated $C_{1-3}$ alkoxy, $C_{1-3}$ alkylamino, amino, oxo, halogen, hydroxyl, and cyano.

5. The compound of Formula (I) or a salt, or an enantiomer thereof as claimed in claim 4, wherein $X_b$ represents cyclopropyl, methoxycyclopropyl, cyclobutyl, fluorocyclobutyl, cyclopentyl, fluorocyclopentyl, cyclohexyl, dimethylcyclohexyl, hydroxycyclohexyl, fluorocyclohexyl, spiro[3.3]heptyl, spiro[2.5]octyl, spiro[3.5]nonyl, spiro[4.4]nonyl, spiro[4.5]decyl, or spiro[5.5]undecyl.

6. The compound of Formula (I) or a salt, or an enantiomer thereof as claimed in claim 1, wherein R is O or NH, or R represents a bond, L represents the linear or branched $C_{1-40}$ alkylene group, wherein the linear or branched $C_{1-40}$ alkylene group is optionally interrupted one or more times by a group selected from the group consisting of: $N(R^7)$, phenylene, and combinations thereof, wherein $R^7$ represents H, $C_{1-3}$ alkyl, or deuterated $C_{1-3}$ alkyl, and the hydrogen atom of one or more $CH_2$ of the linear or branched $C_{1-40}$ alkylene and the phenylene are each independently optionally replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano; and $X_1$ represents the Formula —$X_c$—$X_d$, wherein $X_c$ represents O, $N(R^8)$, $C(O)N(R^8)$, $N(R^8)C(O)$, alkynylene, or alkenylene, wherein $R^8$ represents H, $C_{1-3}$ alkyl, or deuterated $C_{1-3}$ alkyl, or $X_c$ represents a bond, and $X_d$ represents $C_{7-15}$ bridged cycloalkyl optionally substituted with from 1 to 10 substituents selected from the group consisting of: D, $C_{1-3}$ alkyl, deuterated $C_{1-3}$ alkyl, $C_{1-3}$ alkoxy, deuterated $C_{1-3}$ alkoxy, halogen, halogenated $C_{1-3}$ alkyl, hydroxyl, cyano, oxo, $C_{1-3}$ alkylamino, amino, and any combination thereof.

7. The compound of Formula (I) or a salt, or an enantiomer thereof as claimed in claim 6, wherein L represents a linear or branched $C_{1-30}$ alkylene, wherein the hydrogen atom of one or more $CH_2$ of the linear or branched $C_{1-30}$ alkylene is optionally replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano.

8. The compound of Formula (I) or a salt, or an enantiomer thereof as claimed in claim 7, wherein L represents one of the following groups:

$-CH_2-$, $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, $-(CH_2)_{11}-$, $-(CH_2)_{12}-$, $-(CH_2)_{13}-$, $-(CH_2)_{14}-$, $-(CH_2)_{15}-$, $-(CH_2)_{16}-$, $-(CH_2)_{17}-$, $-(CH_2)_{18}-$, $-(CH_2)_{19}-$, or $-(CH_2)_{20}-$;

wherein the hydrogen atom of one or more $CH_2$ of the groups is optionally further replaced with a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano.

9. The compound of Formula (I) or a salt, or an enantiomer thereof as claimed in claim 6, wherein L represents a linear or branched $C_{2-40}$ alkylene, wherein the linear or branched $C_{2-40}$ alkylene is interrupted one or more times by a group selected from the group consisting of: $N(R^7)$, phenylene, and combinations thereof, wherein $R^7$ represents H, $C_{1-3}$ alkyl or deuterated $C_{1-3}$ alkyl, and the hydrogen atom of one or more $CH_2$ of the linear or branched $C_{2-40}$ alkylene and the phenylene are each independently optionally replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano.

10. The compound of Formula (I) or a salt, or an enantiomer thereof as claimed in claim 9, wherein L represents one of the following groups: $*-(CH_2)_{n1}-N(R)-(CH_2)_{n2}-$, $*-(CH_2)_{n1}$-phenylene-$(CH_2)_{12}-$, $*-(CH_2)_{n1}-N(R^7)$-phenylene$-(CH_2)_{n2}-$, $*-(CH_2)_{n1}$-phenylene-$N(R^7)-(CH_2)_{n2}-$, $*-(CH_2)_{n1}-N(R^7)-(CH_2)_{n2}$-phenylene-$(CH_2)_{n3}-$, or $*-(CH_2)_{n1}$-phenylene-$(CH_2)_{n2}-N(R^7)-(CH_2)_{n3}-$, wherein the symbol "*" indicates the point of attachment of L to $X_1$, wherein the hydrogen atom of one or more $CH_2$ of the groups and the phenylene are each independently optionally replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano, wherein $R^7$ represents H, $C_{1-3}$ alkyl, or deuterated $C_{1-3}$ alkyl; and n1, n2, n3 each independently represent an integer of 1, 2, 3, 4, 5, 6, 7, 8, 9, 10, 11, 12, 13, 14, 15, 16, 17, 18, 19 or 20.

11. The compound of Formula (I) or a salt, or an enantiomer thereof as claimed in claim 9, wherein L represents $*-(CH_2)_1-N(R^7)-(CH_2)_1-$, $*-(CH_2)_1-N(R^7)-(CH_2)_2-$, $*-(CH_2)_1-N(R^7)-(CH_2)_3-$, $*-(CH_2)_1-N(R^7)-(CH_2)_4-$, $*-(CH_2)_1-N(R^7)-(CH_2)$ 5—, $*-(CH_2)_1-N(R^7)-(CH_2)_6-$, $*-(CH_2)_1-N(R^7)-(CH_2)_7-$, $*-(CH_2)_1-N(R^7)-(CH_2)_8-$, $*-(CH_2)_1-N(R^7)-(CH_2)_9-$, $*-(CH_2)_1-N(R^7)-(CH_2)_{10}-$, $*-(CH_2)_2-N(R^7)-(CH_2)_1-$, $*-(CH_2)_2-N(R^7)-(CH_2)_2-$, $*-(CH_2)_2-N(R^7)-(CH_2)_3-$, $*-(CH_2)_2-N(R^7)-(CH_2)_4-$, $*-(CH_2)_2-N(R^7)-(CH_2)$ 5—, $*-(CH_2)_2-N(R^7)-(CH_2)_6-$, $*-(CH_2)_2-N(R^7)-(CH_2)_7-$, $*-(CH_2)_2-N(R^7)-(CH_2)_8-$, $*-(CH_2)_2-N(R^7)-(CH_2)_9-$, $*-(CH_2)_2-N(R^7)-(CH_2)_{10}-$, $*-(CH_2)_2-N(R^7)-(CH_2)_{11}-$, $*-(CH_2)_2-N(R^7)-(CH_2)_{12}-$, $*-(CH_2)_3-N(R^7)-(CH_2)_1-$, $*-(CH_2)_3-N(R^7)-(CH_2)_2-$, $*-(CH_2)_3-N(R^7)-(CH_2)_3-$, $*-(CH_2)_4-N(R^7)-(CH_2)_1-$, $*-(CH_2)_4-N(R^7)-(CH_2)_2-$, $*-(CH_2)_5-N(R^7)-(CH_2)_1-$, $*-(CH_2)_5-N(R^7)-(CH_2)_2-$, $*-(CH_2)_5-N(R^7)-(CH_2)_3-$, $*-(CH_2)_5-N(R^7)-(CH_2)_4-$, $*-(CH_2)_5-N(R^7)-(CH_2)$ 5—, $*-(CH_2)_6-N(R^7)-(CH_2)_3-$, $*-(CH_2)_7-N(R^7)-(CH_2)_3-$, $*-(CH_2)_8-N(R^7)-(CH_2)_2-$, $*-CH(CH_3)-N(R^7)-(CH_2)_1-$, $*-CH(CH_3)-N(R^7)-(CH_2)_2-$, $*-CH(CH_3)-N(R^7)-(CH_2)_3-$, $*-CH(CH_3)-N(R^7)-(CH_2)_4-$, $*-CH(CH_3)-N(R^7)-(CH_2)$ 5—, $*-CH(CH_3)-N(R^7)-(CH_2)_6-$, $*-CH(CH_3)-N(R^7)-(CH_2)_7-$, $*-CH(CH_3)-N(R^7)-(CH_2)_8-$, $*-CH(CH_3)-N(R^7)-(CH_2)_9-$, $*-CH(CH_3)-N(R^7)-(CH_2)_{10}-$, $*-CH_2$-phenylene-$CH_2-$, $*-CH_2$-phenylene-$(CH_2)_2-$, $*-CH_2$-phenylene-$(CH_2)_3-$, $*-CH_2$-phenylene-$(CH_2)_4-$, $*-CH_2$-phenylene-$(CH_2)$ 5—, $*-CH_2$-phenylene-$(CH_2)_6-$, $*-CH_2$-phenylene-$(CH_2)_7-$, $*-CH_2$-phenylene-$(CH_2)_8-$, $*-(CH_2)_2$-phenylene$-(CH_2)_1-$, $*-(CH_2)_2$-phenylene-$(CH_2)_2-$, $*-(CH_2)_2$-phenylene-$(CH_2)_3-$, $*-(CH_2)_2$-phenylene-$(CH_2)_4-$, $*-(CH_2)_2$-phenylene-$(CH_2)$ 5—, $*-(CH_2)_2$-phenylene-$(CH_2)_6-$, $*-(CH_2)_2$-phenylene-$(CH_2)_8-$, $*-(CH_2)_3$-phenylene-$CH_2-$, $*-(CH_2)_3$-phenylene-$(CH_2)_2-$, $*-(CH_2)_3$-phenylene-$(CH_2)_3-$, $*-(CH_2)_3$-phenylene-$(CH_2)_8-$, $*-(CH_2)_4$-phenylene-$CH_2-$, $*-(CH_2)_4$-phenylene-$(CH_2)_2-$, $*-(CH_2)_4$-phenylene$-(CH_2)_3-$, $*-(CH_2)_4$-phenylene-$(CH_2)_8-$, $*-(CH_2)_5$-phenylene-$(CH_2)_3-$, $*-(CH_2)_5$-phenylene-$(CH_2)_8-$, $*-(CH_2)_6$-phenylene-$(CH_2)_3-$, $*-(CH_2)_6$-phenylene-$(CH_2)_8-$, $*-(CH_2)_7$-phenylene-$(CH_2)_3-$, $*-(CH_2)_7$-phenylene-$(CH_2)_8-$, $*-(CH_2)_8$-phenylene-$CH_2-$, $*-(CH_2)_8$-phenylene-$(CH_2)_2-$, $*-(CH_2)_8$-phenylene-$(CH_2)_3-$, $*-(CH_2)_8$-phenylene-$(CH_2)_4-$, $*-(CH_2)_8$-phenylene-$(CH_2)$ 5—, $*-(CH_2)_8$-phenylene-$(CH_2)_6-$, $*-(CH_2)_8$-phenylene-$(CH_2)_7-$, $*-(CH_2)_8$-phenylene-$(CH_2)_8-$, $*-CH_2-N(R^7)-CH_2$-phenylene-$CH_2-$, $*-CH_2-N(R^7)-CH_2$-phenylene-$(CH_2)_2-$, $*-CH_2-N(R^7)-CH_2$-phenylene$-(CH_2)_3-$, $*-CH_2-N(R^7)-CH_2$-phenylene-$(CH_2)_4-$, $*-CH_2-N(R^1)-CH_2$-phenylene-$(CH_2)$ 5—, $*-CH_2-N(R^7)-CH_2$-phenylene-$(CH_2)_6-$, $*-CH_2-N(R^7)-CH_2$-phenylene-$(CH_2)_7-$, $*-CH_2-N(R^7)-CH_2$-phenylene-$(CH_2)_8-$, $*-CH_2-N(R^7)-(CH_2)_2$-phenylene-$CH_2-$, $*-CH_2-N(R^7)-(CH_2)_2$-phenylene$-(CH_2)_2-$, $*-CH_2-N(R^7)-(CH_2)_2$-phenylene-$(CH_2)_3-$, $*-CH_2-N(R^7)-(CH_2)_2$-phenylene-$(CH_2)_4-$, $*-CH_2-N(R^7)-(CH_2)_2$-phenylene-$(CH_2)$ 5—, $*-CH_2-N(R^7)-(CH_2)_2$-phenylene-$(CH_2)_6-$, $*-CH_2-N(R^7)-(CH_2)_2$-phenylene-$(CH_2)_7-$, $*-CH_2-N(R^7)-(CH_2)_2$-phenylene-$(CH_2)_8-$, $*-(CH_2)_2-N(R^7)-CH_2$-phenylene-$CH_2-$, $*-(CH_2)_2-N(R^7)-CH_2$-phenylene-$(CH_2)_2-$, $*-(CH_2)_2-N(R^7)-CH_2$-phenylene$-(CH_2)_3-$, $*-(CH_2)_2-N(R^7)-CH_2$-phenylene-$(CH_2)_4-$, $*-(CH_2)_2-N(R^7)-CH_2$-phenylene-$(CH_2)$ 5—, $*-(CH_2)_2-N(R^7)-CH_2$-phenylene-$(CH_2)_6-$, $*-(CH_2)_2-N(R^7)-CH_2$-phenylene-$(CH_2)_7-$, $*-(CH_2)_2-N(R^7)-CH_2$-phenylene-$(CH_2)_8-$, $*-(CH_2)_3-N(R^7)-CH_2$-phenylene-$CH_2-$, $*-(CH_2)_3-N(R^7)-CH_2$-phenylene$-(CH_2)_2-$, $*-(CH_2)_3-N(R^7)-CH_2$-phenylene-$(CH_2)_3-$, $*-(CH_2)_3-N(R^7)-CH_2$-phenylene-$(CH_2)_8-$, $*-(CH_2)_4-N(R^7)-CH_2$-phenylene-$CH_2-$,

*—$(CH_2)_4$—N($R^7$)—$CH_2$-phenylene-$(CH_2)_2$—, *—$(CH_2)_4$—N($R^7$)—$CH_2$-phenylene-$(CH_2)_3$—, *—$(CH_2)_4$—N($R^7$)—$CH_2$-phenylene-$(CH_2)_8$—, *—$(CH_2)_5$—N($R^7$)—$CH_2$-phenylene-$(CH_2)_3$—, *—$(CH_2)_5$—N($R^7$)—$CH_2$-phenylene-$(CH_2)_8$—, *—$(CH_2)_6$—N($R^7$)—$CH_2$-phenylene—$(CH_2)_3$—, *—$(CH_2)_6$—N($R^7$)—$CH_2$-phenylene-$(CH_2)_8$—, *—$(CH_2)_7$—N($R^7$)—$CH_2$-phenylene-$(CH_2)_3$—, *—$(CH_2)_7$—N($R^7$)—$CH_2$-phenylene-$(CH_2)_8$—, *—$(CH_2)_8$—N($R^7$)—$CH_2$-phenylene-$CH_2$—, *—$(CH_2)_8$—N($R^7$)—$CH_2$-phenylene-$(CH_2)_2$—, *—$(CH_2)_8$—N($R^7$)—$CH_2$-phenylene-$(CH_2)_3$—, *—$(CH_2)_8$—N($R^7$)—$CH_2$-phenylene-$(CH_2)_4$—, *—$(CH_2)_8$—N($R^7$)—$CH_2$-phenylene-$(CH_2)$ 5—, *—$(CH_2)_8$—N($R^7$)—$CH_2$-phenylene—$(CH_2)_6$—, *—$(CH_2)_8$—N($R^7$)—$CH_2$-phenylene-$(CH_2)_7$—, or *—$(CH_2)_8$—N($R^7$)—$CH_2$-phenylene-$(CH_2)_8$—;

wherein the symbol "*" indicates the point of attachment of L to $X_1$, wherein the hydrogen atom of one or more $CH_2$ of the group and the phenylene are each independently optionally replaced by substituted with a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano, and wherein $R^7$ represents H, $C_{1-3}$ alkyl, or deuterated $C_{1-3}$ alkyl.

12. The compound of Formula (I) or a salt, or an enantiomer thereof as claimed in claim 9, wherein L represents *—$(CH_2)_1$—NH—$(CH_2)_1$—, *—$(CH_2)_1$—NH—$(CH_2)_2$—, *—$(CH_2)_1$—NH—$(CH_2)_3$—, *—$(CH_2)_1$—NH—$(CH_2)_4$—, *—$(CH_2)_1$—NH—$(CH_2)$ 5—, *—$(CH_2)_1$—NH—$(CH_2)_6$—, *—$(CH_2)_1$—NH—$(CH_2)_7$—, *—$(CH_2)_1$—NH—$(CH_2)_8$—, *—$(CH_2)_1$—NH—$(CH_2)_9$—, *—$(CH_2)_1$—NH—$(CH_2)_{10}$—, *—$(CH_2)_2$—NH—$(CH_2)_1$—, *—$(CH_2)_2$—NH—$(CH_2)_2$—, *—$(CH_2)_2$—NH—$(CH_2)_3$—, *—$(CH_2)_2$—NH—$(CH_2)_4$—, *—$(CH_2)_2$—NH—$(CH_2)$ 5—, *—$(CH_2)_2$—NH—$(CH_2)$ 6—, *—$(CH_2)_2$—NH—$(CH_2)_7$—, *—$(CH_2)_2$—NH—$(CH_2)_8$—, *—$(CH_2)_2$—NH—$(CH_2)_9$—, *—$(CH_2)_2$—NH—$(CH_2)_{10}$—, *—$(CH_2)_2$—NH—$(CH_2)_{11}$—, *—$(CH_2)_2$—NH—$(CH_2)_{12}$—, *—$(CH_2)_3$—NH—$(CH_2)_1$—, *—$(CH_2)_3$—NH—$(CH_2)_2$—, *—$(CH_2)_3$—NH—$(CH_2)_3$—, *—$(CH_2)_4$—NH—$(CH_2)_1$—, *—$(CH_2)_4$—NH—$(CH_2)_2$—, *—$(CH_2)_5$—NH—$(CH_2)_1$—, *—$(CH_2)_5$—NH—$(CH_2)_2$—, *—$(CH_2)_5$—NH—$(CH_2)_3$—, *—$(CH_2)_5$—NH—$(CH_2)_4$—, *—$(CH_2)_5$—NH—$(CH_2)$ 5—, *—$(CH_2)_6$—NH—$(CH_2)_3$—, *—$(CH_2)_7$—NH—$(CH_2)_3$—, *—$(CH_2)_8$—NH—$(CH_2)_2$—, *—CH($CH_3$)—NH—$(CH_2)_1$—, *—CH($CH_3$)—NH—$(CH_2)_2$—, *—CH($CH_3$)—NH—$(CH_2)_3$—, *—CH($CH_3$)—NH—$(CH_2)_4$—, *—CH($CH_3$)—NH—$(CH_2)$ 5—, *—CH($CH_3$)—NH—$(CH_2)_6$—, *—CH($CH_3$)—NH—$(CH_2)_7$—, *—CH($CH_3$)—NH—$(CH_2)_8$—, *—CH($CH_3$)—NH—$(CH_2)_9$—, *—CH($CH_3$)—NH—$(CH_2)_{10}$—, *—$CH_2$-phenylene-$CH_2$—, *—$CH_2$-phenylene—$(CH_2)_2$—, *—$CH_2$-phenylene-$(CH_2)_3$—, *—$CH_2$-phenylene-$(CH_2)_4$—, *—$CH_2$-phenylene-$(CH_2)$ 5—, *—$CH_2$-phenylene-$(CH_2)_6$—, *—$CH_2$-phenylene-$(CH_2)_7$—, *—$CH_2$-phenylene-$(CH_2)_8$—, *—$(CH_2)_2$-phenylene—$(CH_2)_1$—, *—$(CH_2)_2$-phenylene-$(CH_2)_2$—, *—$(CH_2)_2$-phenylene-$(CH_2)_3$—, *—$(CH_2)_2$-phenylene-$(CH_2)_4$—, *—$(CH_2)_2$-phenylene-$(CH_2)_5$—, *—$(CH_2)_2$-phenylene-$(CH_2)_6$—, *—$(CH_2)_2$-phenylene-$(CH_2)_8$—, * $(CH_2)_3$-phenylene-$CH_2$—, *—$(CH_2)_3$-phenylene-$(CH_2)_2$—, *—$(CH_2)_3$-phenylene-$(CH_2)_3$—, *—$(CH_2)_3$-phenylene-$(CH_2)_8$—, *—$(CH_2)_4$-phenylene-$CH_2$—, *—$(CH_2)_4$-phenylene-$(CH_2)_2$—, *—$(CH_2)_4$-phenylene—$(CH_2)_3$—, *—$(CH_2)_4$-phenylene-$(CH_2)_8$—, *—$(CH_2)_5$-phenylene-$(CH_2)_3$—, *—$(CH_2)_5$-phenylene-$(CH_2)_8$—, *—$(CH_2)_6$-phenylene-$(CH_2)_3$—, *—$(CH_2)_6$-phenylene-$(CH_2)_8$—, *—$(CH_2)_7$-phenylene-$(CH_2)_3$—, *—$(CH_2)_7$-phenylene-$(CH_2)_8$—, *—$(CH_2)_8$-phenylene-$CH_2$—, *—$(CH_2)_8$-phenylene-$(CH_2)_2$—, *—$(CH_2)_8$-phenylene-$(CH_2)_3$—, *—$(CH_2)_8$-phenylene-$(CH_2)_4$—, *—$(CH_2)_8$-phenylene-$(CH_2)_5$—, *—$(CH_2)_8$-phenylene-$(CH_2)_6$—, *—$(CH_2)_8$-phenylene-$(CH_2)_7$—, *—$(CH_2)_8$-phenylene-$(CH_2)_8$—, *—$CH_2$—NH—$CH_2$-phenylene-$CH_2$—, *—$CH_2$—NH—$CH_2$-phenylene-$(CH_2)_2$—, *—$CH_2$—NH—$CH_2$-phenylene-$(CH_2)_3$—, *—$CH_2$—NH—$CH_2$-phenylene-$(CH_2)_4$—, *—$CH_2$—NH—$CH_2$-phenylene-$(CH_2)_5$—, *—$CH_2$—NH—$CH_2$-phenylene-$(CH_2)_6$—, *—$CH_2$—NH—$CH_2$-phenylene-$(CH_2)_7$—, *—$CH_2$—NH—$CH_2$-phenylene-$(CH_2)_8$—, *—$CH_2$—NH—$(CH_2)_2$-phenylene-$CH_2$—, *—$CH_2$—NH—$(CH_2)_2$-phenylene-$(CH_2)_2$—, *—$CH_2$—NH—$(CH_2)_2$-phenylene-$(CH_2)_3$—, *—$CH_2$—NH—$(CH_2)_2$-phenylene-$(CH_2)_4$—, *—$CH_2$—NH—$(CH_2)_2$-phenylene-$(CH_2)_5$—, *—$CH_2$—NH—$(CH_2)_2$-phenylene-$(CH_2)_6$—, *—$CH_2$—NH—$(CH_2)_2$-phenylene-$(CH_2)_7$—, *—$CH_2$—NH—$(CH_2)_2$-phenylene-$(CH_2)_8$—, *—$(CH_2)_2$—NH—$CH_2$-phenylene-$CH_2$—, *—$(CH_2)_2$—NH—$CH_2$-phenylene—$(CH_2)_2$—, *—$(CH_2)_2$—NH—$CH_2$-phenylene-$(CH_2)_3$—, *—$(CH_2)_2$—NH—$CH_2$-phenylene-$(CH_2)_4$—, *—$(CH_2)_2$—NH—$CH_2$-phenylene-$(CH_2)_5$—, *—$(CH_2)_2$—NH—$CH_2$-phenylene-$(CH_2)_6$—, *—$(CH_2)_2$—NH—$CH_2$-phenylene-$(CH_2)_7$—, *—$(CH_2)_2$—NH—$CH_2$-phenylene-$(CH_2)_8$—, *—$(CH_2)_3$—NH—$CH_2$-phenylene-$CH_2$—, *—$(CH_2)_3$—NH—$CH_2$-phenylene-$(CH_2)_2$—, *—$(CH_2)_3$—NH—$CH_2$-phenylene-$(CH_2)_3$—, *—$(CH_2)_3$—NH—$CH_2$-phenylene-$(CH_2)_8$—, *—$(CH_2)_4$—NH—$CH_2$-phenylene-$CH_2$—, *—$(CH_2)_4$—NH—$CH_2$-phenylene—$(CH_2)_2$—, *—$(CH_2)_4$—NH—$CH_2$-phenylene-$(CH_2)_3$—, *—$(CH_2)_4$—NH—$CH_2$-phenylene-$(CH_2)_8$—, *—$(CH_2)_5$—NH—$CH_2$-phenylene-$(CH_2)_3$—, *—$(CH_2)_5$—NH—$CH_2$-phenylene-$(CH_2)_8$—, *—$(CH_2)_6$—NH—$CH_2$-phenylene-$(CH_2)_3$—, *—$(CH_2)_6$—NH—$CH_2$-phenylene-$(CH_2)_8$—, *—$(CH_2)_7$—NH—$CH_2$-phenylene-$(CH_2)_3$—, *—$(CH_2)_7$—NH—$CH_2$-phenylene-$(CH_2)_8$—, *—$(CH_2)_8$—NH—$CH_2$-phenylene-$CH_2$—, *—$(CH_2)_8$—NH—$CH_2$-phenylene-$(CH_2)_2$—, *—$(CH_2)_8$—NH—$CH_2$-phenylene-$(CH_2)_3$—, *—$(CH_2)_8$—NH—$CH_2$-phenylene-$(CH_2)_4$—, *—$(CH_2)_8$—NH—$CH_2$-phenylene-$(CH_2)_5$—, *—$(CH_2)_8$—NH—$CH_2$-phenylene-$(CH_2)_6$—, *—$(CH_2)_8$—NH—$CH_2$-phenylene-$(CH_2)_7$—, or *—$(CH_2)_8$—NH—$CH_2$-phenylene-$(CH_2)_8$—;

wherein the symbol "*" indicates the point of attachment of L to $X_1$.

13. The compound of Formula (I) or a salt, or an enantiomer thereof as claimed in claim 6, wherein $X_1$ represents the Formula —$X_c$—$X_a$, wherein $X_c$ represents O, N($R^8$), C(O)N($R^8$), N($R^8$)C(O), $C_{2-6}$ alkynylene, or $C_{2-6}$ alkenylene, wherein $R^8$ represents H, $C_{1-3}$ alkyl or deuterated $C_{1-3}$ alkyl, or $X_c$ represents a bond, and $X_d$ represents noradamantanyl, adamantanyl or bicyclo [2.2.1]heptyl, which are optionally substituted with from 1 to 10 substituents selected from the group consisting of: D, $C_{1-3}$ alkyl, deuterated $C_{1-3}$ alkyl, $C_{1-3}$ alkoxy, deuterated $C_{1-3}$ alkoxy, halogen, halogenated $C_{1-3}$ alkyl, hydroxyl, cyano, oxo, $C_{1-3}$ alkylamino, and amino, or any combination thereof.

14. The compound of Formula (I) or a salt, or an enantiomer thereof as claimed in claim 13, wherein $X_d$ represents:

adamantan-1-yl, adamantan-2-yl, adamantan-3-yl, adamantan-4-yl, adamantan-5-yl, adamantan-6-yl, adamantan-7-yl, adamantan-8-yl, adamantan-9-yl, adamantan-10-yl, halogenated adamantanyl, hydroxyadamantanyl, dimethyladamantanyl, bicyclo[2.2.1]heptan-2-yl, bicyclo[2.2.1]heptan-3-yl, bicyclo[2.2.1]heptan-4-yl, bicyclo[2.2.1]heptan-5-yl, bicyclo[2.2.1]heptan-6-yl, 1,7,7-trimethylbicyclo[2.2.1]heptan-2-yl, 1,7,7-trimethylbicyclo[2.2.1]heptan-3-yl, 1,7,7-trimethylbicyclo[2.2.1]heptan-4-yl, 1,7,7-trimethylbicyclo[2.2.1]heptan-5-yl, 1,7,7-trimethylbicyclo[2.2.1]heptan-6-yl,

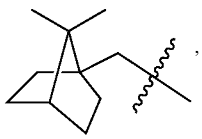
,
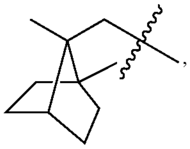
, 7,7-dimethyl-2-oxobicyclo[2.2.1]heptan-1-yl, 7,7-dimethyl-2-oxobicyclo[2.2.1]heptan-3-yl, 7,7-dimethyl-2-oxobicyclo[2.2.1]heptan-4-yl, 7,7-dimethyl-2-oxobicyclo[2.2.1]heptan-5-yl, noradamantanyl, or 7,7-dimethyl-2-oxobicyclo[2.2.1]heptan-6-yl.

15. The compound of Formula (I) or a salt, or an enantiomer thereof as claimed in claim 1, wherein R is $C_{2-6}$ alkynylene or $C_{2-6}$ alkenylene, L represents the linear or branched $C_{1-40}$ alkylene group, wherein the linear or branched $C_{1-40}$ alkylene group is optionally interrupted one or more times by a group selected from the group consisting of: $N(R^9)$, phenylene, and combinations thereof, wherein $R^9$ represents H, $C_{1-3}$ alkyl or deuterated $C_{1-3}$ alkyl, and the hydrogen atom of one or more $CH_2$ of the linear or branched $C_{1-40}$ alkylene and the phenylene are each independently optionally replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano; and $X_1$ represents the Formula $—X_e—X_f$, wherein $X_e$ represents O, $—N(R^{10})$, $C(O)N(R^{10})$, $N(R^{10})C(O)$, alkynylene or alkenylene, wherein $R^{10}$ represents H, $C_{1-3}$ alkyl or deuterated $C_{1-3}$ alkyl, and $X_f$ represents $C_{7-15}$ cycloalkyl, wherein said $C_{7-15}$ cycloalkyl is bicyclic or tricyclic bridged cycloalkyl and is optionally substituted with one or more substituents selected from the group consisting of: D, $C_{1-3}$ alkyl, deuterated $C_{1-3}$ alkyl, $C_{1-3}$ alkoxy, deuterated $C_{1-3}$ alkoxy, halogen, halogenated $C_{1-3}$ alkyl, hydroxyl, cyano, oxo, $C_{1-3}$ alkylamino, amino, and optionally substituted phenyl, wherein the optionally substituted phenyl is optionally substituted with a substituent selected from the group consisting of: cyano, halogen, $C_{1-3}$ alkoxy, halogenated $C_{1-3}$ alkyl, $C_{1-3}$ alkyl, hydroxyl, amino, and $C_{1-3}$ alkylamino.

16. The compound of Formula (I) or a salt, or an enantiomer thereof as claimed in claim 15, wherein L represents the linear or branched $C_{1-40}$ alkylene, wherein the hydrogen atom of one or more $CH_2$ of the linear or branched $C_{1-40}$ alkylene is optionally replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano.

17. The compound of Formula (I) or a salt, or an enantiomer thereof as claimed in claim 16, wherein L represents one of the following groups:

$—CH_2—$, $—(CH_2)_2—$, $—(CH_2)_3—$, $—(CH_2)_4—$, $—(CH_2)_5—$, $—(CH_2)_6—$, $—(CH_2)_7—$, $—(CH_2)_8—$, $—(CH_2)_9—$, $—(CH_2)_{10}—$, $—(CH_2)_{11}—$, $—(CH_2)_{12}—$, $—(CH_2)_{13}—$, $—(CH_2)_{14}—$, $—(CH_2)_{15}—$, $—(CH_2)_{16}—$, $—(CH_2)_{17}—$, $—(CH_2)_{18}—$, $—(CH_2)_{19}—$, or $—(CH_2)_{20}—$;

wherein the hydrogen atom of one or more $CH_2$ of the groups is optionally further replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano.

18. The compound of Formula (I) or a salt, or an enantiomer thereof as claimed in claim 15, wherein L represents a linear or branched $C_{2-40}$ alkylene, wherein the linear or branched $C_{2-40}$ alkylene is interrupted one or more times by a group selected from the group consisting of: $N(R^9)$, phenylene, and combinations thereof, wherein $R^9$ represents H, $C_{1-3}$ alkyl or deuterated $C_{1-3}$ alkyl, and the hydrogen atom of one or more $CH_2$ of the linear or branched $C_{2-40}$ alkylene and the phenylene are each independently optionally replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano.

19. The compound of Formula (I) or a salt, or an enantiomer thereof as claimed in claim 18, wherein L represents one of the following groups: $*—(CH_2)_{n1}—N(R^9)—(CH_2)_{n2}—$, $*—(CH_2)_{n1}$-phenylene-$(CH_2)_{n2}—$, $*—(CH_2)_{n1}—N(R^9)$-phenylene$—(CH_2)_{n2}—$, $*—(CH_2)_{n1}$-phenylene-$N(R^9)—(CH_2)_{n2}—$, $*—(CH_2)_{n1}—N(R^9)—(CH_2)_{n2}$-phenylene-$(CH_2)_{n3}—$, or $*—(CH_2)_{n1}$-phenylene-$(CH_2)_{n2}—N(R^9)—(CH_2)_{n3}—$, wherein the symbol "*" represents the point of attachment of L to $X_1$, wherein the hydrogen atom of one or more $CH_2$ of the groups and the phenylene are each independently optionally replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano, wherein $R^9$ represents H, $C_{1-3}$ alkyl, or deuterated $C_{1-3}$ alkyl; and n1, n2, n3 each independently represent an integer of 1, 2, 3, 4, 5, 6, 7, 8, 9, 10, 11, 12, 13, 14, 15, 16, 17, 18, 19, or 20.

20. The compound of Formula (I) or a salt, or an enantiomer thereof as claimed in claim 18, wherein L represents $*—(CH_2)_1—N(R^7)—(CH_2)_1—$, $*—(CH_2)_1—N(R)—(CH_2)_2—$, $*—(CH_2)_1—N(R^7)—(CH_2)_3—$, $*—(CH_2)_1—N(R^7)—(CH_2)_4—$, $*—(CH_2)_1—N(R^7)—(CH_2)_5—$, $*—(CH_2)_1—N(R^7)—(CH_2)_6—$, $*—(CH_2)_1—N(R^7)—(CH_2)_7—$, $*—(CH_2)_1—N(R^7)—(CH_2)_8—$, $*—(CH_2)_1—N(R^7)—(CH_2)_9—$, $*—(CH_2)_1—N(R^7)—(CH_2)_{10}—$, $*—(CH_2)_2—N(R^7)—(CH_2)_1—$, $*—(CH_2)_2—N(R^7)—(CH_2)_2—$, $*—(CH_2)_2—N(R^7)—(CH_2)_3—$, $*—(CH_2)_2—N(R^7)—(CH_2)_4—$, $*—(CH_2)_2—N(R^7)—(CH_2)_5—$, $*—(CH_2)_2—N(R^7)—(CH_2)_6—$, $*—(CH_2)_2—N(R^7)—(CH_2)_7—$, $*—(CH_2)_2—N(R^7)—(CH_2)_8—$, $*—(CH_2)_2—N(R^7)—(CH_2)_9—$, $*—(CH_2)_2—N(R^7)—(CH_2)_{10}—$, $*—(CH_2)_2—N(R^7)—(CH_2)_{11}—$, $*—(CH_2)_2—N(R^7)—(CH_2)_{12}—$, $*—(CH_2)_3—N(R^7)—(CH_2)_1—$,

*—$(CH_2)_3$—N($R^7$)—$(CH_2)_2$—, *—$(CH_2)_3$—N($R^7$)—$(CH_2)_3$—, *—$(CH_2)_4$—N($R^7$)—$(CH_2)_1$—, *—$(CH_2)_4$—N($R^7$)—$(CH_2)_2$—, *—$(CH_2)_5$—N(R)—$(CH_2)_1$—, *—$(CH_2)_5$—N($R^7$)—$(CH_2)_2$—, *—$(CH_2)_5$—N($R^7$)—$(CH_2)_3$—, *—$(CH_2)_5$—N($R^7$)—$(CH_2)_4$—, *—$(CH_2)_5$—N($R^7$)—$(CH_2)_5$—, *—$(CH_2)_6$—N($R^7$)—$(CH_2)_3$—, * $(CH_2)_7$—N($R^7$)—$(CH_2)_3$—, *—$(CH_2)_8$—N(R)—$(CH_2)_2$—, *—CH($CH_3$)—N(R)—$(CH_2)_1$—, *—CH($CH_3$)—N($R^7$)—$(CH_2)_2$—, *—CH($CH_3$)—N($R^7$)—$(CH_2)_3$—, *—CH($CH_3$)—N($R^7$)—$(CH_2)_4$—, *—CH($CH_3$)—N($R^7$)—$(CH_2)_5$—, *—CH($CH_3$)—N($R^7$)—$(CH_2)_6$—, *—CH($CH_3$)—N($R^7$)—$(CH_2)_7$—, *—CH($CH_3$)—N($R^7$)—$(CH_2)_8$—, *—CH($CH_3$)—N($R^7$)—$(CH_2)_9$—, *—CH($CH_3$)—N($R^7$)—$(CH_2)_{10}$—, *—$CH_2$-phenylene-$CH_2$—, *—$CH_2$-phenylene-$(CH_2)_2$ —, *—$CH_2$-phenylene-$(CH_2)_3$—, *—$CH_2$-phenylene-$(CH_2)_4$—, *—$CH_2$-phenylene-$(CH_2)_5$—, *—$CH_2$-phenylene-$(CH_2)_6$—, *—$CH_2$-phenylene-$(CH_2)_7$—, *—$CH_2$-phenylene-$(CH_2)_8$—, *—$(CH_2)_2$-phenylene—$(CH_2)_1$—, *—$(CH_2)_2$-phenylene-$(CH_2)_2$—, *—$(CH_2)_2$-phenylene-$(CH_2)_3$—, *—$(CH_2)_2$-phenylene-$(CH_2)_4$—, *—$(CH_2)_2$-phenylene-$(CH_2)_5$—, *—$(CH_2)_2$-phenylene-$(CH_2)_6$—, *—$(CH_2)_2$-phenylene-$(CH_2)_8$—, * $(CH_2)_3$-phenylene-$CH_2$—, *—$(CH_2)_3$-phenylene-$(CH_2)_2$—, *—$(CH_2)_3$-phenylene-$(CH_2)_3$—, *—$(CH_2)_3$-phenylene-$(CH_2)_8$—, *—$(CH_2)_4$-phenylene-$CH_2$—, *—$(CH_2)_4$-phenylene-$(CH_2)_2$—, *—$(CH_2)_4$-phenylene—$(CH_2)_3$—, *—$(CH_2)_4$-phenylene-$(CH_2)_8$—, *—$(CH_2)_5$-phenylene-$(CH_2)_3$—, *—$(CH_2)_5$-phenylene-$(CH_2)_8$—, *—$(CH_2)_6$-phenylene-$(CH_2)_3$—, *—$(CH_2)_6$-phenylene-$(CH_2)_8$—, *—$(CH_2)_7$-phenylene-$(CH_2)_3$—, * $(CH_2)_7$-phenylene-$(CH_2)_8$—, *—$(CH_2)_8$-phenylene-$CH_2$—, *—$(CH_2)_8$-phenylene-$(CH_2)_2$—, *—$(CH_2)_8$-phenylene-$(CH_2)_3$—, *—$(CH_2)_8$-phenylene-$(CH_2)_4$— *—$(CH_2)_8$-phenylene-$(CH_2)_5$—, *—$(CH_2)_8$-phenylene-$(CH_2)_6$—, *—$(CH_2)_8$-phenylene-$(CH_2)_7$—, *—$(CH_2)_8$-phenylene-$(CH_2)_8$—, *—$CH_2$—N($R^7$)—$CH_2$-phenylene-$CH_2$—, *—$CH_2$—N($R^7$)—$CH_2$-phenylene-$(CH_2)_2$—, *—$CH_2$—N($R^7$)—$CH_2$-phenylene—$(CH_2)_3$—, *—$CH_2$—N($R^7$)—$CH_2$-phenylene-$(CH_2)_4$—, *—$CH_2$—N($R^7$)—$CH_2$-phenylene-$(CH_2)_5$—, *—$CH_2$—N($R^7$)—$CH_2$-phenylene-$(CH_2)_6$—, *—$CH_2$—N($R^7$)—$CH_2$-phenylene-$(CH_2)_7$—, *—$CH_2$—N($R^7$)—$CH_2$-phenylene-$(CH_2)_8$—, *—$CH_2$—N($R^7$)—$(CH_2)_2$-phenylene-$CH_2$—, *—$CH_2$—N($R^7$)—$(CH_2)_2$-phenylene—$(CH_2)_2$—, *—$CH_2$—N($R^7$)—$(CH_2)_2$-phenylene-$(CH_2)_3$—, *—$CH_2$—N($R^7$)—$(CH_2)_2$-phenylene-$(CH_2)_4$—, *—$CH_2$—N($R^7$)—$(CH_2)_2$-phenylene-$(CH_2)_5$—, *—$CH_2$—N($R^1$)—$(CH_2)_2$-phenylene-$(CH_2)_6$—, *—$CH_2$—N($R^7$)—$(CH_2)_2$-phenylene-$(CH_2)_7$—, *—$CH_2$—N($R^7$)—$(CH_2)_2$-phenylene-$(CH_2)_8$—, *—$(CH_2)_2$—N($R^7$)—$CH_2$-phenylene-$CH_2$—, *—$(CH_2)_2$—N($R^7$)—$CH_2$-phenylene-$(CH_2)_2$—, *—$(CH_2)_2$—N($R^7$)—$CH_2$-phenylene—$(CH_2)_3$—, *—$(CH_2)_2$—N($R^7$)—$CH_2$-phenylene-$(CH_2)_4$—, *—$(CH_2)_2$—N($R^7$)—$CH_2$-phenylene-$(CH_2)_5$—, * $(CH_2)_2$—N($R^7$)—$CH_2$-phenylene-$(CH_2)_6$—, *—$(CH_2)_2$—N($R^1$)—$CH_2$-phenylene-$(CH_2)_7$—, *—$(CH_2)_2$—N($R^7$)—$CH_2$-phenylene-$(CH_2)_8$—, *—$(CH_2)_3$—N($R^7$)—$CH_2$-phenylene-$CH_2$—, *—$(CH_2)_3$—N($R^7$)—$CH_2$-phenylene—$(CH_2)_2$—, *—$(CH_2)_3$—N($R^7$)—$CH_2$-phenylene-$(CH_2)_3$—, *—$(CH_2)_3$—N($R^7$)—$CH_2$-phenylene-$(CH_2)_8$—, *—$(CH_2)_4$—N($R^7$)—$CH_2$-phenylene-$CH_2$—, *—$(CH_2)_4$—N($R^7$)—$CH_2$-phenylene-$(CH_2)_2$—, *—$(CH_2)_4$—N($R^7$)—$CH_2$-phenylene-$(CH_2)_3$—, *—$(CH_2)_4$—N($R^7$)—$CH_2$-phenylene-$(CH_2)_8$—, *—$(CH_2)_5$—N($R^7$)—$CH_2$-phenylene-$(CH_2)_3$—, *—$(CH_2)_5$—N($R^7$)—$CH_2$-phenylene-$(CH_2)_8$—, *—$(CH_2)_6$—N($R^7$)—$CH_2$-phenylene—$(CH_2)_3$—, *—$(CH_2)_6$—N($R^7$)—$CH_2$-phenylene-$(CH_2)_8$—, *—$(CH_2)_7$—N($R^7$)—$CH_2$-phenylene-$(CH_2)_3$—, *—$(CH_2)_7$—N($R^7$)—$CH_2$-phenylene-$(CH_2)_8$—, *—$(CH_2)_8$—N($R^1$)—$CH_2$-phenylene-$CH_2$—, *—$(CH_2)_8$—N($R^7$)—$CH_2$-phenylene-$(CH_2)_2$—, *—$(CH_2)_8$—N($R^7$)—$CH_2$-phenylene-$(CH_2)_3$—, *—$(CH_2)_8$—N($R^7$)—$CH_2$-phenylene-$(CH_2)_4$—, *—$(CH_2)_8$—N($R^7$)—$CH_2$-phenylene-$(CH_2)_5$—, *—$(CH_2)_8$—N($R^7$)—$CH_2$-phenylene—$(CH_2)_6$—, *—$(CH_2)_8$—N($R^7$)—$CH_2$-phenylene-$(CH_2)_7$—, or *—$(CH_2)_8$—N($R^7$)—$CH_2$-phenylene-$(CH_2)_8$—;

wherein the symbol "*" indicates the point of attachment of L to $X_1$, wherein the hydrogen atom of one or more $CH_2$ of the group and the phenylene are each independently optionally replaced by a substituent selected from the group consisting of: D, $C_{1-3}$ alkyl, deuterated $C_{1-3}$ alkyl, $C_{1-3}$ alkoxy, $C_{3-6}$ cycloalkyl, halogen, halogenated $C_{1-3}$ alkyl, hydroxyl, and cyano, wherein $R^7$ represents H, $C_{1-3}$ alkyl, or deuterated $C_{1-3}$ alkyl.

21. The compound of Formula (I) or a salt, or an enantiomer thereof as claimed in claim 18, wherein L represents *—$(CH_2)_1$—NH—$(CH_2)_1$—, *—$(CH_2)_1$—NH—$(CH_2)_2$—, *—$(CH_2)_1$—NH—$(CH_2)_3$—, *—$(CH_2)_1$—NH—$(CH_2)_4$—, *—$(CH_2)_1$—NH—$(CH_2)_5$—, *—$(CH_2)_1$—NH—$(CH_2)_6$—, *—$(CH_2)_1$—NH—$(CH_2)_7$—, *—$(CH_2)_1$—NH—$(CH_2)_8$—, *—$(CH_2)_1$—NH—$(CH_2)_9$—, *—$(CH_2)_1$—NH—$(CH_2)_{10}$—, *—$(CH_2)_2$—NH—$(CH_2)_1$—, *—$(CH_2)_2$—NH—$(CH_2)_2$—, *—$(CH_2)_2$—NH—$(CH_2)_3$—, *—$(CH_2)_2$—NH—$(CH_2)_4$—, *—$(CH_2)_2$—NH—$(CH_2)_5$—, *—$(CH_2)_2$—NH—$(CH_2)_6$—, $(CH_2)_2$—NH—$(CH_2)_7$—, *—$(CH_2)_2$—NH—$(CH_2)_8$—, *—$(CH_2)_2$—NH—$(CH_2)_9$—, *—$(CH_2)_2$—NH—$(CH_2)_{10}$—, *—$(CH_2)_2$—NH—$(CH_2)_{11}$—, *—$(CH_2)_2$—NH—$(CH_2)_{12}$—, *—$(CH_2)_3$—NH—$(CH_2)_1$—, *—$(CH_2)_3$—NH—$(CH_2)_2$—, *—$(CH_2)_3$—NH—$(CH_2)_3$—, *—$(CH_2)_4$—NH—$(CH_2)_1$—, *—$(CH_2)_4$—NH—$(CH_2)_2$—, *—$(CH_2)_5$—NH—$(CH_2)_1$—, * $(CH_2)_5$—NH—$(CH_2)_2$—, *—$(CH_2)_5$ —NH—$(CH_2)_3$—, *—$(CH_2)_5$—NH—$(CH_2)_4$—, *—$(CH_2)_5$—NH—$(CH_2)_5$—, *—$(CH_2)_6$—NH—$(CH_2)_3$—, *—$(CH_2)_7$—NH—$(CH_2)_3$—, *—$(CH_2)_8$—NH—$(CH_2)_2$—, *—CH($CH_3$)—NH—$(CH_2)_1$—, *—CH($CH_3$)—NH—$(CH_2)_2$—, *—CH($CH_3$)—NH—$(CH_2)_3$—, *—CH($CH_3$)—NH—$(CH_2)_4$—, *—CH($CH_3$)—NH—$(CH_2)_5$—, *—CH($CH_3$)—NH—$(CH_2)_6$—, *—CH($CH_3$)—NH—$(CH_2)_7$—, *—CH($CH_3$)—NH—$(CH_2)_8$—, *—CH($CH_3$)—NH—$(CH_2)_9$—, *—CH($CH_3$)—NH—$(CH_2)_{10}$—, *—$CH_2$-phenylene-$CH_2$—, *—$CH_2$-phenylene—$(CH_2)_2$—, *—$CH_2$-phenylene-$(CH_2)_3$—, *—$CH_2$-phenylene-$(CH_2)_4$—, *—$CH_2$-phenylene-$(CH_2)_5$—, *—$CH_2$-phenylene-$(CH_2)_6$—, *—$CH_2$-phenylene-$(CH_2)_7$—, *—$CH_2$-phenylene-$(CH_2)_8$—, *—$(CH_2)_2$-phenylene—$(CH_2)_1$—, *—$(CH_2)_2$-phenylene-$(CH_2)_2$—, *—$(CH_2)_2$-phenylene-$(CH_2)_3$—, *—$(CH_2)_2$-phenylene-$(CH_2)_4$—, *—$(CH_2)_2$-phenylene-$(CH_2)_5$—, *—$(CH_2)_2$-phenylene-$(CH_2)_6$—, *—$(CH_2)_2$-phenylene-$(CH_2)_8$—, *—$(CH_2)_3$-phenylene-$CH_2$—, *—$(CH_2)_3$-phenylene-$(CH_2)_2$—, *—$(CH_2)_3$-phenylene-$(CH_2)_3$—, *—$(CH_2)_3$-phenylene-$(CH_2)_8$—, *—$(CH_2)_4$-phenylene-$CH_2$—, *—$(CH_2)_4$-phenylene- $(CH_2)_2$—, *—$(CH_2)_4$-phenylene—$(CH_2)_3$—, *—$(CH_2)_4$-phenylene-$(CH_2)_8$—, *—$(CH_2)_5$-phenylene-$(CH_2)_3$—, *—$(CH_2)_5$-phenylene-$(CH_2)_8$—, *—$(CH_2)_6$-phenylene-$(CH_2)_3$—, *—$(CH_2)_6$-phenylene-$(CH_2)_8$—, *—$(CH_2)_7$-phenylene-$(CH_2)_3$—, *—$(CH_2)_7$-phenylene-$(CH_2)_8$—, *—$(CH_2)_8$-phenylene-$CH_2$—, *—$(CH_2)_8$-phenylene-$(CH_2)_2$—, *—$(CH_2)_8$-phenylene-$(CH_2)_3$—, *—$(CH_2)_8$-phenylene-$(CH_2)_4$—, *—$(CH_2)_8$-phenylene-$(CH_2)_5$—, *—$(CH_2)_8$-phenylene-$(CH_2)_6$—, *—$(CH_2)_8$-phenylene-$(CH_2)_7$—, *—$(CH_2)_8$-phenylene-$(CH_2)_8$—, *—$CH_2$—NH—$CH_2$-phenylene-$CH_2$—, *—$CH_2$—NH—$CH_2$-phenylene-$(CH_2)_2$—, *—$CH_2$—NH—$CH_2$-phenylene-$(CH_2)_3$—, *—$CH_2$—NH—$CH_2$-phenylene-$(CH_2)_4$—, *—$CH_2$—NH—$CH_2$-phenylene-$(CH_2)_5$—, *—$CH_2$—NH—$CH_2$-phenylene-$(CH_2)_6$—, *—$CH_2$—NH—$CH_2$-phenylene-$(CH_2)_7$—, *—$CH_2$—NH—$CH_2$-phenylene-$(CH_2)_8$—, *—$CH_2$—NH—$(CH_2)_2$-phenylene-$CH_2$—, *—$CH_2$—NH—$(CH_2)_2$-phenylene-$(CH_2)_2$—, *—$CH_2$—NH—$(CH_2)_2$-phenylene-$(CH_2)_3$—, *—$CH_2$—NH—$(CH_2)_2$-phenylene-$(CH_2)_4$—, *—$CH_2$—NH—$(CH_2)_2$-phenylene-$(CH_2)_5$—, *—$CH_2$—NH—$(CH_2)_2$-phenylene-$(CH_2)_6$—, *—$CH_2$—NH—$(CH_2)_2$-phenylene-$(CH_2)_7$—, *—$CH_2$—NH—$(CH_2)_2$-phenylene-$(CH_2)_8$—, *—$(CH_2)_2$—NH—$CH_2$-phenylene-$CH_2$—, *—$(CH_2)_2$—NH—$CH_2$-phenylene—$(CH_2)_2$—, *—$(CH_2)_2$—NH—$CH_2$-phenylene-$(CH_2)_3$—, *—$(CH_2)_2$—NH—$CH_2$-phenylene-$(CH_2)_4$—, *—$(CH_2)_2$—NH—$CH_2$-phenylene-$(CH_2)_5$—, *—$(CH_2)_2$—NH—$CH_2$-phenylene-$(CH_2)_6$—, *—$(CH_2)_2$—NH—$CH_2$-phenylene-$(CH_2)_7$—, *—$(CH_2)_2$—NH—$CH_2$-phenylene-$(CH_2)_8$—, *—$(CH_2)_3$—NH—$CH_2$-phenylene-$CH_2$—, *—$(CH_2)_3$—NH—$CH_2$-phenylene-$(CH_2)_2$—, *—$(CH_2)_3$—NH—$CH_2$-phenylene-$(CH_2)_3$—, *—$(CH_2)_3$—NH—$CH_2$-phenylene-$(CH_2)_8$—, *—$(CH_2)_4$—NH—$CH_2$-phenylene-$CH_2$—, *—$(CH_2)_4$—NH—$CH_2$-phenylene—$(CH_2)_2$—, *—$(CH_2)_4$—NH—$CH_2$-phenylene-$(CH_2)_3$—, *—$(CH_2)_4$—NH—$CH_2$-phenylene-$(CH_2)_8$—, *—$(CH_2)_5$—NH—$CH_2$-phenylene-$(CH_2)_3$—, *—$(CH_2)_5$—NH—$CH_2$-phenylene-$(CH_2)_8$—, *—$(CH_2)_6$—NH—$CH_2$-phenylene-$(CH_2)_3$—, *—$(CH_2)_6$—NH—$CH_2$-phenylene-$(CH_2)_8$—, *—$(CH_2)_7$—NH—$CH_2$-phenylene-$(CH_2)_3$—, *—$(CH_2)_7$—NH—$CH_2$-phenylene-$(CH_2)_8$—, *—$(CH_2)_8$—NH—$CH_2$-phenylene-$CH_2$—, *—$(CH_2)_8$—NH—$CH_2$-phenylene-$(CH_2)_2$—, *—$(CH_2)_8$—NH—$CH_2$-phenylene-$(CH_2)_3$—, *—$(CH_2)_8$—NH—$CH_2$-phenylene-$(CH_2)_4$—, *—$(CH_2)_8$—NH—$CH_2$-phenylene-$(CH_2)_5$—, *—$(CH_2)_8$—NH—$CH_2$-phenylene-$(CH_2)_6$—, *—$(CH_2)_8$—NH—$CH_2$-phenylene-$(CH_2)_7$—, or *—$(CH_2)_8$—NH—$CH_2$-phenylene-$(CH_2)_8$—;

wherein the symbol "*" indicates the point of attachment of L to $X_1$.

22. The compound of Formula (I) or a salt, or an enantiomer thereof as claimed in claim 1, wherein $X_1$ represents the Formula —$X_e$—$X_f$, wherein $X_e$ represents Q, N($R^{10}$), C(O)N($R^{10}$), N($R^{10}$)C(O), alkynylene, or alkenylene, wherein $R^{10}$ represents H, $C_{1-3}$ alkyl, or deuterated $C_{1-3}$ alkyl, and $X_f$ represents one of the following groups:

spiro[3.3]heptyl, spiro[2.5]octyl, spiro[3.5]nonyl, spiro[4.4]nonyl, spiro[4.5]decyl, spiro[5.5]undecyl, adamantanyl, noradamantanyl, or bicyclo[2.2.1]heptyl; wherein the groups are optionally substituted with one or more substituents selected from the group consisting of: D, $C_{1-3}$ alkyl, deuterated $C_{1-3}$ alkyl, $C_{1-3}$ alkoxy, deuterated $C_{1-3}$ alkoxy, halogen, halogenated $C_{1-3}$ alkyl, hydroxyl, cyano, oxo, optionally substituted phenyl, $C_{1-3}$ alkylamino, and amino, wherein the optionally substituted phenyl is optionally substituted with a substituent selected from the group consisting of:

cyano, halogen, $C_{1-3}$ alkoxy, halogenated $C_{1-3}$ alkyl, $C_{1-3}$ alkyl, hydroxyl, amino, and $C_{1-3}$ alkylamino.

23. The compound of Formula (I) or a salt, or an enantiomer thereof as claimed in claim 22, wherein $X_f$ represents the following groups:

spiro[3.3]heptyl, spiro[2.5]octyl, spiro[3.5]nonyl, spiro[4.4]nonyl, spiro[4.5]decyl, spiro[5.5]undecyl, adamantan-1-yl, adamantan-2-yl, adamantan-3-yl, adamantan-4-yl, adamantan-5-yl, adamantan-6-yl, adamantan-7-yl, adamantan-8-yl, adamantan-9-yl, adamantan-10-yl, halogenated adamantanyl, hydroxyadamantanyl, dimethyladamantanyl, noradamantanyl, bicyclo[2.2.1]heptan-2-yl, bicyclo[2.2.1]heptan-3-yl, bicyclo[2.2.1]heptan-4-yl, bicyclo[2.2.1]heptan-5-yl, bicyclo[2.2.1]heptan-6-yl, 1,7,7-trimethylbicyclo[2.2.1]heptan-2-yl, 1,7,7-trimethylbicyclo[2.2.1]heptan-3-yl, 1,7,7-trimethylbicyclo[2.2.1]heptan-4-yl, 1,7,7-trimethylbicyclo[2.2.1]heptan-5-yl, 1,7,7-trimethylbicyclo[2.2.1]heptan-6-yl,

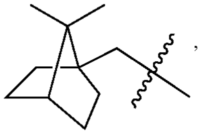
,
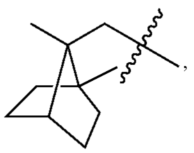
, 7,7-dimethyl-2-oxobicyclo[2.2.1]heptan-1-yl, 7,7-dimethyl-2-oxobicyclo[2.2.1]heptan-3-yl, 7,7-dimethyl-2-oxobicyclo[2.2.1]heptan-4-yl, 7,7-dimethyl-2-oxobicyclo[2.2.1]heptan-5-yl, or 7,7-dimethyl-2-oxobicyclo[2.2.1]heptan-6-yl.

24. The compound of Formula (I) or a salt, or an enantiomer thereof as claimed in claim 1, wherein the compound is selected from:

4-((7-((adamantan-1-yl)amino)heptyl)oxy)-2-(2,6-dioxopiperidin-3-yl)isoindoline-1,3-dione;

5-((7-((adamantan-1-yl)amino)heptyl)oxy)-2-(2,6-dioxopiperidin-3-yl)isoindoline-1,3-dione;

3-(4-((7-(cyclohexylamino)heptyl)oxy)-1-oxoisoindolin-2-yl)piperidine-2,6-dione;

3-(1-oxo-4-((7-(spiro[3.3]heptan-2-ylamino)heptyl)oxy)isoindolin-2-yl)piperidine-2,6-dione;

3-(4-((5-((adamantan-1-yl)amino)pentyl)oxy)-1-oxoisoindolin-2-yl)piperidine-2,6-dione;

3-(4-((6-((adamantan-1-yl)amino)hexyl)oxy)-1-oxoisoindolin-2-yl)piperidine-2,6-dione;

3-(4-((7-((adamantan-1-yl)amino)heptyl)oxy)-1-oxoisoindolin-2-yl)piperidine-2,6-dione;

3-(4-((8-((adamantan-1-yl)amino)octyl)oxy)-1-oxoisoindolin-2-yl)piperidine-2,6-dione;

3-(4-((7-((adamantan-1-yl)(methyl)amino)heptyl)oxy)-1-oxoisoindolin-2-yl)piperidine-2,6-dione;

3-(4-((6-(((adamantan-1-yl)methyl)amino)hexyl)oxy)-1-oxoisoindolin-2-yl)piperidine-2,6-dione;

3-(4-((4-(((adamantan-1-yl)amino)methyl)benzyl)oxy)-1-oxoisoindolin-2-yl)piperidine-2,6-dione;

3-(1-oxo-4-((7-(((1R,2S,4R)-1,7,7-trimethylbicyclo[2.2.1]heptan-2-yl)amino)heptyl)oxy)isoindolin-2-yl)piperidine-2,6-dione;
4-((5-((adamantan-1-yl)amino)pentyl)amino)-2-(2,6-dioxopiperidin-3-yl)isoindoline-1,3-dione;
4-((6-((adamantan-1-yl)amino)hexyl)amino)-2-(2,6-dioxopiperidin-3-yl)isoindoline-1,3-dione;
4-((7-((adamantan-1-yl)amino)heptyl)amino)-2-(2,6-dioxopiperidin-3-yl)isoindoline-1,3-dione;
4-((6-(((adamantan-1-yl)methyl)amino)hexyl)amino)-2-(2,6-dioxopiperidin-3-yl)isoindoline-1,3-dione;
4-((6-((1-(adamantan-1-yl)ethyl)amino)hexyl)amino)-2-(2,6-dioxopiperidin-3-yl)isoindoline-1,3-dione;
4-((7-(adamantan-1-yl)ethyl)amino)heptyl)amino)-2-(2,6-dioxopiperidin-3-yl)isoindoline-1,3-dione;
4-((4-(((adamantan-1-yl)amino)methyl)benzyl)amino)-2-(2,6-dioxopiperidin-3-yl)isoindoline-1,3-dione;
2-(2,6-dioxopiperidin-3-yl)-4-((7-(((1R,2S,4R)-1,7,7-trimethylbicyclo[2.2.1]heptan-2-yl)amino)heptyl)amino)isoindoline-1,3-dione;
2-(2,6-dioxopiperidin-3-yl)-4-((4-((((1R,2S,4R)-1,7,7-trimethylbicyclo[2.2.1]heptan-2-yl)amino)methyl)benzyl)amino)isoindoline-1,3-dione;
5-((7-((adamantan-1-yl)amino)heptyl)amino)-2-(2,6-dioxopiperidin-3-yl)isoindoline-1,3-dione;
4-((7-(cyclohexylamino)heptyl)amino)-2-(2,6-dioxopiperidin-3-yl)isoindoline-1,3-dione;
2-(2,6-dioxopiperidin-3-yl)-4-((7-(spiro[3.3]heptan-2-ylamino)heptyl)amino)isoindoline-1,3-dione;
3-(4-((7-((adamantan-1-yl)amino)heptyl)amino)-1-oxoisoindolin-2-yl)piperidine-2,6-dione;
3-(4-((8-((adamantan-1-yl)amino)octyl)amino)-1-oxoisoindolin-2-yl)piperidine-2,6-dione;
3-(4-((6-(((adamantan-1-yl)methyl)amino)hexyl)amino)-1-oxoisoindolin-2-yl)piperidine-2,6-dione;
3-(4-((4-(((adamantan-1-yl)amino)methyl)benzyl)amino)-1-oxoisoindolin-2-yl)piperidine-2,6-dione;
3-(4-((4-(2-((adamantan-1-yl)amino)ethyl)benzyl)amino)-1-oxoisoindolin-2-yl)piperidine-2,6-dione;
3-(4-((4-(3-((adamantan-1-yl)amino)propyl)benzyl)amino)-1-oxoisoindolin-2-yl)piperidine-2,6-dione;
3-(1-oxo-4-((4-((((1R,2S,4R)-1,7,7-trimethylbicyclo[2.2.1]heptan-2-yl)amino)methyl)benzyl)amino)isoindolin-2-yl)piperidine-2,6-dione;
3-(4-(6-((adamantan-1-yl)amino)hexyl)-1-oxoisoindolin-2-yl)piperidine-2,6-dione;
3-(4-(7-((adamantan-1-yl)amino)heptyl)-1-oxoisoindolin-2-yl)piperidine-2,6-dione;
4-(8-((adamantan-1-yl)amino)octyl)-2-(2,6-dioxopiperidin-3-yl)isoindoline-1,3-dione;
3-(1-oxo-4-(7-(spiro[3.3]heptan-2-ylamino)heptyl)isoindolin-2-yl)piperidine-2,6-dione;
3-(4-(8-(cyclohexylamino) octyl)-1-oxoisoindolin-2-yl)piperidine-2,6-dione;
3-(4-(8-((adamantan-1-yl)(methyl)amino)octyl)-1-oxoisoindolin-2-yl)piperidine-2,6-dione;
3-(4-(8-((adamantan-1-yl)amino)octyl)-1-oxoisoindolin-2-yl)piperidine-2,6-dione;
3-(4-(7-(((adamantan-1-yl)methyl)amino)heptyl)-1-oxoisoindolin-2-yl)piperidine-2,6-dione;
3-(4-(4-(((adamantan-1-yl)amino)methyl)phenethyl)-1-oxoisoindolin-2-yl)piperidine-2,6-dione;
3-(4-(4-((((adamantan-1-yl)methyl)amino)methyl)phenethyl)-1-oxoisoindolin-2-yl)piperidine-2,6-dione;
3-(1-oxo-4-(8-(((1R,2S,4R)-1,7,7-trimethylbicyclo[2.2.1]heptan-2-yl)amino)octyl)isoindolin-2-yl)piperidine-2,6-dione;
3-(1-oxo-4-(4-((((1R,2S,4R)-1,7,7-trimethylbicyclo[2.2.1]heptan-2-yl)amino)methyl)phenethyl)isoindolin-2-yl)piperidine-2,6-dione;
3-(5-(8-((adamantan-1-yl)amino)octyl)-1-oxoisoindolin-2-yl)piperidine-2,6-dione;
4-(8-((adamantan-1-yl)amino) oct-1-yn-1-yl)-2-(2,6-dioxopiperidin-3-yl)isoindoline-1,3-dione;
3-(1-oxo-4-(8-(spiro[3.3]heptan-2-ylamino) oct-1-yn-1-yl)isoindolin-2-yl)piperidine-2,6-dione;
3-(4-(9-morpholinone-1-yn-1-yl)-1-oxoisoindolin-2-yl)piperidine-2,6-dione; nonynyl;
3-(4-(6-((adamantan-1-yl)amino) hex-1-yn-1-yl)-1-oxoisoindolin-2-yl)piperidine-2,6-dione;
3-(4-(7-((adamantan-1-yl)amino) hept-1-yn-1-yl)-1-oxoisoindolin-2-yl)piperidine-2,6-dione;
3-(4-(8-((adamantan-1-yl)amino) oct-1-yn-1-yl)-1-oxoisoindolin-2-yl)piperidine-2,6-dione;
3-(4-(9-((adamantan-1-yl)amino) non-1-yn-1-yl)-1-oxoisoindolin-2-yl)piperidine-2,6-dione;
3-(1-oxo-4-(8-(((1R,2S,4R)-1,7,7-trimethylbicyclo[2.2.1]heptan-2-yl)amino) oct-1-yn-1-yl)isoindolin-2-yl)piperidine-2,6-dione;
3-(5-(8-((adamantan-1-yl)amino) oct-1-yn-1-yl)-1-oxoisoindolin-2-yl)piperidine-2,6-dione;
2-(2,6-dioxopiperidin-3-yl)-4-((7-((hexahydro-2,5-methanopentalen-3a (1H)-yl)amino)heptyl) oxy)isoindoline-1,3-dione;
3-(4-((7-((hexahydro-2,5-methanopentalen-3a (1H)-yl)amino)heptyl)oxy)-1-oxoisoindolin-2-yl)piperidine-2,6-dione;
3-(4-((4-(((hexahydro-2,5-methanopentalen-3a (1H)-yl)amino)methyl)benzyl)oxy)-1-oxoisoindolin-2-yl)piperidine-2,6-dione;
2-(2,6-dioxopiperidin-3-yl)-4-((7-((hexahydro-2,5-methanopentalen-3a (1H)-yl)amino)heptyl)amino)isoindoline-1,3-dione;
2-(2,6-dioxopiperidin-3-yl)-4-((4-(((hexahydro-2,5-methanopentalen-3a (1H)-yl)amino)methyl)benzyl)amino)isoindoline-1,3-dione;
3-(4-((7-((hexahydro-2,5-methanopentalen-3a (1H)-yl)amino)heptyl)amino)-1-oxoisoindolin-2-yl)piperidine-2,6-dione;
3-(4-((4-(((hexahydro-2,5-methanopentalen-3a (1H)-yl)amino)methyl)benzyl)amino)-1-oxoisoindolin-2-yl)piperidine-2,6-dione;
3-(4-((4-(2-((hexahydro-2,5-methanopentalen-3a (1H)-yl)amino)ethyl)benzyl)amino)-1-oxoisoindolin-2-yl)piperidine-2,6-dione;
3-(4-(8-((hexahydro-2,5-methanopentalen-3a (1H)-yl)amino)octyl)-1-oxoisoindolin-2-yl)piperidine-2,6-dione;
N-(adamantan-1-yl)-7-((2-(2,6-dioxopiperidin-3-yl)-1-oxoisoindolin-4-yl)oxy) heptanamide;
N-(6-((2-(2,6-dioxopiperidin-3-yl)-1-oxoisoindolin-4-yl)oxy) hexyl) adamantane-1-carboxamide;
N-(adamantan-1-yl)-2-(4-(((2-(2,6-dioxopiperidin-3-yl)-1-oxoisoindolin-4-yl)oxy)methyl)phenyl) acetamide;
N-(adamantan-1-yl)-7-((2-(2,6-dioxopiperidin-3-yl)-1,3-dioxoisoindolin-4-yl)amino) heptanamide;
N-(6-((2-(2,6-dioxopiperidin-3-yl)-1,3-dioxoisoindolin-4-yl)amino)hexyl) adamantane-1-carboxamide;
N-(adamantan-1-yl)-2-(4-(((2-(2,6-dioxopiperidin-3-yl)-1,3-dioxoisoindolin-4-yl)amino)methyl)phenyl) acetamide;
N-(adamantan-1-yl)-8-(2-(2,6-dioxopiperidin-3-yl)-1-oxoisoindolin-4-yl) octanamide; or N-(7-(2-(2,6-dioxopiperidin-3-yl)-1-oxoisoindolin-4-yl) heptyl) adamantane-1-carboxamide;

5-((6-((adamantan-1-yl)amino)hexyl)amino)-2-(2,6-dioxopiperidin-3-yl)isoindoline-1,3-dione;

5-((5-((adamantan-1-yl)amino)pentyl)amino)-2-(2,6-dioxopiperidin-3-yl)isoindoline-1,3-dione;

5-((4-((adamantan-1-yl)amino)butyl)amino)-2-(2,6-dioxopiperidin-3-yl)isoindoline-1,3-dione;

5-((3-((adamantan-1-yl)amino)propyl)amino)-2-(2,6-dioxopiperidin-3-yl)isoindoline-1,3-dione;

3-(4-((4-(2-((adamantan-1-yl)amino)ethyl)benzyl)oxy)-1-oxoisoindolin-2-yl)piperidine-2,6-dione;

4-((4-(2-((adamantan-1-yl)amino)ethyl)benzyl)oxy)-2-(2,6-dioxopiperidin-3-yl)isoindoline-1,3-dione;

4-((4-(2-((adamantan-1-yl)amino)ethyl)benzyl)amino)-2-(2,6-dioxopiperidin-3-yl)isoindoline-1,3-dione;

2-(2,6-dioxopiperidin-3-yl)-4-((4-(((hexahydro-2,5-methanopentalen-3a (1H)-yl)amino)methyl)benzyl)oxy)isoindoline-1,3-dione;

3-(4-(4-(((hexahydro-2,5-methanopentalen-3a (1H)-yl) amino)methyl)phenethyl)-1-oxoisoindolin-2-yl)piperidine-2,6-dione;

2-(2,6-dioxopiperidin-3-yl)-4-((4-(2-((hexahydro-2,5-methanopentalen-3a (1H)-yl)amino)ethyl)benzyl) amino)isoindoline-1,3-dione;

3-(4-((4-(2-((hexahydro-2,5-methanopentalen-3a (1H)-yl)amino)ethyl)benzyl)oxy)-1-oxoisoindolin-2-yl)piperidine-2,6-dione;

2-(2,6-dioxopiperidin-3-yl)-4-((4-(2-((hexahydro-2,5-methanopentalen-3a (1H)-yl)amino)ethyl)benzyl)oxy) isoindoline-1,3-dione; and 3-(4-(8-((hexahydro-2,5-methanopentalen-3a (1H)-yl) amino) oct-1-yn-1-yl)-1-oxoisoindolin-2-yl)piperidine-2,6-dione.

25. The compound of Formula (I) or a salt, or an enantiomer thereof as claimed in claim 1, which is a hydrochloride salt of the compound of Formula (I).

26. A pharmaceutical composition comprising the compound of Formula (I) as claimed in claim 1 or a pharmaceutically acceptable salt thereof, and at least one pharmaceutically acceptable carrier.

27. The pharmaceutical composition as claimed in claim 26, further comprising at least one therapeutic agent for the treatment of a tumor.

28. A method for treating a tumor, comprising administering to a subject a therapeutically effective amount of the compound of Formula (I) as claimed in claim 1, or a pharmaceutically acceptable salt thereof, or a pharmaceutical composition comprising the compound of Formula (I) or a pharmaceutically acceptable salt thereof.

29. The method as claimed in claim 28, wherein the tumor is selected from the group consisting of: bone marrow disease, neutropenia; leukemia lymphoma, and Unverricht syndrome.

30. The method as claimed in claim 28, wherein the tumor is selected from the group consisting of: myeloma, myelodysplastic syndrome (MDS), transplantation-related cancer, myelofibrosis; acute myeloid leukemia, anemia, chronic myeloid leukemia, B-cell chronic lymphocytic leukemia, acute myeloid leukemia (AML); CD20 positive lymphoma, primary lymphoma, and B-cell lymphoma.

31. The method as claimed in claim 28, wherein the tumor is selected from the group consisting of: multiple myeloma, previously treated myelodysplastic syndrome, plasma cell myeloma, smoldering myeloma, smoldering multiple myeloma; relapsed B-cell non-Hodgkin's lymphoma, relapsed diffuse large B-cell lymphoma, relapsed primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B-cell lymphoma, and refractory transformed non-Hodgkin's lymphoma.

* * * * *